US007135174B2

(12) United States Patent
Corvalan et al.

(10) Patent No.: US 7,135,174 B2
(45) Date of Patent: Nov. 14, 2006

(54) ANTIBODIES DIRECTED TO PDGFD AND USES THEREOF

(75) Inventors: Jose R. F. Corvalan, Foster City, CA (US); Xiao-Chi Jia, San Mateo, CA (US); Xiao Feng, Union City, CA (US); Xiao-dong Yang, Palo Alto, CA (US); Francine Chen, San Francisco, CA (US); Gadi Gazit, Mountain View, CA (US); Richard Weber, San Francisco, CA (US); Binyam Bezabeh, Oakland, CA (US)

(73) Assignee: Amgen Fremont, Inc., Fremont, CA (US)

( * ) Notice: Subject to any disclaimer, the term of this patent is extended or adjusted under 35 U.S.C. 154(b) by 178 days.

(21) Appl. No.: 10/041,860

(22) Filed: Jan. 7, 2002

(65) Prior Publication Data

US 2003/0157109 A1    Aug. 21, 2003

(51) Int. Cl.
*A61K 39/395* (2006.01)
*C07K 16/22* (2006.01)

(52) U.S. Cl. .............................. 424/130.1; 424/133.1; 424/145.1; 530/387.1; 530/387.3; 530/388.23

(58) Field of Classification Search ........... 530/388.15, 530/388.24, 391.3, 388.23; 424/133.1, 134.1, 424/145.1, 178.1, 13, 130.1
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,816,397 A | 3/1989 | Boss et al. | |
| 5,151,510 A | 9/1992 | Stec et al. | |
| 5,194,594 A | 3/1993 | Khawli et al. | |
| 5,733,743 A | 3/1998 | Johnson et al. | |
| 5,916,771 A | 6/1999 | Hori et al. | |
| 6,207,418 B1 | 3/2001 | Hori et al. | |
| 6,432,673 B1 | 8/2002 | Gao et al. | |
| 6,468,543 B1 | 10/2002 | Gilbertson et al. | |
| 6,495,668 B1 | 12/2002 | Gilbert et al. | |
| 6,528,050 B1 | 3/2003 | Gao et al. | |
| 6,630,142 B1 | 10/2003 | Hart et al. | |
| 6,706,687 B1 * | 3/2004 | Eriksson et al. ............. | 514/12 |
| 6,814,965 B1 | 11/2004 | Gao et al. | |
| 6,827,938 B1 | 12/2004 | Hart et al. | |
| 6,866,991 B1 | 3/2005 | Gilbertson et al. | |
| 6,887,982 B1 | 5/2005 | Gao et al. | |
| 6,893,637 B1 | 5/2005 | Gilbertson | |
| 6,962,802 B1 | 11/2005 | Gilbert et al. | |

FOREIGN PATENT DOCUMENTS

| | | |
|---|---|---|
| WO | WO 94/29444 | 12/1994 |
| WO | WO 97/38137 | 10/1997 |
| WO | WO 01/25433 A2 | 4/2001 |

OTHER PUBLICATIONS

Ngo et al., 1994, The Protein Folding Problem and Tertiary Structure Prediction, pp. 492-495.*
Kuby et al., 1994, Immunology, second edition, pp. 85-96.*
Janway et al, p. 3:1-3:3, in Immunobiology, 1994.*
Merriam-Webster's Online Dictionary, 10th Edition.*
Green et al, Nature Genetics 7: 13-21, May 4, 1994.*
Alon et al. *Nat. Med.*, 1(10):1024-1028 (1995).
Athanassiades et al. *Placenta*, 19(7): 465-473 (1998).
Baldrick, *Regul. Toxicol. Pharmacol.*, 32(2):210-218 (2000).
Bellamy et al. *Cancer Res.*, 59(3):728-733 (1999).
Blake et al. *BioConjugate Chem.*, Abstract only, 3:510-513 (1992).
Bowie et al. *Science*, Abstract only, 253:164-170 (1991).
Carmeliet et al. *Cell*, 98(2):147-157 (1999).
Charman, *J. Pharm. Sci.*, 89(8):967-978 (2000).
Chen et al *Hum. Gene Ther.*, Abstract only, 5(5):595-601 (1994).
Chiswell et al. *Trends Biotechnol.*, Abstract only, 10(3):80-84 (1992).
Chothia et al. *J. Mol. Biol.*, Abstract only, 196(4):901-917 (1987).
Chothia et al. *Nature*, 342:878-883 (1989).
Crossen et al. *Cancer Genet. Cytogenet.*, 112:144-148 (1999).
Cwirla et al. *Proc. Natl. Acad. Sci. USA*, 87:6378-6382 (1990).
Deo et al. *Immunol. Today*, 18:127-135 (1997).
Evans et al. *J. Med. Chem.*, Abstract only, 30(7):1229-1239 (1987).
Fanger et al. *Immunomethods.*, Abstract only, 4(1):72-81 (1994).
Ferrara, *Curr. Top Microbiol. Immunol.*, 237:1-30 (1999).
Ferti-Passantonopoulou et al. *Cancer Genet. Cytogenet.*, Abstract only, 51(2):183-188 (1991).
Gerber et al. *J. Biol. Chem.*, 273(46):30336-30343 (1998).
Gorman et al. *Proc. Natl. Acad. Sci. USA*, 79:6777-6781 (1982).
Green et al. *J. Exp. Med.*, 188(3):483-495 (1998).
Green et al. *Nature Genetics*, 7:13-21 (1994).
Grosschedl et al. *Cell*, Abstract only, 41(3):885-897 (1985).
Hanes et al. *Proc. Natl. Acad. Sci. USA*, 94:4937-4942 (1997).
Hoogenboom et al. *Immunol. Rev.*, Abstract only, 130:41-68 (1992).
Houghten et al. *Biotechniques*, 13(3):412-421 (1992).
Houghten *Proc. Natl. Acad. Sci. USA*, 82:5131-5135 (1985).
Ike et al. *Nucl. Acid Res.*, 11(2):477-488 (1983).
Itakura et al. *Annu. Rev. Biochem.*, Abstract only,53:323-356 (1984).
Katoh et al. *J. Gastroenterol.*, 31(1):137-139 (1996).
Kessler et al. *Science*, 271:360-362 (1996).

(Continued)

*Primary Examiner*—Christina Chan
*Assistant Examiner*—Phuong N Huynh
(74) *Attorney, Agent, or Firm*—Mintz, Levin, Cohn, Ferris, Glovsky and Popeo, P.C.; Ivor R. Elrifi

(57) ABSTRACT

The present invention is related to antibodies directed to the antigen PDGFD and uses of such antibodies. In particular, in accordance with the present invention, there are provided fully human monoclonal antibodies directed to the antigen PDGFD. Nucelotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3, are provided. Hybridomas or other cell lines expressing such immunoglobulin molecules and monoclonal antibodies are also provided.

4 Claims, 68 Drawing Sheets

OTHER PUBLICATIONS

Kostelny et al. *J. Immunol.*, 148:1547-1553 (1992).
Kurahashi et al. *Hum. Mol. Genet.*, 9(11):1665-1670 (2000).
LaPlanche et al. *Nucl. Acids Res.*, 14(22):9081-9093 (1986).
LaRochelle et al. *Nat. Cell Biol.*, 3:517-521 (2001).
Li et al. *Cell Res.*, 9:11-25 (1999).
Liu et al. *Proc. Natl. Acad. Sci. USA*, 84:3439-3443 (1987).
Liu et al. *J. Immunol.*, Abstract only,139(10):3521-3526 (1987).
Marasco, *Gene Ther.*, Abstract only, 4(1): 11-15 (1997).
Masood et al., *Proc. Natl. Acad. Sci. USA*, 94(3):979-984 (1997).
Mendez et al. *Nat. Genet.*, 15:146-156 (1997).
Michaux et al. *Genes, Chromosomes & Cancer*, 29:40-47 (2000).
Narang, *Tetrahedron*, Abstract only, 39(1):3-22 (1983).
Needleman et al. *J. Mol. Biol.*, 48:443-453 (1970).
Okayama et al. *Mol. Cell. Biol.*, 3(2):280-289 (1983).
Parmley et al. *Gene*, Abstract only, 73(2):305-318 (1988).
Pearson et al. *Proc. Natl. Acad. Sci. USA*, 85:2444-2448 (1988).
Pinilla et al. *Biotechniques*, Abstract only, 13(6):901-905 (1992).
Pivnick et al. *J. Med. Genet.*, Abstract only, 33(9):772-778 (1996).
Powell et al. *PDA J. Pharm. Sci. Technol.*, Abstract only, 52(5):238-311 (1998).
Risau et al., *Annu. Rev. Cell Dev. Biol.*, 11:73-91 (1995).
Risau, *FASEB J.*, 9(10):926-933 (1995).
Rizo et al. *Annu. Rev. Biochem.*, Abstract only 61:387-418(1992).
Russell et al. *Nucl. Acids Res.*, 21(5):1081-1085 (1993).
Scott, *Trends Biochem. Sci.*, Abstract only, 17(7):241-245 (1992).
Shen et al. *J. Surg. Oncol.*, Abstract only, 74(2):100-107 (2000).
Smith et al. *Adv. Appl. Math.*, Abstract only, 2(4):482-489 (1981).
Songsivilai et al. *Clin. Exp. Immunol.*, Abstract only, 79(3):315-321 (1990).
Speirs et al. *Br. J. Cancer*, 80(5/6):898-903(1999).
Stec et al. *J. Am. Chem. Soc.*, Abstract only, 106:6077-6079 (1984).
Stein et al. *Nucl. Acids Res.*, 16:3209-3221 (1988).
Tarkkanen et al. *Genes, Chromosomes & Cancer*, 25:323-331 (1999).
Thornton et al. *Nature*, 354:105-106 (1991).
Traunecker et al. *Int. J. Cancer (Suppl.)*, Abstract only,7:51-52 (1992).
Uhlmann et al. *Chem. Rev.*, Abstract only, 90(4):543 (1990).
Valerius et al. *Blood*, 90(11):4485-4492 (1997).
Veber et al. *Trends in Neurosci.*, Abstract only, 8:392-396 (1985).
Vitetta et al. *Immunol. Today*, Abstract only,14(6):252-259 (1993).
Wang, *Int. J. Pharm.*, 203(1-2):1-60 (2000).
Warren et al. *J. Clin. Invest.*, 95:1789-1797 (1995).
Winter et al. *Immunol. Today*, Abstract only,14(6):243-246 (1993).
Wozney et al. *Science*, 242:1528-1534 (1988).
Wright et al. *Crit. Rev. Immunol.*, Abstract only, 12(3-4):125-168 (1992).
Yoshikawa et al. *Cancer*, 56:1682-1687 (1985).
Yuan et al. *Proc. Natl. Acad. Sci. USA*, 93:14765-14770 (1996).
Zon et al. *Anti-Cancer Drug Des.*, Abstract only,6(6):539-568 (1991).

* cited by examiner

FIGURE 1

CTAAAAAATATGTTCTCTACAACACCAAGGCTCATTAAAATATTTTAAATATT
AATATACATTTCTTCTGTCAGAAATACATAAAACTTTATTATATCAGCGCAGG
GCGGCGCGGCGTCGGTCCCGGGAGCAGAACCCGGCTTTTTCTTGGAGCGACG
CTGTCTCTAGTCGCTGATCCCAAATGCACCGGCTCATCTTTGTCTACACTCTA
ATCTGCGCAAACTTTTGCAGCTGTCGGGACACTTCTGCAACCCCGCAGAGCG
CATCCATCAAAGCTTTGCGCAACGCCAACCTCAGGCGAGATGAGAGCAATCA
CCTCACAGACTTGTACCGAAGAGATGAGACCATCCAGGTGAAAGGAAACGG
CTACGTGCAGAGTCCTAGATTCCCGAACAGCTACCCCAGGAACCTGCTCCTG
ACATGGCGGCTTCACTCTCAGGAGAATACACGGATACAGCTAGTGTTTGACA
ATCAGTTTGGATTAGAGGAAGCAGAAAATGATATCTGTAGGTATGATTTTGT
GGAAGTTGAAGATATATCCGAAACCAGTACCATTATTAGAGGACGATGGTGT
GGACACAAGGAAGTTCCTCCAAGGATAAAATCAAGAACGAACCAAATTAAA
ATCACATTCAAGTCCGATGACTACTTTGTGGCTAAACCTGGATTCAAGATTTA
TTATTCTTTGCTGGAAGATTTCCAACCCGCAGCAGCTTCAGAGACCAACTGGG
AATCTGTCACAAGCTCTATTTCAGGGGTATCCTATAACTCTCCATCAGTAACG
GATCCCACTCTGATTGCGGATGCTCTGGACAAAAAAATTGCAGAATTTGATA
CAGTGGAAGATCTGCTCAAGTACTTCAATCCAGAGTCATGGCAAGAAGATCT
TGAGAATATGTATCTGGACACCCTCGGTATCGAGGCAGGTCATACCATGAC
CGGAAGTCAAAAGTTGACCTGGATAGGCTCAATGATGATGCCAAGCGTTACA
GTTGCACTCCCAGGAATTACTCGGTCAATATAAGAGAAGAGCTGAAGTTGGC
CAATGTGGTCTTCTTTCCACGTTGCCTCCTCGTGCAGCGCTGTGGAGGAAATT
GTGGCTGTGGAACTGTCAACTGGAGGTCCTGCACATGCAATTCAGGGAAAAC
CGTGAAAAAGTATCATGAGGTATTACAGTTTGAGCCTGGCCACATCAAGAGG
AGGGGTAGAGCTAAGACCATGGCTCTAGTTGACATCCAGTTGGATCACCATG
AACGATGTGATTGTATCTGCAGCTCAAGACCACCTCGATAAGAGAATGTGCA
CATCCTTACATTAAGCCTGAAAGAACCTTTAGTTTAAGGAGGGTGAGATAAG
AGACCCTTTTCCTACCAGCAACCAAACTTACTACTAGCCTGCAATGCAATGA
ACACAAGTGGTTGCTGAGTCTCAGCCTTGCTTTGTTAATGCCATGGCAAGTAG
AAAGGTATATCATCAACTTCTATACCTAAGAATATAGGATTGCATTTAATAAT
AGTGTTTGAGGTTATATATGCACAAACACACAGAAATATATTCATGTCTAT
GTGTATATAGATCAAATGTTTTTTTGGTATATATAACCAGGTACACCAGAGC
TTACATATGTTTGAGTTAGACTCTTAAAATCCTTTGCCAAAATAAGGGATGGT
CAAATATATGAAACATGTCTTTAGAAAATTTAGGAGATAAATTTATTTTTAAA
TTTTGAAACACAAAACAATTTGAATCTTGCTCTCTTAAAGAAAGCATCTTGT
ATATTAAAAATCAAAAGATGAGGCTTTCTTACATATACATCTTAGTTG (SEQ
ID NO:50)

Figure 2A

```
  1 CTAAAAAATATGTTCTCTACAACACCAAGGCTCATTAAAATATTT
 46 TAAATATTAATATACATTTCTTCTGTCAGAAATACATAAAACTTT
 91 ATTATATCAGCGCAGGGCGGCGCGGCGTCGGTCCCGGGAGCAGAA
136 CCCGGCTTTTTCTTGGAGCGACGCTGTCTCTAGTCGCTGATCCCA

181 AATGCACCGGCTCATCTTTGTCTACACTCTAATCTGCGCAAACTT
    MetHisArgLeuIlePheValTyrThrLeuIleCysAlaAsnPhe

226 TTGCAGCTGTCGGGACACTTCTGCAACCCCGCAGAGCGCATCCAT
    CysSerCysArgAspThrSerAlaThrProGlnSerAlaSerIle

271 CAAAGCTTTGCGCAACGCCAACCTCAGGCGAGATGAGAGCAATCA
    LysAlaLeuArgAsnAlaAsnLeuArgArgAspGluSerAsnHis

316 CCTCACAGACTTGTACCGAAGAGATGAGACCATCCAGGTGAAAGG
    LeuThrAspLeuTyrArgArgAspGluThrIleGlnValLysGly

361 AAACGGCTACGTGCAGAGTCCTAGATTCCCGAACAGCTACCCCAG
    AsnGlyTyrValGlnSerProArgPheProAsnSerTyrProArg

406 GAACCTGCTCCTGACATGGCGGCTTCACTCTCAGGAGAATACACG
    AsnLeuLeuLeuThrTrpArgLeuHisSerGlnGluAsnThrArg

451 GATACAGCTAGTGTTTGACAATCAGTTTGGATTAGAGGAAGCAGA
    IleGlnLeuValPheAspAsnGlnPheGlyLeuGluGluAlaGlu

496 AAATGATATCTGTAGGTATGATTTTGTGGAAGTTGAAGATATATC
    AsnAspIleCysArgTyrAspPheValGluValGluAspIleSer

541 CGAAACCAGTACCATTATTAGAGGACGATGGTGTGGACACAAGGA
    GluThrSerThrIleIleArgGlyArgTrpCysGlyHisLysGlu

586 AGTTCCTCCAAGGATAAAATCAAGAACGAACCAAATTAAAATCAC
    ValProProArgIleLysSerArgThrAsnGlnIleLysIleThr

631 ATTCAAGTCCGATGACTACTTTGTGGCTAAACCTGGATTCAAGAT
```

Figure 2B

PheLysSerAspAspTyrPheValAlaLysProGlyPheLysIle

676 TTATTATTCTTTGCTGGAAGATTTCCAACCCGCAGCAGCTTCAGA
TyrTyrSerLeuLeuGluAspPheGlnProAlaAlaAlaSerGlu

721 GACCAACTGGGAATCTGTCACAAGCTCTATTTCAGGGGTATCCTA
ThrAsnTrpGluSerValThrSerSerIleSerGlyValSerTyr

766 TAACTCTCCATCAGTAACGGATCCCACTCTGATTGCGGATGCTCT
AsnSerProSerValThrAspProThrLeuIleAlaAspAlaLeu

811 GGACAAAAAAATTGCAGAATTTGATACAGTGGAAGATCTGCTCAA
AspLysLysIleAlaGluPheAspThrValGluAspLeuLeuLys

856 GTACTTCAATCCAGAGTCATGGCAAGAAGATCTTGAGAATATGTA
TyrPheAsnProGluSerTrpGlnGluAspLeuGluAsnMetTyr

901 TCTGGACACCCCTCGGTATCGAGGCAGGTCATACCATGACCGGAA
LeuAspThrProArgTyrArgGlyArgSerTyrHisAspArgLys

946 GTCAAAAGTTGACCTGGATAGGCTCAATGATGATGCCAAGCGTTA
SerLysValAspLeuAspArgLeuAsnAspAspAlaLysArgTyr

991 CAGTTGCACTCCCAGGAATTACTCGGTCAATATAAGAAGAGCT
SerCysThrProArgAsnTyrSerValAsnIleArgGluGluLeu

1036 GAAGTTGGCCAATGTGGTCTTCTTTCCACGTTGCCTCCTCGTGCA
LysLeuAlaAsnValValPhePheProArgCysLeuLeuValGln

1081 GCGCTGTGGAGGAAATTGTGGCTGTGGAACTGTCAACTGGAGGTC
ArgCysGlyGlyAsnCysGlyCysGlyThrValAsnTrpArgSer

1126 CTGCACATGCAATTCAGGGAAAACCGTGAAAAAGTATCATGAGGT
CysThrCysAsnSerGlyLysThrValLysLysTyrHisGluVal

1171 ATTACAGTTTGAGCCTGGCCACATCAAGAGGAGGGGTAGAGCTAA
LeuGlnPheGluProGlyHisIleLysArgArgGlyArgAlaLys

1216 GACCATGGCTCTAGTTGACATCCAGTTGGATCACCATGAACGATG
     ThrMetAlaLeuValAspIleGlnLeuAspHisHisGluArgCys

1261 TGATTGTATCTGCAGCTCAAGACCACCTCGATAAGAGAATGTGCA
     AspCysIleCysSerSerArgProProArg (SEQ ID NO:12)

1306 CATCCTTACATTAAGCCTGAAAGAACCTTTAGTTTAAGGAGGGTG
1351 AGATAAGAGACCCTTTTCCTACCAGCAACCAAACTTACTACTAGC
1396 CTGCAATGCAATGAACACAAGTGGTTGCTGAGTCTCAGCCTTGCT
1441 TTGTTAATGCCATGGCAAGTAGAAAGGTATATCATCAACTTCTAT
1486 ACCTAAGAATATAGGATTGCATTTAATAATAGTGTTTGAGGTTAT
1531 ATATGCACAAACACACACAGAAATATATTCATGTCTATGTGTATA
1576 TAGATCAAATGTTTTTTTTGGTATATATAACCAGGTACACCAGAG
1621 CTTACATATGTTTGAGTTAGACTCTTAAAATCCTTTGCCAAAATA
1666 AGGGATGGTCAAATATATGAAACATGTCTTTAGAAAATTTAGGAG
1711 ATAAATTTATTTTTAAATTTTGAAACACAAAACAATTTTGAATCT
1756 TGCTCTCTTAAAGAAAGCATCTTGTATATTAAAAATCAAAAGATG
1801 AGGCTTTCTTACATATACATCTTAGTTG (SEQ ID NO:50)

A -- Cur2 1.6 heavy chain nucleotide sequence
GAGGTGCAGCTGGTGGAGTCTGGGGGAGGCCTGGTCAAGCCTGGGGGGTCCC
TGAGACTCTCCTGTGCAGCCTCTGGATTCAACTTCAGAACCTATAACATGAAC
TGGGTCCGCCAGGCTCCAGGGAAGGGGCTGGAGTGGGTCTCATCCATTAGTA
GTAGTAGTAGTAACATATACTACGCAGACTCAGTGAAGGGCCGATTCACCAT
CTCCAGAGACAACGCCAAGAACTCACTGTATCTGCAAATGAACAGCCTGAGA
GCCGAGGACACGGCTGTATATTACTGTGCGAGAGATATTATGATTACGTTTG
GGGGAATTATCGCCTCGTTCTACTTTGACTACTGGGGCCAGGGAACCCTGGTC
ACCGTCTCCTCAG (SEQ ID NO:55)

B -- Cur2 1.6 heavy chain amio acid sequence

EVQLVESGGGLVKPGGSLRLSCAASGFNFRTYNMNWVRQAPGKGLEWVSSISSS
SSNIYYADSVKGRFTISRDNAKNSLYLQMNSLRAEDTAVYYCARDIMITFGGIIAS
FYFDYWGQGTLVTVSS (SEQ ID NO:13)

C -- Cur2 1.6 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TTTCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
ATTCACTCTCACAATCAGCAGCCTGCAGCCTGAAGATTTTGCAACTTATTACT
GTCTACAGCATAATAGTTACCCGCTCACTTTCGGCGGAGGGACCAAGGTGGA
GATCAAAC (SEQ ID NO:56)

D -- Cur2 1.6 light chain amino acid sequence

DIQMTQSPSSLSASVGDRVTITCRASQGIRNDLGWFQQKPGKAPKRLIYAASSLQ
SGVPSRFSGSGSGTEFTLTISSLQPEDFATYYCLQHNSYPLTFGGGTKVEIK (SEQ
ID NO:14)

FIGURE 4

A -- Cur2 1.11 heavy chain nucleotide sequence
GAGGTGCAGCTGGTGCAGTCTGGAGGAGGCTTGATCCAGCCTGGGGGGTCCC
TGAGACTCTCCTGTGCAGCCTCTGGGTTCACCGTCAGTAGCAACTACATGAGC
TGGGTCCGCCAGGCTCCAGGGAAGGGGCTGGAGTGGGTCTCAGTTATTTATA
GCGGTGGTAGCACATACTACGCAGACTCCGTGAAGGGCCGATTCACCATCTC
CAGAGACAATTCCAAGAACACGCTGTATCTTCAAATGAACAGCCTGAGAGCC
GAGGACACGGCCGTGTATTACTGTGCGGGAACGGTGACTACGAATTACTACT
ACGGTATGGACGTCTGGGGCCAAGGGACCACGGTCACCGTCTCCTCAG (SEQ ID NO:57)

B -- Cur2 1.11 heavy chain amino acid sequence
EVQLVQSGGGLIQPGGSLRLSCAASGFTVSSNYMSWVRQAPGKGLEWVSVIYSG
GSTYYADSVKGRFTISRDNSKNTLYLQMNSLRAEDTAVYYCAGTVTTNYYYGM
DVWGQGTTVTVSS (SEQ ID NO:15)

C -- Cur2 1.11 light chain nucleotide sequence
GATATTGTGATGACTCAGTCTCCACTCTCCCTGCCCGTCACCCCTGGAGAGCC
GGCCTCCATCTCCTGCAGGTCTAGTCAGAGCCTCCTGCAAAGTAATGGATAC
AACTATTTGGATTGGTACCTGCAGAAGCCAGGGCAGTCTCCACAGCTCCTGA
TCTATTTGGGTTCTAATCGGGCCTCCGGGGTCCCTGACAGGTTCAGTGGCAGT
GGATCAGGCACAGATTTTACACTGAAAATCAGCAGAGTGGAGGCTGAGGATG
TTGGGGTTTATTACTGCATGCAAGCTCTACAAACTCTCACTTTCGGCGGAGGG
ACCAAGGTGGAGATCAAAC (SEQ ID NO:58)

D -- Cur2 1.11 light chain amino acid sequence
DIVMTQSPLSLPVTPGEPASISCRSSQSLLQSNGYNYLDWYLQKPGQSPQLLIYLG
SNRASGVPDRFSGSGSGTDFTLKISRVEAEDVGVYYCMQALQTLTFGGGTKVEI
K (SEQ ID NO:16)

FIGURE 5

A -- Cur2 1.17 heavy chain nucleotide sequence

CAGGTGCAGCTGGTGGAGTCGGGGGGAGGCGTGGTCCAGCCTGGGAAGTCCC
TGAGACTCTCCTGTGCAGCGTCTGGATTCACCTTCAGTAGCTATGGCATGCAC
TGGGTCCGCCAGGCTCCAGGCAAGGGGCTGGAGTGGGTGGCAGTTATATGGT
ATGATGGAAGTAATAAATACTATGCAGACTCCGTGAAGGGCCGATTCACCAT
CTCCAGAGACAATTCCAAGAACACGCTGTATCTGCAAATGAACAGCCTGAGA
GCCGAGGACACGGCTGTGTATTACTGTGCGAGAGATCAAGGATACAGATATG
CTGGTTACTACTACGACTACGGTATGGACGTCTGGGGCCAAGGGACCACGGT
CACCGTCTCCTCAG (SEQ ID NO:59)

B -- Cur2 1.17 heavy chain protein sequence

QVQLVESGGGVVQPGKSLRLSCAASGFTFSSYGMHWVRQAPGKGLEWVAVIW
YDGSNKYYADSVKGRFTISRDNSKNTLYLQMNSLRAEDTAVYYCARDQGYRYA
GYYYDYGMDVWGQGTTVTVSS (SEQ ID NO:17)

C -- Cur2 1.17 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
ATTCACTCTCACAATCAGCAGCCTGCAGCCTGAAGATTTTGCAACTTATTACT
GTCTACAGCATAATAGTTACCCGCTCACTTTCGGCGGAGGGACCAAGGTGGA
GATCAAAC (SEQ ID NO:60)

D -- Cur2 1.17 light chain protein sequence

DIQMTQSPSSLSASVGDRVTITCRASQGIRNDLGWYQQKPGKAPKRLIYAASSLQ
SGVPSRFSGSGSGTEFTLTISSLQPEDFATYYCLQHNSYPLTFGGGTKVEIK (SEQ
ID NO:18)

FIGURE 6

A -- Cur2 1.18 heavy chain nucleotide sequence

CAGGTGCAGCTGGTGCAGTCGGGGGCTGAGGTGAAGAAGCCTGGGGCCTCA
GTGAAGGTCTCCTGCAAGGCTTCTGGATACACCTTCACCAGTTATGATATCAA
CTGGGTGCGACAGGCCACTGGACAAGGGCTTGAGTGGATGGGATGGATGAA
CCCAAACAGTGGTAACACAGGCTATGCACAGAAGTTCCAGGGCAGAGTCACC
ATGACCAGGAACACCTCCATAAGCACAGCCTACATGGAGCTGAGCAGCCTGA
GATCTGAGGACACGGCCGTGTATTACTGTGCGAGAGAGGGTATAGCAGTGGC
TGGGACATACTACTACTACTACGGTATGGACGTCTGGGGCCAAGGGACCACG
GTCACCGTCTCCTCAG (SEQ ID NO:61)

B -- Cur2 1.18 heavy chain protein sequence

QVQLVQSGAEVKKPGASVKVSCKASGYTFTSYDINWVRQATGQGLEWMGWM
NPNSGNTGYAQKFQGRVTMTRNTSISTAYMELSSLRSEDTAVYYCAREGIAVAG
TYYYYYGMDVWGQGTTVTVSS (SEQ D NO:19)

C -- Cur2 1.18 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
ATTCACTCTCACAATCAGCAGCCTGCAGCCTGAAGATTTTGCAACTTATTTCT
GTCTACAGCATAATAGTTACCCATTCACTTTCGGCCCTGGGACCAAAGTGGAT
ATCAAAC (SEQ ID NO:62)

D -- Cur2 1.18 light chain protein sequence

DIQMTQSPSSLSASVGDRVTITCRASQGIRNDLGWYQQKPGKAPKRLIYAASSLQ
SGVPSRFSGSGSGTEFTLTISSLQPEDFATYFCLQHNSYPFTFGPGTKVDIK (SEQ
ID NO:20)

FIGURE 7

A -- Cur2 1.19 heavy chain nucleotide sequence
CAGGTGCAGCTGGTGCAGTCTGGGGCTGAGGTGAAGAAGCCTGGGGCCTCAG
TGAAGGTCTCCTGCAAGGCTTCTGGATACACCTTCACCAGTTATGATATCAAC
TGGGTGCGACAGGCCACTGGACAAGGGCTTGAGTGGATGGGATGGATGAAC
CCTAACAGTGGTAACACAGGCTATGCACAGAAGTTCCAGGGCAGAGTCACCA
TGACCAGGAACACCTCCATAAGCACAGCCTACATGGAGCTGAGCAGCCTGAG
ATCTGAGGACACGGCCGTGTATTACTGTGCGAGAGACGTTATGATTACGTTTG
GGGGAGTTATCGTGCACTACGGTATGGACGTCTGGGGCCAAGGGACCACGGT
CACCGTCTCCTCAG (SEQ ID NO:63)

B -- Cur2 1.19 heavy chain amino acid sequence

QVQLVQSGAEVKKPGASVKVSCKASGYTFTSYDINWVRQATGQGLEWMGWM
NPNSGNTGYAQKFQGRVTMTRNTSISTAYMELSSLRSEDTAVYYCARDVMITFG
GVIVHYGMDVWGQGTTVTVSS (SEQ ID NO:21)

C -- Cur2 1.19 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
TTTCACTCTCACAATCAGCAGCCTGCAGCCTGAAGATTTTGCAACTTATTACT
GTCTACAGCATAATAGTGACCCGTGCAGTTTTGGCCAGGGGACCAAGCTGGA
GATCAGAC (SEQ ID NO:64)

D -- Cur2 1.19 light chain amino acid sequence

DIQMTQSPSSLSASVGDRVTITCRASQGIRNDLGWYQQKPGKAPKRLIYAASSLQ
SGVPSRFSGSGSGTDFTLTISSLQPEDFATYYCLQHNSDPCSFGQGTKLEIR (SEQ
ID NO:22)

FIGURE 8

A -- Cur2 1.23 heavy chain nucleotide sequence

GAGGTGCAGCTGGTGCAGTCTGGAGCAGAGGTGAAAAAGCCCGGGGAGTCT
CTGAAGATCTCCTGTGAGGGTTCTGGATACAGCTTTACCAGCTACTGGATCGG
CTGGGTGCGCCAGATGCCCGGGAAAGGCCTGGAGTGGATGGGGATCATCTAT
CCTGGTGACTCTGATACCAGATACAGCCCGTCCTTCCAAGGCCAGGTCACCA
TCTCAGCCGACAAGTCCATCAGCACCGCCTACCTGCAGTGGAGCAGCCTGAA
GGCCTCGGACACCGCCATGTATTACTGTGCGAGACATGTATCGTATTACTATG
TTTCGGGGAGTTATTATAACGTCTTTGACTACTGGGGCCAGGGAACCCTGGTC
ACCGTCTCCTCAG (SEQ ID NO:65)

B -- Cur2 1.23 heavy chain amino acid sequence
EVQLVQSGAEVKKPGESLKISCEGSGYSFTSYWIGWVRQMPGKGLEWMGIIYPG
DSDTRYSPSFQGQVTISADKSISTAYLQWSSLKASDTAMYYCARHVSYYYVSGS
YYNVFDYWGQGTLVTVSS (SEQ ID NO:23)

C -- Cur2 1.23 light chain nucleotide sequence
GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGATACCAGGGAAAGCCCCTAAGCGCCTGATCTATGCTGCATCCA
GTTTGCAACGTGGGGTCCCATCAAGGTTCAGCGGCAGTGGATCTGGGACAGA
ATTCACTCTCACAATCAGCAGCCTGCAGCCTGAAGATTTTGCAACTTATTACT
GTCTACAGCATAATAGTTACCCGTGGACGTTCGGCCAAGGGACCAAGGTGGA
AATCAAAC (SEQ ID NO:66)

D -- Cur2 1.23 light chain amino acid sequence
DIQMTQSPSSLSASVGDRVTITCRASQGIRNDLGWYQQIPGKAPKRLIYAASSLQR
GVPSRFSGSGSGTEFTLTISSLQPEDFATYYCLQHNSYPWTFGQGTKVEIK (SEQ
ID NO:24)

FIGURE 9

A -- Cur2 1.24.1 heavy chain nucleotide sequence

CAGGTGCAGCTGGTGGAGTCTGGGGGAGGCGTGGTCCAGCCTGGGAGGTCCC
TGAGACTCTCCTGTGCAGCGTCTGGATTCAGTTTCAGTAGCTATGGCATGCAC
TGGGTCCGCCAGGCTCCAGGCAAGGGGCTGGAGTGGGTGGCAGATATATGGT
ATGATGGAAGTAATAAATACTATGCAGACTCCGTGAAGGGCCGATTCACCAT
CTCCAGAGACAATTCCAAGAACACGCTGTATCTGCAAATGAACAGCCTGAGA
GCCGAGGACACGGCTGTGTATTATTGTGCGAGAGATCAGGGATACAGCTATG
GTTACGTCTACTACGACTACGGTATGGACGTCTGGGGCCAAGGGACCACGGT
CACCGTCTCCTCAG (SEQ ID NO:67)

B -- Cur2 1.24.1 heavy chain protein sequence

QVQLVESGGGVVQPGRSLRLSCAASGFSFSSYGMHWVRQAPGKGLEWVADIW
YDGSNKYYADSVKGRFTISRDNSKNTLYLQMNSLRAEDTAVYYCARDQGYSYG
YVYYDYGMDVWGQGTTVTVSS (SEQ ID NO:25)

C -- Cur2 1.24.1 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
GTTCACTCTCACAATCAGCAGCCTGCAGCCTGAAGATTTTGCAACTTATTACT
GTCTACAGCATAATAGTTACCCGTGGACGTTCGGCCAAGGGACCAAGGTGGA
AATCAAAC (SEQ ID NO:68)

D -- Cur2 1.24.1 light chain protein sequence

DIQMTQSPSSLSASVGDRVTITCRASQGIRNDLGWYQQKPGKAPKRLIYAASSLQ
SGVPSRFSGSGSGTEFTLTISSLQPEDFATYYCLQHNSYPWTFGQGTKVEIK (SEQ
ID NO:26)

FIGURE 10

A -- Cur2 1.25.1 heavy chain nucleotide sequence

GAGGTGCAGCTGGTGCAGTCGGGAGCAGAGGTGAAAAAGCCCGGGGAGTCT
CTGAAGATCTCCTGTAAGGGTTCTGGATACAGGTTTACCAGCTACTGGATCGG
CTGGGTGCGCCAGATGCCCGGGAAAGGCCTGGAGTGGATGGGGATCATCTAT
CCTGGTGACTCTGATACCAGATACAGCCCGTCCTTCCAAGGCCAGGTCACCA
TCTCAGCCGACAAGTCCATCAGCACCGCCTACCTGCAGTGGAGCAGCCTGAA
GGCCTCGGACACCGCCATGTATTACTGTGCGAGACATGGATCGTATTATTATG
GTTCGGAGACTTATTATAATGTCTTTGACTACTGGGGCCAGGGAACCCTGGTC
ACCGTCTCCTCAG (SEQ ID NO:69)

B -- Cur2 1.25.1 heavy chain protein sequence

EVQLVQSGAEVKKPGESLKISCKGSGYRFTSYWIGWVRQMPGKGLEWMGIIYPG
DSDTRYSPSFQGQVTISADKSISTAYLQWSSLKASDTAMYYCARHGSYYYGSET
YYNVFDYWGQGTLVTVSS (SEQ ID NO:27)

C -- Cur2 1.25.1 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
ATTCACTCTCACAATCAGCAGCCTGCAGCCTGAAGATTTTGCAACTTATTACT
GTCTACAGCATAATAGTTACCCGTGGACGTTCGGCCAAGGGACCAAGGTGGA
AATCAAAC (SEQ ID NO:70)

D -- Cur2 1.25.1 light chain protein sequence

DIQMTQSPSSLSASVGDRVTITCRASQGIRNDLGWYQQKPGKAPKRLIYAASSLQ
SGVPSRFSGSGSGTEFTLTISSLQPEDFATYYCLQHNSYPWTFGQGTKVEIK (SEQ
ID NO:28)

FIGURE 11

A -- Cur2 1.29 heavy chain nucleotide sequence

GAGGTGCAGCTGGTGCAGTCGGGAGCAGAGGTGAAAAAGCCCGGGGAGTCT
CTGAAGATCTCCTGTAAGGGTTCTGGATACAGCTTTACCAGCTACTGGATCGG
CTGGGTGCGCCAGATGCCCGGGAAAGGCCTGGAGTGGATGGGGATCATCTAT
CCTGGTGACTCTGATACCAGATACAGCCCGTCCTTCCAAGGCCAGGCCACCA
TCTCAGCCGACAAGTCCATCAGCACCGCCTACCTGCAGTGGAGCAGCCTGAA
GGCCTCGGACACCGCCATGTATTACTGTGCGAGACACGTGGATGTAGGGGCT
ACGATTGGGGGATATTACTATTACTACCACGGTATGGACGTCTGGGGCCAAG
GGACCACGGTCACCGTCTCCTCAG (SEQ ID NO:71)

B -- Cur2 1.29 heavy chain protein sequence

EVQLVQSGAEVKKPGESLKISCKGSGYSFTSYWIGWVRQMPGKGLEWMGIIYPG
DSDTRYSPSFQGQATISADKSISTAYLQWSSLKASDTAMYYCARHVDVGATIGG
YYYYYHGMDVWGQGTTVTVSS (SEQ ID NO:29)

C -- Cur2 1.29 light chain nucleotide sequence

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCAGAAGCCAGGGCAGTCTCCACAACTCCTGATC
TATTTGGGTTCTAATCGGGCCTCCGGGGTCCCTGACAGGTTCAGTGGCAGTGG
ATCAGGCACAGATTTTACACTGAAAATCAGCAGAGTGGAGGCTGACGATGTT
GGGGTTTATTACTGCATGCAAGCTCTACAATCTCTCATGTGCAGTTTTGGCCA
GGGGACCAAGCTGGAGATCAAAC (SEQ ID NO:72)

D -- Cur2 1.29 light chain protein sequence

DIVMTQSPLSLPVTPGEPASISCRSSQSLLHSNGYNYLDWYLQKPGQSPQLLIYLG
SNRASGVPDRFSGSGSGTDFTLKISRVEADDVGVYYCMQALQSLMCSFGQGTKL
EIK (SEQ ID NO:30)

FIGURE 12

A -- Cur2 1.33 heavy chain nucleotide sequence

CAGGTTCAGCTGGTGCAGTCGGGAGCTGAGGTGAAGAAGCCTGGGGCCTCAG
TGAAGGTCTCCTGCAAGGCTTCTGGTTACACCTTTACCAGCTATGGTATCAGC
TGGGTGCGACAGGCCCCTGGACAAGGGCTTGAGTGGATGGGATGGATCAGCG
CTTACAATGGTAACACAAACTATGCACAGAAGCTCCAGGGCAGAGTCACCAT
GACCACAGACACATCCACGAGCACAGCCTACATGGAGCTGAGGAGCCTGAG
ATCTGACGACACGGCCGTGTATTACTGTGCGAGAGATCATTACTATGATAGT
AGTGATTATCTCTACTACTACTACGGTTTGGACGTCTGGGGCCAAGGGACCAC
GGTCACCGTCTCCTCAG (SEQ ID NO:73)

B -- Cur2 1.33 heavy chain protein sequence

QVQLVQSGAEVKKPGASVKVSCKASGYTFTSYGISWVRQAPGQGLEWMGWISA
YNGNTNYAQKLQGRVTMTTDTSTSTAYMELRSLRSDDTAVYYCARDHYYDSS
DYLYYYYGLDVWGQGTTVTVSS (SEQ ID NO:31)

C -- Cur2 1.33 light chain nucleotide sequence

GACATCCAGATGACCCAGTCTCCATCCTCCCTGTCTGCATCTGTAGGAGACAG
AGTCACCATCACTTGCCGGGCGAGTCAGGGCATTAGCAATTATTTAGCCTGGT
ATCAGCAGAAACCAGGGAAAGTTCCTAAGCTCCTGATCTATGCTGCATCCAC
TTTGCAATCAGGGGTCCCATCTCGGTTCAGTGGCAGTGGATCTGGGACAGATT
TCACTCTCACCATCAGCAGCCTGCAGCCTGAAGATGTTGCAACTTATTACTGT
CAAAAGTATAACAGTGCCCCGCTCACTTTCGGCGGAGGGACCAAGGTGGAGA
TCAAAC (SEQ ID NO:74)

D -- Cur2 1.33 light chain protein sequence

DIQMTQSPSSLSASVGDRVTITCRASQGISNYLAWYQQKPGKVPKLLIYAASTLQ
SGVPSRFSGSGSGTDFTLTISSLQPEDVATYYCQKYNSAPLTFGGGTKVEIK (SEQ
ID NO:32)

FIGURE 13

A -- Cur2 1.38.1 heavy chain nucleotide sequence

CAGGTGCAGCTGGTGGAGTCGGGGGGAGGCGTGGTCCAGCCTGGGAGGTCCC
TGAGACTCTCCTGTGCAGCGTCTGGATTCACCTTCAGTAGCTATGGCATGCAC
TGGGTCCGCCAGGCTCCAGGCAAGGGGCTGGAGTGGGTGGCAATTATATGGT
ATGATGGAAATGATAAATACTATGCAGACTCCGTGAAGGGCCGCTTCACCGT
CTCCAGAGACAATTCCAAGAACACGCTGTATCTGCAAATGAACAGCCTGAGA
GCCGAGGACACGGCTGTGTATTACTGTGCGAGAGGATATTACTATGATAGTA
GTGATTATCTCTACTACTACGGTATGGACGTCTGGGGCCAAGGGACCAC
GGTCACCGTCTCCTCAG (SEQ ID NO:75)

B -- Cur2 1.38.1 heavy chain protein sequence

QVQLVESGGGVVQPGRSLRLSCAASGFTFSSYGMHWVRQAPGKGLEWVAIIWY
DGNDKYYADSVKGRFTVSRDNSKNTLYLQMNSLRAEDTAVYYCARGYYYDSS
DYLYYYYGMDVWGQGTTVTVSS (SEQ ID NO:33)

C -- Cur2 1.38.1 light chain nucleotide sequence

GACATCCAGATGACCCAGTCTCCATCCTCCCTGTCTGCATCTGTAGGAGACAG
AGTCACCATCACTTGCCGGGCGAGTCAGGGCATTAGCAATTATTTAGCCTGGT
ATCAGCAGAAACCAGGGAAAGTTCCTAACCTCCTGATCTATGCTGCATCCAC
TTTGCAATCAGGGGTCCCATCTCGGTTCAGTGGCAGTGGATCTGGGACAGATT
TCTCTCTCACCATCAGCAGCCTGCAGCCTGAAGATGTTGCAGCTTATTACTGT
CAAAAGTGTAACAGTGCCCCGTGGACGTTCGGCCAAGGGACCACGGTGGAG
ATCAAAC (SEQ ID NO:76)

D -- Cur2 1.38.1 light chain protein sequence

DIQMTQSPSSLSASVGDRVTITCRASQGISNYLAWYQQKPGKVPNLLIYAASTLQ
SGVPSRFSGSGSGTDFSLTISSLQPEDVAAYYCQKCNSAPWTFGQGTTVEIK (SEQ
ID NO:34)

FIGURE 14

A -- Cur2 1.39.1 heavy chain nucleotide sequence

GAGGTGCAGCTGGTGCAGTCGGGAACAGAGGTGAAAAAGCCCGGGGAGTCT
CTGAAGATCTCCTGTAAGGGTTCTGGATACAGGTTTACCAGCTACTGGATCGG
CTGGGTGCGCCAGATGCCCGGGAAAGGCCTGGAGTGGATGGGGATCATCTAT
CCTGGTGACTCTGATACCAGATACAGCCCGTCCTTCCAAGGCCAGGTCACCA
TCTCAGCCGACAAGTCCATCAGCACCGCCTACCTGCAGTGGAGCAGCCTGAA
GGCCTCGGACACCGCCATGTATTACTGTGCGAGACATGGATCGTATTACTATA
ATTCGGGGAGTTATTATAACGTCTTTGACTACTGGGGCCAGGGAACCCTGGTC
ACCGTCTCCTCAG (SEQ ID NO:77)

B -- Cur2 1.39.1 heavy chain protein sequence

EVQLVQSGTEVKKPGESLKISCKGSGYRFTSYWIGWVRQMPGKGLEWMGIIYPG
DSDTRYSPSFQGQVTISADKSISTAYLQWSSLKASDTAMYYCARHGSYYYNSGS
YYNVFDYWGQGTLVTVSS (SEQ ID NO:35)

C -- Cur2 1.39.1 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATCTATGCTGCATCCA
GTTTGCAAAGTGGGGTCCCATCAAGGTTCAGCGGCAGTGGATCTGGGACAGA
ATTCACTCTCACAATCAGCAGCCTGCAGCCTGAAGATTTTGCAACTTATTACT
GTCTACAGCATAATAGTTACCCGTGGACGTTCGGCCAAGGGACCAAGGTGGA
AATCAAAC (SEQ ID NO:78)

D -- Cur2 1.39.1 light chain protein sequence

DIQMTQSPSSLSASVGDRVTITCRASQGIRNDLGWYQQKPGKAPKRLIYAASSLQ
SGVPSRFSGSGSGTEFTLTISSLQPEDFATYYCLQHNSYPWTFGQGTKVEIK (SEQ
ID NO:36)

FIGURE 15

A -- Cur2 1.40.1 heavy chain nucleotide sequence

CAGGTGCAGCTGGTGCAGTCGGGGGCTGAGGTGAAGAAGCCTGGGGCCTCA
GTGAAGGTCTCCTGCAAGGCTTCTGGATACACCTTCACCACTTATGATATCAA
CTGGGTGCGACAGGCCACTGGACAAGGGCTTGAGTGGATGGGATGGATGAA
CCCTAACAGTGGTAACACAGGCTATGCACAGAAGTTCCAGGGCAGAGTCACC
ATGACCAGGAACACCTCCCTAAGCACAGCCTACATGGAGCTGAGCAGCCTGA
GATCTGAGGACACGGCCGTGTATTACTGTGCGAGAGATATTGTAGTGGTGGT
AGCTGCTACCAACTACTACAACGGTATGGACGTCTGGGGCCAAGGGACCACG
GTCACCGTCTCCTCAG (SEQ ID NO:79)

B -- Cur2 1.40.1 heavy chain protein sequence

QVQLVQSGAEVKKPGASVKVSCKASGYTFTTYDINWVRQATGQGLEWMGWM
NPNSGNTGYAQKFQGRVTMTRNTSLSTAYMELSSLRSEDTAVYYCARDIVVVV
AATNYYNGMDVWGQGTTVTVSS (SEQ ID NO:37)

FIGURE 16

A -- Cur2 1.45 heavy chain nucleotide sequence

CAGGTGCAGCTGGTGCAGTCGGGGGCTGAGGTGAAGAAGCCTGGGGCCTCA
GTGAAGGTCTCCTGCAAGGCTTCTGGATACACCTTCACCAGTTATGATATCAA
CTGGGTGCGACAGGCCACTGGACAAGGGCTTGAGTGGATGGGATGGATGAA
CCCTAACAGTGGTAACACAGGCTATGCACAGAAGTTCCAGGGCAGAGTCACC
ATGACCAGGAACACCTCCATAAGCACAGCCTACATGGAGCTGAGCAGCCTGA
GATCTGAGGACACGGCCGTGTATTACTGTGCGAGAGGCAGTGGATACAGCTA
TGGTTACGACTACTACTACGGTATGGACGTCTGGGGCCAAGGGACCACGGTC
ACCGTCTCCTCAG (SEQ ID NO:80)

B -- Cur2 1.45 heavy chain protein sequence

QVQLVQSGAEVKKPGASVKVSCKASGYTFTSYDINWVRQATGQGLEWMGWM
NPNSGNTGYAQKFQGRVTMTRNTSISTAYMELSSLRSEDTAVYYCARGSGYSYG
YDYYYGMDVWGQGTTVTVSS (SEQ ID NO:38)

C -- Cur2 1.45 light chain nucleotide sequence

GACATCCAGATGACCCAGTCTCCATCCTCCCTGTCTGCATCTGTAGGAGACAG
AGTCACCATCAATTGCCGGGCGAGTCAGGGCATTAGCAATGATTTAGCCTGG
TATCAGCAGAAACCAGGGAAAGTTCCTAAGCTCCTGATCTATGCTGCATCCA
CTTTGCAATTAGGGGTCCCATCTCGGTTCAGTGGCAGTGGATCTGGGACAGAT
TTCACTCTCACCATCAGCAGCCTGCAGCCTGAAGATGTTGCAACTTATTACTG
TCAAAAGTATAACAGTGCCCCATTCACTTTCGGCCCTGGGACCAAAGTGGAT
ATCAAAC (SEQ ID NO:81)

D -- Cur2 1.45 light chain protein sequence

DIQMTQSPSSLSASVGDRVTINCRASQGISNDLAWYQQKPGKVPKLLIYAASTLQ
LGVPSRFSGSGSGTDFTLTISSLQPEDVATYYCQKYNSAPFTFGPGTKVDIK (SEQ
ID NO:39)

FIGURE 17

A -- Cur2 1.46.1 heavy chain nucleotide sequence

CAGGTGCAGCTGGTGCAGTCGGGGGCTGAGGTGAAGAAGCCTGGGGCCTCA
GTGAAGGTCTCCTGCAAGGCTTCTGGATACTCCTTCACCAGTTATGATATCAA
CTGGGTGCGACAGGCCACTGGACAAGGGCTTGAGTGGATGGGATGGATGAA
CCCTAACAATGGTAACACAGGCTATGCACAGAAGTTCCAGGGCAGAGTCACC
ATGACCAGGAACACCTCCATAAGCACAGCCTACATGGAGCTGAGCAGCCTGA
GATCTGAGGACACGGCCGTGTATTACTGTGCGAGAGATATTGTAGTGGTGGT
AACTGCTACGGACTACTACTACGGTATGGACGTCTGGGGCCAAGGGACCACG
GTCACCGTCTCCTCAG (SEQ ID NO:82)

B -- Cur2 1.46.1 heavy chain protein sequence

QVQLVQSGAEVKKPGASVKVSCKASGYSFTSYDINWVRQATGQGLEWMGWM
NPNNGNTGYAQKFQGRVTMTRNTSISTAYMELSSLRSEDTAVYYCARDIVVVVT
ATDYYYGMDVWGQGTTVTVSS (SEQ ID NO:40)

C -- Cur2 1.46.1 light chain nucleotide sequence

GACATCCAGATGACCCAGTCTCCATCCTCCCTGTCTGCATCTGTAGGAGACAG
AGTCACCATCACTTGCCGGGCAAGTCAGGGCATTAGAAATGATTTAGGCTGG
TATCAGCAGAAACCAGGGAAAGCCCCTAAGCGCCTGATTTTTGCTGCATCCA
GTTTGCCAAGTGGGGTCCCATCAAGGTTCAGCGGCAGTGGATCTGGGACAGA
ATTCACTCTCACAATCAGCAGCCTGCAGCCTGAAGATTTTGCAACTTATTACT
GTCTACAGCATAGTGGTTACCCTCCGACGTTCGGCCAAGGGACCAAGGTGGA
AATCAAAC (SEQ ID NO:83)

D -- Cur2 1.46.1 light chain protein sequence

DIQMTQSPSSLSASVGDRVTITCRASQGIRNDLGWYQQKPGKAPKRLIFAASSLPS
GVPSRFSGSGSGTEFTLTISSLQPEDFATYYCLQHSGYPPTFGQGTKVEIK (SEQ ID NO:41)

FIGURE 18

A -- Cur2 1.48.1 heavy chain nucleotide sequence

CAGGTTCAGCTGGTGCAGTCGGGAGCTGAGGTGAAGAAGCCTGGGGCCTCAG
TGAAGGTCTCCTGCAAGGCTTCTGGTTACACCTTTACCAGCTATGGTATCAGC
TGGGTGCGACAGGCCCCTGGACAAGGGCTTGAGTGGATGGGATGGATCAGCG
CTTACAATGGTAACACAAACTATGCACAGAAGCTCCAGGGCAGAGTCACCAT
GACCACAGACACATCCACGAGCACAGCCTACATGGAGCTGAGGAGCCTGAG
ATCTGACGACACGGCCGTGTATTACTGTGCGAGAGATGTTGAATATTACTATG
ATGGTAGTGGTTATTACTACTTTGACTACTGGGGCCAGGGAACCCTGGTCACC
GTCTCCTCAG (SEQ ID NO:84)

B -- Cur2 1.48.1 heavy chain protein sequence

QVQLVQSGAEVKKPGASVKVSCKASGYTFTSYGISWVRQAPGQGLEWMGWISA
YNGNTNYAQKLQGRVTMTTDTSTSTAYMELRSLRSDDTAVYYCARDVEYYYD
GSGYYYFDYWGQGTLVTVSS (SEQ ID NO:42)

C -- Cur2 1.48.1 light chain nucleotide sequence

GACATCCAGATGACCCAGTCTCCATCTTCCGTGTCTGCATCTGTAGGAGACAG
AGTCACCATCACTTGTCGGGCGAGTCAGGGTATTAGCAGCTGGTTAGCCTGG
TATCAGCAGAAACCAGGGAAAGCCCCTAAGCTCCTGATCTATGCTGCATCCA
TTTTGCAAAGTGGGGTCCCATCAAGGTTCAGCGGCAGTGGATCTGGGACAGA
TTTCACTCTCACCATCAGCAGCCTGCAGCCTGAGGATTTTGCATCTTACTATT
GTCAACAGTCTAACAGTTTCCCTCGGACGTTCGGCCAAGGGACCAAGGTGGA
GATCAAAC (SEQ ID NO:85)

D -- Cur2 1.48.1 light chain protein sequence

DIQMTQSPSSVSASVGDRVTITCRASQGISSWLAWYQQKPGKAPKLLIYAASILQ
SGVPSRFSGSGSGTDFTLTISSLQPEDFASYYCQQSNSFPRTFGQGTKVEIK (SEQ
ID NO:43)

FIGURE 19

A -- Cur2 1.49.1 heavy chain nucleotide sequence

CAGGTGCAGCTGGTGCAGTCGGGGGCTGAGGTGAAGAAGCCTGGGGCCTCA
GTGAAGGTCTCCTGCAAGGCTTCTGGATACACCTTCACCAGTTATGATATCAA
CTGGGTGCGACAGGCCACTGGACAAGGGCTTGAGTGGATGGGATGGATGAA
CCCTAACAGTGGTGACACAGGCTATGCACAGAAGTTCCAGGGCAGAGTCACC
ATGACCAGGAACACCTCCATAAGCACAGCCTACATGGAGCTGAGCAGCCTGA
GATCTGAGGACACGGCCGTGTATTTCTGTGCGAGAATGAGGGATATAGTGGC
TACGAGCTATTACTACTACTTCTACGGTATGGACGTCTGGGGCCAAGGGACC
ACGGTCACCGTCTCCTCAG (SEQ ID NO:86)

B -- Cur2 1.49.1 heavy chain protein sequence

QVQLVQSGAEVKKPGASVKVSCKASGYTFTSYDINWVRQATGQGLEWMGWM
NPNSGDTGYAQKFQGRVTMTRNTSISTAYMELSSLRSEDTAVYFCARMRDIVAT
SYYYYFYGMDVWGQGTTVTVSS (SEQ ID NO:44)

C -- Cur2 1.49.1 light chain nucleotide sequence

GATATTGTGATGACTCAGTCTCCACTCTCCCTGCCCGTCACCCCTGGAGAGCC
GGCCTCCATCTCCTGCAGGTCTAGTCAGAGCCTCCTGCATAGTAATGGATACA
ACTATTTGGATTGGTACCTGCTGAAGCCAGGGCAGTCTCCACAGCTCCTGATC
TATTTGGGTTCTAGTCGGGCCTCCGGGGTCCCTGACAGGTTCAGTGGCAGTGG
ATCAGGCACAGATTTTACACTGAAAATCAGCAGAGTGGAGGCTGAGGATGTT
GGGGTTTATTACTGCATGCAAACTCTACAAACTATCACCTTCGGCCAAGGGA
CACGACTGGAGATTAAAC (SEQ ID NO:87)

D -- Cur2 1.49.1 light chain protein sequence

DIVMTQSPLSLPVTPGEPASISCRSSQSLLHSNGYNYLDWYLLKPGQSPQLLIYLG
SSRASGVPDRFSGSGSGTDFTLKISRVEAEDVGVYYCMQTLQTITFGQGTRLEIK
(SEQ ID NO:45)

FIGURE 20

A -- Cur2 1.51 heavy chain nucleotide sequence

GAGGTGCAGCTGGTGCAGTCGGGAGCTGAGGTGAAAAAGCCCGGGGAGTCT
CTGAAGATCTCCTGTAAGGGTTCTGGATACAGCTTTACCAGCTACTGGATCGG
CTGGGTGCGCCAGATGCCCGGGAAAGGCCTGGAGTGGATGGGGATCATCTAT
CCTGGTGACTCTGATGCCAAATACAGCCCGTCCTTCCAAGGCCAGGTCACCA
TCTCAGCCGACAAGTCCATCAGCACCGCCTACCTGCAGTGGAGCAGCCTGAA
GGCCTCGGACACCGCCATGTATTACTGTGCGAGACACTATGATTACGTTTGGA
GGAATTATCGGTATACAGGGTGGTTCGACCCCTGGGGCCAGGGAACCCTGGT
CACCGTCTCCTCAG (SEQ ID NO:88)

B -- Cur2 1.51.1 heavy chain protein sequence

EVQLVQSGAEVKKPGESLKISCKGSGYSFTSYWIGWVRQMPGKGLEWMGIIYPG
DSDAKYSPSFQGQVTISADKSISTAYLQWSSLKASDTAMYYCARHYDYVWRNY
RYTGWFDPWGQGTLVTVSS (SEQ ID NO:46)

C -- Cur2 1.51.1 light chain nucleotide sequence

GAAATTGTGTTGACGCAGTCTCCAGGCACCCTGTCTTTGTCTCCAGGGGAAAG
AGCCACCCTCTCCTGCAGGGCCAGTCAGAGTGTTAGCAGCAGCTACTTAGCC
TGGTACCAGCAGAAACCTGGCCAGGCTCCCAGGCTCCTCATCTATGGTGCAT
CCAACAGGGCCACTGGCATCCCAGACAGGTTCAGTGGCAGTGGGTCTGGGAC
AGACTTCACTCTCACCATCAGCAGACTGGAGCCTGAAGATTTTGCAGTGTATT
ACTGTCAGCAGTATGGTAGCTCACTATTCACTTTCGGCCCTGGGACCAAAGTG
GATATCAAAC (SEQ ID NO:89)

D -- Cur2 1.51.1 light chain protein sequence

EIVLTQSPGTLSLSPGERATLSCRASQSVSSSYLAWYQQKPGQAPRLLIYGASNRA
TGIPDRFSGSGSGTDFTLTISRLEPEDFAVYYCQQYGSSLFTFGPGTKVDIK (SEQ
ID NO:47)

FIGURE 21

A -- Cur2 6.4 heavy chain nucleotide sequence
CAGGTGCAGCTGGTGCAGTCTGGGGCTGAGGTGAAGAAGCCTGGGGCCTCAG
TGAAGGTCTCCTGCAAGGCTTCTGGATACACCTTCACCAGTTATGATATCAAC
TGGGTGCGACAGGCCACTGGACAAGGGCTTGAGTGGATGGGATGGATAAAC
CCTAATAGTGGTAACACAGACTATGCACAGAAGTTCCAGGGCAGAGTCACCA
TGACCAGGGACACCTCCATAAGCACAGCCTACATGGAGCTGAGCAGCCTGAG
ATCTGAGGACACGGCCATATATTATTGTGTGAGAGGCTTTGGATACAGCTAT
AATTACGACTACTATTACGGTATGGACGTCTGGGGCCAAGGGACCACGGTCA
CCGTCTCCTCAGT (SEQ ID NO:90)

B -- Cur2 6.4 heavy chain amino acid sequence
QVQLVQSGAEVKKPGASVKVSCKASGYTFTSYDINWVRQATGQGLEWMGWIN
PNSGNTDYAQKFQGRVTMTRDTSISTAYMELSSLRSEDTAIYYCVRGFGYSYNY
DYYYGMDVWGQGTTVTVSS (SEQ ID NO:48)

C -- Cur2 6.4 light chain nucleotide sequence
GAAATTGTGTTGACGCAGTCTCCAGGCACCCTGTCTTTGTCTCCAGGGGAAAG
AGCCACCCTCTCCTGCAGGGCCAGTCAGAGTGTTAGTAGTAGTTACTTAGCCT
GGTACCAGCAGAAGCCTGGCCAGGCTCCCAGGCTCCTCATCTATGCTACATC
CAGCAGGGCCACTGGCATCCCAGACAGGTTCAGTGGCAGTGGGTCTGGGACA
GACTTCACTCTCACCATCAGCAGACTGGAGCCTGAAGATTTTGCAGTGTATTA
CTGTCAGCAGTATGGTAGTTCACCGTGCAGTTTTGGCCAGGGGACCAAGCTG
GAAATCAAGC (SEQ ID NO:91)

D -- Cur2 6.4 light chain amino acid sequence
EIVLTQSPGTLSLSPGERATLSCRASQSVSSSYLAWYQQKPGQAPRLLIYATSSRA
TGIPDRFSGSGSGTDFTLTISRLEPEDFAVYYCQQYGSSPCSFGQGTKLEIK (SEQ
ID NO:49)

FIGURE 22A

| Clone | Germline genes used | | | No. of Nucleotide/ Amino acid changes | | | | | | |
|---|---|---|---|---|---|---|---|---|---|---|
| | | | | FR1 | CDR1 | FR2 | CDR2 | FR3 | CDR3 | FR4 |
| CR2 | | V | D | J | V | | | | | D & J |
| 1.19.1 | VH | V1-8 | D3-16 | JH6B | 0/0 | 0/0 | 0/0 | 0/0 | 0/0 | 0/0 | 0/0 |
| | VK | A30 | | JK2 | 0/0 | 0/0 | 0/0 | 0/0 | 1/1 | 1/1 | 0/0 |
| 6.4.1 | VH | V1-8 | D5-18 | JH6B | 0/0 | 0/0 | 0/0 | 3/2 | 5/3 | 0/0 | 0/0 |
| | VK | A27 | | JK2 | 0/0 | 3/0 | 1/0 | 2/2 | 0/0 | 1/0 | 0/0 |
| 1.18 | VH | V1-8 | D6-19 | JH6B | 1/0 | 0/0 | 0/0 | 1/0 | 0/0 | 0/0 | 0/0 |
| | VK | A30 | | JK3 | 0/0 | 0/0 | 0/0 | 0/0 | 1/1 | 0/0 | 0/0 |
| 1.40.1 | VH | V1-8 | D2 | JH6B | 1/0 | 1/1 | 0/0 | 0/0 | 1/1 | 0/0 | 0/0 |
| | VK | mix | | | | | | | | | |
| 1.45 | VH | V1-8 | DK4 | JH6B | 1/0 | 0/0 | 0/0 | 0/0 | 0/0 | 0/0 | 0/0 |
| | VK | A20 | | JK3 | 1/1 | 1/1 | 0/0 | 1/1 | 0/0 | 0/0 | 0/0 |
| 1.46.1 | VH | V1-8 | D2 | JH6B | 1/0 | 1/1 | 0/0 | 0/0 | 1/1 | 0/0 | 0/0 |
| | VK | A30 | | JK1 | 0/0 | 0/0 | 2/1 | 1/1 | 0/0 | 2/2 | 0/0 |
| 1.49.1 | VH | V1-8 | D5-12 | JH6B | 1/0 | 0/0 | 0/0 | 1/1 | 1/1 | 0/0 | 0/0 |
| | VK | A19 | | JK5 | 0/0 | 0/0 | 1/1 | 1/1 | 0/0 | 1/1 | 0/0 |
| 1.33 | VH | V1-18 | D21-9 | JH6B | 1/0 | 0/0 | 0/0 | 0/0 | 0/0 | 0/0 | 0/0 |
| | VK | A20 | | JK4 | 0/0 | 0/0 | 0/0 | 0/0 | 0/0 | 0/0 | 0/0 |
| 1.48.1 | VH | V1-18 | D21-9 | JH4B | 1/0 | 0/0 | 0/0 | 0/0 | 0/0 | 0/0 | 0/0 |
| | VK | L5 | | JK1 | 0/0 | 0/0 | 0/0 | 1/1 | 2/1 | 1/1 | 0/0 |
| 1.6.1 | VH | V3-21 | D3-16 | JH4B | 0/0 | 4/4 | 0/0 | 1/1 | 1/0 | 0/0 | 0/0 |
| | VK | A30 | | JK4 | 0/0 | 0/0 | 1/1 | 0/0 | 0/0 | 0/0 | 0/0 |
| 1.17.1 | VH | V3-33 | D5-18 | JH6B | 2/1 | 0/0 | 0/0 | 0/0 | 0/0 | 0/0 | 0/0 |
| | VK | A30 | | JK4 | 0/0 | 0/0 | 0/0 | 0/0 | 0/0 | 0/0 | 0/0 |
| 1.24.1 | VH | V3-33 | D5-18 | JH6B | 0/0 | 2/1 | 0/0 | 1/1 | 0/0 | 0/0 | 0/0 |
| | VK | A30 | | JK1 | 0/0 | 0/0 | 0/0 | 0/0 | 1/0 | 0/0 | 0/0 |
| 1.38.1 | VH | V3-33 | D21-9 | JH6B | 1/0 | 0/0 | 0/0 | 3/3 | 2/1 | 0/0 | 0/0 |
| | VK | A20 | | JK1 | 0/0 | 0/0 | 1/1 | 0/0 | 2/2 | 1/1 | 0/0 |
| 1.11.1 | VH | V3-53 | D4-17 | JH6B | 0/0 | 0/0 | 0/0 | 0/0 | 0/0 | 0/0 | 0/0 |
| | VK | A19 | | JK4 | 0/0 | 1/1 | 0/0 | 0/0 | 0/0 | 0/0 | 0/0 |
| 1.23.1 | VH | V5-51 | D3-10 | JH4B | 1/1 | 0/0 | 0/0 | 0/0 | 0/0 | 0/0 | 0/0 |
| | VK | A30 | | JK1 | 0/0 | 0/0 | 1/1 | 1/1 | 0/0 | 0/0 | 0/0 |
| 1.25.1 | VH | V5-51 | D3-10 | JH4B | 1/0 | 1/1 | 0/0 | 0/0 | 0/0 | 0/0 | 0/0 |
| | VK | A30 | | JK1 | 0/0 | 0/0 | 0/0 | 0/0 | 0/0 | 0/0 | 0/0 |
| 1.29 | VH | V5-51 | D5-12 | JH6B | 1/0 | 0/0 | 0/0 | 0/0 | 1/1 | 0/0 | 0/0 |
| | VK | A19 | | JK2 | 0/0 | 0/0 | 1/0 | 1/1 | 0/0 | 0/0 | 0/0 |
| 1.39.1 | VH | V5-51 | D3-10 | JH4B | 2/1 | 1/1 | 0/0 | 0/0 | 0/0 | 0/0 | 0/0 |
| | VK | A30 | | JK1 | 0/0 | 0/0 | 0/0 | 0/0 | 0/0 | 0/0 | 0/0 |
| 1.51.1 | VH | 5-51 | D3-16 | JH5B | 2/0 | 0/0 | 0/0 | 1/1 | 1/1 | 0/0 | 0/0 |
| | VK | A27 | | JK3 | 0/0 | 0/0 | 0/0 | 1/1 | 0/0 | 0/0 | 0/0 |

FIGURE 22B

| Clone | Germline genes used | | | No. of Nucleotide/ Amino acid changes | | | | | | |
|---|---|---|---|---|---|---|---|---|---|---|
| | | | | FR1 | CDR1 | FR2 | CDR2 | FR3 | CDR3 | FR4 |
| CR2 | | V | D | J | | V | | | | D & J |
| 1.40.1 | VH | V1-8 | D2 | JH6B | 1/0 | 1/1 | 0/0 | 0/0 | 1/1 | 0/0 | 0/0 |
| | VK | mix | | | | | | | | | |
| 1.48.1 | VH | V1-18 | D21-9 | JH4B | 1/0 | 0/0 | 0/0 | 0/0 | 0/0 | 0/0 | 0/0 |
| | VK | L5 | | JK1 | 0/0 | 0/0 | 0/0 | 1/1 | 2/1 | 1/1 | 0/0 |
| 1.49.1 | VH | V1-8 | D5-12 | JH6B | 1/0 | 0/0 | 0/0 | 0/0 | 1/1 | 0/0 | 0/0 |
| | VK | A19 | | JK5 | 0/0 | 0/0 | 1/1 | 1/1 | 0/0 | 1/1 | 0/0 |
| 1.11.1 | VH | V3-53 | D4-17 | JH6B | 0/0 | 0/0 | 0/0 | 0/0 | 0/0 | 0/0 | 0/0 |
| | VK | A19 | | JK4 | 0/0 | 1/1 | 0/0 | 0/0 | 0/0 | 0/0 | 0/0 |
| 1.29 | VH | V5-51 | D5-12 | JH6B | 1/0 | 0/0 | 0/0 | 0/0 | 1/1 | 0/0 | 0/0 |
| | VK | A19 | | JK2 | 0/0 | 0/0 | 1/0 | 0/0 | 1/1 | 0/0 | 0/0 |
| 1.45 | VH | V1-8 | DK4 | JH6B | 1/0 | 0/0 | 0/0 | 0/0 | 0/0 | 0/0 | 0/0 |
| | VK | A20 | | JK3 | 1/1 | 1/1 | 0/0 | 1/1 | 0/0 | 0/0 | 0/0 |
| 1.33 | VH | V1-18 | D21-9 | JH6B | 1/0 | 0/0 | 0/0 | 0/0 | 0/0 | 0/0 | 0/0 |
| | VK | A20 | | JK4 | 0/0 | 0/0 | 0/0 | 0/0 | 0/0 | 0/0 | 0/0 |
| 1.38.1 | VH | V3-33 | D21-9 | JH6B | 1/0 | 0/0 | 0/0 | 3/3 | 2/1 | 0/0 | 0/0 |
| | VK | A20 | | JK1 | 0/0 | 0/0 | 1/1 | 0/0 | 2/2 | 1/1 | 0/0 |
| 6.4.1 | VH | V1-8 | D5-18 | JH6B | 0/0 | 0/0 | 0/0 | 3/2 | 5/3 | 0/0 | 0/0 |
| | VK | A27 | | JK2 | 0/0 | 3/0 | 1/0 | 2/2 | 0/0 | 1/0 | 0/0 |
| 1.51.1 | VH | 5-51 | D3-16 | JH5B | 2/0 | 0/0 | 0/0 | 1/1 | 1/1 | 0/0 | 0/0 |
| | VK | A27 | | JK3 | 0/0 | 0/0 | 0/0 | 1/1 | 0/0 | 0/0 | 0/0 |
| 1.19.1 | VH | V1-8 | D3-16 | JH6B | 0/0 | 0/0 | 0/0 | 0/0 | 0/0 | 0/0 | 0/0 |
| | VK | A30 | | JK2 | 0/0 | 0/0 | 0/0 | 0/0 | 1/1 | 1/1 | 0/0 |
| 1.18 | VH | V1-8 | D6-19 | JH6B | 1/0 | 0/0 | 0/0 | 1/0 | 0/0 | 0/0 | 0/0 |
| | VK | A30 | | JK3 | 0/0 | 0/0 | 0/0 | 0/0 | 1/1 | 0/0 | 0/0 |
| 1.6.1 | VH | V3-21 | D3-16 | JH4B | 0/0 | 4/4 | 0/0 | 1/1 | 1/0 | 0/0 | 0/0 |
| | VK | A30 | | JK4 | 0/0 | 0/0 | 1/1 | 0/0 | 0/0 | 0/0 | 0/0 |
| 1.23.1 | VH | V5-51 | D3-10 | JH4B | 1/1 | 0/0 | 0/0 | 0/0 | 0/0 | 0/0 | 0/0 |
| | VK | A30 | | JK1 | 0/0 | 0/0 | 1/1 | 1/1 | 0/0 | 0/0 | 0/0 |
| 1.25.1 | VH | V5-51 | D3-10 | JH4B | 1/0 | 1/1 | 0/0 | 0/0 | 0/0 | 0/0 | 0/0 |
| | VK | A30 | | JK1 | 0/0 | 0/0 | 0/0 | 0/0 | 0/0 | 0/0 | 0/0 |
| 1.39.1 | VH | V5-51 | D3-10 | JH4B | 2/1 | 1/1 | 0/0 | 0/0 | 0/0 | 0/0 | 0/0 |
| | VK | A30 | | JK1 | 0/0 | 0/0 | 0/0 | 0/0 | 0/0 | 0/0 | 0/0 |
| 1.17.1 | VH | V3-33 | D5-18 | JH6B | 2/1 | 0/0 | 0/0 | 0/0 | 0/0 | 0/0 | 0/0 |
| | VK | A30 | | JK4 | 0/0 | 0/0 | 0/0 | 0/0 | 0/0 | 0/0 | 0/0 |
| 1.24.1 | VH | V3-33 | D5-18 | JH6B | 0/0 | 2/1 | 0/0 | 1/1 | 0/0 | 0/0 | 0/0 |
| | VK | A30 | | JK1 | 0/0 | 0/0 | 0/0 | 0/0 | 1/0 | 0/0 | 0/0 |
| 1.46.1 | VH | V1-8 | D2 | JH6B | 1/0 | 1/1 | 0/0 | 0/0 | 1/1 | 0/0 | 0/0 |
| | VK | A30 | | JK1 | 0/0 | 0/0 | 2/1 | 1/1 | 0/0 | 2/2 | 0/0 |

```
                                                                    Section 1
           (1)  1         10         20         30         40        51
CUR2-1.6.1_HC (1) EVQLVESGGGLVKPGGSLRLSCAASGFNFR YNMNWVRQAPGKGLEWVSSI
        VH3-21 (1) EVQLVESGGGLVKPGGSLRLSCAASGFTFS SYSMNWVRQAPGKGLEWVSSI
     Consensus (1) EVQLVESGGGLVKPGGSLRLSCAASGF  F SY MNWVRQAPGKGLEWVSSI
                                                                    Section 2
          (52) 52        60         70         80         90        102
CUR2-1.6.1_HC (52) SSSSS NIYYADSVKGRFTISRDNAKNSLYLQMNSLRAEDTAVYYCARDIMI
        VH3-21 (52) SSSSS YIYYADSVKGRFTISRDNAKNSLYLQMNSLRAEDTAVYYCAR----
     Consensus (52) SSSSS  IYYADSVKGRFTISRDNAKNSLYLQMNSLRAEDTAVYYCAR
                                                                    Section 3
         (103) 103       110        126
CUR2-1.6.1_HC (103) TFGGIIASFYFDYWGQGTLVTVSS  SEQ ID NO:13
        VH3-21  (99) ------------------------  SEQ ID NO:3
     Consensus (103)
```

Figure 23B

```
                                                                    Section 1
           (1)  1         10         20         30         40        51
CUR2-1.6.1_LC (1) DIQMTQSPSSLSASVGDRVTITCRASQGIRNDLGW QQKPGKAPKRLIYAA
           A30 (1) DIQMTQSPSSLSASVGDRVTITCRASQGIRNDLGW QQKPGKAPKRLIYAA
     Consensus (1) DIQMTQSPSSLSASVGDRVTITCRASQGIRNDLGWFQQKPGKAPKRLIYAA
                                                                    Section 2
          (52) 52        60         70         80         90        102
CUR2-1.6.1_LC (52) SSLQSGVPSRFSGSGSGTEFTLTISSLQPEDFATYYCLQHNSYPLTFGGGT
           A30 (52) SSLQSGVPSRFSGSGSGTEFTLTISSLQPEDFATYYCLQHNSYP------
     Consensus (52) SSLQSGVPSRFSGSGSGTEFTLTISSLQPEDFATYYCLQHNSYP
                                                                    Section 3
         (103) 103 107
CUR2-1.6.1_LC (103) KVEIK  SEQ ID NO:14
           A30  (96) -----  SEQ ID NO:11
     Consensus (103)
```

```
                                                                            Section 1
              (1)  1          10         20         30         40        51
Cur2-1.11.1 HC (1) EVQLVESGGGLIQPGGSLRLSCAASGFTVSSNYMSWVRQAPGKGLEWVSVI
        VH3-53 (1) EVQLVESGGGLIQPGGSLRLSCAASGFTVSSNYMSWVRQAPGKGLEWVSVI
      Consensus (1) EVQLVESGGGLIQPGGSLRLSCAASGFTVSSNYMSWVRQAPGKGLEWVSVI
                                                                            Section 2
              (52) 52         60         70         80         90       102
Cur2-1.11.1_HC (52) YSGGSTYYADSVRGRFTISRDNSKNTLYLQMNSLRAEDTAVYYCAGTVTTN
        VH3-53 (52) YSGGSTYYADSVRGRFTISRDNSKNTLYLQMNSLRAEDTAVYYCAR-----
      Consensus (52) YSGGSTYYADSVRGRFTISRDNSKNTLYLQMNSLRAEDTAVYYCA
                                                                            Section 3
             (103) 103      110        120
Cur2-1.11.1_HC (103) YYYGMDVWGQGTTVTVSS    SEQ ID NO:15
        VH3-53 (98) ------------------    SEQ ID NO:5
     Consensus (103)
```

Figure 24B

```
                                                                            Section 1
              (1)  1          10         20         30         40        51
CUR2-1.11.1 LC (1) DIVMTQSPLSLPVTPGEPASISCRSSQSLLQSNGYNYLDWYLQKPGQSPQL
           A19 (1) DIVMTQSPLSLPVTPGEPASISCRSSQSLLHSNGYNYLDWYLQKPGQSPQL
      Consensus (1) DIVMTQSPLSLPVTPGEPASISCRSSQSLL SNGYNYLDWYLQKPGQSPQL
                                                                            Section 2
              (52) 52         60         70         80         90       102
CUR2-1.11.1_LC (52) LIYLGSNRASGVPDRFSGSGSGTDFTLKISRVEAEDVGVYYCMQALQTLTF
           A19 (52) LIYLGSNRASGVPDRFSGSGSGTDFTLKISRVEAEDVGVYYCMQALQTP--
      Consensus (52) LIYLGSNRASGVPDRFSGSGSGTDFTLKISRVEAEDVGVYYCMQALQT
                                                                            Section 3
             (103) 103     111
CUR2-1.11.1_LC (103) GGGTKVEIK    SEQ ID NO:16
          A19 (101) ---------    SEQ ID NO:8
      Consensus (103)
```

```
                                                                              Section 1
              (1)  1         10        20        30        40         51
CR2-1.17.1 HC (1)  QVQLVESGGGVVQPGRSLRLSCAASGFTFSSYGMHWVRQAPGKGLEWVAVI
         VH3-33 (1) QVQLVESGGGVVQPGRSLRLSCAASGFTFSSYGMHWVRQAPGKGLEWVAVI
      Consensus (1) QVQLVESGGGVVQPGKSLRLSCAASGFTFSSYGMHWVRQAPGKGLEWVAVI
                                                                              Section 2
              (52) 52        60        70        80        90        102
CR2-1.17.1_HC (52) WYDGSNKYYADSVKGRFTISRDNSKNTLYLQMNSLRAEDTAVYYCARDQGY
         VH3-33 (52) WYDGSNKYYADSVKGRFTISRDNSKNTLYLQMNSLRAEDTAVYYCAR----
      Consensus (52) WYDGSNKYYADSVKGRFTISRDNSKNTLYLQMNSLRAEDTAVYYCAR
                                                                              Section 3
              (103) 103       110             126
CR2-1.17.1_HC (103) RYAGYYYDYGMDVWGQGTTVTVSS  SEQ ID NO:17
         VH3-33 (99) ------------------------  SEQ ID NO:4
      Consensus (103)
```

Figure 25B

```
                                                                              Section 1
              (1)  1         10        20        30        40        52
CR2-1.17.1 LC (1)  DIQMTQSPSSLSASVGDRVTITCRASQGIRNDLGWYQQKPGKAPKRLIYAAS
         A30 (1)  DIQMTQSPSSLSASVGDRVTITCRASQGIRNDLGWYQQKPGKAPKRLIYAAS
      Consensus (1) DIQMTQSPSSLSASVGDRVTITCRASQGIRNDLGWYQQKPGKAPKRLIYAAS
                                                                              Section 2
              (53) 53        60        70        80        90       104
CR2-1.17.1_LC (53) SLQSGVPSRFSGSGSGTEFTLTISSLQPEDFATYYCLQHNSYPLTFGGGTKV
         A30 (53) SLQSGVPSRFSGSGSGTEFTLTISSLQPEDFATYYCLQHNSYP---------
      Consensus (53) SLQSGVPSRFSGSGSGTEFTLTISSLQPEDFATYYCLQHNSYP
                                                                              Section 3
              (105) 1067
CR2-1.17.1_LC (105) EIK  SEQ ID NO:18
         A30 (96)  ---  SEQ ID NO:11
      Consensus (105)
```

```
                                                                              Section 1
              (1)  1          10         20         30         40          52
CR2-1.18_HC   (1)  QVQLVQSGAEVKKPGASVKVSCKASGYTFTSYDINWVRQATGQGLEWMGWMN
       VH1-8  (1)  QVQLVQSGAEVKKPGASVKVSCKASGYTFTSYDINWVRQATGQGLEWMGWMN
   Consensus  (1)  QVQLVQSGAEVKKPGASVKVSCKASGYTFTSYDINWVRQATGQGLEWMGWMN
                                                                              Section 2
              (53) 53         60         70         80         90         104
CR2-1.18_HC   (53) PNSGNTGYAQRFQGRVTMTRNTSISTAYMELSSLRSEDTAVYYCAREGIAVA
       VH1-8  (53) PNSGNTGYAQRFQGRVTMTRNTSISTAYMELSSLRSEDTAVYYCAR------
   Consensus  (53) PNSGNTGYAQRFQGRVTMTRNTSISTAYMELSSLRSEDTAVYYCAR
                                                                              Section 3
              (105) 105   110        125
CR2-1.18_HC   (105) GTYYYYYGMDVWGQGTTVTVSS      SEQ ID NO:19
       VH1-8  (99)  ----------------------      SEQ ID NO:1
   Consensus  (105)
```

Figure 26B

```
                                                                              Section 1
              (1)  1          10         20         30         40         53
CR2-1.18_LC   (1)  DIQMTQSPSSLSASVGDRVTITCRASQGIRNDLGWYQQKPGKAPKRLIYAASS
         A30  (1)  DIQMTQSPSSLSASVGDRVTITCRASQGIRNDLGWYQQKPGKAPKRLIYAASS
   Consensus  (1)  DIQMTQSPSSLSASVGDRVTITCRASQGIRNDLGWYQQKPGKAPKRLIYAASS
                                                                              Section 2
              (54) 54         60         70         80         90         106
CR2-1.18_LC   (54) LQSGVPSRFSGSGSGTEFTLTISSLQPEDFATYFCLQHNSYPFTPGPGTKVDI
         A30  (54) LQSGVPSRFSGSGSGTEFTLTISSLQPEDFATYFCLQHNSYP-----------
   Consensus  (54) LQSGVPSRFSGSGSGTEFTLTISSLQPEDFATYFCLQHNSYP
                                                                              Section 3
              (107) RC7
CR2-1.18_LC   (107) K          SEQ ID NO:20
         A30  (96)  -          SEQ ID NO:11
   Consensus  (107)
```

```
                                                                                    Section 1
              (1) 1         10         20         30         40        52
Cur2-1.19.1_hc (1) QVQLVQSGAEVKKPGASVKVSCKASGYTFTSYDINWVRQATGQGLEWMGWMN
        VH1-8  (1) QVQLVQSGAEVKKPGASVKVSCKASGYTFTSYDINWVRQATGQGLEWMGWMN
    Consensus  (1) QVQLVQSGAEVKKPGASVKVSCKASGYTFTSYDINWVRQATGQGLEWMGWMN
                                                                                    Section 2
              (53) 53        60         70         80         90        104
Cur2-1.19.1_hc (53) PNSGNTGYAQKFQGRVTMTRNTSISTAYMELSSLRSEDTAVYYCARDVMITF
        VH1-8 (53) PNSGNTGYAQKFQGRVTMTRNTSISTAYMELSSLRSEDTAVYYCAR------
    Consensus (53) PNSGNTGYAQKFQGRVTMTRNTSISTAYMELSSLRSEDTAVYYCAR
                                                                                    Section 3
             (105) 105   110        126
Cur2-1.19.1_hc (105) GGVIVHYGMDVWGQGTTVTVSS    SEQ ID NO:21
        VH1-8  (99) ----------------------    SEQ ID NO:1
    Consensus (105)
```

Figure 27B

```
                                                                                    Section 1
              (1) 1         10         20         30         40        52
Cur2-1.19.1_lc (1) DIQMTQSPSSLSASVGDRVTITCRASQGIRNDLGWYQQKPGKAPKRLIYAAS
         A30   (1) DIQMTQSPSSLSASVGDRVTITCRASQGIRNDLGWYQQKPGKAEKRLIYAAS
    Consensus  (1) DIQMTQSPSSLSASVGDRVTITCRASQGIRNDLGWYQQKPGKAPKRLIYAAS
                                                                                    Section 2
              (53) 53        60         70         80         90        104
Cur2-1.19.1_lc (53) SLQSGVPSRFSGSGSGTDFTLTISSLQPEDFATYYCLQHNSDPCSFGQGTKL
         A30  (53) SLQSGVPSRFSGSGSGTDFTLTISSLQPEDFATYYCLQHNSYP---------
    Consensus (53) SLQSGVPSRFSGSGSGTDFTLTISSLQPEDFATYYCLQHNS P
                                                                                    Section 3
             (105) 1067
Cur2-1.19.1_lc (105) EIR    SEQ ID NO:22
         A30   (96) ---    SEQ ID NO:11
    Consensus (105)
```

```
                                                                    Section 1
                (1)  1         10        20        30        40        51
Cur2-1.23.1_HC  (1)  EVQLVQSGAEVKRPGESLKISCEGSGYSFTSYWIGWVRQMPGKGLEWMGII
        VH5-51  (1)  EVQLVQSGAEVKKPGESLKISCKGSGYSFTSYWIGWVRQMPGKGLEWMGII
     Consensus  (1)  EVQLVQSGAEVKRPGESLKISC GSGYSFTSYWIGWVRQMPGKGLEWMGII
                                                                    Section 2
                (52) 52        60        70        80        90       102
Cur2-1.23.1_HC  (52) YPGDSDTRYSPSFQGQVTISADKSISTAYLQWSSLKASDTAMYYCARHVSY
        VH5-51  (52) YPGDSDTRYSPSFQGQVTISADKSISTAYLQWSSLKASDTAMYYCAR----
     Consensus  (52) YPGDSDTRYSPSFQGQVTISADKSISTAYLQWSSLKASDTAMYYCAR
                                                                    Section 3
                (103) 103       110       126
Cur2-1.23.1_HC  (103) YYVSGSYYNVFDYWGQGTLVTVSS    SEQ ID NO:23
        VH5-51  (99)  ------------------------    SEQ ID NO:6
     Consensus  (103)
```

Figure 28B

```
                                                                    Section 1
                (1)  1         10        20        30        40        51
Cur2-1.23.1_LC  (1)  DIQMTQSPSSLSASVGDRVTITCRASQSIRNDLGWYQQIPGKAPKRLIYAA
           A30  (1)  DIQMTQSPSSLSASVGDRVTITCRASQGIRNDLGWYQQKPGKAPKRLIYAA
     Consensus  (1)  DIQMTQSPSSLSASVGDRVTITCRASQGIRNDLGWYQQ PGKAPKRLIYAA
                                                                    Section 2
                (52) 52        60        70        80        90       102
Cur2-1.23.1_LC  (52) SSLQRGVPSRFSGSGSGTEFTLTISSLQPEDFATYYCLQHNSYPWTFGQGT
           A30  (52) SSLQSGVPSRFSGSGSGTEFTLTISSLQPEDFATYYCLQHNSYP------
     Consensus  (52) SSLQ GVPSRFSGSGSGTEFTLTISSLQPEDFATYYCLQHNSYP
                                                                    Section 3
                (103) 103 107
Cur2-1.23.1_LC  (103) RVEIK     SEQ ID NO:24
           A30  (96)  -----     SEQ ID NO:11
     Consensus  (103)
```

```
                                                                                    Section 1
              (1) 1         10         20         30         40         51
CR2-1.24.1 HC (1) QVQLVESGGGVVQPGRSLRLSCAASGF S SYGMHWVRQAPGKGLEWVADI
        VH3-33 (1) QVQLVESGGGVVQPGRSLRLSCAASGF P SSYGMHWVRQAPGKGLEWVAVI
     Consensus (1) QVQLVESGGGVVQPGRSLRLSCAASGFSF SSYGMHWVRQAPGKGLEWVA I
                                                                                    Section 2
              (52) 52        60         70         80         90        102
CR2-1.24.1 HC (52) WYDGSNKYYADSVKGRFTISRDNSKNTLYLQMNSLRAEDTAVYYCARDQGY
        VH3-33 (52) WYDGSNKYYADSVKGRFTISRDNSKNTLYLQMNSLRAEDTAVYYCAR----
     Consensus (52) WYDGSNKYYADSVKGRFTISRDNSKNTLYLQMNSLRAEDTAVYYCAR
                                                                                    Section 3
              (103) 103      110        126
CR2-1.24.1 HC (103) SYGYVYYDYGMDVWGQGTTVTSS          SEQ ID NO:25
        VH3-33  (99) --------------------            SEQ ID NO:4
     Consensus (103)
```

Figure 29B

```
                                                                                    Section 1
              (1) 1         10         20         30         40         52
CR2-1.24.1 LC (1) DIQMTQSPSSLSASVGDRVTITCRASQGIRNDLGWYQQKPGKAPKRLIYAAS
           A30 (1) DIQMTQSPSSLSASVGDRVTITCRASQGIRNDLGWYQQKPGKAPKRLIYAAS
     Consensus (1) DIQMTQSPSSLSASVGDRVTITCRASQGIRNDLGWYQQKPGKAPKRLIYAAS
                                                                                    Section 2
              (53) 53        60         70         80         90        104
CR2-1.24.1 LC (53) SLQSGVPSRFSGSGSGTEFTLTISSLQPEDFATYYCLQHNSYPWTPGQGTKV
           A30 (53) SLQSGVPSRFSGSGSGTEFTLTISSLQPEDFATYYCLQHNSYP--------
     Consensus (53) SLQSGVPSRFSGSGSGTEFTLTISSLQPEDFATYYCLQHNSYP
                                                                                    Section 3
              (105) 1067
CR2-1.24.1 LC (105) EIK      SEQ ID NO:26
           A30  (96) ---      SEQ ID NO:11
     Consensus (105)
```

```
                                                                                    Section 1
            (1)  1          10         20         30         40        51
   VH5-51   (1)  EVQLVQSGAEVKKPGESLKISCKGSGYSFTSYWIGWVRQMPGKGLEWMGII
CR2-1.25.1_HC (1) EVQLVQSGAEVKKPGESLKISCKGSGYRFTSYWIGWVRQMPGKGLEWMGII
 Consensus  (1)  EVQLVQSGAEVKKPGESLKISCKGSGY FTSYWIGWVRQMPGKGLEWMGII
                                                                                    Section 2
            (52) 52         60         70         80         90        102
   VH5-51   (52) YPGDSDTRYSPSFQGQVTISADKSISTAYLQWSSLKASDTAMYYCAR----
CR2-1.25.1_HC (52) YPGDSDTRYSPSFQGQVTISADKSISTAYLQWSSLKASDTAMYYCARHGSY
 Consensus  (52) YPGDSDTRYSPSFQGQVTISADKSISTAYLQWSSLKASDTAMYYCAR
                                                                                    Section 3
            (103) 103   110         126
   VH5-51   (99)  ----------------------    SEQ ID NO:6
CR2-1.25.1_HC (103) YYGSETYYNVFDYWGQGTLVTVSS  SEQ ID NO:27
 Consensus  (103)
```

Figure 30B

```
                                                                                    Section 1
            (1)  1          10         20         30         40        52
     A30    (1)  DIQMTQSPSSLSASVGDRVTITCRASQGIRNDLGWYQQKPGKAPKRLIYAAS
CR2-1.25.1_LC (1) DIQMTQSPSSLSASVGDRVTITCRASQGIRNDLGWYQQKPGKAPKRLIYAAS
 Consensus  (1)  DIQMTQSPSSLSASVGDRVTITCRASQGIRNDLGWYQQKPGKAPKRLIYAAS
                                                                                    Section 2
            (53) 53         60         70         80         90        104
     A30    (53) SLQSGVPSRFSGSGSGTEFTLTISSLQPEDFATYYCLQHNSYP--------
CR2-1.25.1_LC (53) SLQSGVPSRFSGSGSGTEFTLTISSLQPEDFATYYCLQHNSYPWTFGQGTKV
 Consensus  (53) SLQSGVPSRFSGSGSGTEFTLTISSLQPEDFATYYCLQHNSYP
                                                                                    Section 3
            (105) 1067
     A30    (96)  ---         SEQ ID NO:11
CR2-1.25.1_LC (105) EIK        SEQ ID NO:28
 Consensus  (105)
```

```
                                                                    Section 1
         (1)  1         10        20        30        40        52
VH5-51   (1)  EVQLVQSGAEVKKPGESLKISCKGSGYSFTSYWIGWVRQMPGKGLEWMGIIY
CR2-1.29_HC (1) EVQLVQSGAEVKKPGESLKISCKGSGYSFTSYWIGWVRQMPGKGLEWMGIIY
Consensus (1) EVQLVQSGAEVKKPGESLKISCKGSGYSFTSYWIGWVRQMPGKGLEWMGIIY
                                                                    Section 2
         (53) 53        60        70        80        90        104
VH5-51   (53) PGDSDTRYSPSFQGQVTISADKSISTAYLQWSSLKASDTAMYYCAR------
CR2-1.29_HC (53) PGDSDTRYSPSFQGQATISADKSISTAYLQWSSLKNSDTAMYYCARHVDVGA
Consensus (53) PGDSDTRYSPSFQGQ TISADKSISTAYLQWSSLKASDTAMYYCAR
                                                                    Section 3
         (105) 105    110              129
VH5-51   (99)  ------------------------------  SEQ ID NO:6
CR2-1.29_HC (105) TIGGYYYYYHGMDVWGQGTTVTVSS      SEQ ID NO:29
Consensus (105)
```

Figure 31B

```
                                                                    Section 1
         (1)  1         10        20        30        40        53
A19      (1)  DIVMTQSPLSLPVTPGEPASISCRSSQSLLHSNGYNYLDWYLQKPGQSPQLLI
CR2-1.29_LC (1) DIVMTQSPLSLPVTPGEPASISCRSSQSLLHSNGYNYLDWYLQKPGQSPQLLI
Consensus (1) DIVMTQSPLSLPVTPGEPASISCRSSQSLLHSNGYNYLDWYLQKPGQSPQLLI
                                                                    Section 2
         (54) 54        60        70        80        90        106
A19      (54) YLGSNRASGVPDRFSGSGSGTDFTLKISRVEADDVGVYYCMQALQP------
CR2-1.29_LC (54) YLGSNRASGVPDRFSGSGSGTDFTLKISRVEADDVGVYYCMQALQLMCSFGQ
Consensus (54) YLGSNRASGVPDRFSGSGSGTDFTLKISRVEADDVGVYYCMQALQS
                                                                    Section 3
         (107) 107    113
A19      (101)  ------   SEQ ID NO:8
CR2-1.29_LC (107) GTKLEIK SEQ ID NO:30
Consensus (107)
```

```
                                                                    Section 1
            (1)  1         10         20         30         40        52
    VH1-18  (1)  QVQLVQSGAEVKKDGASVKVSCKASGYTFTSYGISWVRQAPGQGLEWMGWIS
 CR2-1.33_HC (1)  QVQLVQSGAEVKKPGASVKVSCKASGYTFTSYGISWVRQAPGQGLEWMGWIS
  Consensus (1)  QVQLVQSGAEVKKPGASVKVSCKASGYTFTSYGISWVRQAPGQGLEWMGWIS
                                                                    Section 2
            (53) 53        60         70         80         90       104
    VH1-18  (53) AYNGNTNYAQKLQGRVTMTTDTSTSTAYMELRSLRSDDTAVYYCAR------
 CR2-1.33_HC (53) AYNGNTNYAQKLQGRVTMTTDTSTSTAYMELRSLRSDDTAVYYCARDHYYDS
  Consensus (53) AYNGNTNYAQKLQGRVTMTTDTSTSTAYMELRSLRSDDTAVYYCAR
                                                                    Section 3
           (105) 105    110       127
    VH1-18  (99) -----------------------       SEQ ID NO:2
 CR2-1.33_HC (105) SDYLYYYGLDVWGQGTTVTVSS       SEQ ID NO:31
  Consensus (105)
```

Figure 32B

```
                                                                    Section 1
            (1)  1         10         20         30         40        53
        A20 (1)  DIQMTQSPSSLSASVGDRVTITCRASQGISNYLAWYQQKPGKVPKLLIYAAST
 CR2-1.33_LC (1)  DIQMTQSPSSLSASVGDRVTITCRASQGISNYLAWYQQKPGKVPKLLIYAAST
  Consensus (1)  DIQMTQSPSSLSASVGDRVTITCRASQGISNYLAWYQQKPGKVPKLLIYAAST
                                                                    Section 2
            (54) 54        60         70         80         90       106
        A20 (54) LQSGVPSRFSGSGSGTDFTLTISSLQPEDVATYYCQKYNSAP-----------
 CR2-1.33_LC (54) LQSGVPSRFSGSGSGTDFTLTISSLQPEDVATYYCQKYNSAPLTFGGGTKVEI
  Consensus (54) LQSGVPSRFSGSGSGTDFTLTISSLQPEDVATYYCQKYNSAP
                                                                    Section 3
           (107) 107
        A20 (96) -       SEQ ID NO:9
 CR2-1.33_LC (107) K     SEQ ID NO:32
  Consensus (107)
```

```
                                                                          Section 1
              (1)  1          10         20         30         40         51
   VH3-33     (1)  QVQLVESGGGVVQPGRSLRLSCAASGFTFSSYGMHWVRQAPGKGLEWVAII
CR2-1.38.1_HC (1)  QVQLVESGGGVVQPGRSLRLSCAASGFTFSSYGMHWVRQAPGKGLEWVAII
   Consensus  (1)  QVQLVESGGGVVQPGRSLRLSCAASGFTFSSYGMHWVRQAPGKGLEWVAII
                                                                          Section 2
              (52) 52         60         70         80         90         102
   VH3-33     (52) WYDGSNKYYADSVKGRFTISRDNSKNTLYLQMNSLRAEDTAVYYCAR----
CR2-1.38.1_HC (52) WYDGNDKYYADSVKGRFTISRDNSKNTLYLQMNSLRAEDTAVYYCARGYYY
   Consensus  (52) WYDG  KYYADSVKGRFTISRDNSKNTLYLQMNSLRAEDTAVYYCAR
                                                                          Section 3
              (103) 103       110        127
   VH3-33     (99)  ------------------------           SEQ ID NO:4
CR2-1.38.1_HC (103) DSSDYLYYYYGMDVWGQGTTVTVSS          SEQ ID NO:33
   Consensus  (103)
```

Figure 33B

```
                                                                          Section 1
              (1)  1          10         20         30         40         52
       A20    (1)  DIQMTQSPSSLSASVGDRVTITCRASQGISNYLAWYQQKPGKVPRLLIYAAS
CR2-1.38.1_LC (1)  DIQMTQSPSSLSASVGDRVTITCRASQGISNYLAWYQQKPGKVPNLLIYAAS
   Consensus  (1)  DIQMTQSPSSLSASVGDRVTITCRASQGISNYLAWYQQKPGKVP LLIYAAS
                                                                          Section 2
              (53) 53         60         70         80         90         104
       A20    (53) TLQSGVPSRFSGSGSGTDFLTISSLQPEDVATYYCQKYNSAP---------
CR2-1.38.1_LC (53) TLQSGVPSRFSGSGSGTDFLTISSLQPEDVAAYYCQKCNSAPWTFGQGTTV
   Consensus  (53) TLQSGVPSRFSGSGSGTDFSLTISSLQPEDVA  YYCQK NSAP
                                                                          Section 3
              (105) 1897
       A20    (96)  ---         SEQ ID NO:9
CR2-1.38.1_LC (105) EIK         SEQ ID NO:34
   Consensus  (105)
```

```
                                                                              Section 1
              (1)  1         10        20        30        40        51
    VH5-51    (1)  EVQLVQSGAEVKKPGESLKISCKGSGYSFTSYWIGWVRQMPGKGLEWMGII
CR2-1.39.1_HC (1)  EVQLVQSGTEVRKPGESLKISCKGSGYRFTSYWIGWVRQMPGKGLEWMGII
  Consensus   (1)  EVQLVQSG EVKKPGESLKISCKGSGY FTSYWIGWVRQMPGKGLEWMGII
                                                                              Section 2
              (52) 52        60        70        80        90       102
    VH5-51    (52) YPGDSDTRYSPSFQGQVTISADKSISTAYLQWSSLKASDTAMYYCAR----
CR2-1.39.1_HC (52) YPGDSDTRYSPSFQGQVTISADKSISTAYLQWSSLKASDTAMYYCARHGSY
  Consensus   (52) YPGDSDTRYSPSFQGQVTISADKSISTAYLQWSSLKASDTAMYYCAR
                                                                              Section 3
              (103) 103    110         126
    VH5-51    (99)  ---------------------   SEQ ID NO:6
CR2-1.39.1_HC (103) YYNSGSYYNVFDYWGQGTLVTVSS  SEQ ID NO:35
  Consensus   (103)
```

Figure 34B

```
                                                                               Section 1
              (1)  1         10        20        30        40        52
     A30      (1)  DIQMTQSPSSLSASVGDRVTITCRASQGIRNDLGWYQQKPGKAPKRLIYAAS
CR2-1.39.1_LC (1)  DIQMTQSPSSLSASVGDRVTITCRASQGIRNDLGWYQQKPGKAPKRLIYAAS
  Consensus   (1)  DIQMTQSPSSLSASVGDRVTITCRASQGIRNDLGWYQQKPGKAPKRLIYAAS
                                                                               Section 2
              (53) 53        60        70        80        90       104
     A30      (53) SLQSGVPSRFSGSGSGTEFTLTISSLQPEDFATYYCLQHNSYP---------
CR2-1.39.1_LC (53) SLQSGVPSRFSGSGSGTEFTLTISSLQPEDFATYYCLQHNSYPWTFGQGTKV
  Consensus   (53) SLQSGVPSRFSGSGSGTEFTLTISSLQPEDFATYYCLQHNSYP
                                                                               Section 3
              (105) 1057
     A30      (96)  ---      SEQ ID NO:11
CR2-1.39.1_LC (105) EIK      SEQ ID NO:36
  Consensus   (105)
```

```
                                                                                    Section 1
              (1)  1         10        20        30        40        52
    VH1-8     (1)  QVQLVQSGAEVKRPGASVKVSCKASGYTFTSYDINWVRQATGQGLEWMGWMN
    CR2-1.45_HC (1) QVQLVQSGAEVKRPGASVKVSCKASGYTFTSYDINWVRQATGQGLEWMGWMN
    Consensus (1)  QVQLVQSGAEVKRPGASVKVSCKASGYTFTSYDINWVRQATGQGLEWMGWMN
                                                                                    Section 2
              (53) 53        60        70        80        90        104
    VH1-8     (53) PNSGNTGYAQKFQGRVTMTRNTSISTAYMELSSLRSEDTAVYYCAR-----
    CR2-1.45_HC (53) PNSGNTGYAQKFQGRVTMTRNTSISTAYMELSSLRSEDTAVYYCARGSGYSY
    Consensus (53) PNSGNTGYAQKFQGRVTMTRNTSISTAYMELSSLRSEDTAVYYCAR
                                                                                    Section 3
              (105) 105      110        125
    VH1-8     (99)  --------------------    SEQ ID NO:1
    CR2-1.45_HC (105) GYDYYYGMDVWGQGTTVTVSS  SEQ ID NO:38
    Consensus (105)
```

Figure 35B

```
                                                                                    Section 1
              (1)  1         10        20        30        40        53
    A20       (1)  DIQMTQSPSSLSASVGDRVTITCRASQGISNYLAWYQQKPGKVPKLLIYAAST
    CR2-1.45_LC (1) DIQMTQSPSSLSASVGDRVTINCRASQGISNDLAWYQQKPGKVPKLLIYAAST
    Consensus (1)  DIQMTQSPSSLSASVGDRVTI CRASQGISN LAWYQQKPGKVPKLLIYAAST
                                                                                    Section 2
              (54) 54        60        70        80        90        106
    A20       (54) LQSGVPSRFSGSGSGTDFTLTISSLQPEDVATYYCQKYNSAP----------
    CR2-1.45_LC (54) LQLGVPSRFSGSGSGTDFTLTISSLQPEDVATYYCQKYNSAPFTPGPGTKVDI
    Consensus (54) LQ GVPSRFSGSGSGTDFTLTISSLQPEDVATYYCQKYNSAP
                                                                                    Section 3
              (107) 107
    A20       (96)  -    SEQ ID NO:9
    CR2-1.45_LC (107) K    SEQ ID NO:39
    Consensus (107)
```

```
                                                                          Section 1
            (1)  1          10         20         30         40        51
    VH1-8   (1)  QVQLVQSGAEVKKPGASVKVSCKASGYTFTSYDINWVRQATGQGLEWMGWM
CR2-1.46.1_HC (1) QVQLVQSGAEVKKPGASVRVSCRASGYSFTSYDINWVRQATGQGLEWMGWM
  Consensus (1)  QVQLVQSGAEVKKPGASVKVSCKASGYSFTSYDINWVRQATGQGLEWMGWM
                                                                          Section 2
           (52) 52         60         70         80         90        102
    VH1-8  (52) NPNSGNTGYAQKFQGRVTMTRNTSISTAYMELSSLRSEDTAVYYCAR----
CR2-1.46.1_HC (52) NPNNGNTGYAQKFQGRVTMTRNTSISTAYMELSSLRSEDTAVYYCARDIVV
  Consensus (52) NPN GNTGYAQKFQGRVTMTRNTSISTAYMELSSLRSEDTAVYYCAR
                                                                          Section 3
          (103) 103        110                126
    VH1-8  (99) --------------------------         SEQ ID NO:1
CR2-1.46.1_HC (103) VVTATDYYYGMDVWGQGTTVTVSS          SEQ ID NO:40
  Consensus (103)
```

Figure 36B

```
                                                                          Section 1
            (1)  1          10         20         30         40        52
      A30   (1)  DIQMTQSPSSLSASVGDRVTITCRASQGIRNDLGWYQQKPGKAPKRLIYAAS
CR2-1.46.1_LC (1) DIQMTQSPSSLSASVGDRVTITCRASQGIRNDLGWYQQKPGKAPKRLIFAAS
  Consensus (1)  DIQMTQSPSSLSASVGDRVTITCRASQGIRNDLGWYQQKPGKAPKRLIFAAS
                                                                          Section 2
           (53) 53         60         70         80         90       104
      A30  (53) SLQSGVPSRFSGSGSGTEFTLTISSLQPEDFATYYCLQHNSYP--------
CR2-1.46.1_LC (53) SLPSGVPSRFSGSGSGTEFTLTISSLQPEDFATYYCLQHSGYPPTPGQGTKV
  Consensus (53) SL SGVPSRFSGSGSGTEFTLTISSLQPEDFATYYCLQH  YP
                                                                          Section 3
          (105) 105  107
      A30   (96) ---          SEQ ID NO:11
CR2-1.46.1_LC (105) EIK         SEQ ID NO:41
  Consensus (105)
```

```
                                                                          Section 1
              (1) 1         10         20         30         40        51
CR2-1.48.1_HC (1) QVQLVQSGAEVKKPGASVKVSCKASGYTFTSYGISWVRQAPGQGLEWMGWI
       VH1-18 (1) QVQLVQSGAEVKKPGASVKVSCKASGYTFTSYGISWVRQAPGQGLEWMGWI
    Consensus (1) QVQLVQSGAEVKKPGASVKVSCKASGYTFTSYGISWVRQAPGQGLEWMGWI
                                                                          Section 2
              (52) 52        60         70         80         90       102
CR2-1.48.1_HC (52) SAYNGNTNYAQRLQGRVTMTTDTSTSTAYMELRSLRSDDTAVYYCARDVEY
       VH1-18 (52) SAYNGNTNYAQRLQGRVTMTTDTSTSTAYMELRSLRSDDTAVYYCAR----
    Consensus (52) SAYNGNTNYAQRLQGRVTMTTDTSTSTAYMELRSLRSDDTAVYYCAR
                                                                          Section 3
              (103) 103       110        125
CR2-1.48.1_HC (103) YYDGSGYYYFDYWGQGTLVTVSS  SEQ ID NO:42
       VH1-18 (99)  -----------------------  SEQ ID NO:2
    Consensus (103)
```

Figure 37B

```
                                                                          Section 1
              (1) 1         10         20         30         40        52
CR2-1.48.1_LC (1) DIQMTQSPSSVSASVGDRVTITCRASQGISSWLAWYQQKPGKAPKLLIYAAS
           L5 (1) DIQMTQSPSSVSASVGDRVTITCRASQGISSWLAWYQQKPGKAPKLLIYAAS
    Consensus (1) DIQMTQSPSSVSASVGDRVTITCRASQGISSWLAWYQQKPGKAPKLLIYAAS
                                                                          Section 2
              (53) 53        60         70         80         90       104
CR2-1.48.1_LC (53) ILQSGVPSRFSGSGSGTDFTLTISSLQPEDFATYCQQYNSFPRTFGQGTKV
           L5 (53) SLQSGVPSRFSGSGSGTDFTLTISSLQPEDFATYCQQYNSFP--------
    Consensus (53)  LQSGVPSRFSGSGSGTDFTLTISSLQPEDFASYYCQQANSFP
                                                                          Section 3
              (105) 1067
CR2-1.48.1_LC (105) EIK  SEQ ID NO:43
           L5 (96)  ---  SEQ ID NO:7
    Consensus (105)
```

```
                                                                            Section 1
                   (1) 1         10        20        30        40       51
    CR2-1.49.1_HC  (1) QVQLVQSGAEVKKPGASVKVSCKASGYTPTSYDINWVRQATGQGLEWMGWM
           VH1-8   (1) QVQLVQSGAEVKKPGASVKVSCKASGYTPTSYDINWVRQATGQGLEWMGWM
        Consensus  (1) QVQLVQSGAEVKKPGASVKVSCKASGYTPTSYDINWVRQATGQGLEWMGWM
                                                                            Section 2
                  (52) 52        60        70        80        90       102
    CR2-1.49.1_HC (52) NPNSGDTGYAQKFQGRVTMTPNTSISTAYMELSSLRSEDTAVYFCARMRDI
           VH1-8  (52) NPNSGNTGYAQKFQGRVTMTRNTSISTAYMELSSLRSEDTAVYFCAR----
        Consensus (52) NPNSG TGYAQKFQGRVTMTRNTSISTAYMELSSLRSEDTAVYFCAR
                                                                            Section 3
                 (103) 103       110               127
    CR2-1.49.1_HC(103) VATSYYYYPYGMDVWGQGTTVTVSS     SEQ ID NO:44
           VH1-8  (99) -------------------------     SEQ ID NO:1
        Consensus(103)
```

Figure 38B

```
                                                                            Section 1
                   (1) 1         10        20        30        40       52
    CR2-1.49.1_LC  (1) DIVMTQSPLSLPVTPGEPASISCRSSQSLLHSNGYNYLDWYLLKPGQSPQLL
             A19   (1) DIVMTQSPLSLPVTPGEPASISCRSSQSLLHSNGYNYLDWYLQKPGQSPQLL
        Consensus  (1) DIVMTQSPLSLPVTPGEPASISCRSSQSLLHSNGYNYLDWYL KPGQSPQLL
                                                                            Section 2
                  (53) 53        60        70        80        90      104
    CR2-1.49.1_LC (53) IYLGSSRASGMPDRFSGSGSGTVFTLKISRVEAEDVGVYYCMQTLQTITPGQ
             A19  (53) IYLGSNRASGVPDRFSGSGSGTDFTLKISRVEAEDVGVYYCMQALQTP----
        Consensus (53) IYLGS RASGVPDRFSGSGSGTDFTLKISRVEAEDVGVYYCMQ LQT
                                                                            Section 3
                 (105) 105    111
    CR2-1.49.1_LC(105) GTRLEIK         SEQ ID NO:45
             A19 (101) -------         SEQ ID NO:8
        Consensus(105)
```

```
                                                                          Section 1
              (1) 1       10        20        30        40       51
CR2-1.51.1 HC (1) EVQLVQSGAEVRKPGESLKISCKGSGYSPTSYWIGWVRQMPGKGLEWMGII
       VH5-51 (1) EVQLVQSGAEVRKPGESLKISCKGSGYSPTSYWIGWVRQMPGKGLEWMGII
    Consensus (1) EVQLVQSGAEVKKPGESLKISCKGSGYSPTSYWIGWVRQMPGKGLEWMGII
                                                                          Section 2
              (52) 52      60        70        80        90       102
CR2-1.51.1_HC (52) YPGDSDA  YSPSFQGQVTISADKSISTAYLQWSSLRASDTAMYYCARHYDY
       VH5-51 (52) YPGDSDT  YSPSFQGQVTISADKSISTAYLQWSSLRASDTAMYYCAR----
    Consensus (52) YPGDSD   KYSPSFQGQVTISADKSISTAYLQWSSLRASDTAMYYCAR
                                                                          Section 3
              (103) 103     110       126
CR2-1.51.1_HC (103) VWRNYRYTGWFDPWGQGTLVTVSS              SEQ ID NO:46
       VH5-51 (99)  -----------------------              SEQ ID NO:6
    Consensus (103)
```

Figure 39B

```
                                                                           Section 1
              (1) 1       10        20        30        40        52
CR2-1.51.1 LC (1) EIVLTQSPGTLSLSPGERATLSCRASQSVSSSYLAWYQQKPGQAPRLLIYGA
          A27 (1) EIVLTQSPGTLSLSPGERATLSCRASQSVSSSYLAWYQQKPGQAPRLLIYGA
    Consensus (1) EIVLTQSPGTLSLSPGERATLSCRASQSVSSSYLAWYQQKPGQAPRLLIYGA
                                                                           Section 2
              (53) 53      60        70        80        90        104
CR2-1.51.1_LC (53) SNRATGIPDRFSGSGSGTDFTLTISRLEPEDFAVYYCQQYGSSLFTFGPGTK
          A27 (53) SSRATGIPDRFSGSGSGTDFTLTISRLEPEDFAVYYCQQYGSSP--------
    Consensus (53) S RATGIPDRFSGSGSGTDFTLTISRLEPEDFAVYYCQQYGSS
                                                                           Section 3
               (105) 105108
CR2-1.51.1_LC (105) VDIK           SEQ ID NO:47
          A27  (97) ----           SEQ ID NO:10
    Consensus (105)
```

```
                                                                         Section 1
                  (1)  1         10         20         30         40        52
Cur2-6.4.1_hc     (1)  QVQLVQSGAEVRKPGASVKVSCKASGYTPTSYDINWVRQATGQGLEWMGWIN
        VH1-8     (1)  QVQLVQSGAEVKKPGASVKVSCKASGYTFTSYDINWVRQATGQGLEWMGWIN
    Consensus     (1)  QVQLVQSGAEVRKPGASVKVSCKASGYTPTSYDINWVRQATGQGLEWMGWIN
                                                                         Section 2
                 (53) 53         60         70         80         90       104
Cur2-6.4.1_hc    (53)  PNSGNTDYAQKFQGRVTMTRDTSISTAYMELSSLRSEDTAIYYCVRGFGYSY
        VH1-8    (53)  PNSGNTGYAQKFQGRVTMTRNTSISTAYMELSSLRSEDTAIYYCAR-----
    Consensus   (53)  PNSGNT YAQKFQGRVTMTR TSISTAYMELSSLRSEDTAIYYC R
                                                                         Section 3
                (105) 105   110       125
Cur2-6.4.1_hc  (105)  NYDYYYGMDVWGQGTTVTVSS    SEQ ID NO:48
        VH1-8   (99)  ---------------------    SEQ ID NO:1
    Consensus  (105)
```

Figure 40B

```
                                                                         Section 1
                  (1)  1         10         20         30         40        52
Cur2-6.4.1_Lc     (1)  EIVLTQSPGTLSLSPGERATLSCRASQSVSSSYLAWYQQKPGQAPRLLIYT
          A27     (1)  EIVLTQSPGTLSLSPGERATLSCRASQSVSSSYLAWYQQKPGQAPRLLIYA
    Consensus     (1)  EIVLTQSPGTLSLSPGERATLSCRASQSVSSSYLAWYQQKPGQAPRLLIYA
                                                                         Section 2
                 (53) 53         60         70         80         90       104
Cur2-6.4.1_Lc   (53)  SSRATGIPDRFSGSGSGTDFTLTISRLEPEDFAVYYCQQYGSSPCSPGQGTK
          A27   (53)  SSRATGIPDRFSGSGSGTDFTLTISRLEPEDFAVYYCQQYGSSP--------
    Consensus  (53)  SSRATGIPDRFSGSGSGTDFTLTISRLEPEDFAVYYCQQYGSSP
                                                                         Section 3
                (105) 10508
Cur2-6.4.1_Lc  (105)  LEIK     SEQ ID NO:49
          A27   (97)  ----     SEQ ID NO:10
    Consensus  (105)
```

Figure 41A

| CLONE # | VH | #del | VH END | # N's | N Sequence | DH | Size of D | D Sequence | # N's | N Sequence | JH | # del | JH Segment |
|---|---|---|---|---|---|---|---|---|---|---|---|---|---|
| 1.19.1 | DP-15/1-8 | -1 | CGAGAG (SEQ ID NO:92) | 3 | ACG | D3-16 | 28 | TTATGATTACGTTT GGGGAGTTATCGT (SEQ ID NO:93) | 2 | GC | JH6 B | -12 | ACTACG (SEQ ID NO:94) |
| 1.19.2 | DP-15/1-8 | -1 | CGAGAG (SEQ ID NO:92) | 3 | ACG | D3-16 | 28 | TTATGATTACGTTT GGGGAGTTATCGT (SEQ ID NO:93) | 2 | GC | JH6 B | -12 | ACTACG (SEQ ID NO:94) |
| 1.19.3 | DP-15/1-8 | -1 | CGAGAG (SEQ ID NO:92) | 3 | ACG | D3-16 | 28 | TTATGATTACGTTT GGGGAGTTATCGT (SEQ ID NO:93) | 2 | GC | JH6 B | -12 | ACTACG (SEQ ID NO:94) |
| 6.4.1 | DP-15/1-8 | 0 | GAGAGG (SEQ ID NO:95) | 3 | CTT | D5-18 | 12 | TGGATACAGCTA (SEQ ID NO:96) | 2 | TA | JH6 B | 0 | ATTACTAC (SEQ ID NO:97) |
| 6.4.2 | DP-15/1-8 | 0 | GAGAGG (SEQ ID NO:95) | 3 | CTT | D5-18 | 12 | TGGATACAGCTA (SEQ ID NO:96) | 2 | TA | JH6 B | 0 | ATTACTAC (SEQ ID NO:97) |
| 6.4.3 | DP-15/1-8 | 0 | GAGAGG (SEQ ID NO:95) | 3 | CTT | D5-18 | 12 | TGGATACAGCTA (SEQ ID NO:96) | 2 | TA | JH6 B | 0 | ATTACTAC (SEQ ID NO:97) |

| CLONE | Vk | #del | Vk end | # N | N SEQ | Jk | # del | JK end |
|---|---|---|---|---|---|---|---|---|
| 1.19.1 | A30 | -3 | TTACCC (SEQ ID NO:98) | 6 | GTGCAG (SEQ ID NO:99) | JK3 | -7 | TTTTCG (SEQ ID NO:100) |
| 1.19.2 | A30 | -3 | TTACCC (SEQ ID NO:98) | 6 | GTGCAG (SEQ ID NO:99) | JK2 | -7 | TTTTCG (SEQ ID NO:100) |

Figure 41B

| 1.19.3 | A30 | -3 | TTAACC (SEQ ID NO:98) | 6 | GTGCAG (SEQ ID NO:99) | JK2 | -7 | TTTTGG (SEQ ID NO:100) |
|---|---|---|---|---|---|---|---|---|
| 6.4.1 | A27/A27A | -3 | CTGACC (SEQ ID NO:101) | 6 | GTGCAG (SEQ ID NO:102) | JK2 | -7 | TTTTGG (SEQ ID NO:103) |
| 6.4.2 | A27/A27A | -3 | CTGACC (SEQ ID NO:101) | 6 | GTGCAG (SEQ ID NO:102) | JK2 | -7 | TTTTGG (SEQ ID NO:103) |
| 6.4.3 | A27/A27A | -3 | CTGACC (SEQ ID NO:101) | 6 | GTGCAG (SEQ ID NO:102) | JK2 | -7 | TTTTGG (SEQ ID NO:103) |

Figure 42A

| CLONE # | VH | #DEL | VH END | # N's | N Sequence | DH | Size of D | D Sequence | # N's | N Sequence | JH | # del | JH Segment |
|---|---|---|---|---|---|---|---|---|---|---|---|---|---|
| 1.6.1 | DP-77/3-21 | 0 | GAGAGA (SEQ ID NO:104) | 0 | 0 | D3-16 | 22 | TATTATGATTAC GTTGGGGA (SEQ ID NO:105) | 14 | ATTATGGCC TCGTT (SEQ ID NO:106) | JH4B | -1 | CTACTT (SEQ ID NO:107) |
| 1.6.1 | DP-77/3-21 | 0 | GAGAGA (SEQ ID NO:104) | 0 | 0 | D3-16 | 22 | TATTATGATTAC GTTGGGGA (SEQ ID NO:105) | 14 | ATTATGGCC TCGTT (SEQ ID NO:106) | JH4B | -1 | CTACTT (SEQ ID NO:107) |
| 1.6.1 | DP-77/3-21 | 0 | GAGAGA (SEQ ID NO:104) | 0 | 0 | D3-16 | 22 | TATTATGATTAC GTTGGGGA (SEQ ID NO:105) | 14 | ATTATGGCC TCGTT (SEQ ID NO:106) | JH4B | -1 | CTACTT (SEQ ID NO:107) |
| 1.11.1 | DP-42/3-53 | -5 | AGAGA (SEQ ID NO:108) | 3 | GGA | D4-17 | 10 | ACGGTGACTA (SEQ ID NO:109) | 5 | CGAAT (SEQ ID NO:110) | JH6B | -2 | TACTACT A (SEQ ID NO:111) |
| 1.11.2 | DP-42/3-53 | -5 | AGAGA (SEQ ID NO:108) | 3 | GGA | D4-17 | 10 | ACGGTGACTA (SEQ ID NO:109) | 5 | CGAAT (SEQ ID NO:110) | JH6B | -2 | TACTACT A (SEQ ID NO:111) |
| 1.23.1 | DP-73/5-51 | 0 | GAGACA (SEQ ID NO:112) | 18 | TGTATCGTATTACT AVT (SEQ ID NO:113) | D3-10 | 19 | TTCGGGGAGTTA TTATAAC (SEQ ID NO:114) | 2 | GT | JH4B | -4 | CTTTGA (SEQ ID NO:115) |
| 1.23.2 | DP-73/5-51 | 0 | GAGACA (SEQ ID NO:112) | 18 | TGTATCGTATTACT AVT (SEQ ID NO:113) | D3-10 | 19 | TTCGGGGAGTTA TTATAAC (SEQ ID NO:114) | 2 | GT | JH4B | -4 | CTTTGA (SEQ ID NO:115) |

| CLONE # | Vk | #del | Vk end | # N's | N SEQ | Jk | Jk # del | JK end |
|---|---|---|---|---|---|---|---|---|

Figure 42B

| | | | | | | | #n | | | | |
|---|---|---|---|---|---|---|---|---|---|---|---|
| 1.6.1 | A30 | -3 | TTACCC (SEQ ID NO:116) | 0 | 0 | JK4 | 0 | GCTCACT (SEQ ID NO:117) |
| 1.6.2 | A30 | -3 | TTACCC (SEQ ID NO:116) | 0 | 0 | JK4 | 0 | GCTCACT (SEQ ID NO:117) |
| 1.6.3 | A30 | -3 | TTACCC (SEQ ID NO:116) | 0 | 0 | JK4 | 0 | GCTCACT (SEQ ID NO:117) |
| 1.11.1 | A3/A19/DPK | -4 | AAACTTC (SEQ ID NO:118) | 0 | 0 | JK4 | -2 | TCACTTC (SEQ ID NO:119) |
| 1.11.2 | A3/A19/DPK | -4 | AAACTTC (SEQ ID NO:118) | 0 | 0 | JK4 | -2 | TCACTTC (SEQ ID NO:119) |
| 1.23.1 | A30 | -3 | TTACCC (SEQ ID NO:120) | 0 | 0 | JK1 | 0 | GTGGAC (SEQ ID NO:120) |
| 1.23.2 | A30 | -3 | TTACCC (SEQ ID NO:120) | 0 | 0 | JK1 | 0 | GTGGAC (SEQ ID NO:120) |

Figure 43A

| CLONE # | VH | %DEL | VH END | # N's | N Sequence | DH | Size of D | D Sequence | # N's | N Sequence | JH | # del | JH Segment |
|---|---|---|---|---|---|---|---|---|---|---|---|---|---|
| 1.17.1 | DP-50/3-33 | 0 | GAGAGA (SEQ ID NO:121) | 4 | TCAA | D6-19 | 8 | GGATACA (SEQ ID NO:122) | 9 | ATATGCTGG (SEQ ID NO:123) | JH6B | -1 | TTACTACT (SEQ ID NO:124) |
| 1.17.2 | DP-50/3-33 | 0 | GAGAGA (SEQ ID NO:121) | 4 | TCAA | D6-19 | 8 | GGATACA (SEQ ID NO:122) | 9 | ATATGCTGG (SEQ ID NO:123) | JH6B | -1 | TTACTACT (SEQ ID NO:124) |
| 1.17.3 | DP-50/3-33 | 0 | GAGAGA (SEQ ID NO:121) | 4 | TCAA | D6-19 | 8 | GGATACA (SEQ ID NO:122) | 9 | ATATGCTGG (SEQ ID NO:123) | JH6B | -1 | TTACTACT (SEQ ID NO:124) |
| 1.18 | DP-15/1-8 | 1 | CGAGAG (SEQ ID NO:125) | 1 | A | D6-19 | 19 | GGGTATAGCAGTGGCTGG (SEQ ID NO:126) | 4 | GACA | JH6B | -2 | TACTAC (SEQ ID NO:127) |
| 1.24.1 | DP-50/3-33 | 0 | GAGAGA (SEQ ID NO:128) | 4 | TCAG | DK4 | 18 | GGATACAGCTATGGTTAC (SEQ ID NO:129) | 2 | GT | JH6B | -1 | CTACTA (SEQ ID NO:130) |
| 1.24.2 | DP-50/3-33 | 0 | GAGAGA (SEQ ID NO:128) | 4 | TCAG | DK4 | 18 | GGATACAGCTATGGTTAC (SEQ ID NO:129) | 2 | GT | JH6B | -1 | CTACTA (SEQ ID NO:130) |
| 1.25.1 | DP-73/5-51 | 0 | GAGACA (SEQ ID NO:131) | 6 | TGGATC (SEQ ID NO:132) | D3-10 | 30 | GTATTATTGGTTCGGAGAGTTATTATAA | 3 | TGT | JH4B | -1 | CTTTGA (SEQ ID NO:133) |

Figure 43B

| CLONE # | VH | #DEL | VH END | # N's | N Sequence | DH | Size of D | D Sequence | # N's | N Sequence | JH | # del | JH Segment |
|---|---|---|---|---|---|---|---|---|---|---|---|---|---|
| 1.25.2 | DP-73/5-51 | 0 | GAGACA (SEQ ID NO:131) | 6 | TGGATC (SEQ ID NO:132) | D3-10 | 30 | GTATATTA TGGTTCGG AGAaTTATT ATAA (SEQ ID NO:133) | 3 | TGT | JH4B | 4 | CTTTGA (SEQ ID NO:134) |
| 1.29 | DP-73/5-51 | 0 | GAGAGA (SEQ ID NO:135) | 1 | C | D5-12 | 21 | GTGGATGT AGGGGCT ACGATT (SEQ ID NO:136) | 7 | GGGGAT (SEQ ID NO:137) | JH6B | 0 | ATTACTAC (SEQ ID NO:138) |
| 1.33 | DP-14/1-18 | 0 | GAGAGA (SEQ ID NO:139) | 2 | TC | D21-9 | 18 | ATTACTAT GATAGTAG TG (SEQ ID NO:140) | 7 | ATTATCT (SEQ ID NO:141) | JH6B | 4 | CTACTA (SEQ ID NO:142) |
| 1.38.1 | DP-50/3-33 | 1 | CGAGAG (SEQ ID NO:143) | 2 | GA | D21-9 | 19 | TATTACTA TGATAGTA GTG (SEQ ID NO:144) | 7 | ATTATCT (SEQ ID NO:145) | JH6B | 4 | CTACTA (SEQ ID NO:146) |
| 1.39.1 | DP-73/5-51 | 0 | GAGACA (SEQ ID NO:147) | 6 | TGGATC (SEQ ID NO:148) | D3-10 | 31 | GTATTACT ATaaTTCG GGGAGTTA TTATAAC (SEQ ID NO:149) | 2 | GT | JH4B | 4 | CTTTGA (SEQ ID NO:150) |
| 1.39.2 | DP-73/5-51 | 0 | GAGACA (SEQ ID NO:147) | 6 | TGGATC (SEQ ID NO:148) | D3-10 | 31 | GTATTACT ATaaTTCG GGGAGTTA TTATAAC (SEQ ID NO:149) | 2 | GT | JH4B | 4 | CTTTGA (SEQ ID NO:150) |

Figure 43C

| CLONE # | VH | #DEL | VH END | # N's | N Sequence | DH | Size of D | D Sequence | # N's | N Sequence | JH | # del | JH Segment |
|---|---|---|---|---|---|---|---|---|---|---|---|---|---|
| 1.40.1 | DP-15/1-8 | 1 | CGAGAG (SEQ ID NO:151) | 0 | 0 | D2 | 25 | ATATTGTA GTGGTGGT AGCTGCTA C (SEQ ID NO:152) | 2 | CA | JH6B | -6 | ACTACT (SEQ ID NO:153) |
| 1.40.2 | DP-15/1-8 | 1 | CGAGAG (SEQ ID NO:151) | 0 | 0 | D2 | 25 | ATATTGTA GTGGTGGT AGCTGCTA C (SEQ ID NO:152) | 2 | CA | JH6B | -6 | ACTACT (SEQ ID NO:153) |
| 1.45 | DP-15/1-8 | 0 | GAGAG (SEQ ID NO:154) | 2 | CA | DK4 | 20 | GTGGATAC AGCTATGG TTAC (SEQ ID NO:155) | 1 | G | JH6B | -6 | ACTACT (SEQ ID NO:156) |
| 1.46.1 | DP-15/1-8 | 1 | CGAGAG (SEQ ID NO:157) | 0 | 0 | D2 | 25 | ATATTGTA GT GGTGGTA GCTGCTAC (SEQ ID NO:158) | 2 | GG | JH6B | -6 | ACTACT (SEQ ID NO:159) |
| 1.46.2 | DP-15/1-8 | 1 | CGAGAG (SEQ ID NO:157) | 0 | 0 | D2 | 25 | ATATTGTA GTGGTGGT AGCTGCTA C (SEQ ID NO:158) | 2 | GG | JH6B | -6 | ACTACT (SEQ ID NO:159) |
| 1.48.1 | DP-14/1-18 | 1 | CGAGAG (SEQ ID NO:160) | 7 | TGTTGAA (SEQ ID NO:161) | D21-9 | 20 | TATTACTA TGATgGTA GTTGGTTAT (SEQ ID NO:162) | 1 | T | JH4B | 0 | ACTACT (SEQ ID NO:163) |
| 1.48.2 | DP-14/1-18 | 1 | CGAGAG | 7 | TGTTGAA | D21-9 | 20 | TATTACTA | 1 | T | JH4B | 0 | ACTACT |

Figure 43D

| CLONE # | VH | #DEL | VH END | # N's | N Sequence | DH | Size of D | D Sequence | # N's | N Sequence | JH | # del | JH Segment |
|---|---|---|---|---|---|---|---|---|---|---|---|---|---|
|  |  |  | (SEQ ID NO:160) |  | (SEQ ID NO:161) |  |  | TGATgGTA GTGGTTAT (SEQ ID NO:162) |  |  |  |  | (SEQ ID NO:163) |
| 1.49.1 | DP-15/1-8 | 2 | GCGAGA (SEQ ID NO:164) | 5 | ATGAG (SEQ ID NO:165) | D6-12 | 17 | GGATATAG TGGCTACG A (SEQ ID NO:166) | 3 | GCT | JH6B | 0 | ATTACTAC (SEQ ID NO:167) |
| 1.49.2 | DP-15/1-8 | 2 | GCGAGA (SEQ ID NO:164) | 5 | ATGAG (SEQ ID NO:165) | D6-12 | 17 | GGATATAG TGGCTACG A (SEQ ID NO:166) | 3 | GCT | JH6B | 0 | ATTACTAC (SEQ ID NO:167) |
| 1.51.1 | DP-73/5-51 | 0 | GAGACA (SEQ ID NO:168) | 1 | C | D3-16 | 31 | TATGATTA CGTTTGGa GGAgTTAT CGGTATA (SEQ ID NO:169) | 5 | CAGGG (SEQ ID NO:170) | JH5B | -5 | TGGTTC (SEQ ID NO:171) |
| 1.51.2 | DP-73/5-51 | 0 | GAGACA (SEQ ID NO:168) | 1 | C | D3-16 | 31 | TATGATTA CGTTTGGa GGAgTTAT CGGTATA (SEQ ID NO:169) | 5 | CAGGG (SEQ ID NO:170) | JH5B | -5 | TGGTTC (SEQ ID NO:171) |

| CLONE | vk | #del | vk end | #n | N SEQ | Jk | # del | JK end |
|---|---|---|---|---|---|---|---|---|
| 1.17.1 | A30 | 3 | TTACCC (SEQ ID NO:172) | 0 | 0 | JK4 | 0 | GCTCACT (SEQ ID NO:173) |

Figure 43E

| CLONE | vk | #del | vk end | #n | N SEQ | Jk | # del | JK end |
|---|---|---|---|---|---|---|---|---|
| 1.17.2 | A30 | 3 | TTACCC (SEQ ID NO:172) | 0 | 0 | JK4 | 0 | GCTCACT (SEQ ID NO:172) |
| 1.17.3 | A30 | 3 | TTACCC (SEQ ID NO:172) | 0 | 0 | JK4 | 0 | GCTCACT (SEQ ID NO:173) |
| 1.18 | A30 | 3 | TTACCC (SEQ ID NO:174) | 0 | 0 | JK3 | 0 | ATTCAC (SEQ ID NO:175) |
| 1.24.1 | A30 | 3 | TTACCC (SEQ ID NO:176) | 0 | 0 | JK1 | 0 | GTGGAC (SEQ ID NO:177) |
| 1.24.2 | A30 | 3 | TTACCC (SEQ ID NO:176) | 0 | 0 | JK1 | 0 | GTGGAC (SEQ ID NO:177) |
| 1.25.1 | A30 | 3 | TTACCC (SEQ ID NO:178) | 0 | 0 | JK1 | 0 | GTGGAC (SEQ ID NO:179) |
| 1.25.2 | A30 | 3 | TTACCC (SEQ ID NO:178) | 0 | 0 | JK1 | 0 | GTGGAC (SEQ ID NO:179) |
| 1.29 | A3/A19/DPK | 7 | CTACAA (SEQ ID NO:180) | 14 | TCTCTCATG TGCAG (SEQ ID NO:181) | JK2 | 7 | TTTTGG (SEQ ID NO:182) |
| 1.33 | A20/DPK4 | 3 | TGCCCC (SEQ ID NO:183) | 0 | 0 | JK4 | 0 | GCTCAC (SEQ ID NO:184) |
| 1.38.1 | A20/DPK4 | 3 | TGCCCC (SEQ ID NO:185) | 0 | 0 | JK1 | 0 | GTGGAC (SEQ ID NO:186) |
| 1.39.1 | A30 | 3 | TTACCC (SEQ ID NO:187) | 0 | 0 | JK1 | 0 | GTGGAC (SEQ ID NO:186) |

Figure 43F

| CLONE | vk | #del | vk end | #n | N SEQ | jk | # del | JK end |
|---|---|---|---|---|---|---|---|---|
| 1.39.2 | A30 | 3 | TTACCC (SEQ ID NO:187) | 0 | 0 | JK1 | 0 | GTGGAC (SEQ ID NO:188) |
| 1.46 | A20/DPK4 | 3 | TGCCCC (SEQ ID NO:189) | 0 | 0 | JK3 | 0 | ATTCAC (SEQ ID NO:190) |
| 1.46.1 | A30 | 0 | CCCTCC (SEQ ID NO:191) | 0 | 0 | JK1 | -3 | GACGTT (SEQ ID NO:192) |
| 1.46.2 | A30 | 0 | CCCTCC (SEQ ID NO:191) | 0 | 0 | JK1 | -3 | GACGTT (SEQ ID NO:192) |
| 1.48.1 | L5/DPK5V | 1 | TCCCTC (SEQ ID NO:193) | 0 | 0 | JK1 | -2 | GGACGTT (SEQ ID NO:194) |
| 1.48.2 | L5/DPK5V | 1 | TCCCTC (SEQ ID NO:193) | 0 | 0 | JK1 | -2 | GGACGTT (SEQ ID NO:194) |
| 1.49.1 | A3/A19/DPK | 5 | CAAACT (SEQ ID NO:195) | 0 | 0 | JK5 | -1 | ATCACC (SEQ ID NO:196) |
| 1.49.2 | A3/A19/DPK | 5 | CAAACT (SEQ ID NO:195) | 0 | 0 | JK5 | -1 | ATCACC (SEQ ID NO:196) |
| 1.51.1 | A27/A27A | 4 | GCTCAC (SEQ ID NO:197) | 1 | T | JK3 | 0 | ATTCAC (SEQ ID NO:198) |
| 1.51.1 | A27/A27A | 4 | GCTCAC (SEQ ID NO:197) | 1 | T | JK3 | 0 | ATTCAC (SEQ ID NO:198) |

FIGURE 48

```
1.19  H   1   Q           A        A V V   K   T       D N    T  Q    WMNPNSGN   G   60
6.4   H   1   Q           A        A V V   K   T       D N    T  Q    WINPNSGN   D   60
1.18  H   1   Q           A        A V V   K   T       D N    T  Q    WMNPNSGN   G   60
1.40  H   1   Q           A        A V V   K   T   T   D N    T  Q    WMNPNSGN   G   60
1.45  H   1   Q           A        A V V   K   T       D N    T  Q    WMNPNSGN   G   60
1.46  H   1   Q           A        A V V   K   S       D N    T  Q    WMNPNNGN   G   60
1.49  H   1   Q           A        A V V   K   T       D N    T  Q    WMNPNSGD   G   60
1.33  H   1   Q           A        A V V   K   T       G S    P  Q    WISAYNGN   N   60
1.48  H   1   Q           A        A V V   K   T       G S    P  Q    WISAYNGN   N   60
1.6   H   1   E    E    GGLV     G LRL    A   FN  RT  NMN    P  K    VSSISSSSSNIY  60
1.17  H   1   Q    E    GG VQ    K LRL    A   FT  S   GMH    P  K    VAVIWYDGSNKY  60
1.24  H   1   Q    E    GG VQ    R LRL    A   FS  S   GMH    P  K    VADIWYDGSNKY  60
1.38  H   1   Q    E    GG VQ    R LRL    A   FT  S   GMH    P  K    VAIIWYDGNDKY  60
1.11  H   1   E         GGLIQ    G LRL    A   FTVS    NYMS   P  K    VSVIYSGGS-  Y   59
1.23  H   1   E           A      E L I   EG   S       W G    MP K    IIYPGDSD    R   60
1.25  H   1   E           A      E L I   KG   R       W G    MP K    IIYPGDSD    R   60
1.29  H   1   E           A      E L I   KG   S       W G    MP K    IIYPGDSD    R   60
1.39  H   1   E           T      E L I   KG   R       W G    MP K    IIYPGDSD    R   60
1.51  H   1   E           A      E L I   KG   S       W G    MP K    IIYPGDSDAK      60
                                           [   CDR1  ]              [    CDR2    ]

1.19  H   61   QKF    V MTRNT  I    MELS    SE    V       --DVM-ITFGGVIVH-YGM  V  116
6.4   H   61   QKF    V MTRDT  I    MELS    SE    I    V  --GFG-YSYN-YD    -YGM  V  115
1.18  H   61   QKF    V MTRNT  I    MELS    SE    V       --EG--IAVAGTY    YYGM  V  116
1.40  H   61   QKF    V MTRNT  L    MELS    SE    V       --DIV-VVVAATN    -NGM  V  116
1.45  H   61   QKF    V MTRNT  I    MELS    SE    V       --GSG-YSYG-YD    -YGM  V  115
1.46  H   61   QKF    V MTRNT  I    MELS    SE    V       --DIV-VVVTATD    -YGM  V  116
1.49  H   61   QKF    V MTRNT  I    MELS    SE    V F     --MRD-IVATSYY    FYGM  V  117
1.33  H   61   QKL    V MTTDT  T    MELR    SD    V       --DHY-YDSSDYL    YYGL  V  117
1.48  H   61   QKL    V MTTDT  T    MELR    SD    V       DVEYY-YDGSGYY    FDY----  115
1.6   H   61   DSVK   F ISRDNAKNSL  LQMN    AE    V       DIMI----TFG-GIIASFYF  Y  116
1.17  H   61   DSVK   F ISRDN KN L  LQMN    AE    V       DQGY---RYA-GY    DYGM  V  116
1.24  H   61   DSVK   F ISRDN KN L  LQMN    AE    V       DQGY---SYG-YV    DYGM  V  116
1.38  H   61   DSVK   F ISRDN KN L  LQMN    AE    V       GYYYD--SSD-YL    YYGM  V  117
1.11  H   60   DSVK   F VSRDN KN L  LQMN    AE    V       GTVTT---------N  YYGM  V  110
1.23  H   61   SPSF   QV ISADK  I   LQWS    KAS   M       HVSY---YYVSGS    -NVF  Y  116
1.25  H   61   SPSF   QV ISADK  I   LQWS    KAS   M       HGSY---YYGSET    -NVF  Y  116
1.29  H   61   SPSF   QA ISADK  I   LQWS    KAS   M       HVDVGATIGGYYY    -HGM  V  119
1.39  H   61   SPSF   QV ISADK  I   LQWS    KAS   M       HGSY---YYNSGS    -NVF  Y  116
1.51  H   61   SPSF   QV ISADK  I   LQWS    KAS   M       HYDY---VWRNYR    T-GWF P  116
                               ]                                   [       CDR3      ]
```

FIGURE 48 (CONT)

| | | | |
|---|---|---|---|
| 1.19 H | 117 | T | 126 |
| 6.4 H | 116 | T | 125 |
| 1.18 H | 117 | T | 126 |
| 1.40 H | 117 | T | 126 |
| 1.45 H | 116 | T | 125 |
| 1.46 H | 117 | T | 126 |
| 1.49 H | 118 | T | 127 |
| 1.33 H | 118 | T | 127 |
| 1.48 H | 116 | L | 125 |
| 1.6 H | 117 | L | 126 |
| 1.17 H | 117 | T | 126 |
| 1.24 H | 117 | T | 126 |
| 1.38 H | 118 | T | 127 |
| 1.11 H | 111 | T | 120 |
| 1.23 H | 117 | L | 126 |
| 1.25 H | 117 | L | 126 |
| 1.29 H | 120 | T | 129 |
| 1.39 H | 117 | L | 126 |
| 1.51 H | 117 | L | 126 |

FIGURE 49

```
1.48  L  1                    V         T       SS-----W  A      A  KL       I Q  55
1.49  L  1        V        L  PVTP EPAS S   S   SLLHSNGYNY D LL  QS QL    LG SRA 60
1.11  L  1        V        L  PVTP EPAS S   S   SLLQSNGYNY D L   QS QL    LG NRA 60
1.29  L  1        V        L  PVTP EPAS S   S   SLLHSNGYNY D L   QS QL    LG NRA 60
1.45  L  1                              N       SN-----D   A     V  KL       T Q  55
1.33  L  1                              T       SN-----Y   A     V  KL       T Q  55
1.38  L  1                              T       SN-----Y   A     V  NL       T Q  55
6.4   L  1        E VL   GT  L P E A LS         SVSSS----Y A     QA RL    T  SRA 56
1.51  L  1        E VL   GT  L P E A LS         SVSSS----Y A     QA RL    G  NRA 56
1.19  L  1                              T       RN-----D  G      A  KR       S Q  55
1.18  L  1                              T       RN-----D  G      A  KR       S Q  55
1.16  L  1                              T       RN-----D  G  F   A  KR       S Q  55
1.23  L  1                              T       RN-----D  G    I A  KR       S Q  55
1.25  L  1                              T       RN-----D  G      A  KR       S Q  55
1.39  L  1                              T       RN-----D  G      A  KR       S Q  55
1.17  L  1                              T       RN-----D  G      A  KR       S Q  55
1.24  L  1                              T       RN-----D  G      A  KR       S Q  55
1.46  L  1                              T       RN-----D  G      A  KR    F  S P  55
                                              [    CDR1     ]           [  CDR2
```

```
1.48  L  56                   D           F S   Q SN  F R -   Q          107
1.49  L  61          D        D   K  RVEA   VGV M TLQTIT--    Q  RL      111
1.11  L  61          D        D   K  RVEA   VGV M ALQTLT--    G          111
1.29  L  61          D        D   K  RVEAD  VGV M ALQSLMCS    Q  L       113
1.45  L  56    L              D           V T   QKYN A F -    P  D       107
1.33  L  56                   D           V T   QKYN A L -    G          107
1.38  L  56                   D S         V A   QKCN A W -    Q  T       107
6.4   L  57    T I D          D     R E   F V   Q YG S CS-    Q  L       108
1.51  L  57    T I D          D     R E   F V   Q YG SLF -    P  D       108
1.19  L  56                   D           F T   L HN D CS-    Q  L R     107
1.18  L  56                   E           F T F L HN Y F -    P  D       107
1.16  L  56                   E           F T   L HN Y L -    G          107
1.23  L  56    R              E           F T   L HN Y W -    Q          107
1.25  L  56                   E           F T   L HN Y W -    Q          107
1.39  L  56                   E           F T   L HN Y W -    Q          107
1.17  L  56                   E           F T   L HN Y L -    G          107
1.24  L  56                   E           F T   L HN Y W -    Q          107
1.46  L  56                   E           F T   L HSGY P -    Q          107
            ]                                 [   CDR3  ]
```

FIGURE 50

```
1.19 H   1                                                              60
6.4  H   1                                             I       D        60
1.18 H   1                                                              60
1.40 H   1                         T                                    60
1.45 H   1                                                              60
1.46 H   1                     S                           N            60
1.49 H   1                                                     D        60
                             [   CDR1   ]             [    CDR2    ]

1.19 H  61                              DVMITFGG-VIVH                  119
6.4  H  61         D           I  V     GFGYSYN--YD                    118
1.18 H  61                              EGIAVAGT-YY                    119
1.40 H  61              L               DIVVVVAA-TN   N                119
1.45 H  61                              GSGYSYG--YD                    118
1.46 H  61                              DIVVVVTA-TD                    119
1.49 H  61                         F    MRDIVATSYYY F                  120
                        ]                [    CDR3      ]

```
1.33 H    1                                                                                    60
1.48 H    1                                                                                    60
                                        [   CDR1   ]                    [    CDR2    ]

1.33 H   61                                              --DH   S D L YY GLDV                 118
1.48 H   61                                              DVEY   G G Y FD ----                 116
                      ___ ]                              [           CDR3          ]

```
1.17 H   1              K        T                    V    SN    60
1.24 H   1              R        S                    D    SN    60
1.38 H   1              R        T                    I    ND    60
                                 [   CDR1   ]              [   CDR2    ]

1.17 H  61       I                       DQG -RYAGY   D          119
1.24 H  61       I                       DQG -SYGYV   D          119
1.38 H  61       V                       GYY DSSDYL   Y          120
                  ___]                      [    CDR3         ]

```
1.23 H   1                       E    S                                          60
1.25 H   1                            R                                          60
1.29 H   1                            S                                          60
1.39 H   1          T                 R                                          60
1.51 H   1                            S                              AK          60
                                 [   CDR1   ]              [    CDR2

1.23 H  61                                   VS YYVSG---S    NV   Y             117
1.25 H  61                                   GS YYGSE---T    NV   Y             117
1.29 H  61          A                        VDVGATIGGYYY   HGM   V             120
1.39 H  61                                   GS YYNSG---S    NV   Y             117
1.51 H  61                                   YD VWRNY---R   TGW   P             117
                       ___]                  [         CDR3           ]

```
1.49 L  1                         H         L              S   60
1.11 L  1                         Q         Q              N   60
1.29 L  1                         H         Q              N   60
                            [     CDR1     ]           [ CDR2   ]

1.49 L  61                   E       T   TIT--   Q   RL   111
1.11 L  61                   E       A   TLT--   G   KV   111
1.29 L  61                   D       A   SLMCS   Q   KL   113
             _]                      [     CDR3    ]
```

FIGURE 55

```
1.45 L  1                      N        D           K        L      60
1.33 L  1                      T        Y           K        S      60
1.38 L  1                      T        Y           N        S      60
                              [    CDR1    ]              [ CDR2 ]

1.45 L 61      T               T    Y    F   P  K D   107
1.33 L 61      T               T    Y    L   G  K E   107
1.38 L 61      S               A    C    W   Q  T E   107
                              [    CDR3   ]
```

FIGURE 56

```
                                              AT  S      60
6.4  L    1                                   GA  N      60
1.51 L    1            [    CDR1    ]        [  CDR2  ]

PCS  Q    LE   108
6.4  L   61                   LFT  P    VD   108
1.51 L   61            [    CDR3    ]
```

FIGURE 57

```
1.19 L  1                                                              60
1.18 L  1                                                              60
1.16 L  1                         F                                    60
1.23 L  1                                    I                 R       60
1.25 L  1                                                              60
1.39 L  1                                                              60
1.17 L  1                                                              60
1.24 L  1                                                              60
1.46 L  1                                                     F   P    60
                               [   CDR1   ]               [   CDR2   ]

1.19 L 61            D                        D  CS  Q     L  R  107
1.18 L 61                              F          F   P       D  107
1.16 L 61                                         L   G          107
1.23 L 61                                         W   Q          107
1.25 L 61                                         W   Q          107
1.39 L 61                                         W   Q          107
1.17 L 61                                         L   G          107
1.24 L 61                                         W   Q          107
1.46 L 61                                    SG   P   Q          107
                                             [  CDR3  ]
```

ANTIBODIES DIRECTED TO PDGFD AND USES THEREOF

BACKGROUND OF THE INVENTION

1. Summary of the Invention

The present invention is related to antibodies directed to the antigen PDGFD and uses of such antibodies. In particular, in accordance with the present invention, there are provided fully human monoclonal antibodies directed to the antigen PDGFD. Nuceltoide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3, are provided. Hybridomas or other cell lines expressing such immunoglobulin molecules and monoclonal antibodies are also provided.

2. Background of the Technology

Polypeptide growth factors exerting effects in a variety of tissues have been described. Such growth factors include platelet-derived growth factor (PDGF).

The platelet derived growth factor (PDGF) family currently consists of at least 3 distinct genes, PDGF A, PDGF B, and PDGF C whose gene products selectively signal through two PDGFRs to regulate diverse cellular functions. PDGF A, PDGF B, and PDGF C dimerize in solution to form homodimers, as well as the heterodimer.

Expression of RNA encoding the PDGF A and PDGF B subunits of has been reported in vascular tissues involved in atherosclerosis. PDGF A and PDGF B mRNA have been reported to be present in mesenchymal-appearing intimal cells and endothelial cells, respectively, of atherosclerotic plaques. In addition, PDGF receptor mRNA has also been localized predominantly in plaque intimal cells.

The PDGF B is related to the transforming gene (v-sis) of simian sarcoma virus. The PDGF B has also been reported to be mitogen for cells of mesenchymal origin. The PDGF B has in addition been implicated in autocrine growth stimulation in the pathologic proliferation of endothelial cells characteristically found in glioblastomas. PDGF has also been reported to promote cellular proliferation and inhibits apoptosis.

A novel PDGF, PDGF-D, has recently been cloned and characterized. See LaRochelle et al. *Nature Cell Biology* 3:517 (2001), GenBank Accession No. AF335584, International Patent Application No. WO 01/25433, U.S. Ser. No. 60/158,083, filed Oct. 7, 1999; U.S. Ser. No. 60/159,231, filed Oct. 13, 1999; U.S. Ser. No. 60/174,485 filed Jan. 4, 2000; U.S. Ser. No. 60/186,707 filed Mar. 3, 2000; U.S. Ser. No. 60/188,250, filed Mar. 10, 2000; U.S. Ser. No. 60/223,879, filed Aug. 8, 2000; U.S. Ser. No. 60/234,082, filed on Sep. 20, 2000; U.S. Ser. No. 09/685,330, filed on Oct. 5, 2000; PCT Application US00/27671, filed Oct. 6, 2000; U.S. Ser. No. 09/688,312, filed Oct. 13, 2000 and U.S. Ser. No. 09/715,332, filed Nov. 16, 2000. Each of these applications is incorporated by reference in its entirety., the disclosures of which are hereby incorporated by reference. Because of its expression profile and sequence homology and/or similarity to the above-discussed genes and gene products, antibodies to the PDGF-D antigen could be useful therapeutically.

BRIEF DESCRIPTION OF THE DRAWING FIGURES

FIG. 1 is a representation of the nucleotide sequence of the human PDGFD gene (SEQ ID NO:50).

FIG. 2 is a representation of the nucleotide (SEQ ID NO:50) and deduced amino acid (SEQ ID NO:12) sequence of the human PDGF D gene.

Figure 44:
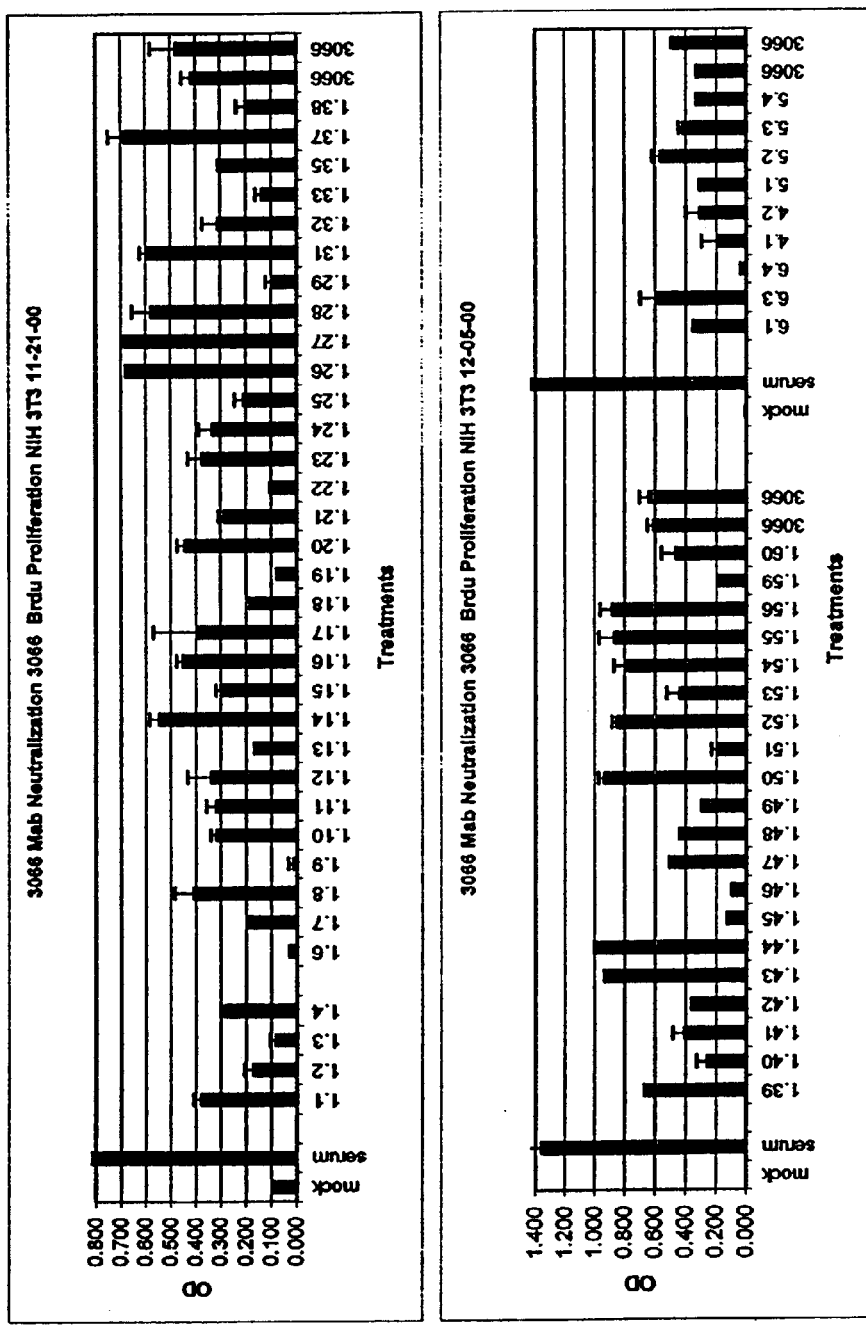

FIG. 3 is a series of representations of the heavy chain and light chain variable region nucleotide and amino acid sequences of the human anti-PDGFD antibody expressed by the hybridoma cell line designated Cur 2-1.6 of the invention, with FIG. 3A representing the nucleotide sequence encoding the variable region of the heavy chain (SEQ.ID.NO: 55), FIG. 3B (SEQ.ID.NO: 13) representing the amino acid sequence encoded by the nucleotide sequence shown in FIG. 3A, FIG. 3C (SEQ.ID.NO: 56) representing the nucleotide sequence encoding the variable region of the light chain, and FIG. 3D (SEQ.ID.NO: 14) representing the amino acid sequence encoded by the nucleotide sequence shown in FIG. 3C.

FIG. 4 is a series of representations of the heavy chain and light chain variable region nucleotide and amino acid sequences of the human anti-PDGFD antibody expressed by the hybridoma cell line designated Cur 2-1.11 of the invention, with FIG. 4A representing the nucleotide sequence encoding the variable region of the heavy chain (SEQ.ID.NO: 57) FIG. 4B (SEQ.ID.NO: 15) representing the amino acid sequence encoded by the nucleotide sequence shown in FIG. 4A, FIG. 4C (SEQ.ID.NO: 58) representing the nucleotide sequence encoding the variable region of the light chain, and FIG. 4D (SEQ.ID.NO: 16) representing the amino acid sequence encoded by the nucleotide sequence shown in FIG. 4C.

FIG. 5 is a series of representations of the heavy chain and light chain variable region nucleotide and amino acid sequences of the human anti-PDGFD antibody expressed by the hybridoma cell line designated Cur 2-1.17 of the invention, with FIG. 5A (SEQ.ID.NO: 59) representing the nucleotide sequence encoding the variable region of the heavy chain, FIG. 5B (SEQ.ID.NO: 17) representing the amino acid sequence encoded by the nucleotide sequence shown in FIG. 5A, FIG. 5C (SEQ.ID.NO: 60) representing the nucleotide sequence encoding the variable region of the light chain, and FIG. 5D (SEQ.ID.NO: 18) representing the amino acid sequence encoded by the nucleotide sequence shown in FIG. 5C.

FIG. 6 is a series of representations of the heavy chain and light chain variable region nucleotide and amino acid sequences of the human anti-PDGFD antibody expressed by the hybridoma cell line designated Cur 2-1.18 of the invention, with FIG. 6A (SEQ.ID.NO: 61) representing the nucleotide sequence encoding the variable region of the heavy chain, FIG. 6B (SEQ.ID.NO: 19) representing the amino acid sequence encoded by the nucleotide sequence shown in FIG. 6A, FIG. 6C (SEQ.ID.NO: 62) representing the nucleotide sequence encoding the variable region of the light chain, and FIG. 6D (SEQ.ID.NO: 20) representing the amino acid sequence encoded by the nucleotide sequence shown in FIG. 6C.

FIG. 7 is a series of representations of the heavy chain and light chain variable region nucleotide and amino acid sequences of the human anti-PDGFD antibody expressed by the hybridoma cell line designated Cur 2-1.19 of the invention, with FIG. 7A (SEQ.ID.NO: 63) representing the nucleotide sequence encoding the variable region of the heavy chain, FIG. 7B (SEQ.ID.NO: 21) representing the amino acid sequence encoded by the nucleotide sequence shown in FIG. 7A, FIG. 7C (SEQ.ID.NO: 64) representing the nucleotide sequence encoding the variable region of the light chain, and FIG. 7D (SEQ.ID.NO: 22) representing the amino acid sequence encoded by the nucleotide sequence shown in FIG. 7C.

FIG. 8 is a series of representations of the heavy chain and light chain variable region nucleotide and amino acid sequences of the human anti-PDGFD antibody expressed by the hybridoma cell line designated Cur 2-1.23 of the invention, with FIG. 8A (SEQ.ID.NO: 65) representing the nucleotide sequence encoding the variable region of the heavy chain, FIG. 8B (SEQ.ID.NO: 23) representing the amino acid sequence encoded by the nucleotide sequence shown in FIG. 8A, FIG. 8C (SEQ.ID.NO: 66) representing the nucleotide sequence encoding the variable region of the light chain, and FIG. 8D (SEQ.ID.NO: 24) representing the amino acid sequence encoded by the nucleotide sequence shown in FIG. 8C.

FIG. 9 is a series of representations of the heavy chain and light chain variable region nucleotide and amino acid sequences of the human anti-PDGFD antibody expressed by the hybridoma cell line designated Cur 2-1.24 of the invention, with FIG. 9A (SEQ.ID.NO: 67) representing the nucleotide sequence encoding the variable region of the heavy chain, FIG. 9B (SEQ.ID.NO: 25) representing the amino acid sequence encoded by the nucleotide sequence shown in FIG. 9A, FIG. 9C (SEQ.ID.NO: 68) representing the nucleotide sequence encoding the variable region of the light chain, and FIG. 9D (SEQ.ID.NO: 26) representing the amino acid sequence encoded by the nucleotide sequence shown in FIG. 9C.

FIG. 10 is a series of representations of the heavy chain and light chain variable region nucleotide and amino acid sequences of the human anti-PDGFD antibody expressed by the hybridoma cell line designated Cur 2-1.25 of the invention, with FIG. 10A (SEQ.ID.NO: 69) representing the nucleotide sequence encoding the variable region of the heavy chain, FIG. 10B (SEQ.ID.NO: 27) representing the amino acid sequence encoded by the nucleotide sequence shown in FIG. 10A, FIG. 10C (SEQ.ID.NO: 70) representing the nucleotide sequence encoding the variable region of the light chain, and FIG. 10D (SEQ.ID.NO: 28) representing the amino acid sequence encoded by the nucleotide sequence shown in FIG. 10C.

FIG. 11 is a series of representations of the heavy chain and light chain variable region nucleotide and amino acid sequences of the human anti-PDGFD antibody expressed by the hybridoma cell line designated Cur 2-1.29 of the invention, with FIG. 11A (SEQ.ID.NO: 71) representing the nucleotide sequence encoding the variable region of the heavy chain, FIG. 11B (SEQ.ID.NO: 29) representing the amino acid sequence encoded by the nucleotide sequence shown in FIG. 11A, FIG. 11C (SEQ.ID.NO: 72) representing the nucleotide sequence encoding the variable region of the light chain, and FIG. 11D (SEQ.ID.NO: 30) representing the amino acid sequence encoded by the nucleotide sequence shown in FIG. 11C.

FIG. 12 is a series of representations of the heavy chain and light chain variable region nucleotide and amino acid sequences of the human anti-PDGFD antibody expressed by the hybridoma cell line designated Cur 2-1.33 of the invention, with FIG. 12A (SEQ.ID.NO: 73) representing the nucleotide sequence encoding the variable region of the heavy chain, FIG. 12B (SEQ.ID.NO: 31) representing the amino acid sequence encoded by the nucleotide sequence shown in FIG. 12A, FIG. 12C (SEQ.ID.NO: 74) representing the nucleotide sequence encoding the variable region of the light chain, and FIG. 12D (SEQ.ID.NO: 32) representing the amino acid sequence encoded by the nucleotide sequence shown in FIG. 12C.

FIG. 13 is a series of representations of the heavy chain and light chain variable region nucleotide and amino acid sequences of the human anti-PDGFD antibody expressed by the hybridoma cell line designated Cur 2-1.38 of the invention, with FIG. 13A (SEQ.ID.NO: 75) representing the nucleotide sequence encoding the variable region of the heavy chain, FIG. 13B (SEQ.ID.NO: 33) representing the amino acid sequence encoded by the nucleotide sequence shown in FIG. 13A, FIG. 13C (SEQ.ID.NO: 76) representing the nucleotide sequence encoding the variable region of the light chain, and FIG. 13D (SEQ.ID.NO: 34) representing the amino acid sequence encoded by the nucleotide sequence shown in FIG. 13C.

FIG. 14 is a series of representations of the heavy chain and light chain variable region nucleotide and amino acid sequences of the human anti-PDGFD antibody expressed by the hybridoma cell line designated Cur 2-1.39 of the invention, with FIG. 14A (SEQ.ID.NO: 77) representing the nucleotide sequence encoding the variable region of the heavy chain, FIG. 14B (SEQ.ID.NO: 35) representing the amino acid sequence encoded by the nucleotide sequence shown in FIG. 14A, FIG. 14C (SEQ.ID.NO: 78) representing the nucleotide sequence encoding the variable region of the light chain, and FIG. 14D (SEQ.ID.NO: 36) representing the amino acid sequence encoded by the nucleotide sequence shown in FIG. 14C.

FIG. 15 is a series of representations of the heavy chain and light chain variable region nucleotide and amino acid sequences of the human anti-PDGFD antibody expressed by the hybridoma cell line designated Cur 2-1.40 of the invention, with FIG. 15A (SEQ.ID.NO: 79) representing the nucleotide sequence encoding the variable region of the heavy chain and FIG. 15B (SEQ.ID.NO: 37) representing the amino acid sequence encoded by the nucleotide sequence shown in FIG. 15A.

FIG. 16 is a series of representations of the heavy chain and light chain variable region nucleotide and amino acid sequences of the human anti-PDGFD antibody expressed by the hybridoma cell line designated Cur 2-1.45 of the invention, with FIG. 16A (SEQ.ID.NO: 80) representing the nucleotide sequence encoding the variable region of the heavy chain, FIG. 16B (SEQ.ID.NO: 38) representing the amino acid sequence encoded by the nucleotide sequence shown in FIG. 16A, FIG. 16C (SEQ.ID.NO: 81) representing the nucleotide sequence encoding the variable region of the light chain, and FIG. 16D (SEQ.ID.NO: 39) representing the amino acid sequence encoded by the nucleotide sequence shown in FIG. 16C.

FIG. 17 is a series of representations of the heavy chain and light chain variable region nucleotide and amino acid sequences of the human anti-PDGFD antibody expressed by the hybridoma cell line designated Cur 2-1.46 of the invention, with FIG. 17A (SEQ.ID.NO: 82) representing the nucleotide sequence encoding the variable region of the heavy chain, FIG. 17B (SEQ.ID.NO: 40) representing the amino acid sequence encoded by the nucleotide sequence shown in FIG. 17A, FIG. 17C (SEQ.ID.NO: 83) representing the nucleotide sequence encoding the variable region of the light chain, and FIG. 17D (SEQ.ID.NO: 41) representing the amino acid sequence encoded by the nucleotide sequence shown in FIG. 17C.

FIG. 18 is a series of representations of the heavy chain and light chain variable region nucleotide and amino acid sequences of the human anti-PDGFD antibody expressed by the hybridoma cell line designated Cur 2-1.48 of the invention, with FIG. 18A (SEQ.ID.NO: 84) representing the nucleotide sequence encoding the variable region of the heavy chain, FIG. 18B (SEQ.ID.NO: 42) representing the amino acid sequence encoded by the nucleotide sequence shown in FIG. 18A, FIG. 18C (SEQ.ID.NO: 85) representing the nucleotide sequence encoding the variable region of the light chain, and FIG. 18D (SEQ.ID.NO: 43) representing the amino acid sequence encoded by the nucleotide sequence shown in FIG. 18C.

FIG. 19 is a series of representations of the heavy chain and light chain variable region nucleotide and amino acid sequences of the human anti-PDGFD antibody expressed by the hybridoma cell line designated Cur 2-1.49 of the invention, with FIG. 19A (SEQ.ID.NO: 86) representing the nucleotide sequence encoding the variable region of the heavy chain, FIG. 19B (SEQ.ID.NO: 44) representing the amino acid sequence encoded by the nucleotide sequence shown in FIG. 19A, FIG. 19C (SEQ.ID.NO: 87) representing the nucleotide sequence encoding the variable region of the light chain, and FIG. 19D (SEQ.ID.NO: 45) representing the amino acid sequence encoded by the nucleotide sequence shown in FIG. 19C.

FIG. 20 is a series of representations of the heavy chain and light chain variable region nucleotide and amino acid sequences of the human anti-PDGFD antibody expressed by the hybridoma cell line designated Cur 2-1.51 of the invention, with FIG. 20A (SEQ.ID.NO: 88) representing the nucleotide sequence encoding the variable region of the heavy chain, FIG. 20B (SEQ.ID.NO: 46) representing the amino acid sequence encoded by the nucleotide sequence shown in FIG. 20A, FIG. 20C (SEQ.ID.NO: 89) representing the nucleotide sequence encoding the variable region of the light chain, and FIG. 20D (SEQ.ID.NO: 47) representing the amino acid sequence encoded by the nucleotide sequence shown in FIG. 20C.

FIG. 21 is a series of representations of the heavy chain and light chain variable region nucleotide and amino acid sequences of the human anti-PDGFD antibody expressed by the hybridoma cell line designated Cur 2-6.4 of the invention, with FIG. 21A (SEQ.ID.NO: 90) representing the nucleotide sequence encoding the variable region of the heavy chain, FIG. 21B (SEQ.ID.NO: 48) representing the amino acid sequence encoded by the nucleotide sequence shown in FIG. 21A, FIG. 21C (SEQ.ID.NO: 91) representing the nucleotide sequence encoding the variable region of the light chain, and FIG. 21D (SEQ.ID.NO: 49) representing the amino acid sequence encoded by the nucleotide sequence shown in FIG. 21C.

FIG. 22 is a table showing VDJ gene utilization of antibodies of the invention and indicating nucleotide/amino acid changes between the antibodies and the V, D, or J genes from which they are derived in the antibodies FR1, CDR1, FR2, CDR2, FR3, CDR3, and FR4 regions.

FIG. 23 is a series of alignments of the heavy chain and light chain variable region amino acid sequences of the human anti-PDGFD antibody expressed by the hybridoma cell line designated Cur 2-1.6 of the invention and the V gene from which it is derived. FIG. 23A representing the alignment of the heavy chain amino acid sequence CUR2.1.6.1. HC (SEQ. ID. NO: 270) and VH2-21 (SEQ. ID. NO: 271), the consensus being shown below (SEQ. ID. NO: 272). FIG. 23B representing the alignment of the light chain amino acid sequence of .CUR2.1.6.1 LC (SEQ. ID. NO: 273) and A30 (SEQ. ID. NO: 274), with the consensus sequence being shown below (SEQ. ID. NO: 275).

FIG. 24 is a series of alignments of the heavy chain and light chain variable region amino acid sequences of the human anti-PDGFD antibody expressed by the hybridoma cell line designated Cur 2-1.11 of the invention and the V gene from which it is derived. FIG. 24A represents the alignment of the heavy chain amino acid sequence CUR2.1.11.1 HC (SEQ. ID. NO: 276) and VH3-53 (SEQ. ID. NO: 277), the consensus being shown below (SEQ. ID. NO: 278). FIG. 24B represents the alignment of the light chain amino acid sequence of CUR2.1.11.1 LC (SEQ. ID. NO: 279) and A19 (SEQ. ID. NO: 280), with the consensus sequence shown below (SEQ. ID. NO: 281).

FIG. 25 is a series of alignments of the heavy chain and light chain variable region amino acid sequences of the human anti-PDGFD antibody expressed by the hybridoma cell line designated Cur 2-1.17 of the invention and the V gene from which it is derived. FIG. 25A represents the alignment of the heavy chain amino acid sequence CR 2-1.17.1 HC (SEQ. ID. NO: 282) and VH3-53 (SEQ. ID. NO: 283), the consensus being shown below (SEQ. ID. NO: 284). FIG. 25B represents the alignment of the light chain amino acid sequence of CR 2-1.17.1 LC (SEQ. ID. NO: 285) and A30 (SEQ. ID. NO: 286), with the consensus sequence being shown below (SEQ. ID. NO: 287).

FIG. 26 is a series of alignments of the heavy chain and light chain variable region amino acid sequences of the human anti-PDGFD antibody expressed by the hybridoma cell line designated Cur 2-1.18 of the invention and the V gene from which it is derived. FIG. 26A represents the alignment of the heavy chain amino acid sequence CR2-1.18 HC (SEQ. ID. NO: 288) and VH1-8 (SEQ. ID. NO: 289), the consensus being shown below (SEQ. ID. NO: 290). FIG. 26B represents the alignment of the light chain amino acid sequence of CR2-1.18 LC (SEQ. ID. NO: 291) and A30 (SEQ. ID. NO: 292), with the consensus sequence being shown below (SEQ. ID. NO: 293).

FIG. 27 is a series of alignments of the heavy chain and light chain variable region amino acid sequences of the human anti-PDGFD antibody expressed by the hybridoma cell line designated Cur 2-1.19 of the invention and the V gene from which it is derived FIG. 27A represents the alignment of the heavy chain amino acid sequence CUR2.1.19.1 HC (SEQ. ID. NO: 294) and VH1-8 (SEQ. ID. NO: 295), the consensus being shown below (SEQ. ID. NO: 296). FIG. 27B represents the alignment of the light chain amino acid sequence of CUR2.1.19.1 LC (SEQ. ID. NO: 297) and A30 (SEQ. ID. NO: 298), with the consensus sequence begin shown below (SEQ. ID. NO: 299).

FIG. 28 is a series of alignments of the heavy chain and light chain variable region amino acid sequences of the human anti-PDGFD antibody expressed by the hybridoma cell line designated Cur 2-1.23 of the invention and the V gene from which it is derived. FIG. 28A represents the alignment of the heavy chain amino acid sequence CUR2.1.23.1 HC (SEQ. ID. NO: 300) and VH5-51 (SEQ. ID. NO: 301), the consensus being shown below (SEQ. ID. NO: 302). FIG. 28B represents the alignment of the light chain amino acid sequence of CUR2.1.23.1 LC (SEQ. ID. NO: 303) and A30 (SEQ. ID. NO: 304), with the consensus sequence being shown below (SEQ. ID. NO: 305).

FIG. 29 is a series of alignments of the heavy chain and light chain variable region amino acid sequences of the human anti-PDGFD antibody expressed by the hybridoma cell line designated Cur 2-1.24 of the invention and the V gene from which it is derived, with FIG. 29A represents the alignment of the heavy chain amino acid sequence CUR2.1.24.1 HC (SEQ. ID. NO: 306) and VH3-33 (SEQ.

ID. NO: 307), the consensus being shown below (SEQ. ID. NO: 308). FIG. 29B represents the alignment of the light chain amino acid sequence of CUR2.1.24.1 LC (SEQ. ID. NO: 309) and A30 (SEQ. ID. NO: 310), with the consensus sequence being shown below (SEQ. ID. NO: 311).

FIG. 30 is a series of alignments of the heavy chain and light chain variable region amino acid sequences of the human anti-PDGFD antibody expressed by the hybridoma cell line designated Cur 2-1.25 of the invention and the V gene from which it is derived. FIG. 30A represents the alignment of the heavy chain amino acid sequence VH5-51 (SEQ. ID. NO: 312) and CUR2.1.25.1 HC (SEQ. ID. NO: 313), the consensus being shown below (SEQ. ID. NO: 314). FIG. 30B represents the alignment of the light chain amino acid sequence of A30 (SEQ. ID. NO: 315) and CUR2.1.25.1 LC (SEQ. ID. NO: 316), with the consensus sequence shown below (SEQ. ID. NO: 317).

FIG. 31 is a series of alignments of the heavy chain and light chain variable region amino acid sequences of the human anti-PDGFD antibody expressed by the hybridoma cell line designated Cur 2-1.29 of the invention and the V gene from which it is derived. FIG. 31A represents the alignment of the heavy chain amino acid sequence VH5-51 (SEQ. ID. NO: 318) and CUR2.1.29 HC (SEQ. ID. NO: 319), the consensus being shown below (SEQ. ID. NO: 320). FIG. 31B represents the alignment of the light chain amino acid sequence of A19 (SEQ. ID. NO: 321) and CUR2.1.29 LC (SEQ. ID. NO: 322), with the consensus sequence being shown below.

FIG. 32 is a series of alignments of the heavy chain and light chain variable region amino acid sequences of the human anti-PDGFD antibody expressed by the hybridoma cell line designated Cur 2-1.33 of the invention and the V gene from which it is derived. FIG. 32A represents the alignment of the heavy chain amino acid sequence VH1-18 (SEQ. ID. NO: 324) and CR2.1.33 HC (SEQ. ID. NO: 325), the consensus being shown below (SEQ. ID. NO: 326). FIG. 32B represents the alignment of the light chain amino to acid sequence of A20 (SEQ. ID. NO: 327) and CR2.1.33 LC (SEQ. ID. NO: 328), with the consensus sequence being shown below (SEQ. ID. NO: 329).

FIG. 33 is a series of alignments of the heavy chain and light chain variable region amino acid sequences of the human anti-PDGFD antibody expressed by the hybridoma cell line designated Cur 2-1.38 of the invention and the V gene from which it is derived. FIG. 33A represents the alignment of the heavy chain amino acid sequence VH3-33 (SEQ. ID. NO: 330) and CR2.1.38.1 HC (SEQ. ID. NO: 331), the consensus being shown below (SEQ. ID. NO: 322). FIG. 33B represents the alignment of the light chain amino acid sequence of A20 (SEQ. ID. NO: 334) and CUR2.1.38.1 LC (SEQ. ID. NO: 335), with the consensus sequence begin shown below (SEQ. ID. NO: 336).

FIG. 34 is a series of alignments of the heavy chain and light chain variable region amino acid sequences of the human anti-PDGFD antibody expressed by the hybridoma cell line designated Cur 2-1.39 of the invention and the V gene from which it is derived. FIG. 34A represents the alignment of the heavy chain amino acid sequence VH5-51 (SEQ. ID. NO: 336) and CR2.1.39.1 HC (SEQ. ID. NO: 337), the consensus being shown below (SEQ. ID. NO: 338). FIG. 34B represents the alignment of the light chain amino acid sequence of A30 (SEQ. ID. NO: 339) and CR2.1.39.1 LC (SEQ. ID. NO: 340), with the consensus sequence being shown below (SEQ. ID. NO: 341).

FIG. 35 is a series of alignments of the heavy chain and light chain variable region amino acid sequences of the human anti-PDGFD antibody expressed by the hybridoma cell line designated Cur 2-1.45 of the invention and the V gene from which it is derived. FIG. 35A represents the alignment of the heavy chain amino acid sequence VH1-8 (SEQ. ID. NO: 342) and CR2.1.45.1 HC (SEQ. ID. NO: 343), the consensus being shown below (SEQ. ID. NO: 344). FIG. 35B represents the alignment of the light chain amino acid sequence of A20 (SEQ. ID. NO: 345) and CUR2.1.45.1 LC (SEQ. ID. NO: 346), with the consensus sequence being shown below (SEQ. ID. NO: 347).

FIG. 36 is a series of alignments of the heavy chain and light chain variable region amino acid sequences of the human anti-PDGFD antibody expressed by the hybridoma cell line designated Cur 2-1.46 of the invention and the V gene from which it is derived. FIG. 36A represents the alignment of the heavy chain amino acid sequence VH1-8 (SEQ. ID. NO: 348) and CR2.1.46.1 HC (SEQ. ID. NO: 349), the consensus being shown below (SEQ. ID. NO: 350). FIG. 36B represents the alignment of the light chain amino acid sequence of A30 (SEQ. ID. NO: 351) and CR2.1.46.1 LC (SEQ. ID. NO: 352), with the consensus sequence being shown below (SEQ. ID. NO: 353).

FIG. 37 is a series of alignments of the heavy chain and light chain variable region amino acid sequences of the human anti-PDGFD antibody expressed by the hybridoma cell line designated Cur 2-1.48 of the invention and the V gene from which it is derived. FIG. 37A represents the alignment of the heavy chain amino acid sequence CR2.1.48.1 HC (SEQ. ID. NO: 354) and VH1-18 (SEQ. ID. NO: 355), the consensus being shown below (SEQ. ID. NO: 356). FIG. 37B represents the alignment of the light chain amino acid sequence of CR2.1.48.1 LC (SEQ. ID. NO: 357) and L5 (SEQ. ID. NO: 358), with the consensus sequence being shown below (SEQ. ID. NO: 359).

FIG. 38 is a series of alignments of the heavy chain and light chain variable region amino acid sequences of the human anti-PDGFD antibody expressed by the hybridoma cell line designated Cur 2-1.49 of the invention and the V gene from which it is derived. FIG. 38A represents the alignment of the heavy chain amino acid sequence CR2.1.49.1 HC (SEQ. ID. NO: 360) and VH1-8 (SEQ. ID. NO: 361), the consensus being shown below (SEQ. ID. NO: 362). FIG. 38B representing the alignment of the light chain amino acid sequence of CUR2.1.49.1 LC (SEQ. ID. NO: 363) and A19 (SEQ. ID. NO: 364), with the consensus sequence being shown below (SEQ. ID. NO: 365).

FIG. 39 is a series of alignments of the heavy chain and light chain variable region amino acid sequences of the human anti-PDGFD antibody expressed by the hybridoma cell line designated Cur 2-1.51 of the invention and the V gene from which it is derived. FIG. 39A represents the alignment of the heavy chain amino acid sequence CR2.1.51.1 HC (SEQ. ID. NO: 366) and VH5-51 (SEQ. ID. NO: 367), the consensus being shown below (SEQ. ID. NO: 368). FIG. 39B representing the alignment of the light chain amino acid sequence of CR2.1.51.1 LC (SEQ. ID. NO: 369) and A27 (SEQ. ID. NO: 370), with the consensus sequence being below (SEQ. ID. NO: 371).

FIG. 40 is a series of alignments of the heavy chain and light chain variable region amino acid sequences of the human anti-PDGFD antibody expressed by the hybridoma cell line designated Cur 2-6.4 of the invention and the V gene from which it is derived. FIG. 40A represents the alignment of the heavy chain amino acid sequence CUR2.6.4.1 HC (SEQ. ID. NO: 372) and VH1-8 (SEQ. ID. NO: 373), the consensus being shown below (SEQ. ID. NO: 374). FIG. 40B representing the alignment of the light chain amino acid sequence of CUR2.6.4.1 LC (SEQ. ID. NO: 375) and A27 (SEQ. ID. NO: 376), with the consensus sequence being shown below (SEQ. ID. NO: 377).

FIG. 41 is a table showing VDJ gene utilization of the 1.19.1 and 6.4.1 antibodies of the invention and indicating nucleotide changes between the antibodies and the VH, DH, and JH and VK and JK genes from which they are derived.

FIG. 42 is a table showing VDJ gene utilization of the 1.6.1, 1.11.1, and 1.23.1 antibodies of the invention and indicating nucleotide changes between the antibodies and the VH, DH, and JH and VK and JK genes from which they are derived.

FIG. 43 is a table showing VDJ gene utilization of the 1.19.1, 6.4.1, 1.6.1, 1.11.1, 1.23.1, 1.17.1, 1.18, 1.24.1, 1.25.1, 1.29, 1.33, 1.38.1, 1.39.1, 1.40.1, 1.45, 1.46.1, 1.46.2, 1.48.1, 1.49.1, and 1.51.1 antibodies of the invention and indicating nucleotide changes between the antibodies and the VH, DH, and JH and VK and JK genes from which they are derived.

FIG. 44 is a bar graphic representation comparing the levels of BrdU incorporation in NIH 3T3 cells upon exposure to various human anti-PDGFD monoclonal antibodies of the invention.

Figure 45:
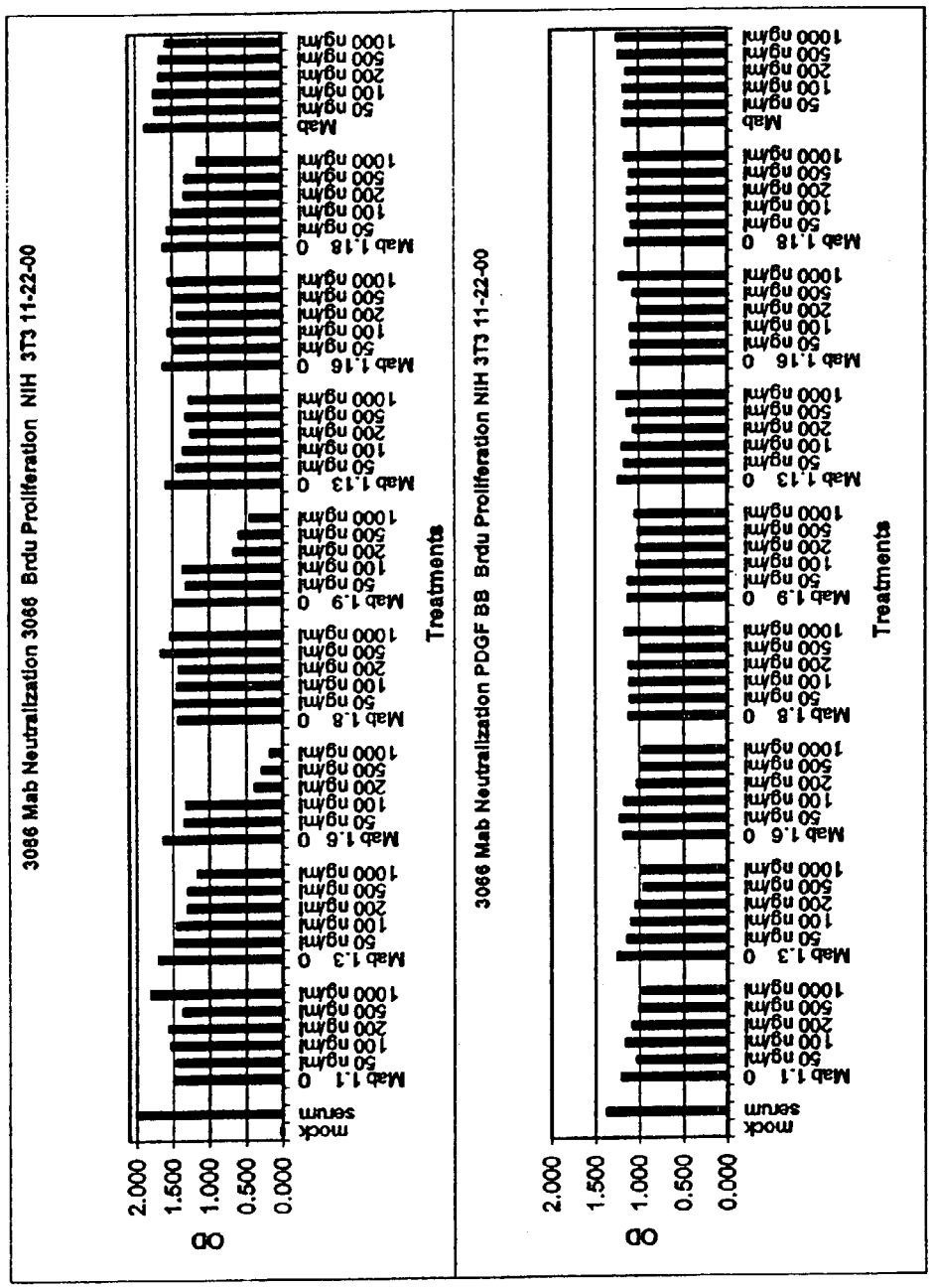

FIG. 45 is a bar graphic representation comparing the levels of BrdU incorporation in NIH 3T3 cells upon exposure to various human anti-PDGFD monoclonal antibodies of the invention at varying doses as compared to a control run utilizing PDGFBB at varying concentrations.

Figure 46:
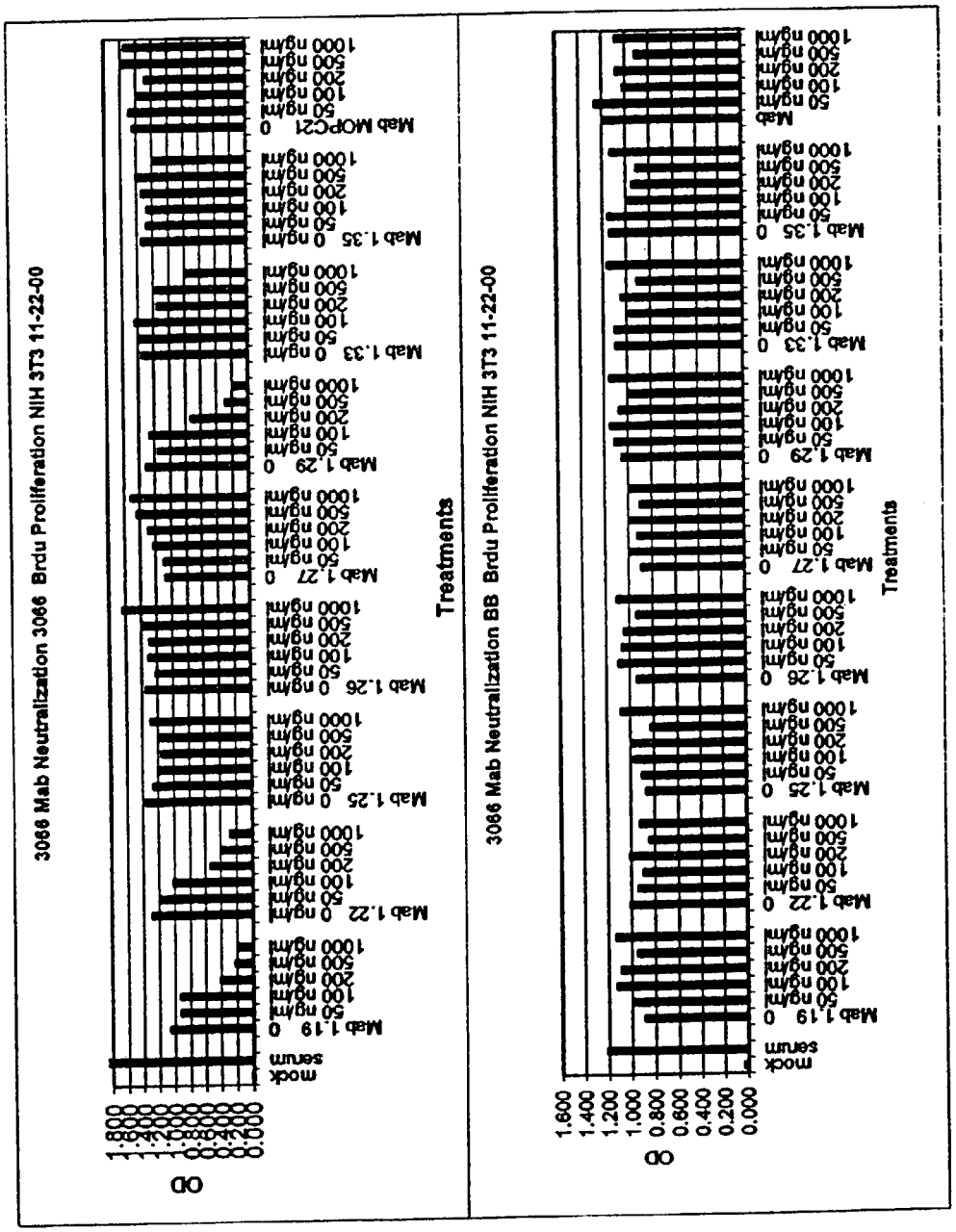

FIG. 46 is a bar graphic representation comparing the levels of BrdU incorporation in NIH 3T3 cells upon exposure to various human anti-PDGFD monoclonal antibodies of the invention at varying doses as compared to a control run utilizing PDGFBB at varying concentrations.

Figure 47:
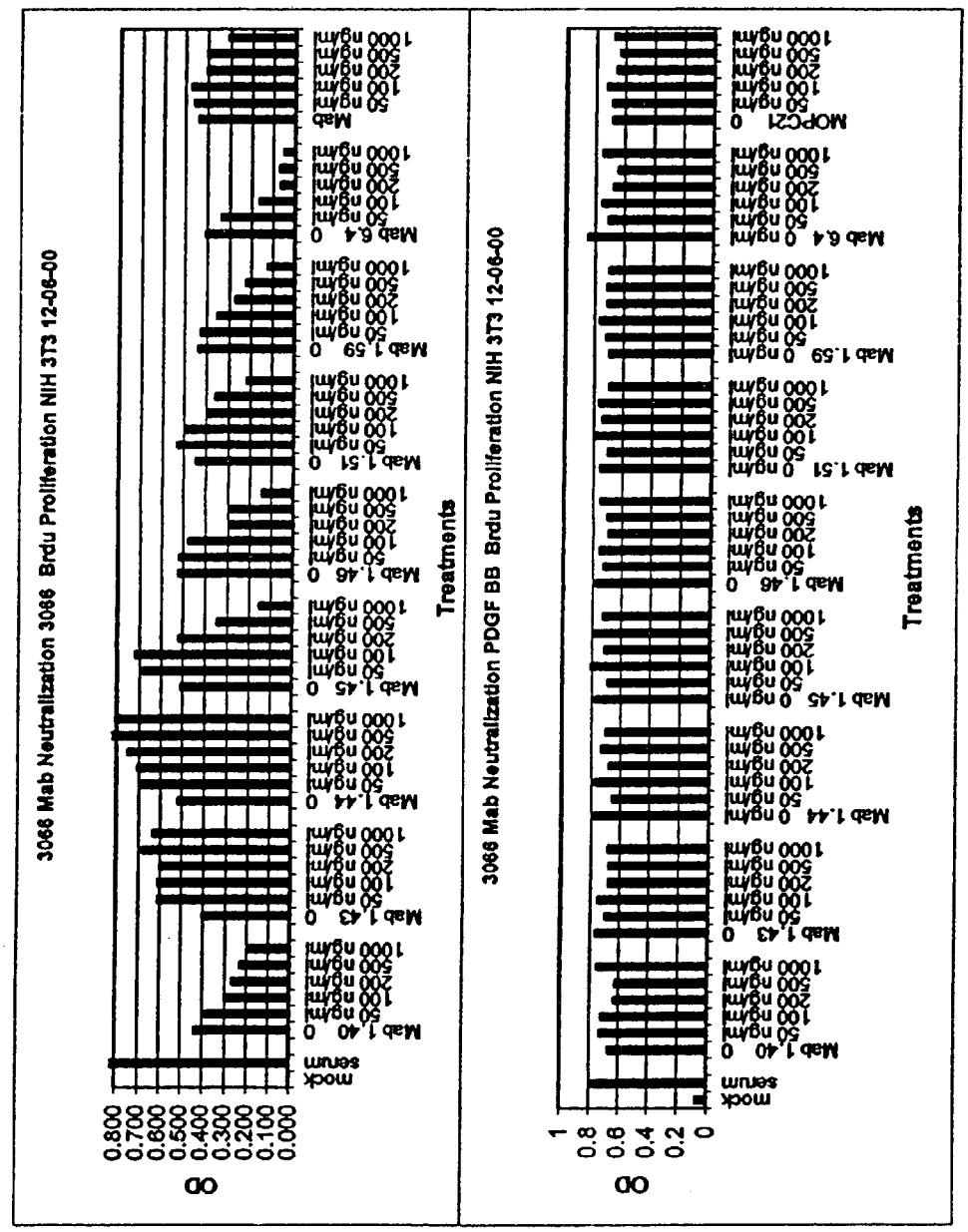

FIG. 47 is a bar graphic representation comparing the levels of BrdU incorporation in NIH 3T3 cells upon exposure to various human anti-PDGFD monoclonal antibodies of the invention at varying doses as compared to a control run utilizing PDGFBB at varying concentrations.

FIG. 48 is a representation of a ClustalW sequence alignment between the heavy chain amino acid sequences of antibodies of the invention indicating locations of the CDRs of the antibodies. Heavy chain sequences shown are: 1.19H (SEQ. ID. NO: 199); 6.4H (SEQ. ID. NO: 200); 1.18H (SEQ. ID. NO: 201); 1.40H (SEQ. ID. NO: 202); 1.45H (SEQ. ID. NO: 203); 1.46H (SEQ. ID. NO: 204); 1.49H (SEQ. ID. NO: 205); 1.33H (SEQ. ID. NO: 206); 1.48H (SEQ. ID. NO: 207); 1.6H (SEQ. ID. NO: 208); 1.17H (SEQ. ID. NO: 209); 1.24H (SEQ. ID. NO: 210); 1.38H (SEQ. ID. NO: 211); 1.11H (SEQ. ID. NO: 212); 1.23H (SEQ. ID. NO: 213); 1.25H (SEQ. ID. NO: 214); 1.29H (SEQ. ID. NO: 215); 1.39H (SEQ. ID. NO: 216); and 1.51H (SEQ. ID. NO: 217).

FIG. 49 is a representation of a ClustalW sequence alignment between the light chain amino acid sequences of antibodies of the invention indicating locations of the CDRs of the antibodies. Light chain sequences shown are: 1.48L (SEQ. ID. NO: 218); 1.49L (SEQ. ID. NO: 219); 1.11L (SEQ. ID. NO: 220); 1.29L (SEQ. ID. NO: 221); 1.45L (SEQ. ID. NO: 222); 1.33L (SEQ. ID. NO: 223); 1.38L (SEQ. ID. NO: 224); 6.4L (SEQ. ID. NO: 225); 1.51L (SEQ. ID. NO: 226); 1.19L (SEQ. ID. NO: 227); 1.18L (SEQ. ID. NO: 228); 1.16L (SEQ. ID. NO: 229); 1.23L (SEQ. ID. NO: 230); 1.25L (SEQ. ID. NO: 231); 1.39L (SEQ. ID. NO: 232); 1.17L (SEQ. ID. NO: 233); 1.24L (SEQ. ID. NO: 234); and 1.46L (SEQ. ID. NO: 235).

FIG. 50 is a representation of a ClustalW sequence alignment between the heavy chain amino acid sequences of antibodies of the invention that possess heavy chains derived from the VH 1-8 gene with CDRs indicated. Heavy chains sequences shown are: 1.19H (SEQ. ID. NO: 236); 6.4H (SEQ. ID. NO: 237); 1.18H (SEQ. ID. NO: 238); 1.40H (SEQ. ID. NO: 239); 1.45H (SEQ. ID. NO: 240); 1.46H (SEQ. ID. NO: 241); and 1.49H (SEQ. ID. NO: 242);

FIG. 51 is a representation of a ClustalW sequence alignment between the heavy chain amino acid sequences of antibodies of the invention that possess heavy chains derived from the VH 1-18 gene with CDRs indicated. Heavy chain sequences shown are: 1.33H (SEQ. ID. NO: 243); and 1.48H (SEQ. ID. NO: 244).

FIG. 52 is a representation of a ClustalW sequence alignment between the heavy chain amino acid sequences of antibodies of the invention that possess heavy chains derived from the VH 3-33 gene with CDRs indicated. Heavy chain sequences shown are: 1.17H (SEQ. ID. NO: 245); 1.24H (SEQ. ID. NO: 246); and 1.38H (SEQ. ID. NO: 247).

FIG. 53 is a representation of a ClustalW sequence alignment between the heavy chain amino acid sequences of antibodies of the invention that possess heavy chains derived from the VH 5-51 gene with CDRs indicated. Heavy chain sequences shown are: 1.23H (SEQ. ID. NO: 248); 1.25H (SEQ. ID. NO: 249); 1.29H (SEQ. ID. NO: 250); 1.39H (SEQ. ID. NO: 251); and 1.51H (SEQ. ID. NO: 252).

FIG. 54 is a representation of a ClustalW sequence alignment between the light chain amino acid sequences of antibodies of the invention that possess light chains derived from the VK A19 gene with CDRs indicated. Light chain sequences shown are: 1.49L (SEQ. ID. NO: 253); 1.11L (SEQ. ID. NO: 254); and 1.29L (SEQ. ID. NO: 255).

FIG. 55 is a representation of a ClustalW sequence alignment between the light chain amino acid sequences of antibodies of the invention that possess light chains derived from the VK A20 gene with CDRs indicated. Light chain sequences are shown are: 1.45L (SEQ. ID. NO: 256); 1.33L (SEQ. ID. NO: 257); and 1.38L (SEQ. ID. NO: 258).

FIG. 56 is a representation of a ClustalW sequence alignment between the light chain amino acid sequences of antibodies of the invention that possess light chains derived from the VK A27 gene with CDRs indicated. Light chain sequences shown are: 6.4L (SEQ. ID. NO: 259) and 1.5L (SEQ. ID. NO: 260).

FIG. 57 is a representation of a ClustalW sequence alignment between the light chain amino acid sequences of antibodies of the invention that possess light chains derived from the VK A30 gene with CDRs indicated. Light chain sequences shown are: 1.19L (SEQ. ID. NO: 261); 1.18L (SEQ. ID. NO: 262); 1.16L (SEQ. ID. NO: 263); 1.23L (SEQ. ID. NO: 264); 1.25L (SEQ. ID. NO: 265); 1.39L (SEQ. ID. NO: 266); 1.17L (SEQ. ID. NO: 267); 1.24L (SEQ. ID. NO: 268); and 1.46L (SEQ. ID. NO: 269).

SUMMARY OF THE INVENTION

In accordance with a first aspect of the present invention, there is provided a human monoclonal antibody that binds to PDGFD and has a heavy chain amino acid sequence selected from the group consisting of SEQ ID NOS: 13, 15, 17, 19, 21, 23, 25, 27, 29, 31, 33, 35, 37, 38, 40, 42, 44, 46, and 48. In one embodiment, the antibody further comprises a light chain amino acid sequence selected from the group consisting of SEQ ID NOS: 14, 16, 18, 20, 22, 24, 26, 28, 30, 32, 34, 36, 39, 41, 43, 45, 47, and 49.

In accordance with a second aspect of the present invention there is provided a human antibody that binds to PDGFD that comprises a heavy chain amino acid sequence corresponding substantially to the amino acid sequence encoded by the VH 1-8 gene and any of the amino acid differences shown in FIG. 50 and comprising a CDR3 sequence selected from the group consisting of the CDR3 sequences shown in FIG. 50.

In accordance with a third aspect of the present invention there is provided a human antibody that binds to PDGFD that comprises a heavy chain amino acid sequence corresponding substantially to the amino acid sequence encoded by the VH 1-18 gene and any of the amino acid differences shown in FIG. 51 and comprising a CDR3 sequence selected from the group consisting of the CDR3 sequences shown in FIG. 51.

In accordance with a fourth aspect of the present invention there is provided a human antibody that binds to PDGFD that comprises a heavy chain amino acid sequence corresponding substantially to the amino acid sequence encoded by the VH 3-33 gene and any of the amino acid differences shown in FIG. 52 and comprising a CDR3 sequence selected from the group consisting of the CDR3 sequences shown in FIG. 52.

In accordance with a fifth aspect of the present invention there is provided a human antibody that binds to PDGFD that comprises a heavy chain amino acid sequence corresponding substantially to the amino acid sequence encoded by the VH 5-51 gene and any of the amino acid differences shown in FIG. 53 and comprising a CDR3 sequence selected from the group consisting of the CDR3 sequences shown in FIG. 53.

In accordance with a sixth aspect of the present invention there is provided a human antibody that binds to PDGFD that comprises a light chain amino acid sequence corresponding substantially to the amino acid sequence encoded by the VK A19 gene and any of the amino acid differences shown in FIG. 54 and comprising a CDR3 sequence selected from the group consisting of the CDR3 sequences shown in FIG. 54.

In accordance with a seventh aspect of the present invention there is provided a human antibody that binds to PDGFD that comprises a light chain amino acid sequence corresponding substantially to the amino acid sequence encoded by the VK A20 gene and any of the amino acid differences shown in FIG. 55 and comprising a CDR3 sequence selected from the group consisting of the CDR3 sequences shown in FIG. 55.

In accordance with an eighth aspect of the present invention there is provided a human antibody that binds to PDGFD that comprises a light chain amino acid sequence corresponding substantially to the amino acid sequence encoded by the VK A27 gene and any of the amino acid differences shown in FIG. 56 and comprising a CDR3 sequence selected from the group consisting of the CDR3 sequences shown in FIG. 56.

In accordance with a ninth aspect of the present invention there is provided a human antibody that binds to PDGFD that comprises a light chain amino acid sequence corresponding substantially to the amino acid sequence encoded by the VK A30 gene and any of the amino acid differences shown in FIG. 57 and comprising a CDR3 sequence selected from the group consisting of the CDR3 sequences shown in FIG. 57.

DETAILED DESCRIPTION OF THE PREFERRED EMBODIMENTS

A novel PDGF, PDGF-D, has recently been cloned and characterized. See LaRochelle et al. *Nature Cell Biology* 3:517 (2001), GenBank Accession No. AF335584, International Patent Application No. WO 01/25433, U.S. Ser. No. 60/158,083, filed Oct. 7, 1999; U.S. Ser. No. 60/159,231, filed Oct. 13, 1999; U.S. Ser. No. 60/174,485 filed Jan. 4, 2000; U.S. Ser. No. 60/186,707 filed Mar. 3, 2000; U.S. Ser. No. 60/188,250, filed Mar. 10, 2000; U.S. Ser. No. 60/223,879, filed Aug. 8, 2000; U.S. Ser. No. 60/234,082, filed on Sep. 20, 2000; U.S. Ser. No. 09/685,330, filed on Oct. 5, 2000; PCT Application US00/27671, filed Oct. 6, 2000; U.S. Ser. No. 09/688,312, filed Oct. 13, 2000 and U.S. Ser. No. 09/715,332, filed Nov. 16, 2000. Each of these applications is incorporated by reference in its entirety., the disclosures of which are hereby incorporated by reference. Because of its expression profile and sequence homology and/or similarity to the above-discussed genes and gene products, antibodies to the PDGF-D antigen could be useful therapeutically. Because of its expression profile and sequence homology and/or similarity to the above-discussed genes and gene products, antibodies to the PDGF-D antigen could be useful therapeutically.

The nucleotide and translated amino acid sequence, respectively, of PDGF-D is set forth in FIGS. 1 and 2.

The similarities of the disclosed PDGFD polypeptides to previously described BMP-1 VEGF-E and PDGF polypeptides indicate a similarity of functions by the PDGFD nucleic acids and polypeptides of the invention. These utilities are described in more detail below.

PDGFD nucleic acids and polypeptides may be use to induce formation of cartilage, as BMP-1 is also capable of inducing formation of cartilage in vivo (Wozney et al., *Science* 242: 1528–1534 (1988)).

An additional use for the PDGFD nucleic acids and polypeptides is in the modulation of collagen formation. Recombinantly expressed BMP1 and purified procollagen C proteinase (PCP), a secreted metalloprotease requiring calcium and needed for cartilage and bone formation, are, in fact, identical. See, Kessler et al., *Science* 271:360–62 (1996). BMP-1 cleaves the C-terminal propeptides of procollagen I, II, and III and its activity is increased by the procollagen C-endopeptidase enhancer protein. PDGFD nucleic acids and polypeptides may play similar roles in collagen modulation pathways.

PDGFD nucleic acids and polypeptides can also be used to stage various cancers. For example, bone metastases can almost universally be correlated to the morbidity and mortality of certain prostate cancers. For example, bone morphogenetic proteins are implicated as having important roles in various cancers. Overexpression of bone morphogenetic protein-4 ("BMP-4") and BMP-2 mRNA has been reported in gastric cancer cell lines of poorly differentiated type. See, Katoh et al., *J. Gastroenterol* 31(1):137–9 (1996). This observation may have implications regarding the poor prognosis of patients with diffuse osteoplastic bone metastasis of gastric cancer. Additionally, osteosarcomas producing bone morphogenetic protein ("BMP") differed in clinical features from those not producing BMP. See, Yoshikawa et al *Cancer* 56: 1682–7 (1985) They were characterized radiologically by perpendicular spicules, histologically by osteoblastic type cells, and clinically by an increased serum alkaline phosphatase level, relative resistance to preoperative chemotherapy with Adriamycin (doxorubicin) plus high-dose methotrexate, and a tendency to metastasize to other bones and the lungs.

The relatedness of PDGFD polypeptides to VEGF—reveals uses for PDGFD nucleic acids and polypeptides in modulating angiogenesis. Angiogenesis is a process which contributes to the development of new blood vessels. During angiogenesis, new capillaries sprout from existing vessels. See, Risau *FASEB J.* 9(10): 926–33 (1995); Risau et al., *Ann.Rev. Cell Dev Biol.* 11: 73–91 (1995). In adult mammals, new blood vessels are produced through angiogenesis. Pathological states in which angiogenesis contributes to the appearance and maintenance of the pathology include tumor development and growth vascular endothelial growth factor F has been reported to be involved in angiogenesis.

Vascular endothelial growth factor ("VEGF") is a multifunctional cytokine expressed and secreted at high levels by many tumor cells in both nonhumans and humans. See review in Ferrara, *Curr Top Microbiol Immunol* 237: 1–30 (1999). VEGF exerts its effects on the vascular endothelium through at least two receptors that are expressed on the cell surface. The first is kinase insert domain-containing receptor ("KDR")/fetal liver kinase 1 ("Flk-1"), and the second is FLT-1 (Warren et al., *J Clin Invest* 95: 1789–97 (1995)). These two receptors have different affinities for VEGF and appear to have different cellular responses. See, Athanassiades et al., *Placenta* 19(7): 465–73 (1998); Li et al. *Cell Res* 9: 11–25 (1999). FLT-1 null mice die in the embryonic stage, at about day 8.5, whereas KDR null mice survive through birth and retain endothelial and hematopoietic cell development. Activation of KDR leads to mitogenesis and to up-regulation of e-nitric oxide synthase (eNOS) and inducible NOS, enzymes in the nitric oxide pathway that contribute to regulation of vasodilation and that play a role in vascular tumor development.

It has been also been reported that VEGF acts as a survival factor for newly formed blood vessels. In the developing retina, for example, vascular regression in response to hyperoxia has been correlated with inhibition of VEGF release by glial cells. See, Alon et al, *Nat Med* 1: 1024–8 (1995). Furthermore, administration of anti-VEGF monoclonal antibodies results in regression of already established tumor-associated vasculature in xenograft models. See, Yuan, et al., *Proc Natl Acad Sci U S A* 93: 14765–70 (1996). Therefore, antibodies to PDGFD polypeptides may also be used to induce or promote regression of newly formed blood vessels.

Tumor cells additionally respond to hypoxia by secreting VEGF. This response promotes neovascularization and consequently permits tumor growth. Furthermore, it has been found that several tumor cells, including hematopoietic cells (Bellamy et al., *Cancer Res* 59(3): 728–33 (1999)), breast cancer cells (Speirs et al., *Br J Cancer* 80(5–6): 898–903 (1999)), and Kaposi's sarcoma (Masood et al., *Proc Natl Acad Sci U S A* 94(3): 979–84 (1997)), express the KDR receptor. Such results suggest that in these tumors VEGF is acting not only in a paracrine fashion to stimulate angiogenesis, but also via an autocrine mechanism as well to stimulate proliferation and/or survival of endothelial cells, and/or promoting survival of tumor cells. Accordingly, modulation of angiogenesis by PDGFD antibodies, or other antagonists of PDGFD nucleic acid or polypeptide function, can be used in anoxia-associated conditions to inhibit endothelial cell proliferation, and/or tumor cells such as hematopoietic cells, breast cancer cells, and Kaposi's sarcoma cells.

The similarity between PDGFD polypeptides and VEGF polypeptides suggests that PDGFD nucleic acids and their encoded polypeptides can be used to modulate cell survival. It has been reported that VEGF signaling is important for cell survival. Binding of VEGF to its receptor, VEGF receptor-2 (VEGFR-2/Flk1/KDR), is reported to induce the formation of a complex of VE-cadherin, β-catenin, phosphoinositide-3-OH kinase (PI3-K), and KDR. PI3-K in this complex activates the serine/threonine protein kinase Akt (protein kinase B) by phosphorylation. See, Carmeliet et al., 1999 *Cell* 98(2): 147–57. Activated Akt is then thought to be necessary and sufficient to mediate the VEGF-dependent survival signal. See, Gerber et al. 1998 *J. Biol. Chem.* 273(46): 30336–43. These findings indicate that there is a relationship between VEGF signaling and cell survival.

The similarity between PDGFD polypeptides and PDGF polypeptides suggests that PDGFD nucleic acids and their encoded polypeptides can be used in various therapeutic and diagnostic applications. For example, PDGFD nucleic acids and their encoded polypeptides can be used to treat cancer, cardiovascular and fibrotic diseases and diabetic ulcers. In addition, PDGFD nucleic acids and their encoded polypeptides will be therapeutically useful for the prevention of aneurysms and the acceleration of wound closure through gene therapy. Furthermore, PDGFD nucleic acids and their encoded polypeptides can be utilized to stimulate cellular growth.

PDGFD nucleic acids according to the invention can be used to identify various cell types, including cancerous cells. For example, PDGFD is strongly expressed specifically in CNS cancer, lung cancer and ovarian cancer. It is also shown in the PDGFD produces a gene product which either persists intact in conditioned medium arising from transfecting HEK 293 cells, or is processed to provide fragments of the gene product. The activities ascribed to either one or both of these substances include the ability to stimulate net DNA synthesis as monitored by incorporation of BrdU into DNA, proliferation of cell number, the ability to transform cells in culture, and the ability to induce tumor formation in vivo. These various activities occur in a variety of cell types. Additional activities include inducing the phosphorylation of tyrosine residues of receptor protein molecules.

A PDGFD nucleic acid or gene product, is useful as a therapeutic agent in promoting wound healing, neovascularization and tissue growth, and similar tissue regeneration needs. More specifically, a PDGFD nucleic acid or polypeptide may be useful in treatment of anemia and leukopenia, intestinal tract sensitivity and baldness. Treatment of such conditions may be indicated in, e.g., patients having undergone radiation or chemotherapy. It is intended in such cases that administration of a PDGFD nucleic acid or polypeptide or a nucleic acid sequence encoding these polypeptides will be controlled in dose such that any hyperproliferative side effects are minimized.

Alternatively, in cases of tumors, such as CNS cancer and ovarian cancer, in which PDGFD nucleic acids is expressed at high levels it is desired to inhibit or eliminate the effects of production of a PDGFD nucleic acid or gene product. For example, this may be accomplished by administration of an antibody directed against PDGFD identified herein. An alternative example involves identifying the putative protease implicated in the formation of p35 from p85 (see WO 01/25433 Apr. 12, 2001). Administration of a substance that specifically inhibits the activity of this protease, but not the activity of other proteases, will be effective to prevent formation of the active p35 form of a PDGFD polypeptide.

Based on the roles of molecules related to PDGFD polypeptides and nucleic acids, (e.g., BMP-1 and VEGF-like polypeptides such as fallotein) in malignant disease progression and the gene expression profile described herein, it is foreseen that, for a subset of human gliomas and ovarian epithelial carcinomas, targeting of a PDGFD polypeptide using an antibody has an inhibitory effect on tumor growth, matrix invasion, chemo-resistance, radio-resistance, and metastatic dissemination. In various embodiments, the PDGFD polypeptide is linked to a monoclonal antibody, a humanized antibody or a fully human antibody.

Furthermore, based on chromosomal location analysis (see WO 01/25433 Apr. 12, 2001) the PDGFD nucleic acids localize to chromosome 11q23–24. This chromosomal locus to D maps is a region of genomic instability (Kurahashi et al., Hum. Mol. Genet. 9, 1665–1670 (2000)) altered in various neoplasias (Ferti-Passantonopoulou, et al. Cancer Genet. Cytogenet. 51, 183–188 (1991); Tarkkanen et al., Genes Chromosomes Cancer 25, 323–331 (1999)) and Jacobsen's syndrome (Pivnick et al., J. Med. Genet. 33, 772–778 (1996)) that might be explained in part through abnormal growth factor expression. Jacobsen's syndrome is marked by craniofacial abnormalities, heart defects, glandular abnormalities and lack of brain development (Pivnick et al. (1996)). Accordingly, the PDGFD nucleic acids and polypeptides according to the invention may be used in various diagnostic and therapeutic applications of these disease states.

Additionally, rearrangements resulting in amplification or deletions about the 11q23–24 locus have been reported in breast cancer (Ferti-Passantonopoulou, et al. Cancer Genet. Cytogenet. 51, 183–188 (1991); Shen et al., *J. Surg. Oncol.* 74, 100–107 (2000)), primary sarcomas, their pulmonary metastasis (Tarkkanen et al. (1999)), and myeloid leukemias (Michaux et al., *Genes Chromosomes Cancer* 29, 4047 (2000); Crossen, et al. *Cancer Genet. Cytogenet.* 112, 144–148 (1999)). Thus, PDGFD nucleic acids polypeptides and antibodies according to the invention may also have diagnostic and therapeutic applications in the detection and treatment these cancers.

A PDGFD polypeptide can potentially block or limit the extent of tumor neovascularization. In addition to classical modes of administration of potential antibody therapeutics newly developed modalities of administration may be useful. For example, local administration of $^{131}$I-labeled monoclonal antibody for treatment of primary brain tumors after surgical resection has been reported. Additionally, direct stereotactic intracerebral injection of monoclonal antibodies and their fragments is also being studied clinically and pre-clinically. Intracarotid hyperosmolar perfusion is an experimental strategy to target primary brain malignancy with drug conjugated human monoclonal antibodies.

Additionally, the nucleic acids of the invention, and fragments and variants thereof, may be used, by way of nonlimiting example, (a) to direct the biosynthesis of the corresponding encoded proteins, polypeptides, fragments and variants as recombinant or heterologous gene products, (b) as probes for detection and quantification of the nucleic acids disclosed herein, (c) as sequence templates for preparing antisense molecules, and the like. Such uses are described more fully in the following disclosure.

Furthermore, the proteins and polypeptides of the invention, and fragments and variants thereof, may be used, in ways that include (a) serving as an immunogen to stimulate the production of an anti-PDGFD antibody, (b) a capture antigen in an immunogenic assay for such an antibody, (c) as a target for screening for substances that bind to a PDGFD polypeptide of the invention, and (d) a target for a PDGFD-specific antibody such that treatment with the antibody inhibits cell growth. These utilities and other utilities for PDGFD nucleic acids, polypeptides, antibodies, agonists, antagonists, and other related compounds uses are disclosed more fully below. In view of its strong effects in modulating cell growth, an increase of PDGFD polypeptide expression or activity can be used to promote cell survival. Conversely, a decrease in PDGFD polypeptide expression can be used to induce cell death.

PDGFD Agonists and Antagonists

The present invention also pertains to variants of a PDGFD protein that function as either PDGFD agonists (mimetics) or as PDGFD antagonists. Variants of a PDGFD protein can be generated by mutagenesis, e.g., discrete point mutation or truncation of the PDGFD protein. An agonist of the PDGFD protein can retain substantially the same, or a subset of, the biological activities of the naturally occurring form of the PDGFD protein. An antagonist of the PDGFD protein can inhibit one or more of the activities of the naturally occurring form of the PDGFD protein by, for example, competitively binding to a downstream or upstream member of a cellular signaling cascade which includes the PDGFD protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PDGFD protein.

Variants of the PDGFD protein that function as either PDGFD agonists (mimetics) or as PDGFD antagonists can be identified by screening combinatorial libraries of mutants, e.g., truncation mutants, of the PDGFD protein for PDGFD protein agonist or antagonist activity. In one embodiment, a variegated library of PDGFD variants is generated by combinatorial mutagenesis at the nucleic acid level and is encoded by a variegated gene library. A variegated library of PDGFD variants can be produced by, for example, enzymatically ligating a mixture of synthetic oligonucleotides into gene sequences such that a degenerate set of potential PDGFD sequences is expressible as individual polypeptides, or alternatively, as a set of larger fusion proteins (e.g., for phage display) containing the set of PDGFD sequences therein. There are a variety of methods which can be used to produce libraries of potential PDGFD variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PDGFD variant sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules represented by FIGS. 1, 5, 9, 13, 17, 21, 25, and 29 and the human kappa light chain immunoglobulin molecules represented by FIGS. 3, 7, 11, 15, 19, 23, 27, and 31, as well as antibody molecules formed by combinations comprising the heavy chain immunoglobulin molecules with light chain immunoglobulin molecules, such as the kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87–108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101–110 (Volume 5, National Biomedical Research Foundation (1972)) and Supplement 2 to this volume, pp. 1–10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24–48 nucleotide (8–16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a PDGFD, under suitable binding conditions, (2) ability to block appropriate PDGFD binding, or (3) ability to inhibit PDGFD expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drus with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ μM, preferably $\leq 100$ nM and most preferably $\leq 10$ nM.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, 35S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibody Structure

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. *See generally,* Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901–917 (1987); Chothia et al. *Nature* 342:878–883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315–321 (1990), Kostelny et al. *J. Immunol.* 148:1547–1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce fully human antibodies.

Human Antibodies

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al. *Nature Genetics* 7:13–21 (1994). The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genetics* 15:146–156 (1997) and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. *Nature Genetics* 15:146–156 (1997) and Green and Jakobovits *J. Exp. Med.* 188:483–495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B 1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

The inventors of Surani et al., cited above and assigned to the Medical Research Counsel (the "MRC"), produced a transgenic mouse possessing an Ig locus through use of the minilocus approach. The inventors on the GenPharm International work, cited above, Lonberg and Kay, following the lead of the present inventors, proposed inactivation of the endogenous mouse Ig locus coupled with substantial duplication of the Surani et al. work.

An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against PDGFD in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris *Immunol Today* 14:43–46 (1993) and Wright et al. *Crit, Reviews in Immunol.* 12125–168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. *P.N.A.S.* 84:3439 (1987) and *J. Immunol.* 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab').sub.2 and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. *Mol. Cell. Bio.* 3:280 (1983)), Rous sarcoma virus LTR (Gorman et al. *P.N.A.S.* 79:6777 (1982)), and moloney murine leukemia virus LTR (Grosschedl et al. *Cell* 41:885 (1985)). Also, as will be appreciated, native Ig promoters and the like may be used.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau *PNAS USA* 94:4937–4942 (1997) (ribosomal display), Parmley and Smith *Gene* 73:305–318 (1988) (phage display), Scott *TIBS* 17:241–245 (1992), Cwirla et al. *PNAS USA* 87:6378–6382 (1990), Russel et al. *Nucl. Acids Research* 21:1081–1085 (1993), Hoganboom et al. *Immunol. Reviews* 130:43–68 (1992), Chiswell and McCafferty *TIBTECH* 10:80–84 (1992), and U.S. Pat. No. 5,733,743. If display technologies are utilized to produce antibodies that are not human, such antibodies can be humanized as described above.

Using these techniques, antibodies can be generated to PDGFD expressing cells, PDGFD itself, forms of PDGFD, epitopes or peptides thereof, and expression libraries thereto (see e.g. U.S. Pat. No. 5,703,057) which can thereafter be screened as described above for the activities described above.

Additional Criteria for Antibody Therapeutics

As discussed herein, the function of the PDGFD antibody appears important to at least a portion of its mode of operation. By function, we mean, by way of example, the activity of the PDGFD antibody in operation PDGFD. Accordingly, in certain respects, it may be desirable in connection with the generation of antibodies as therapeutic candidates against PDGFD that the antibodies be capable of fixing complement and participating in CDC. There are a number of isotypes of antibodies that are capable of the same, including, without limitation, the following: murine IgM, murine IgG2a, murine IgG2b, murine IgG3, human IgM, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816, 397), cell-cell fusion techniques (see e.g., U.S. Pat. Nos. 5,916,771 and 6,207,418), among others.

In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, the PDGFD antibody discussed herein is a human anti-PDGFD IgG2 antibody. If such antibody possessed desired binding to the PDGFD molecule, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC.

Accordingly, as antibody candidates are generated that meet desired "structural" attributes as discussed above, they can generally be provided with at least certain of the desired "functional" attributes through isotype switching.

Design and Generation of Other Therapeutics

In accordance with the present invention and based on the activity of the antibodies that are produced and characterized herein with respect to PDGFD, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecifics, immunotoxins, or radiolabels, for example.

For example, in connection with bispecific antibodies, bispecific antibodies can be generated that comprise (i) two antibodies one with a specificity to PDGFD and another to a second molecule that are conjugated together, (ii) a single antibody that has one chain specific to PDGFD and a second chain specific to a second molecule, or (iii) a single chain antibody that has specificity to PDGFD and the other molecule. Such bispecific antibodies can be generated using techniques that are well known for example, in connection with (i) and (ii) see e.g., Fanger et al. *Immunol Methods* 4:72–81 (1994) and Wright and Harris, supra. and in connection with (iii) see e.g., Traunecker et al. *Int. J. Cancer* (Suppl.) 7:51–52 (1992). In each case, the second specificity can be made to the heavy chain activation receptors, including, without limitation, CD16 or CD64 (see e.g., Deo et al. 18:127 (1997)) or CD89 (see e.g., Valerius et al. *Blood* 90:4485–4492 (1997)). Bispecific antibodies prepared in accordance with the foregoing would be likely to kill cells expressing PDGFD, and particularly those cells in which the PDGFD antibodies of the invention are effective.

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655–686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing PDGFD, and particularly those cells in which the antibodies of the invention are effective.

In connection with the generation of therapeutic peptides, through the utilization of structural information related to PDGFD and antibodies thereto, such as the antibodies of the invention (as discussed below in connection with small molecules) or screening of peptide libraries, therapeutic peptides can be generated that are directed against PDGFD. Design and screening of peptide therapeutics is discussed in connection with Houghten et al. *Biotechniques* 13:412–421 (1992), Houghten *PNAS USA* 82:5131–5135 (1985), Pinalla et al. *Biotechniques* 13:901–905 (1992), Blake and Litzi-Davis *BioConjugate Chem.* 3:510–513 (1992). Immunotoxins and radiolabeled molecules can also be prepared, and in a similar manner, in connection with peptidic moieties as discussed above in connection with antibodies.

Assuming that the PDGFD molecule (or a form, such as a splice variant or alternate form) is functionally active in a disease process, it will also be possible to design gene and antisense therapeutics thereto through conventional techniques. Such modalities can be utilized for modulating the function of PDGFD. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. *Human Gene Therapy* 5:595–601 (1994) and Marasco *Gene Therapy* 4:11–15 (1997). General design of and considerations related to gene therapeutics is also discussed in International Patent Application No. WO 97/38137.

Small molecule therapeutics can also be envisioned in accordance with the present invention. Drugs can be designed to modulate the activity of PDGFD based upon the present invention. Knowledge gleaned from the structure of the PDGFD molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of PDGFD. Such structures can be synthesized chemically or expressed in biological systems. This approach has been reviewed in Capsey et al. *Genetically Engineered Human Therapeutic Drugs* (Stockton Press, NY (1988)). Further, combinatorial libraries can be designed and synthesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15$^{th}$ ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210–8 (2000), Wang W. "Lyophilization and development of solid protein pharmaceuticals." *Int. J. Pharm.* 203(1–2): 1–60 (2000), Charman W N "Lipids, lipophilic drugs, and oral drug delivery-some emerging concepts." *J Pharm Sci* 89(8):967–78 (2000), Powell et al. "Compendium of excipients for parenteral formulations" *PDA J Pharm Sci Technol.* 52:238–311 (1998) and the citations therein for additional information related to formulations, excipients and carriers well known to pharmaceutical chemists.

Preparation of Antibodies

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the Background, herein. In particular, however, a preferred embodiment of transgenic production of mice and antibodies therefrom is disclosed in U.S. patent application Ser. No. 08759, 620, filed Dec. 3, 1996 and International Patent Application Nos. WO 98/24893, published Jun. 11, 1998 and WO 00176310, published Dec. 21, 2000, the disclosures of which are hereby incorporated by reference. See also Mendez et al. *Nature Genetics* 15:146–156 (1997), the disclosure of which is hereby incorporated by reference.

Through use of such technology, we have produced fully human monoclonal antibodies to a variety of antigens. Essentially, we immunize XenoMouse™ lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to PDGFD. Herein, we describe the production of multiple hybridoma cell lines that produce antibodies specific to PDGFD. Further, we provide a characterization of the antibodies produced by such cell lines, including nucleotide and amino acid sequence analyses of the heavy and light chains of such antibodies.

The hybridoma cell lines discussed herein are designated 1.6.1, 1.11.1, 1.17.1, 1.18.1, 1.19.1, 1.23.1, 1.24, 1.25, 1.29, 1.33, 1.38, 1.39, 1.40, 1.45, 1.46, 1.48, 1.49, 1.51, and 6.4.1. Each of the antibodies produced by the aforementioned cell lines possess fully human IgG2 heavy chains with human kappa light chains. In general, antibodies in accordance with the invention possess high affinities, typically possessing Kd's of from about $10^{-6}$ through about $10^{-11}$ M, when measured by either solid phase and solution phase.

As will be appreciated, antibodies in accordance with the present invention can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912, 040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive PDGFD binding properties.

Antibodies in accordance with the present invention are capable of binding to PDGFD. Further, antibodies of the invention are useful in the detection of PDGFD in patient samples and accordingly are useful as diagnostics as described hereinbelow. In addition, based on the potent inhibition of growth of fibroblast cells observed through use of antibodies of the invention, it is expected that such antibodies will have therapeutic effect in the treatment of malignant tissue growth and/or disease, such as cancer and obstructive tissue growths as discussed hereinbelow.

EXAMPLES

The following examples, including the experiments conducted and results achieved are provided for illustrative purposes only and are not to be construed as limiting upon the present invention.

Example 1

Antibodies to PDGFD were generated as described in International Patent Application No. WO 01/25433 using an active protein fragment of the gene product from clone 30664188.0.99 arises in the conditioned medium obtained when HEK293 cells are transfected with the plasmid pCEP4/Sec-30664188 This vector harbors a fragment of the gene product of clone 30664188.0.99 that encompasses the entire amino acid sequence except for the predicted N-terminal signal peptide. The active fragment is termed the p35 form of the 30664188.0.99, or "p35" herein.

The active fragment p35 was employed as the immunogen to stimulate an immune response in XenoMouse® animals. Monoclonal antibodies directed against p35 were prepared by hybridoma technology from p35-immunized XenoMouse animals in standard fashion.

Several fully human monoclonal antibody clones were isolated from such immunizations and their ability to neutralize the growth promoting effects of the 30664188 p35 immunogen were analyzed using the BrdU incorporation assay on NIH 3T3 cells (described in International Patent Application No. WO 01/25433). The results for thirteen of the clones are presented in Table 1. An additional fully human monoclonal antibody, CURA2-1.17, was also identified that immunospecifically binds p35. In addition, ten other clones exhibited $IC_{50}$ values >1000 ng/mL. Importantly, all of the monoclonal antibodies identified in this work had no inhibitory activity when added with PDGF BB to the comparable BrdU incorporation assay, up to 1000 ng/mL. Thus the neutralizing fully human monoclonal antibodies identified were specific for the p35 antigen.

In the BrdU assay, murine NIH 3T3 (ATCC No. CRL-1658, Manassas, Va.) fibroblast cells were cultured in DMEM supplemented with 10% fetal bovine serum or 10% calf serum respectively. Fibroblasts were grown to confluence at 37° C. in 10% $CO_2$/air. Cells were then starved in DMEM for 24 hours. Enriched conditioned medium was added (10 microL/100 microL of culture) for 18 h. BrdU (10 microM) was then added and incubated with the cells for 5 h. BrdU incorporation was assayed by calorimetric immunoassay according to the manufacturer's specifications (Boehringer Mannheim, Indianapolis, Ind.).

FIGS. 44–47 show BrdU incorporation assay results from experiments in which the neutralization of various human anti-PDGFD monoclonal antibodies of the invention was assessed. FIG. 44 is a bar graphic representation comparing the levels of BrdU incorporation in NIH 3T3 cells upon exposure to various human anti-PDGFD monoclonal antibodies of the invention. FIGS. 45–47 are bar graphic representations comparing the levels of BrdU incorporation in NIH 3T3 cells upon exposure to various human anti-PDGFD monoclonal antibodies of the invention at varying doses as compared to a control run utilizing PDGFBB at varying concentrations.

TABLE 1

| CURA2 MAb | $IC_{50}$ (ng/ml) |
|---|---|
| 1.6 | 75 |
| 1.9 | 100 |
| 1.18 | >1000 |
| 1.19 | 75 |
| 1.22 | 100 |
| 1.29 | 150 |
| 1.35 | 1000 |
| 1.40 | >1000 |
| 1.45 | 750 |
| 1.46 | 500 |
| 1.51 | 1000 |
| 1.59 | 500 |
| 6.4 | 75 |

Example 2

An Enzyme-Linked Immunosorbent Assay (ELISA) for the detection of PDGFD Antigen in a Sample was developed. In the assay, wells of a microtiter plate, such as a 96-well microtiter plate or a 384-well microtiter plate, were adsorbed for several hours with a first fully human monoclonal antibody CURA2-1.6 (see Example 1) directed against the antigen. The immobilized CURA2-1.6 serves as a capture antibody for any of the antigen that may be present in a test sample. The wells were rinsed and treated with a blocking agent such as milk protein or albumin to prevent nonspecific adsorption of the analyte.

Subsequently the wells were treated with a test sample suspected of containing the antigen, or with a solution containing a standard amount of the antigen. Such a sample may be, for example, a serum sample from a subject suspected of having levels of circulating antigen considered to be diagnostic of a pathology.

After rinsing away the test sample or standard, the wells were treated with a second fully human monoclonal antibody CURA2-1.17 (see Example 1) that has been labeled by conjugation with biotin. The labeled CURA2-1.17 serves as a detecting antibody. After rinsing away excess second antibody, the wells were treated with avidin-conjugated horseradish peroxidase (HRP) and a suitable chromogenic substrate. The concentration of the antigen in the test samples was determined by comparison with a standard curve developed from the standard samples. The results obtained for such a standard curve are shown in Table 2.

This ELISA assay provides a highly specific and very sensitive assay for the antigen in a test sample.

TABLE 2

Two site, or sandwich, ELISA for the detection of
a p35 antigen in a test sample.
PDGFD (ng/ml)

| conc.nanog/ml | OD 490 |
|---|---|
| 1000 | 2.354 |
| 300 | 2.145 |
| 100 | 1.017 |
| 30 | 0.375 |
| 10 | 0.172 |
| 3 | 0.1 |
| 1 | 0.072 |

Example 3

In order to determine the concentration of the PDGFD antigen in the serum of cancer patients, serum from human subjects diagnosed as suffering from various types of cancer, or as harboring various kinds of tumor, were obtained. In particular, serum from five patients suffering from cancer of the tongue, five patients suffering from Hodgkin's lymphoma, five patients suffering from prostate cancer, three patients suffering from lung cancer, four patients suffering from renal cancer, five patients suffering from melanoma and five patients suffering from myeloma were examined. The concentration of the antigen in the serum of these patients was assessed using an ELISA procedure described in Example 2. The results are shown in Table 3. The results show that samples from 5 of the 5 tongue cancer patients contain high levels of the antigen, samples from 2 of 5 Hodgkin disease patients contain detectable amounts of the antigen (one of these at a high level), samples from 2 of 3 lung cancer patients contain detectable levels of antigen, a sample from 1 of 5 patients with prostate cancer contains a high level of the antigen, and a sample from 1 of 4 renal cancer patients contains a detectable concentration of the antigen. In addition to the results in Table 3, it was found that 1 of 5 patients with scleroderma has a low concentration of the antigen.

The results in this Example indicate that an immunoassay directed against circulating the antigen is a useful diagnostic procedure in the detection of certain cancers. The use of the assay in staging such cancers and in assessing a response to therapeutic treatment is also suggested by these results.

TABLE 3

| Sera number | Designation | Concentration PDGFD (ng/ml) |
|---|---|---|
| 809001 | Melanoma | <3 |
| 809002 | Melanoma | <3 |
| 809003 | Melanoma | <3 |
| 809004 | Melanoma | <3 |
| 809005 | Melanoma | <3 |
| 809006 | Renal Cancer | <3 |
| 809007 | Renal Cancer | <3 |
| 809008 | Renal Cancer | <3 |
| 809010 | Renal Cancer | 5.8 |
| 809010 | Lung Cancer | <3 |
| 809011 | Lung Cancer | 20 |
| 809012 | Lung Cancer | 10.04 |
| 809013 | Myeloma | <3 |
| 809014 | Myeloma | <3 |
| 809015 | Myeloma | <3 |
| 809016 | Myeloma | <3 |
| 809017 | Myeloma | <3 |
| 809018 | Tongue Cancer | 116.6 |
| 809019 | Tongue Cancer | 114.9 |
| 809020 | Tongue Cancer | 70.9 |
| 809021 | Tongue Cancer | 86.3 |
| 809022 | Tongue Cancer | 101.3 |
| 809023 | Hodgkins | <3 |
| 809024 | Hodgkins | <3 |
| 809025 | Hodgkins | 6.9 |
| 809026 | Hodgkins | <3 |
| 809027 | Hodgkins | 82.8 |
| 809028 | Prostate Cancer | 81.8 |
| 809029 | Prostate Cancer | <3 |
| 809030 | Prostate Cancer | <3 |
| 809031 | Prostate Cancer | <3 |
| 809032 | Prostate Cancer | <3 |
| BRH00861 | Cardiovascular | |
| BRH00862 | Cardiovascular | |
| BRH00863 | Cardiovascular | |
| BRH00864 | Cardiovascular | |
| BRH00865 | Cardiovascular | |
| 817001 | Scleroderma | |
| 817002 | Scleroderma | 15.4 |
| 817003 | Scleroderma | |
| 817004 | Scleroderma | |
| 817005 | Scleroderma | |

Example 4

It will be appreciated that based on the results set forth and discussed in Examples 2 and 3, through use of the present invention, it is possible to stage a cancer in a subject based on expression levels of the PDGFD antigen. For a given type of cancer, samples of blood are taken from subjects diagnosed as being at various stages in the progression of the disease, and/or at various points in the therapeutic treatment of the cancer. The concentration of the PDGFD antigen present in the blood samples is determined using a method that specifically determines the amount of the antigen that is present. Such a method includes a ELISA method, such as the method described in Examples 2 and 3. Using a population of samples that provides statistically significant results for each stage of progression or therapy, a range of concentrations of the antigen that may be considered characteristic of each stage is designated.

In order to stage progression of the cancer in a subject under study, or to characterize the response of the subject to a course of therapy, a sample of blood is taken from the subject and the concentration of the PDGFD antigen present in the sample is determined. The concentration so obtained is used to identify in which range of concentrations the value falls. The range so identified correlates with a stage of progression or a stage of therapy identified in the various populations of diagnosed subjects, thereby providing a stage in the subject under study.

Example 5

A sandwich ELISA was developed to quantify PDGF D levels in human serum. The 2 fully human mabs (1.6 and 1.17) used in the sandwich ELISA, recognized different epitopes on the PDGF D molecule (data not shown). The ELISA was performed as follows: 50 µl of capture antibody (mAb 1.6) in coating buffer (0.1 M NaHCO$_3$, pH 9.6) at a concentration of 2 µg/ml was coated on ELISA plates (Fisher). After incubation at 4° C. overnight, the plates were treated with 200 μl of blocking buffer (0.5% BSA, 0.1% Tween 20, 0.01% Thimerosal in PBS) for 1 hr at 25° C. The plates were washed (3×) using 0.05% Tween 20 in PBS (washing buffer, WB). Normal or patient sera (Clinomics, Bioreclaimation) were diluted in blocking buffer containing 50% human serum. The plates were incubated with serum samples overnight at 4° C., washed with WB, and then incubated with 100 μl/well of biotinylated detection antibody mAb 1.17 for 1 hr at 25° C. After washing, the plates were incubated with BPP-Streptavidin for 15 min, washed as before, and then treated with 100 μl/well of o-phenylenediamine in $H_2O_2$ (Sigma developing solution) for color generation. The reaction was stopped with 50 μl/well of $H_2SO_4$ (2M) and analyzed using an ELISA plate reader at 492 nm. Concentration of PDGF D in serum samples was calculated by comparison to dilutions of purified PDGF D using a four parameter curve fitting program.

Example 6

PDGF D immunohistochemistry was performed with biotinylated fully human mAb 6.4 and streptavidin-HRP was used for detection. Briefly, tissues were deparaffinized using conventional techniques, and treated with trypsin (0.15%) for 10 min at 37 ° C. Sections were incubated with 10% normal goat serum for 10 minutes. Normal goat serum solution was drained and wiped to remove excess solution. Sections were incubated with the biotinylated anti-PDGF D mAb at 5 μg/ml for 30 min at 25° C., and washed thoroughly with PBS. After incubation with streptavidin-HRP conjugate for 10 min, a solution of diaminobenzidine (DAB) was applied onto the sections to visualize the immunoreactivity. For the isotype control, sections were incubated with biotinylated isotype matched negative control mAb at 5 μg/ml for 30 minutes at 25 ° C. instead of biotinylated PDGF D mAb.

Example 7

In the following discussion, structural information related to antibodies prepared in accordance with the invention is provided.

In order to analyze structures of antibodies produced in accordance with the invention, we cloned genes encoding the heavy and light chain fragments out of the particular hybridoma. Gene cloning and sequencing was accomplished as follows:

Poly(A)$^+$ mRNA was isolated from approximately 2×10$^5$ hybridoma cells derived from immunized XenoMouse mice using a Fast-Track kit (Invitrogen). The generation of random primed cDNA was followed by PCR. Human $V_H$ or human $V_\kappa$ family specific variable region primers (Marks et. al., 1991) or a universal human $V_H$ primer, MG-30 (CAG-GTGCAGCTGGAGCAGTCIGG) (SEQ ID NO: 51) was used in conjunction with primers specific for the human:

above. PCR products were also cloned into pCRII using a TA cloning kit (Invitrogen) and both strands were sequenced using Prism dye-terminator sequencing kits and an ABI 377 sequencing machine. All sequences were analyzed by alignments to the "V BASE sequence directory" (Tomlinson et al., MRC Centre for Protein Engineering, Cambridge, UK) using MacVector and Geneworks software programs.

FIG. 3 is a series of representations of the heavy chain and light chain variable region nucleotide and amino acid sequences of the human anti-PDGFD antibody expressed by the hybridoma cell line designated Cur 2-1.6 of the invention, with FIG. 3A representing the nucleotide sequence encoding the variable region of the heavy chain, FIG. 3B representing the amino acid sequence encoded by the nucleotide sequence shown in FIG. 3A, FIG. 3C representing the nucleotide sequence encoding the variable region of the light chain, and FIG. 3D representing the amino acid sequence encoded by the nucleotide sequence shown in FIG. 3C.

FIG. 4 is a series of representations of the heavy chain and light chain variable region nucleotide and amino acid sequences of the human anti-PDGFD antibody expressed by the hybridoma cell line designated Cur 2-1.11 of the invention, with FIG. 4A representing the nucleotide sequence encoding the variable region of the heavy chain, FIG. 4B representing the amino acid sequence encoded by the nucleotide sequence shown in FIG. 4A, FIG. 4C representing the nucleotide sequence encoding the variable region of the light chain, and FIG. 4D representing the amino acid sequence encoded by the nucleotide sequence shown in FIG. 4C.

FIG. 5 is a series of representations of the heavy chain and light chain variable region nucleotide and amino acid sequences of the human anti-PDGFD antibody expressed by the hybridoma cell line designated Cur 2-1.17 of the invention, with FIG. 5A representing the nucleotide sequence encoding the variable region of the heavy chain, FIG. 5B representing the amino acid sequence encoded by the nucleotide sequence shown in FIG. 5A, FIG. 5C representing the nucleotide sequence encoding the variable region of the light chain, and FIG. 5D representing the amino acid sequence encoded by the nucleotide sequence shown in FIG. 5C.

FIG. 6 is a series of representations of the heavy chain and light chain variable region nucleotide and amino acid sequences of the human anti-PDGFD antibody expressed by the hybridoma cell line designated Cur 2-1.18 of the invention, with FIG. 6A representing the nucleotide sequence encoding the variable region of the heavy chain, FIG. 6B representing the amino acid sequence encoded by the nucleotide sequence shown in FIG. 6A, FIG. 6C representing the nucleotide sequence encoding the variable region of the light chain, and FIG. 6D representing the amino acid sequence encoded by the nucleotide sequence shown in FIG. 6C.

FIG. 7 is a series of representations of the heavy chain and light chain variable region nucleotide and amino acid

```
Cγ2 constant region (MG-40d; 5'-GCT GAG GGA GTA GAG TCC TGA GGA-3'; (SEQ ID NO:52))

Cγ1 constant region (HG1; 5'CAC ACC GCG GTC ACA TGG C; or         (SEQ ID NO:53))

Cγ3 constant region (HG3; 5'CTA CTC TAG GGC ACC TGT CC            (SEQ ID NO:54))
``` or the human Cκ constant region (hκP2; as previously described in Green et al., 1994). Sequences of human Mabs-derived heavy and kappa chain transcripts from hybridomas were obtained by direct sequencing of PCR products generated from poly(A$^+$) RNA using the primers described sequences of the human anti-PDGFD antibody expressed by the hybridoma cell line designated Cur 2-1.19 of the invention, with FIG. 7A representing the nucleotide sequence encoding the variable region of the heavy chain, FIG. 7B representing the amino acid sequence encoded by the nucleotide sequence shown in FIG. 7A, FIG. 7C representing the nucleotide sequence encoding the variable region of the light chain, and FIG. 7D representing the amino acid sequence encoded by the nucleotide sequence shown in FIG. 7C.

FIG. 8 is a series of representations of the heavy chain and light chain variable region nucleotide and amino acid sequences of the human anti-PDGFD antibody expressed by the hybridoma cell line designated Cur 2-1.23 of the invention, with FIG. 8A representing the nucleotide sequence encoding the variable region of the heavy chain, FIG. 8B representing the amino acid sequence encoded by the nucleotide sequence shown in FIG. 8A, FIG. 8C representing the nucleotide sequence encoding the variable region of the light chain, and FIG. 8D representing the amino acid sequence encoded by the nucleotide sequence shown in FIG. 8C.

FIG. 9 is a series of representations of the heavy chain and light chain variable region nucleotide and amino acid sequences of the human anti-PDGFD antibody expressed by the hybridoma cell line designated Cur 2-1.24 of the invention, with FIG. 9A representing the nucleotide sequence encoding the variable region of the heavy chain, FIG. 9B representing the amino acid sequence encoded by the nucleotide sequence shown in FIG. 9A, FIG. 9C representing the nucleotide sequence encoding the variable region of the light chain, and FIG. 9D representing the amino acid sequence encoded by the nucleotide sequence shown in FIG. 9C.

FIG. 10 is a series of representations of the heavy chain and light chain variable region nucleotide and amino acid sequences of the human anti-PDGFD antibody expressed by the hybridoma cell line designated Cur 2-1.25 of the invention, with FIG. 10A representing the nucleotide sequence encoding the variable region of the heavy chain, FIG. 10B representing the amino acid sequence encoded by the nucleotide sequence shown in FIG. 10A, FIG. 10C representing the nucleotide sequence encoding the variable region of the light chain, and FIG. 10D representing the amino acid sequence encoded by the nucleotide sequence shown in FIG. 10C.

FIG. 11 is a series of representations of the heavy chain and light chain variable region nucleotide and amino acid sequences of the human anti-PDGFD antibody expressed by the hybridoma cell line designated Cur 2-1.29 of the invention, with FIG. 11A representing the nucleotide sequence encoding the variable region of the heavy chain, FIG. 11B representing the amino acid sequence encoded by the nucleotide sequence shown in FIG. 11A, FIG. 11C representing the nucleotide sequence encoding the variable region of the light chain, and FIG. 11D representing the amino acid sequence encoded by the nucleotide sequence shown in FIG. 11C.

FIG. 12 is a series of representations of the heavy chain and light chain variable region nucleotide and amino acid sequences of the human anti-PDGFD antibody expressed by the hybridoma cell line designated Cur 2-1.33 of the invention, with FIG. 12A representing the nucleotide sequence encoding the variable region of the heavy chain, FIG. 12B representing the amino acid sequence encoded by the nucleotide sequence shown in FIG. 12A, FIG. 12C representing the nucleotide sequence encoding the variable region of the light chain, and FIG. 12D representing the amino acid sequence encoded by the nucleotide sequence shown in FIG. 12C.

FIG. 13 is a series of representations of the heavy chain and light chain variable region nucleotide and amino acid sequences of the human anti-PDGFD antibody expressed by the hybridoma cell line designated Cur 2-1.38 of the invention, with FIG. 13A representing the nucleotide sequence encoding the variable region of the heavy chain, FIG. 13B representing the amino acid sequence encoded by the nucleotide sequence shown in FIG. 13A, FIG. 13C representing the nucleotide sequence encoding the variable region of the light chain, and FIG. 13D representing the amino acid sequence encoded by the nucleotide sequence shown in FIG. 13C.

FIG. 14 is a series of representations of the heavy chain and light chain variable region nucleotide and amino acid sequences of the human anti-PDGFD antibody expressed by the hybridoma cell line designated Cur 2-1.39 of the invention, with FIG. 14A representing the nucleotide sequence encoding the variable region of the heavy chain, FIG. 14B representing the amino acid sequence encoded by the nucleotide sequence shown in FIG. 14A, FIG. 14C representing the nucleotide sequence encoding the variable region of the light chain, and FIG. 14D representing the amino acid sequence encoded by the nucleotide sequence shown in FIG. 14C.

FIG. 15 is a series of representations of the heavy chain and light chain variable region nucleotide and amino acid sequences of the human anti-PDGFD antibody expressed by the hybridoma cell line designated Cur 2-1.40 of the invention, with FIG. 15A representing the nucleotide sequence encoding the variable region of the heavy chain and FIG. 15B representing the amino acid sequence encoded by the nucleotide sequence shown in FIG. 15A.

FIG. 16 is a series of representations of the heavy chain and light chain variable region nucleotide and amino acid sequences of the human anti-PDGFD antibody expressed by the hybridoma cell line designated Cur 2-1.45 of the invention, with FIG. 16A representing the nucleotide sequence encoding the variable region of the heavy chain, FIG. 16B representing the amino acid sequence encoded by the nucleotide sequence shown in FIG. 16A, FIG. 16C representing the nucleotide sequence encoding the variable region of the light chain, and FIG. 16D representing the amino acid sequence encoded by the nucleotide sequence shown in FIG. 16C.

FIG. 17 is a series of representations of the heavy chain and light chain variable region nucleotide and amino acid sequences of the human anti-PDGFD antibody expressed by the hybridoma cell line designated Cur 2-1.46 of the invention, with FIG. 17A representing the nucleotide sequence encoding the variable region of the heavy chain, FIG. 17B representing the amino acid sequence encoded by the nucleotide sequence shown in FIG. 17A, FIG. 17C representing the nucleotide sequence encoding the variable region of the light chain, and FIG. 17D representing the amino acid sequence encoded by the nucleotide sequence shown in FIG. 17C.

FIG. 18 is a series of representations of the heavy chain and light chain variable region nucleotide and amino acid sequences of the human anti-PDGFD antibody expressed by the hybridoma cell line designated Cur 2-1.48 of the invention, with FIG. 18A representing the nucleotide sequence encoding the variable region of the heavy chain, FIG. 18B representing the amino acid sequence encoded by the nucleotide sequence shown in FIG. 18A, FIG. 18C representing the nucleotide sequence encoding the variable region of the light chain, and FIG. 18D representing the amino acid sequence encoded by the nucleotide sequence shown in FIG. 18C.

FIG. 19 is a series of representations of the heavy chain and light chain variable region nucleotide and amino acid sequences of the human anti-PDGFD antibody expressed by the hybridoma cell line designated Cur 2-1.49 of the invention, with FIG. 19A representing the nucleotide sequence encoding the variable region of the heavy chain, FIG. 19B representing the amino acid sequence encoded by the nucleotide sequence shown in FIG. 19A, FIG. 19C representing the nucleotide sequence encoding the variable region of the light chain, and FIG. 19D representing the amino acid sequence encoded by the nucleotide sequence shown in FIG. 19C.

FIG. 20 is a series of representations of the heavy chain and light chain variable region nucleotide and amino acid sequences of the human anti-PDGFD antibody expressed by the hybridoma cell line designated Cur 2-1.51 of the invention, with FIG. 20A representing the nucleotide sequence encoding the variable region of the heavy chain, FIG. 20B representing the amino acid sequence encoded by the nucleotide sequence shown in FIG. 20A, FIG. 20C representing the nucleotide sequence encoding the variable region of the light chain, and FIG. 20D representing the amino acid sequence encoded by the nucleotide sequence shown in FIG. 20C.

FIG. 21 is a series of representations of the heavy chain and light chain variable region nucleotide and amino acid sequences of the human anti-PDGFD antibody expressed by the hybridoma cell line designated Cur 2-6.4 of the invention, with FIG. 21A representing the nucleotide sequence encoding the variable region of the heavy chain, FIG. 21B representing the amino acid sequence encoded by the nucleotide sequence shown in FIG. 21A, FIG. 21C representing the nucleotide sequence encoding the variable region of the light chain, and FIG. 21D representing the amino acid sequence encoded by the nucleotide sequence shown in FIG. 21C.

FIG. 22 is a table showing VDJ gene utilization of antibodies of the invention and indicating nucleotide/amino acid changes between the antibodies and the V, D, or J genes from which they are derived in the antibodies FR1, CDR1, FR2, CDR2, FR3, CDR3, and FR4 regions.

As will be observed in FIG. 22A, the following antibodies have the following V heavy chain gene utilization:
VH 1-8: 1.19.1, 6.4.1, 1.18, 1.40.1, 1.45, 1.46.1, 1.49.1
VH 1-18: 1.33, 1.48.1
VH 3-21: 1.6.1
VH 3-33: 1.17.1, 1.24.1, 1.38.1
VH 3-53: 1.11.1
VH 5-51: 1.23.1, 1.25.1, 1.29, 1.39.1, 1.51.1

As will be observed in FIG. 22B, the following antibodies have the following V light chain gene utilization:
VL L5: 1.48
VL A19: 1.49, 1.11, 1.29
VL A20: 1.45, 1.33, 1.38
VL A27: 6.4.1, 1.51
VL A30: 1.19, 1.18, 1.6, 1.23, 1.25, 1.29, 1.39, 1.17, 1.24, 1.46

For convenience, sequences of the protein sequences of the foregoing VH and VK genes are provided:

```
VH 1-8:
QVQLVQSGAEVKKPGASVKVSCKASGYTFTSYDINWVRQATGQGLEWMGWM        (SEQ ID NO:1)

NPNSGNTGYAQKFQGRVTMTRNTSISTAYMELSSLRSEDTAVYYCAR

VH 1-18:
QVQLVQSGAEVKKPGASVKVSCKASGYTFTSYGISWVRQAPGQGLEWGWISA        (SEQ ID NO:2)

YNGNTNYAQKLQGRVTMTTDTSTSTAYMELRSLRSDDTAVYYCAR

VH 3-21:
EVQLVESGGGLVKPGGSLRLSCAASGFTFSSYSMNWVRQAPGKGLEWVSSISSSS        (SEQ ID NO:3)

SYIYYADSVKGRFTISRDNAKNSLYLQMNSLRAEDTAVYYCAR

VH 3-33:
QVQLVESGGGVVQPGRSLRLSCAASGFTFSSYGMHWVRQAPGKGLEWVAVIW        (SEQ ID NO:4)

YDGSNKYYADSVKGRFTISRDNSKNTLYLQMNSLRAEDTAVYYCAR

VH 3-53:
EVQLVESGGGLIQPGGSLRLSCAASGFTVSSNYMSWVRQAPGKGLEWVSVIYSG        (SEQ ID NO:5)

GSTYYADSVKGRFTISRDNSKNTLYLQMNSLRAEDTAVYYCAR

VH 5-51:
EVQLVQSGAEVKKPGESLKISCKGSGYSFTSYWIGWVRQMPGKGLEWMGIIYPG        (SEQ ID NO:6)

DSDTRYSPSFQGQVTISADKSISTAYLQWSSLKASDTAMYYCAR

VK L5:
DIQMTQSPSSVSASVGDRVTITCRASQGISSWLAWYQQKPGKAPKLLIYAASSLQ        (SEQ ID NO:7)

SGVPSRFSGSGSGTDFTLTISSLQPEDFATYYCQQANSFP

VK A19:
DLVMTQSPLSLPVTPGEPASISCRSSQSLLHSNGYNYLDWYLQKPGQSPQLLIYLG        (SEQ ID NO:8)

SNRASGVPDRESGSGSGTDFTLKISRVEAEDVGVYYCMQALQTP

VK A20:
DIQMTQSPSSLSASVGDRVTITCRASQGISNYLAWYQQKPGKVPKLLIYAASTLQ        (SEQ ID NO:9)

SGVPSRFSGSGSGTDFTLTISSLQPEDVATYYCQKYNSAP
```

-continued

VK A27:
EIVLTQSPGTLSLSPGERATLSCRASQSVSSSYLAWYQQKPGQAPRLLIYGASSRA (SEQ ID NO:10)

TGTPDRFSGSGSGTDFTLTISRLEPEDFAVYYCQQYGSSP

VK A30:
DIQMTQSPSSLSASVGDRVTITCRASQGJRNDLGWYQQKPGKAPKRLIYAASSLQ (SEQ ID NO:11)

SGVPSRFSGSGSGTEFTLTISSLQPEDFATYYCLQHNSYP

FIG. 23 is a series of alignments of the heavy chain and light chain variable region amino acid sequences of the human anti-PDGFD antibody expressed by the hybridoma cell line designated Cur 2-1.6 of the invention and the V gene from which it is derived, with FIG. 23A representing the alignment of the heavy chain amino acid sequence alignment and FIG. 23B representing the alignment of the light chain amino acid sequence.

FIG. 24 is a series of alignments of the heavy chain and light chain variable region amino acid sequences of the human anti-PDGFD antibody expressed by the hybridoma cell line designated Cur 2-1.11 of the invention and the V gene from which it is derived, with FIG. 24A representing the alignment of the heavy chain amino acid sequence alignment and FIG. 24B representing the alignment of the light chain amino acid sequence.

FIG. 25 is a series of alignments of the heavy chain and light chain variable region amino acid sequences of the human anti-PDGFD antibody expressed by the hybridoma cell line designated Cur 2-1.17 of the invention and the V gene from which it is derived, with FIG. 25A representing the alignment of the heavy chain amino acid sequence alignment and FIG. 25B representing the alignment of the light chain amino acid sequence.

FIG. 26 is a series of alignments of the heavy chain and light chain variable region amino acid sequences of the human anti-PDGFD antibody expressed by the hybridoma cell line designated Cur 2-1.18 of the invention and the V gene from which it is derived, with FIG. 26A representing the alignment of the heavy chain amino acid sequence alignment and FIG. 26B representing the alignment of the light chain amino acid sequence.

FIG. 27 is a series of alignments of the heavy chain and light chain variable region amino acid sequences of the human anti-PDGFD antibody expressed by the hybridoma cell line designated Cur 2-1.19 of the invention and the V gene from which it is derived, with FIG. 27A representing the alignment of the heavy chain amino acid sequence alignment and FIG. 27B representing the alignment of the light chain amino acid sequence.

FIG. 28 is a series of alignments of the heavy chain and light chain variable region amino acid sequences of the human anti-PDGFD antibody expressed by the hybridoma cell line designated Cur 2-1.23 of the invention and the V gene from which it is derived, with FIG. 28A representing the alignment of the heavy chain amino acid sequence alignment and FIG. 28B representing the alignment of the light chain amino acid sequence.

FIG. 29 is a series of alignments of the heavy chain and light chain variable region amino acid sequences of the human anti-PDGFD antibody expressed by the hybridoma cell line designated Cur 2-1.24 of the invention and the V gene from which it is derived, with FIG. 29A representing the alignment of the heavy chain amino acid sequence alignment and FIG. 29B representing the alignment of the light chain amino acid sequence.

FIG. 30 is a series of alignments of the heavy chain and light chain variable region amino acid sequences of the human anti-PDGFD antibody expressed by the hybridoma cell line designated Cur 2-1.25 of the invention and the V gene from which it is derived, with FIG. 30A representing the alignment of the heavy chain amino acid sequence alignment and FIG. 30B representing the alignment of the light chain amino acid sequence.

FIG. 31 is a series of alignments of the heavy chain and light chain variable region amino acid sequences of the human anti-PDGFD antibody expressed by the hybridoma cell line designated Cur 2-1.29 of the invention and the V gene from which it is derived, with FIG. 31A representing the alignment of the heavy chain amino acid sequence alignment and FIG. 31B representing the alignment of the light chain amino acid sequence.

FIG. 32 is a series of alignments of the heavy chain and light chain variable region amino acid sequences of the human anti-PDGFD antibody expressed by the hybridoma cell line designated Cur 2-1.33 of the invention and the V gene from which it is derived, with FIG. 32A representing the alignment of the heavy chain amino acid sequence alignment and FIG. 32B representing the alignment of the light chain amino acid sequence.

FIG. 33 is a series of alignments of the heavy chain and light chain variable region amino acid sequences of the human anti-PDGFD antibody expressed by the hybridoma cell line designated Cur 2-1.38 of the invention and the V gene from which it is derived, with FIG. 33A representing the alignment of the heavy chain amino acid sequence alignment and FIG. 33B representing the alignment of the light chain amino acid sequence.

FIG. 34 is a series of alignments of the heavy chain and light chain variable region amino acid sequences of the human anti-PDGFD antibody expressed by the hybridoma cell line designated Cur 2-1.39 of the invention and the V gene from which it is derived, with FIG. 34A representing the alignment of the heavy chain amino acid sequence alignment and FIG. 34B representing the alignment of the light chain amino acid sequence.

FIG. 35 is a series of alignments of the heavy chain and light chain variable region amino acid sequences of the human anti-PDGFD antibody expressed by the hybridoma cell line designated Cur 2-1.45 of the invention and the V gene from which it is derived, with FIG. 35A representing the alignment of the heavy chain amino acid sequence alignment and FIG. 35B representing the alignment of the light chain amino acid sequence.

FIG. 36 is a series of alignments of the heavy chain and light chain variable region amino acid sequences of the human anti-PDGFD antibody expressed by the hybridoma cell line designated Cur 2-1.46 of the invention and the V gene from which it is derived, with FIG. 36A representing the alignment of the heavy chain amino acid sequence alignment and FIG. 36B representing the alignment of the light chain amino acid sequence.

FIG. 37 is a series of alignments of the heavy chain and light chain variable region amino acid sequences of the human anti-PDGFD antibody expressed by the hybridoma cell line designated Cur 2-1.48 of the invention and the V gene from which it is derived, with FIG. 37A representing the alignment of the heavy chain amino acid sequence alignment and FIG. 37B representing the alignment of the light chain amino acid sequence.

FIG. 38 is a series of alignments of the heavy chain and light chain variable region amino acid sequences of the human anti-PDGFD antibody expressed by the hybridoma cell line designated Cur 2-1.49 of the invention and the V gene from which it is derived, with FIG. 38A representing the alignment of the heavy chain amino acid sequence alignment and FIG. 38B representing the alignment of the light chain amino acid sequence.

FIG. 39 is a series of alignments of the heavy chain and light chain variable region amino acid sequences of the human anti-PDGFD antibody expressed by the hybridoma cell line designated Cur 2-1.51 of the invention and the V gene from which it is derived, with FIG. 39A representing the alignment of the heavy chain amino acid sequence alignment and FIG. 39B representing the alignment of the light chain amino acid sequence.

FIG. 40 is a series of alignments of the heavy chain and light chain variable region amino acid sequences of the human anti-PDGFD antibody expressed by the hybridoma cell line designated Cur 2-6.4 of the invention and the V gene from which it is derived, with FIG. 40A representing the alignment of the heavy chain amino acid sequence alignment and FIG. 40B representing the alignment of the light chain amino acid sequence.

FIG. 41 is a table showing VDJ gene utilization of the 1.19.1 and 6.4.1 antibodies of the invention and indicating nucleotide changes between the antibodies and the VH, DH, and JH and VK and JK genes from which they are derived.

FIG. 42 is a table showing VDJ gene utilization of the 1.6.1, 1.11.1, and 1.23.1 antibodies of the invention and indicating nucleotide changes between the antibodies and the VH, DH, and JH and VK and JK genes from which they are derived.

FIG. 43 is a table showing VDJ gene utilization of the 1.19.1, 6.4.1, 1.6.1, 1.11.1, 1.23.1, 1.17.1, 1.18, 1.24.1, 1.25.1, 1.29, 1.33, 1.38.1, 1.39.1, 1.40.1, 1.45, 1.46.1, 1.46.2, 1.48.1, 1.49.1, and 1.51.1 antibodies of the invention and indicating nucleotide changes between the antibodies and the VH, DH, and JH and VK and JK genes from which they are derived.

FIG. 48 is a representation of a ClustalW sequence alignment between the heavy chain amino acid sequences of antibodies of the invention indicating locations of the CDRs of the antibodies.

FIG. 49 is a representation of a ClustalW sequence alignment between the light chain amino acid sequences of antibodies of the invention indicating locations of the CDRs of the antibodies.

FIG. 50 is a representation of a ClustalW sequence alignment between the heavy chain amino acid sequences of antibodies of the invention that possess heavy chains derived from the VH 1-8 gene with CDRs indicated.

FIG. 51 is a representation of a ClustalW sequence alignment between the heavy chain amino acid sequences of antibodies of the invention that possess heavy chains derived from the VH 1-18 gene with CDRs indicated.

FIG. 52 is a representation of a ClustalW sequence alignment between the heavy chain amino acid sequences of antibodies of the invention that possess heavy chains derived from the VH 3-33 gene with CDRs indicated.

FIG. 53 is a representation of a ClustalW sequence alignment between the heavy chain amino acid sequences of antibodies of the invention that possess heavy chains derived from the VH 5-51 gene with CDRs indicated.

FIG. 54 is a representation of a ClustalW sequence alignment between the light chain amino acid sequences of antibodies of the invention that possess light chains derived from the VK A19 gene with CDRs indicated.

FIG. 55 is a representation of a ClustalW sequence alignment between the light chain amino acid sequences of antibodies of the invention that possess light chains derived from the VK A20 gene with CDRs indicated.

FIG. 56 is a representation of a ClustalW sequence alignment between the light chain amino acid sequences of antibodies of the invention that possess light chains derived from the VK A27 gene with CDRs indicated.

FIG. 57 is a representation of a ClustalW sequence alignment between the light chain amino acid sequences of antibodies of the invention that possess light chains derived from the VK A30 gene with CDRs indicated.

In each of FIGS. 48–57, CDR domains were determined in accordance with the Kabat numbering system. See Kabat Sequences of *Proteins of Immunological Interest* (National Institutes of Health, Bethesda, Md. (1987 and 1991)).

Example 8

In the following discussion, structural information related to relative epitopes that antibodies prepared in accordance with the invention bind to is provided.

Certain antibodies in accordance with the present invention were "binned" in accordance relative epitope to which they bind. In order to conduct such binning, we followed the protocol described in U.S. patent application No.60/337,245, filed Dec. 3, 2001, entitled Antibody Categorization Based On Binding Characteristics. As shown in the following Tables, we detected antibodies that bound to at least three distinct epitopes on the PDGFD antigen. Results are shown for two different experiments utilizing the binning procedure described in the foregoing patent application as well as results derived from competition studies using BiaCore affinity cross-competition studies.

| Epitope Type | | | |
|---|---|---|---|
| I | II | III | IV |
| 1.6 | 1.9 | 1.45 | 1.33 |
| 1.19 | 1.22 | 1.46 | |
| | 1.29 | | |
| | 6.4 | | |

| Epitope Type | | | |
|---|---|---|---|
| I | II | III | IV |
| 1.6 | 1.9 | 1.19 | 1.33 |
| | 1.29 | 1.22 | |
| | 1.45 | 6.4 | |
| | 1.46 | | |

-continued

| Epitope Type (by BiaCore) | | | |
|---|---|---|---|
| I | II | IV | ? |
| 1.6 | 1.9 | 6.4 | 1.33 |
| 1.45 | 1.19 | | 1.46 |
| | 1.22 | | |
| | 1.29 | | |

INCORPORATION BY REFERENCE

All references cited herein, including patents, patent applications, papers, text books, and the like, and the references cited therein, to the extent that they are not already, are hereby incorporated herein by reference in their entirety. In addition, the following references are also incorporated by reference herein in their entirety, including the references cited in such references:

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What we claim is:

1. A human monoclonal antibody that binds to Platelet Derived Growth Factor D (PDGFD) and comprises a heavy chain amino acid sequence comprising SEQ ID NO: 48 and a light chain amino acid sequence comprising SEQ ID NO: 49.

2. A human monoclonal antibody or antigen-binding portion thereof that specifically binds to Platelet Derived Growth Factor D (PDGFD) and is encoded by human $V_H1$-8 gene and $J_H6B$ gene, wherein said monoclonal antibody comprises a heavy chain polypeptide comprising the sequence of SEQ ID NO:48 and a light chain polypeptide comprising the sequence of SEQ ID NO:49.

3. A human monoclonal antibody that binds to Platelet Derived Growth Factor D (PDGFD) and is derived from $V_H1$-8 and $J_H6B$, wherein said monoclonal antibody comprises a heavy chain polypeptide comprising the sequence of SEQ ID NO:48 and a light chain polypeptide comprising the sequence of SEQ ID NO:49.

4. A composition comprising a human monoclonal antibody or antigen-binding portion thereof that specifically binds to Platelet Derived Growth Factor D (PDGFD) and is encoded by human $V_H1$-8 gene and $J_H6B$ gene, wherein said human monoclonal antibody or antigen-binding portion thereof comprises a heavy chain polypeptide comprising the sequence of SEQ ID NO:48 and a light chain polypeptide comprising the sequence of SEQ ID NO:49 in association with a pharmaceutically acceptable carrier.

* * * * *

SEQUENCE LISTING

<160> NUMBER OF SEQ ID NOS: 377

<210> SEQ ID NO 1
<211> LENGTH: 99
<212> TYPE: PRT
<213> ORGANISM: homo sapiens

<400> SEQUENCE: 1

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly

<210> SEQ ID NO 2
<211> LENGTH: 98
<212> TYPE: PRT
<213> ORGANISM: homo sapiens

<400> SEQUENCE: 2

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

-continued

<210> SEQ ID NO 3
<211> LENGTH: 98
<212> TYPE: PRT
<213> ORGANISM: homo sapiens

<400> SEQUENCE: 3

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 4
<211> LENGTH: 98
<212> TYPE: PRT
<213> ORGANISM: homo sapiens

<400> SEQUENCE: 4

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 5
<211> LENGTH: 97
<212> TYPE: PRT
<213> ORGANISM: homo sapiens

<400> SEQUENCE: 5

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Ala
                85                  90                  95
Arg

<210> SEQ ID NO 6
<211> LENGTH: 98
<212> TYPE: PRT
<213> ORGANISM: homo sapiens

<400> SEQUENCE: 6

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg

<210> SEQ ID NO 7
<211> LENGTH: 95
<212> TYPE: PRT
<213> ORGANISM: homo sapiens

<400> SEQUENCE: 7

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                85                  90                  95

<210> SEQ ID NO 8
<211> LENGTH: 100
<212> TYPE: PRT
<213> ORGANISM: homo sapiens

<400> SEQUENCE: 8

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 9
<211> LENGTH: 95
<212> TYPE: PRT
<213> ORGANISM: homo sapiens

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95
```

<210> SEQ ID NO 10
<211> LENGTH: 96
<212> TYPE: PRT
<213> ORGANISM: homo sapiens

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 11
<211> LENGTH: 95
<212> TYPE: PRT
<213> ORGANISM: homo sapiens

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45
```

```
Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95
```

<210> SEQ ID NO 12
<211> LENGTH: 381
<212> TYPE: PRT
<213> ORGANISM: homo sapiens

<400> SEQUENCE: 12

```
Pro Met His Arg Leu Ile Phe Val Tyr Thr Leu Ile Cys Ala Asn Phe
 1               5                  10                  15

Cys Ser Cys Arg Asp Thr Ser Ala Thr Pro Gln Ser Ala Ser Ile Lys
                 20                  25                  30

Ala Leu Arg Asn Ala Asn Leu Arg Asp Glu Ser Asn His Leu Thr
             35                  40                  45

Asp Leu Tyr Arg Arg Asp Glu Thr Ile Gln Val Lys Gly Asn Gly Tyr
 50                  55                  60

Val Gln Ser Pro Arg Phe Pro Asn Ser Tyr Pro Arg Asn Leu Leu Leu
 65                  70                  75                  80

Thr Trp Arg Leu His Ser Gln Glu Asn Thr Arg Ile Gln Leu Val Phe
                 85                  90                  95

Asp Asn Gln Phe Gly Leu Glu Glu Ala Glu Asn Asp Ile Cys Arg Tyr
                 100                 105                 110

Asp Phe Val Glu Val Glu Asp Ile Ser Glu Thr Ser Thr Ile Ile Arg
             115                 120                 125

Gly Arg Trp Cys Gly His Lys Glu Val Pro Pro Arg Ile Lys Ser Arg
 130                 135                 140

Thr Asn Gln Ile Lys Ile Thr Phe Lys Ser Asp Asp Tyr Phe Val Ala
 145                 150                 155                 160

Leu Ala Lys Pro Gly Phe Lys Ile Tyr Tyr Ser Leu Leu Glu Asp Phe
                 165                 170                 175

Gln Pro Ala Ala Ala Ser Glu Thr Asn Trp Glu Ser Val Thr Ser Ser
                 180                 185                 190

Ile Ser Gly Val Ser Tyr Asn Ser Pro Ser Val Thr Asp Pro Thr Leu
             195                 200                 205

Ile Ala Asp Ala Leu Asp Lys Lys Ile Ala Glu Phe Asp Thr Val Glu
 210                 215                 220

Asp Leu Leu Lys Tyr Phe Asn Pro Glu Ser Trp Gln Glu Asp Leu Glu
 225                 230                 235                 240

Asn Met Tyr Leu Asp Thr Pro Arg Tyr Arg Gly Arg Ser Tyr His Asp
                 245                 250                 255

Arg Lys Ser Lys Val Ala Ser Pro Leu Asp Arg Leu Asn Asp Asp Ala
                 260                 265                 270

Lys Arg Tyr Ser Cys Thr Pro Arg Asn Tyr Ser Val Ala Ser Asn Ile
             275                 280                 285

Arg Glu Glu Leu Lys Leu Ala Asn Val Val Phe Phe Pro Arg Cys Leu
 290                 295                 300

Leu Val Gln Arg Cys Gly Gly Asn Cys Gly Cys Gly Thr Val Ala Ser
 305                 310                 315                 320

Asn Trp Arg Ser Cys Thr Cys Asn Ser Gly Lys Thr Val Lys Lys Tyr
                 325                 330                 335
```

His Glu Val Leu Gln Phe Glu Pro Gly His Ile Lys Arg Arg Gly Arg
                340                 345                 350

Ala Lys Thr Met Ala Leu Val Ala Ser Pro Ile Gln Leu Asp His His
            355                 360                 365

Glu Arg Cys Asp Cys Ile Cys Ser Ser Arg Pro Pro Arg
        370                 375                 380

<210> SEQ ID NO 13
<211> LENGTH: 126
<212> TYPE: PRT
<213> ORGANISM: homo sapiens

<400> SEQUENCE: 13

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Asn Phe Arg Thr Tyr
            20                  25                  30

Asn Met Asn Trp Val Arg Gln Ala Pro Gly Lys Gly Leu Glu Trp Val
        35                  40                  45

Ser Ser Ile Ser Ser Ser Ser Asn Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Ile Met Ile Thr Phe Gly Ile Ile Ala Ser Phe Tyr
            100                 105                 110

Phe Asp Tyr Trp Gly Gln Gly Thr Leu Val Thr Val Ser Ser
        115                 120                 125

<210> SEQ ID NO 14
<211> LENGTH: 107
<212> TYPE: PRT
<213> ORGANISM: homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 15
<211> LENGTH: 120
<212> TYPE: PRT
<213> ORGANISM: homo sapiens

<400> SEQUENCE: 15

```
Glu Val Gln Leu Val Gln Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
 50                      55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Gly Thr Val Thr Thr Asn Tyr Tyr Tyr Gly Met Asp Val Trp Gly Gln
            100                 105                 110

Gly Thr Thr Val Thr Val Ser Ser
            115                 120
```

<210> SEQ ID NO 16
<211> LENGTH: 111
<212> TYPE: PRT
<213> ORGANISM: homo sapiens

<400> SEQUENCE: 16

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Gln Ser
             20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
             85                  90                  95

Leu Gln Thr Leu Thr Phe Gly Gly Gly Thr Lys Val Glu Ile Lys
            100                 105                 110
```

<210> SEQ ID NO 17
<211> LENGTH: 126
<212> TYPE: PRT
<213> ORGANISM: homo sapiens

<400> SEQUENCE: 17

```
Gln Val Gln Leu Val Glu Ser Gly Gly Gly Val Val Gln Pro Gly Lys
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

-continued

Ala Arg Asp Gln Gly Tyr Arg Tyr Ala Gly Tyr Tyr Asp Tyr Gly
            100                 105                 110

Met Asp Val Trp Gly Gln Gly Thr Thr Val Thr Val Ser Ser
        115                 120                 125

<210> SEQ ID NO 18
<211> LENGTH: 107
<212> TYPE: PRT
<213> ORGANISM: homo sapiens

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 19
<211> LENGTH: 126
<212> TYPE: PRT
<213> ORGANISM: homo sapiens

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Ala Val Ala Gly Thr Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 20
<211> LENGTH: 107
<212> TYPE: PRT
<213> ORGANISM: homo sapiens

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp

```
                    20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln His Asn Ser Tyr Pro Phe
                85                  90                  95

Thr Phe Gly Pro Gly Thr Lys Val Asp Ile Lys
            100                 105

<210> SEQ ID NO 21
<211> LENGTH: 126
<212> TYPE: PRT
<213> ORGANISM: homo sapiens

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Met Ile Thr Phe Gly Gly Val Ile Val His Tyr Gly
                100                 105                 110

Met Asp Val Trp Gly Gln Gly Thr Thr Val Thr Val Ser Ser
            115                 120                 125

<210> SEQ ID NO 22
<211> LENGTH: 107
<212> TYPE: PRT
<213> ORGANISM: homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Asp Pro Cys
                85                  90                  95

Ser Phe Gly Gln Gly Thr Lys Leu Glu Ile Arg
            100                 105
```

```
<210> SEQ ID NO 23
<211> LENGTH: 126
<212> TYPE: PRT
<213> ORGANISM: homo sapiens

<400> SEQUENCE: 23

Glu Val Gln Leu Val Gln Ser Gly Ala Glu Val Lys Lys Pro Gly Glu
 1               5                  10                  15

Ser Leu Lys Ile Ser Cys Glu Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Val Ser Tyr Tyr Val Ser Gly Ser Tyr Tyr Asn Val
            100                 105                 110

Phe Asp Tyr Trp Gly Gln Gly Thr Leu Val Thr Val Ser Ser
        115                 120                 125

<210> SEQ ID NO 24
<211> LENGTH: 107
<212> TYPE: PRT
<213> ORGANISM: homo sapiens

<400> SEQUENCE: 24

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Ile Pro Gly Lys Ala Pro Lys Arg Leu Ile
         35                  40                  45

Tyr Ala Ala Ser Ser Leu Gln Arg Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 25
<211> LENGTH: 126
<212> TYPE: PRT
<213> ORGANISM: homo sapiens

<400> SEQUENCE: 25

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
             20                  25                  30

Gly Met His Trp Val Arg Gln Ala Pro Gly Lys Gly Leu Glu Trp Val
         35                  40                  45

Ala Asp Ile Trp Tyr Asp Gly Ser Asn Lys Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr Ser Tyr Gly Tyr Val Tyr Tyr Asp Tyr Gly
            100                 105                 110

Met Asp Val Trp Gly Gln Gly Thr Thr Val Thr Val Ser Ser
            115                 120                 125

<210> SEQ ID NO 26
<211> LENGTH: 107
<212> TYPE: PRT
<213> ORGANISM: homo sapiens

<400> SEQUENCE: 26

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 27
<211> LENGTH: 126
<212> TYPE: PRT
<213> ORGANISM: homo sapiens

<400> SEQUENCE: 27

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Arg Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Gly Ser Tyr Tyr Gly Ser Glu Thr Tyr Tyr Asn Val
            100                 105                 110

Phe Asp Tyr Trp Gly Gln Gly Thr Leu Val Thr Val Ser Ser
            115                 120                 125

<210> SEQ ID NO 28
<211> LENGTH: 107
<212> TYPE: PRT
<213> ORGANISM: homo sapiens
```

```
<400> SEQUENCE: 28

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 29
<211> LENGTH: 129
<212> TYPE: PRT
<213> ORGANISM: homo sapiens

<400> SEQUENCE: 29

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60

Gln Gly Gln Ala Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg His Val Asp Val Gly Ala Thr Ile Gly Gly Tyr Tyr Tyr Tyr
            100                 105                 110

Tyr His Gly Met Asp Val Trp Gly Gln Gly Thr Thr Val Thr Val Ser
        115                 120                 125

Ser

<210> SEQ ID NO 30
<211> LENGTH: 113
<212> TYPE: PRT
<213> ORGANISM: homo sapiens

<400> SEQUENCE: 30

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
```

```
                65                  70                  75                  80
Ser Arg Val Glu Ala Asp Asp Val Gly Val Tyr Tyr Cys Met Gln Ala
                    85                  90                  95

Leu Gln Ser Leu Met Cys Ser Phe Gly Gln Gly Thr Lys Leu Glu Ile
                    100                 105                 110

Lys

<210> SEQ ID NO 31
<211> LENGTH: 127
<212> TYPE: PRT
<213> ORGANISM: homo sapiens

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp His Tyr Tyr Asp Ser Ser Asp Tyr Leu Tyr Tyr Tyr Tyr
                100                 105                 110

Gly Leu Asp Val Trp Gly Gln Gly Thr Thr Val Thr Val Ser Ser
            115                 120                 125

<210> SEQ ID NO 32
<211> LENGTH: 107
<212> TYPE: PRT
<213> ORGANISM: homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
                100                 105

<210> SEQ ID NO 33
<211> LENGTH: 127
<212> TYPE: PRT
<213> ORGANISM: homo sapiens

<400> SEQUENCE: 33
```

-continued

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ile Ile Trp Tyr Asp Gly Asn Asp Lys Tyr Tyr Ala Asp Ser Val
 50                      55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Tyr Tyr Asp Ser Ser Asp Tyr Leu Tyr Tyr Tyr Tyr
             100                 105                 110

Gly Met Asp Val Trp Gly Gln Gly Thr Thr Val Thr Val Ser Ser
         115                 120                 125
```

<210> SEQ ID NO 34
<211> LENGTH: 107
<212> TYPE: PRT
<213> ORGANISM: homo sapiens

<400> SEQUENCE: 34

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Asn Leu Leu Ile
         35                  40                  45

Tyr Ala Ala Ser Thr Leu Gln Ser Gly Val Pro Ser Arg Phe Ser Gly
 50                      55                  60

Ser Gly Ser Gly Thr Asp Phe Ser Leu Thr Ile Ser Ser Leu Gln Pro
 65                  70                  75                  80

Glu Asp Val Ala Ala Tyr Tyr Cys Gln Lys Cys Asn Ser Ala Pro Trp
                 85                  90                  95

Thr Phe Gly Gln Gly Thr Thr Val Glu Ile Lys
             100                 105
```

<210> SEQ ID NO 35
<211> LENGTH: 126
<212> TYPE: PRT
<213> ORGANISM: homo sapiens

<400> SEQUENCE: 35

```
Glu Val Gln Leu Val Gln Ser Gly Thr Glu Val Lys Lys Pro Gly Glu
  1               5                  10                  15

Ser Leu Lys Ile Ser Cys Lys Gly Ser Gly Tyr Arg Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                      55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95
```

Ala Arg His Gly Ser Tyr Tyr Asn Ser Gly Ser Tyr Tyr Asn Val
            100                 105                 110

Phe Asp Tyr Trp Gly Gln Gly Thr Leu Val Thr Val Ser Ser
        115                 120                 125

<210> SEQ ID NO 36
<211> LENGTH: 107
<212> TYPE: PRT
<213> ORGANISM: homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 37
<211> LENGTH: 126
<212> TYPE: PRT
<213> ORGANISM: homo sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Leu Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Val Val Val Ala Ala Thr Asn Tyr Tyr Asn Gly
            100                 105                 110

Met Asp Val Trp Gly Gln Gly Thr Val Thr Val Ser Ser
        115                 120                 125

<210> SEQ ID NO 38
<211> LENGTH: 125
<212> TYPE: PRT
<213> ORGANISM: homo sapiens

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr

```
            20                  25                  30
Asp Ile Asn Trp Val Arg Gln Ala Thr Gly Gln Gly Leu Glu Trp Met
        35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Ser Gly Tyr Ser Tyr Gly Tyr Asp Tyr Tyr Tyr Gly Met
            100                 105                 110
Asp Val Trp Gly Gln Gly Thr Thr Val Thr Val Ser Ser
        115                 120                 125

<210> SEQ ID NO 39
<211> LENGTH: 107
<212> TYPE: PRT
<213> ORGANISM: homo sapiens

<400> SEQUENCE: 39

Asp Ile Gln Met Thr Gln Ser Pro Ser Ser Leu Ser Ala Ser Val Gly
1               5                   10                  15
Asp Arg Val Thr Ile Asn Cys Arg Ala Ser Gln Gly Ile Ser Asn Asp
            20                  25                  30
Leu Ala Trp Tyr Gln Gln Lys Pro Gly Lys Val Pro Lys Leu Leu Ile
        35                  40                  45
Tyr Ala Ala Ser Thr Leu Gln Leu Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Lys Tyr Asn Ser Ala Pro Phe
                85                  90                  95
Thr Phe Gly Pro Gly Thr Lys Val Asp Ile Lys
            100                 105

<210> SEQ ID NO 40
<211> LENGTH: 126
<212> TYPE: PRT
<213> ORGANISM: homo sapiens

<400> SEQUENCE: 40

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Tyr
            20                  25                  30
Asp Ile Asn Trp Val Arg Gln Ala Thr Gly Gln Gly Leu Glu Trp Met
        35                  40                  45
Gly Trp Met Asn Pro Asn Asn Gly Asn Thr Gly Tyr Ala Gln Lys Phe
    50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Ile Val Val Val Thr Ala Thr Asp Tyr Tyr Tyr Gly
            100                 105                 110
Met Asp Val Trp Gly Gln Gly Thr Thr Val Thr Val Ser Ser
```

```
            115                 120                 125

<210> SEQ ID NO 41
<211> LENGTH: 107
<212> TYPE: PRT
<213> ORGANISM: homo sapiens

<400> SEQUENCE: 41

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Phe Ala Ala Ser Ser Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Ser Gly Tyr Pro Pro
                85                  90                  95

Thr Phe Gly Gln Gly Thr Lys Val Glu Ile Lys
            100                 105

<210> SEQ ID NO 42
<211> LENGTH: 125
<212> TYPE: PRT
<213> ORGANISM: homo sapiens

<400> SEQUENCE: 42

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Glu Tyr Tyr Asp Gly Ser Gly Tyr Tyr Tyr Phe
            100                 105                 110

Asp Tyr Trp Gly Gln Gly Thr Leu Val Thr Val Ser Ser
        115                 120                 125

<210> SEQ ID NO 43
<211> LENGTH: 107
<212> TYPE: PRT
<213> ORGANISM: homo sapiens

<400> SEQUENCE: 43

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Ala Ala Ser Ile Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Ser Tyr Tyr Cys Gln Gln Ser Asn Ser Phe Pro Arg
                 85                  90                  95
Thr Phe Gly Gln Gly Thr Lys Val Glu Ile Lys
            100                 105

<210> SEQ ID NO 44
<211> LENGTH: 127
<212> TYPE: PRT
<213> ORGANISM: homo sapiens

<400> SEQUENCE: 44

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
                 20                  25                  30
Asp Ile Asn Trp Val Arg Gln Ala Thr Gly Gln Gly Leu Glu Trp Met
             35                  40                  45
Gly Trp Met Asn Pro Asn Ser Gly Asp Thr Gly Tyr Ala Gln Lys Phe
 50                  55                  60
Gln Gly Arg Val Thr Met Thr Arg Asn Thr Ser Ile Ser Thr Ala Tyr
 65                  70                  75                  80
Met Glu Leu Ser Ser Leu Arg Ser Glu Asp Thr Ala Val Tyr Phe Cys
                 85                  90                  95
Ala Arg Met Arg Asp Ile Val Ala Thr Ser Tyr Tyr Tyr Tyr Phe Tyr
                100                 105                 110
Gly Met Asp Val Trp Gly Gln Gly Thr Thr Val Thr Val Ser Ser
            115                 120                 125

<210> SEQ ID NO 45
<211> LENGTH: 111
<212> TYPE: PRT
<213> ORGANISM: homo sapiens

<400> SEQUENCE: 45

Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
                 20                  25                  30
Asn Gly Tyr Asn Tyr Leu Asp Trp Tyr Leu Leu Lys Pro Gly Gln Ser
             35                  40                  45
Pro Gln Leu Leu Ile Tyr Leu Gly Ser Ser Arg Ala Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Thr
                 85                  90                  95
Leu Gln Thr Ile Thr Phe Gly Gln Gly Thr Arg Leu Glu Ile Lys
                100                 105                 110

<210> SEQ ID NO 46
<211> LENGTH: 126
<212> TYPE: PRT
<213> ORGANISM: homo sapiens
```

<400> SEQUENCE: 46

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Ala Lys Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Tyr Asp Tyr Val Trp Arg Asn Tyr Arg Tyr Thr Gly Trp
            100                 105                 110

Phe Asp Pro Trp Gly Gln Gly Thr Leu Val Thr Val Ser Ser
        115                 120                 125

<210> SEQ ID NO 47
<211> LENGTH: 108
<212> TYPE: PRT
<213> ORGANISM: homo sapiens

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Phe Thr Phe Gly Pro Gly Thr Lys Val Asp Ile Lys
            100                 105

<210> SEQ ID NO 48
<211> LENGTH: 125
<212> TYPE: PRT
<213> ORGANISM: homo sapiens

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Ile Asn Pro Asn Ser Gly Asn Thr Asp Tyr Ala Gln Lys Phe
    50                  55                  60

Gln Gly Arg Val Thr Met Thr Arg Asp Thr Ser Ile Ser Thr Ala Tyr
65                  70                  75                  80

```
Met Glu Leu Ser Ser Leu Arg Ser Glu Asp Thr Ala Ile Tyr Tyr Cys
                85                  90                  95

Val Arg Gly Phe Gly Tyr Ser Tyr Asn Tyr Asp Tyr Tyr Gly Met
            100                 105                 110

Asp Val Trp Gly Gln Gly Thr Thr Val Thr Val Ser Ser
        115                 120                 125

<210> SEQ ID NO 49
<211> LENGTH: 108
<212> TYPE: PRT
<213> ORGANISM: homo sapiens

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Ala Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Ser Phe Gly Gln Gly Thr Lys Leu Glu Ile Lys
            100                 105

<210> SEQ ID NO 50
<211> LENGTH: 1828
<212> TYPE: DNA
<213> ORGANISM: homo sapiens

<400> SEQUENCE: 50
ctaaaaaata tgttctctac aacaccaagg ctcattaaaa tattttaaat attaatatac      60
atttcttctg tcagaaatac ataaaacttt attatatcag cgcagggcgg cgcggcgtcg     120
gtcccgggag cagaacccgg cttttcttg gagcgacgct gtctctagtc gctgatccca     180
aatgcaccgg ctcatctttg tctacactct aatctgcgca aacttttgca gctgtcggga     240
cacttctgca accccgcaga gcgcatccat caaagctttg cgcaacgcca acctcaggcg     300
agatgagagc aatcacctca cagacttgta ccgaagagat gagaccatcc aggtgaaagg     360
aaacggctac gtgcagagtc ctagattccc gaacagctac cccaggaacc tgctcctgac     420
atggcggctt cactctcagg agaatacacg gatacagcta gtgtttgaca atcagtttgg     480
attagaggaa gcagaaaatg atatctgtag gtatgatttt gtggaagttg aagatatatc     540
cgaaaccagt accattatta gaggacgatg gtgtggacac aaggaagttc ctccaaggat     600
aaaatcaaga acgaaccaaa ttaaaatcac attcaagtcc gatgactact ttgtggctaa     660
acctggattc aagattttat ttcttgct ggaagatttc caacccgcag cagcttcaga     720
gaccaactgg gaatctgtca caagctctat ttcaggggta tcctataact ctccatcagt     780
aacggatccc actctgattg cggatgctct ggacaaaaaa attgcagaat tgatacagt     840 ggaagatctg ctcaagtact tcaatccaga gtcatggcaa gaagatcttg agaatatgta     900
tctggacacc cctcggtatc gaggcaggtc ataccatgac cggaagtcaa aagttgacct     960
ggataggctc aatgatgatg ccaagcgtta cagttgcact cccaggaatt actcggtcaa    1020
```

-continued

```
tataagagaa gagctgaagt tggccaatgt ggtcttcttt ccacgttgcc tcctcgtgca    1080
gcgctgtgga ggaaattgtg gctgtggaac tgtcaactgg aggtcctgca catgcaattc    1140
agggaaaacc gtgaaaaagt atcatgaggt attacagttt gagcctggcc acatcaagag    1200
gaggggtaga gctaagacca tggctctagt tgacatccag ttggatcacc atgaacgatg    1260
tgattgtatc tgcagctcaa gaccacctcg ataagagaat gtgcacatcc ttacattaag    1320
cctgaaagaa cctttagttt aaggagggtg agataagaga cccttttcct accagcaacc    1380
aaacttacta ctagcctgca atgcaatgaa cacaagtggt tgctgagtct cagccttgct    1440
ttgttaatgc catggcaagt agaaaggtat atcatcaact tctataccta agaatatagg    1500
attgcattta ataatagtgt ttgaggttat atatgcacaa acacacacag aaatatattc    1560
atgtctatgt gtatatagat caaatgtttt ttttggtata tataaccagg tacaccagag    1620
cttacatatg tttgagttag actcttaaaa tcctttgcca aaataaggga tggtcaaata    1680
tatgaaacat gtctttagaa aatttaggag ataaatttat ttttaaattt tgaaacacaa    1740
aacaattttg aatcttgctc tcttaaagaa agcatcttgt atattaaaaa tcaaaagatg    1800
aggctttctt acatatacat cttagttg                                      1828
```

<210> SEQ ID NO 51
<211> LENGTH: 22
<212> TYPE: DNA
<213> ORGANISM: homo sapiens

<400> SEQUENCE: 51
caggtgcagc tggagcagtc gg                                             22

<210> SEQ ID NO 52
<211> LENGTH: 24
<212> TYPE: DNA
<213> ORGANISM: homo sapiens

<400> SEQUENCE: 52
gctgagggag tagagtcctg agga                                           24

<210> SEQ ID NO 53
<211> LENGTH: 19
<212> TYPE: DNA
<213> ORGANISM: homo sapiens

<400> SEQUENCE: 53
cacaccgcgg tcacatggc                                                 19

<210> SEQ ID NO 54
<211> LENGTH: 20
<212> TYPE: DNA
<213> ORGANISM: homo sapiens

<400> SEQUENCE: 54
ctactctagg gcacctgtcc                                                20

<210> SEQ ID NO 55
<211> LENGTH: 379
<212> TYPE: DNA
<213> ORGANISM: homo sapiens

<400> SEQUENCE: 55
gaggtgcagc tggtggagtc tgggggaggc ctggtcaagc ctgggggggtc cctgagactc    60

```
tcctgtgcag cctctggatt caacttcaga acctataaca tgaactgggt ccgccaggct    120
ccagggaagg ggctggagtg ggtctcatcc attagtagta gtagtagtaa catatactac    180
gcagactcag tgaagggccg attcaccatc tccagagaca acgccaagaa ctcactgtat    240
ctgcaaatga acagcctgag agccgaggac acggctgtat attactgtgc gagagatatt    300
atgattacgt ttggggggaat tatcgcctcg ttctactttg actactgggg ccagggaacc    360
ctggtcaccg tctcctcag                                                  379

<210> SEQ ID NO 56
<211> LENGTH: 322
<212> TYPE: DNA
<213> ORGANISM: homo sapiens

<400> SEQUENCE: 56
gacatccaga tgacccagtc tccatcctcc ctgtctgcat ctgtaggaga cagagtcacc     60
atcacttgcc gggcaagtca gggcattaga aatgatttag gctggtttca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgctcac tttcggcgga    300
gggaccaagg tggagatcaa ac                                             322

<210> SEQ ID NO 57
<211> LENGTH: 361
<212> TYPE: DNA
<213> ORGANISM: homo sapiens

<400> SEQUENCE: 57
gaggtgcagc tggtgcagtc tggaggaggc ttgatccagc ctgggggtc cctgagactc      60 tcctgtgcag cctctgggtt caccgtcagt agcaactaca tgagctgggt ccgccaggct    120
ccagggaagg ggctggagtg ggtctcagtt atttatagcg gtggtagcac atactacgca    180
gactccgtga agggccgatt caccatctcc agagacaatt ccaagaacac gctgtatctt    240
caaatgaaca gcctgagagc cgaggacacg gccgtgtatt actgtgcggg aacggtgact    300
acgaattact actacggtat ggacgtctgg ggccaaggga ccacggtcac cgtctcctca    360
g                                                                    361

<210> SEQ ID NO 58
<211> LENGTH: 334
<212> TYPE: DNA
<213> ORGANISM: homo sapiens

<400> SEQUENCE: 58
gatattgtga tgactcagtc tccactctcc ctgcccgtca cccctggaga gccggcctcc     60
atctcctgca ggtctagtca gagcctcctg caaagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagatttac actgaaaatc    240 agcagagtgg aggctgagga tgttggggtt tattactgca tgcaagctct acaaactctc    300
actttcggcg gagggaccaa ggtggagatc aaac                                334

<210> SEQ ID NO 59
<211> LENGTH: 379
<212> TYPE: DNA
<213> ORGANISM: homo sapiens
```

<400> SEQUENCE: 59

```
caggtgcagc tggtggagtc gggggaggc gtggtccagc ctgggaagtc cctgagactc    60
tcctgtgcag cgtctggatt caccttcagt agctatggca tgcactgggt ccgccaggct   120
ccaggcaagg gctggagtg gtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatcaa   300
ggatacagat atgctggtta ctactacgac tacggtatgg acgtctgggg ccaagggacc   360
acggtcaccg tctcctcag                                                379
```

<210> SEQ ID NO 60
<211> LENGTH: 322
<212> TYPE: DNA
<213> ORGANISM: homo sapiens

<400> SEQUENCE: 60

```
gacatccaga tgacccagtc tccatcctcc ctgtctgcat ctgtaggaga cagagtcacc    60
atcacttgcc gggcaagtca ggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgctcac tttcggcgga   300
gggaccaagg tggagatcaa ac                                            322
```

<210> SEQ ID NO 61
<211> LENGTH: 379
<212> TYPE: DNA
<213> ORGANISM: homo sapiens

<400> SEQUENCE: 61

```
caggtgcagc tggtgcagtc gggggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atgaacccaa acagtggtaa cacaggctat   180
gcacagaagt tccagggcag agtcaccatg accaggaaca cctccataag cacagcctac   240
atggagctga gcagcctgag atctgaggac acggccgtgt attactgtgc gagagagggt   300
atagcagtgg ctgggacata ctactactac tacggtatgg acgtctgggg ccaagggacc   360
acggtcaccg tctcctcag                                                379
```

<210> SEQ ID NO 62
<211> LENGTH: 322
<212> TYPE: DNA
<213> ORGANISM: homo sapiens

<400> SEQUENCE: 62

```
gacatccaga tgacccagtc tccatcctcc ctgtctgcat ctgtaggaga cagagtcacc    60
atcacttgcc gggcaagtca ggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttattt ctgtctacag cataatagtt acccattcac tttcggccct   300
gggaccaaag tggatatcaa ac                                            322
```

<210> SEQ ID NO 63
<211> LENGTH: 379
<212> TYPE: DNA
<213> ORGANISM: homo sapiens

<400> SEQUENCE: 63

| | | | | | |
|---|---|---|---|---|---|
| caggtgcagc | tggtgcagtc | tggggctgag | gtgaagaagc | ctggggcctc | agtgaaggtc | 60 |
| tcctgcaagg | cttctggata | caccttcacc | agttatgata | tcaactgggt | gcgacaggcc | 120 |
| actggacaag | ggcttgagtg | gatgggatgg | atgaaccctg | acagtggtaa | cacaggctat | 180 |
| gcacagaagt | tccagggcag | agtcaccatg | accaggaaca | cctccataag | cacagcctac | 240 |
| atggagctga | gcagcctgag | atctgaggac | acggccgtgt | attactgtgc | gagagacgtt | 300 |
| atgattacgt | ttgggggagt | tatcgtgcac | tacggtatgg | acgtctgggg | ccaagggacc | 360 |
| acggtcaccg | tctcctcag | | | | | 379 |

<210> SEQ ID NO 64
<211> LENGTH: 322
<212> TYPE: DNA
<213> ORGANISM: homo sapiens

<400> SEQUENCE: 64

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gggcattaga | aatgatttag | gctggtatca | gcagaaacca | 120 |
| gggaaagccc | ctaagcgcct | gatctatgct | gcatccagtt | tgcaaagtgg | ggtcccatca | 180 |
| aggttcagcg | gcagtggatc | tgggacagat | ttcactctca | caatcagcag | cctgcagcct | 240 |
| gaagattttg | caacttatta | ctgtctacag | cataatagtg | acccgtgcag | ttttggccag | 300 |
| gggaccaagc | tggagatcag | ac | | | | 322 |

<210> SEQ ID NO 65
<211> LENGTH: 379
<212> TYPE: DNA
<213> ORGANISM: homo sapiens

<400> SEQUENCE: 65

| | | | | | |
|---|---|---|---|---|---|
| gaggtgcagc | tggtgcagtc | tggagcagag | gtgaaaaagc | ccggggagtc | tctgaagatc | 60 |
| tcctgtgagg | gttctggata | cagctttacc | agctactgga | tcggctgggt | gcgccagatg | 120 |
| cccgggaaag | gcctggagtg | gatggggatc | atctatcctg | gtgactctga | taccagatac | 180 |
| agcccgtcct | tccaaggcca | ggtcaccatc | tcagccgaca | agtccatcag | caccgcctac | 240 |
| ctgcagtgga | gcagcctgaa | ggcctcggac | accgccatgt | attactgtgc | gagacatgta | 300 |
| tcgtattact | atgtttcggg | gagttattat | aacgtctttg | actactgggg | ccaggggaacc | 360 |
| ctggtcaccg | tctcctcag | | | | | 379 |

<210> SEQ ID NO 66
<211> LENGTH: 322
<212> TYPE: DNA
<213> ORGANISM: homo sapiens

<400> SEQUENCE: 66

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gggcattaga | aatgatttag | gctggtatca | gcagatacca | 120 |
| gggaaagccc | ctaagcgcct | gatctatgct | gcatccagtt | tgcaacgtgg | ggtcccatca | 180 |
| aggttcagcg | gcagtggatc | tgggacagaa | ttcactctca | caatcagcag | cctgcagcct | 240 |

```
gaagattttg caacttatta ctgtctacag cataatagtt acccgtggac gttcggccaa     300
gggaccaagg tggaaatcaa ac                                             322
```

<210> SEQ ID NO 67
<211> LENGTH: 379
<212> TYPE: DNA
<213> ORGANISM: homo sapiens

<400> SEQUENCE: 67

```
caggtgcagc tggtggagtc tgggggaggc gtggtccagc ctgggaggtc cctgagactc     60
tcctgtgcag cgtctggatt cagtttcagt agctatggca tgcactgggt ccgccaggct    120
ccaggcaagg ggctggagtg ggtggcagat atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attattgtgc gagagatcag    300
ggatacagct atggttacgt ctactacgac tacggtatgg acgtctgggg ccaagggacc    360
acggtcaccg tctcctcag                                                 379
```

<210> SEQ ID NO 68
<211> LENGTH: 322
<212> TYPE: DNA
<213> ORGANISM: homo sapiens

<400> SEQUENCE: 68

```
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagag ttcactctca caatcagcag cctgcagcct    240
gaagattttg caacttatta ctgtctacag cataatagtt acccgtggac gttcggccaa    300
gggaccaagg tggaaatcaa ac                                             322
```

<210> SEQ ID NO 69
<211> LENGTH: 379
<212> TYPE: DNA
<213> ORGANISM: homo sapiens

<400> SEQUENCE: 69

```
gaggtgcagc tggtgcagtc gggagcagag gtgaaaaagc ccggggagtc tctgaagatc     60
tcctgtaagg gttctggata caggtttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagacatgga    300
tcgtattatt atggttcgga gacttattat aatgtctttg actactgggg ccagggaacc    360
ctggtcaccg tctcctcag                                                 379
```

<210> SEQ ID NO 70
<211> LENGTH: 322
<212> TYPE: DNA
<213> ORGANISM: homo sapiens

<400> SEQUENCE: 70

```
gacatccaga tgacccagtc tccatcctcc ctgtctgcat ctgtaggaga cagagtcacc     60
```

```
atcacttgcc gggcaagtca gggcattaga aatgatttag ctggtatca gcagaaacca      120 gggaaagccc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt acccgtggac gttcggccaa      300
gggaccaagg tggaaatcaa ac                                               322
```

<210> SEQ ID NO 71
<211> LENGTH: 388
<212> TYPE: DNA
<213> ORGANISM: homo sapiens

<400> SEQUENCE: 71

```
gaggtgcagc tggtgcagtc gggagcagag gtgaaaaagc ccggggagtc tctgaagatc       60
tcctgtaagg gttctggata cagctttacc agctactgga tcggctgggt gcgccagatg      120
cccgggaaag cctggagtg gatggggatc atctatcctg gtgactctga taccagatac      180
agcccgtcct ccaaggcca ggccaccatc tcagccgaca gtccatcag caccgcctac       240 ctgcagtgga gcagcctgaa ggcctcggac accgccatgt attactgtgc gagacacgtg      300
gatgtagggg ctacgattgg gggatattac tattactacc acggtatgga cgtctgggggc      360 caagggacca cggtcaccgt ctcctcag                                         388
```

<210> SEQ ID NO 72
<211> LENGTH: 340
<212> TYPE: DNA
<213> ORGANISM: homo sapiens

<400> SEQUENCE: 72

```
gatattgtga tgactcagtc tccactctcc ctgcccgtca cccctggaga gccggcctcc       60
atctcctgca ggtctagtca gagcctcctg catagtaatg gatacaacta tttggattgg      120
tacctgcaga agccagggca gtctccacaa ctcctgatct atttgggttc taatcgggcc      180
tccggggtcc ctgacaggtt cagtggcagt ggatcaggca cagattttac actgaaaatc      240
agcagagtgg aggctgacga tgttggggtt tattactgca tgcaagctct acaatctctc      300
atgtgcagtt ttggccaggg gaccaagctg gagatcaaac                            340
```

<210> SEQ ID NO 73
<211> LENGTH: 382
<212> TYPE: DNA
<213> ORGANISM: homo sapiens

<400> SEQUENCE: 73

```
caggttcagc tggtgcagtc gggagctgag gtgaagaagc ctggggcctc agtgaaggtc       60
tcctgcaagg cttctggtta cacctttacc agctatggta tcagctgggt gcgacaggcc      120
cctggacaag gcttgagtg gatgggatgg atcagcgctt acaatggtaa cacaaactat      180
gcacagaagc tccagggcag agtcaccatg accacagaca catccacgag cacagcctac      240
atggagctga ggagcctgag atctgacgac acggccgtgt attactgtgc gagagatcat      300
tactatgata gtagtgatta tctctactac tactacggtt ggacgtctg gggccaaggg      360 accacggtca ccgtctcctc ag                                               382
```

<210> SEQ ID NO 74
<211> LENGTH: 322
<212> TYPE: DNA
<213> ORGANISM: homo sapiens

<400> SEQUENCE: 74

```
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg ccccgctcac tttcggcgga   300
gggaccaagg tggagatcaa ac                                            322
```

<210> SEQ ID NO 75
<211> LENGTH: 382
<212> TYPE: DNA
<213> ORGANISM: homo sapiens

<400> SEQUENCE: 75

```
caggtgcagc tggtggagtc ggggggaggc gtggtccagc ctgggaggtc cctgagactc    60
tcctgtgcag cgtctggatt caccttcagt agctatggca tgcactgggt ccgccaggct   120
ccaggcaagg gctggagtg gtggcaatt atatggtatg atggaaatga taaatactat   180
gcagactccg tgaagggccg cttcaccgtc tccagagaca attccaagaa cacgctgtat   240
ctgcaaatga acagcctgag agccgaggac acggctgtgt attactgtgc gagaggatat   300
tactatgata gtagtgatta tctctactac tactacggta tggacgtctg gggccaaggg   360
accacggtca ccgtctcctc ag                                            382
```

<210> SEQ ID NO 76
<211> LENGTH: 322
<212> TYPE: DNA
<213> ORGANISM: homo sapiens

<400> SEQUENCE: 76

```
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaacctcct gatctatgct gcatccactt tgcaatcagg ggtcccatct   180
cggttcagtg gcagtggatc tgggacagat ttctctctca ccatcagcag cctgcagcct   240
gaagatgttg cagcttatta ctgtcaaaag tgtaacagtg ccccgtggac gttcggccaa   300
gggaccacgg tggagatcaa ac                                            322
```

<210> SEQ ID NO 77
<211> LENGTH: 379
<212> TYPE: DNA
<213> ORGANISM: homo sapiens

<400> SEQUENCE: 77

```
gaggtgcagc tggtgcagtc gggaacagag gtgaaaaagc ccggggagtc tctgaagatc    60
tcctgtaagg gttctggata caggtttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca agtccatcag caccgcctac   240
ctgcagtgga gcagcctgaa ggcctcggac accgccatgt attactgtgc gagacatgga   300
tcgtattact ataattcggg gagttattat aacgtctttg actactgggg ccagggaacc   360
ctggtcaccg tctcctcag                                                379
```

<210> SEQ ID NO 78
<211> LENGTH: 322
<212> TYPE: DNA
<213> ORGANISM: homo sapiens

<400> SEQUENCE: 78

| gacatccaga tgacccagtc tccatcctcc ctgtctgcat ctgtaggaga cagagtcacc | 60 |
| atcacttgcc gggcaagtca gggcattaga aatgatttag gctggtatca gcagaaacca | 120 |
| gggaaagccc ctaagcgcct gatctatgct gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataatagtt acccgtggac gttcggccaa | 300 |
| gggaccaagg tggaaatcaa ac | 322 |

<210> SEQ ID NO 79
<211> LENGTH: 379
<212> TYPE: DNA
<213> ORGANISM: homo sapiens

<400> SEQUENCE: 79

| caggtgcagc tggtgcagtc gggggctgag gtgaagaagc ctggggcctc agtgaaggtc | 60 |
| tcctgcaagg cttctggata caccttcacc acttatgata tcaactgggt gcgacaggcc | 120 |
| actggacaag gcttgagtg gatgggatgg atgaaccta acagtggtaa cacaggctat | 180 |
| gcacagaagt tccagggcag agtcaccatg accaggaaca cctccctaag cacagcctac | 240 |
| atggagctga gcagcctgag atctgaggac acggccgtgt attactgtgc gagagatatt | 300 |
| gtagtggtgg tagctgctac caactactac aacggtatgg acgtctgggg ccaagggacc | 360 |
| acggtcaccg tctcctcag | 379 |

<210> SEQ ID NO 80
<211> LENGTH: 376
<212> TYPE: DNA
<213> ORGANISM: homo sapiens

<400> SEQUENCE: 80

| caggtgcagc tggtgcagtc gggggctgag gtgaagaagc ctggggcctc agtgaaggtc | 60 |
| tcctgcaagg cttctggata caccttcacc agttatgata tcaactgggt gcgacaggcc | 120 |
| actggacaag gcttgagtg gatgggatgg atgaaccta acagtggtaa cacaggctat | 180 |
| gcacagaagt tccagggcag agtcaccatg accaggaaca cctccataag cacagcctac | 240 |
| atggagctga gcagcctgag atctgaggac acggccgtgt attactgtgc gagaggcagt | 300 |
| ggatacagct atggttacga ctactactac ggtatggacg tctggggcca agggaccacg | 360 |
| gtcaccgtct cctcag | 376 |

<210> SEQ ID NO 81
<211> LENGTH: 322
<212> TYPE: DNA
<213> ORGANISM: homo sapiens

<400> SEQUENCE: 81

| gacatccaga tgacccagtc tccatcctcc ctgtctgcat ctgtaggaga cagagtcacc | 60 |
| atcaattgcc gggcgagtca gggcattagc aatgatttag cctggtatca gcagaaacca | 120 |
| gggaaagttc ctaagctcct gatctatgct gcatccactt tgcaattagg ggtcccatct | 180 |
| cggttcagtg gcagtggatc tgggacagat ttcactctca ccatcagcag cctgcagcct | 240 |

```
gaagatgttg caacttatta ctgtcaaaag tataacagtg ccccattcac tttcggccct      300
gggaccaaag tggatatcaa ac                                              322

<210> SEQ ID NO 82
<211> LENGTH: 379
<212> TYPE: DNA
<213> ORGANISM: homo sapiens

<400> SEQUENCE: 82
caggtgcagc tggtgcagtc gggggctgag gtgaagaagc ctggggcctc agtgaaggtc       60
tcctgcaagg cttctggata ctccttcacc agttatgata tcaactgggt gcgacaggcc     120
actggacaag gcttgagtg gatgggatgg atgaacccta acaatggtaa cacaggctat      180
gcacagaagt tccagggcag agtcaccatg accaggaaca cctccataag cacagcctac     240
atggagctga gcagcctgag atctgaggac acggccgtgt attactgtgc gagagatatt     300
gtagtggtgg taactgctac ggactactac tacggtatgg acgtctgggg ccaagggacc     360
acggtcaccg tctcctcag                                                  379

<210> SEQ ID NO 83
<211> LENGTH: 322
<212> TYPE: DNA
<213> ORGANISM: homo sapiens

<400> SEQUENCE: 83
gacatccaga tgacccagtc tccatcctcc ctgtctgcat ctgtaggaga cagagtcacc       60
atcacttgcc gggcaagtca gggcattaga aatgatttag ctggtatca gcagaaacca      120 gggaaagccc ctaagcgcct gatttttgct gcatccagtt tgccaagtgg ggtcccatca     180
aggttcagcg gcagtggatc tgggacagaa ttcactctca caatcagcag cctgcagcct     240
gaagattttg caacttatta ctgtctacag catagtggtt accctccgac gttcggccaa     300
gggaccaagg tggaaatcaa ac                                              322

<210> SEQ ID NO 84
<211> LENGTH: 376
<212> TYPE: DNA
<213> ORGANISM: homo sapiens

<400> SEQUENCE: 84
caggttcagc tggtgcagtc gggagctgag gtgaagaagc ctggggcctc agtgaaggtc       60
tcctgcaagg cttctggtta cacctttacc agctatggta tcagctgggt gcgacaggcc     120
cctggacaag gcttgagtg gatgggatgg atcagcgctt acaatggtaa cacaaactat      180
gcacagaagc tccagggcag agtcaccatg accacagaca catccacgag cacagcctac     240
atggagctga ggagcctgag atctgacgac acggccgtgt attactgtgc gagagatgtt     300
gaatattact atgatggtag tggttattac tactttgact actggggcca gggaaccctg     360
gtcaccgtct cctcag                                                     376

<210> SEQ ID NO 85
<211> LENGTH: 322
<212> TYPE: DNA
<213> ORGANISM: homo sapiens

<400> SEQUENCE: 85
gacatccaga tgacccagtc tccatcttcc gtgtctgcat ctgtaggaga cagagtcacc       60
```

| | |
|---|---|
| atcacttgtc gggcgagtca gggtattagc agctggttag cctggtatca gcagaaacca | 120 |
| gggaaagccc ctaagctcct gatctatgct gcatccattt tgcaaagtgg ggtcccatca | 180 |
| aggttcagcg gcagtggatc tgggacagat ttcactctca ccatcagcag cctgcagcct | 240 |
| gaggattttg catcttacta ttgtcaacag tctaacagtt ccctcggac gttcggccaa | 300 |
| gggaccaagg tggagatcaa ac | 322 |

<210> SEQ ID NO 86
<211> LENGTH: 382
<212> TYPE: DNA
<213> ORGANISM: homo sapiens

<400> SEQUENCE: 86

| | |
|---|---|
| caggtgcagc tggtgcagtc gggggctgag gtgaagaagc ctggggcctc agtgaaggtc | 60 |
| tcctgcaagg cttctggata caccttcacc agttatgata tcaactgggt gcgacaggcc | 120 |
| actggacaag gcttgagtg gatgggatgg atgaaccta acagtggtga cacaggctat | 180 |
| gcacagaagt tccagggcag agtcaccatg accaggaaca cctccataag cacagcctac | 240 |
| atggagctga gcagcctgag atctgaggac acggccgtgt atttctgtgc gagaatgagg | 300 |
| gatatagtgg ctacgagcta ttactactac ttctacggta tggacgtctg gggccaaggg | 360 |
| accacggtca ccgtctcctc ag | 382 |

<210> SEQ ID NO 87
<211> LENGTH: 334
<212> TYPE: DNA
<213> ORGANISM: homo sapiens

<400> SEQUENCE: 87

| | |
|---|---|
| gatattgtga tgactcagtc tccactctcc ctgcccgtca cccctggaga gccggcctcc | 60 |
| atctcctgca ggtctagtca gagcctcctg catagtaatg gatacaacta tttggattgg | 120 |
| tacctgctga agccagggca gtctccacag ctcctgatct atttggggttc tagtcgggcc | 180 |
| tccggggtcc ctgacaggtt cagtggcagt ggatcaggca cagattttac actgaaaatc | 240 |
| agcagagtgg aggctgagga tgttggggtt tattactgca tgcaaactct acaaactatc | 300 |
| accttcggcc aagggacacg actggagatt aaac | 334 |

<210> SEQ ID NO 88
<211> LENGTH: 379
<212> TYPE: DNA
<213> ORGANISM: homo sapiens

<400> SEQUENCE: 88

| | |
|---|---|
| gaggtgcagc tggtgcagtc gggagctgag gtgaaaaagc ccggggagtc tctgaagatc | 60 |
| tcctgtaagg gttctggata cagctttacc agctactgga tcggctgggt gcgccagatg | 120 |
| cccgggaaag gcctggagtg gatggggatc atctatcctg gtgactctga tgccaaatac | 180 |
| agcccgtcct tccaaggcca ggtcaccatc tcagccgaca agtccatcag caccgcctac | 240 |
| ctgcagtgga gcagcctgaa ggcctcggac accgccatgt attactgtgc gagacactat | 300 |
| gattacgttt ggaggaatta tcggtataca gggtggttcg accctgggg ccagggaacc | 360 |
| ctggtcaccg tctcctcag | 379 |

<210> SEQ ID NO 89
<211> LENGTH: 325
<212> TYPE: DNA
<213> ORGANISM: homo sapiens

<400> SEQUENCE: 89

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca cagggccac tggcatccca     180
gacaggttca gtggcagtgg gtctgggaca gacttcactc tcaccatcag cagactggag    240
cctgaagatt ttgcagtgta ttactgtcag cagtatggta gctcactatt cactttcggc    300
cctgggacca agtggatat caaac                                           325
```

<210> SEQ ID NO 90
<211> LENGTH: 377
<212> TYPE: DNA
<213> ORGANISM: homo sapiens

<400> SEQUENCE: 90

```
caggtgcagc tggtgcagtc tggggctgag gtgaagaagc ctggggcctc agtgaaggtc     60
tcctgcaagg cttctggata caccttcacc agttatgata tcaactgggt gcgacaggcc    120
actggacaag ggcttgagtg gatgggatgg ataaacccta atagtggtaa cacagactat    180
gcacagaagt tccagggcag agtcaccatg accaggaca cctccataag cacagcctac     240
atggagctga gcagcctgag atctgaggac acggccatat attattgtgt gagaggcttt    300
ggatacagct ataattacga ctactattac ggtatggacg tctggggcca agggaccacg    360
gtcaccgtct cctcagt                                                   377
```

<210> SEQ ID NO 91
<211> LENGTH: 325
<212> TYPE: DNA
<213> ORGANISM: homo sapiens

<400> SEQUENCE: 91

```
gaaattgtgt tgacgcagtc tccaggcacc ctgtctttgt ctccagggga aagagccacc     60
ctctcctgca gggccagtca gagtgttagt agtagttact tagcctggta ccagcagaag    120
cctggccagg ctcccaggct cctcatctat gctacatcca gcagggccac tggcatccca    180
gacaggttca gtggcagtgg gtctgggaca gacttcactc tcaccatcag cagactggag    240
cctgaagatt ttgcagtgta ttactgtcag cagtatggta gttcaccgtg cagttttggc    300
caggggacca agctggaaat caagc                                          325
```

<210> SEQ ID NO 92
<211> LENGTH: 6
<212> TYPE: DNA
<213> ORGANISM: homo sapiens

<400> SEQUENCE: 92

```
cgagag                                                                 6
```

<210> SEQ ID NO 93
<211> LENGTH: 28
<212> TYPE: DNA
<213> ORGANISM: homo sapiens

<400> SEQUENCE: 93

```
ttatgattac gtttggggga gttatcgt                                         28
```

<210> SEQ ID NO 94

```
<211> LENGTH: 6
<212> TYPE: DNA
<213> ORGANISM: homo sapiens

<400> SEQUENCE: 94 actacg                                                                    6

<210> SEQ ID NO 95
<211> LENGTH: 6
<212> TYPE: DNA
<213> ORGANISM: homo sapiens

<400> SEQUENCE: 95 gagagg                                                                    6

<210> SEQ ID NO 96
<211> LENGTH: 12
<212> TYPE: DNA
<213> ORGANISM: homo sapiens

<400> SEQUENCE: 96
tggatacagc ta                                                            12

<210> SEQ ID NO 97
<211> LENGTH: 8
<212> TYPE: DNA
<213> ORGANISM: homo sapiens

<400> SEQUENCE: 97 attactac                                                                  8

<210> SEQ ID NO 98
<211> LENGTH: 6
<212> TYPE: DNA
<213> ORGANISM: homo sapiens

<400> SEQUENCE: 98 ttaccc                                                                    6

<210> SEQ ID NO 99
<211> LENGTH: 6
<212> TYPE: DNA
<213> ORGANISM: homo sapiens

<400> SEQUENCE: 99 gtgcag                                                                    6

<210> SEQ ID NO 100
<211> LENGTH: 6
<212> TYPE: DNA
<213> ORGANISM: homo sapiens

<400> SEQUENCE: 100 ttttgg                                                                    6

<210> SEQ ID NO 101
<211> LENGTH: 6
<212> TYPE: DNA
<213> ORGANISM: homo sapiens

<400> SEQUENCE: 101 ctcacc                                                                    6
```

```
<210> SEQ ID NO 102
<211> LENGTH: 6
<212> TYPE: DNA
<213> ORGANISM: homo sapiens

<400> SEQUENCE: 102 gtgcag                                                                  6

<210> SEQ ID NO 103
<211> LENGTH: 6
<212> TYPE: DNA
<213> ORGANISM: homo sapiens

<400> SEQUENCE: 103 ttttgg                                                                  6

<210> SEQ ID NO 104
<211> LENGTH: 6
<212> TYPE: DNA
<213> ORGANISM: homo sapiens

<400> SEQUENCE: 104 gagaga                                                                  6

<210> SEQ ID NO 105
<211> LENGTH: 22
<212> TYPE: DNA
<213> ORGANISM: homo sapiens

<400> SEQUENCE: 105
tattatgatt acgtttgggg ga                                               22

<210> SEQ ID NO 106
<211> LENGTH: 14
<212> TYPE: DNA
<213> ORGANISM: homo sapiens

<400> SEQUENCE: 106
attatcgcct cgtt                                                        14

<210> SEQ ID NO 107
<211> LENGTH: 6
<212> TYPE: DNA
<213> ORGANISM: homo sapiens

<400> SEQUENCE: 107 ctactt                                                                  6

<210> SEQ ID NO 108
<211> LENGTH: 5
<212> TYPE: DNA
<213> ORGANISM: homo sapiens

<400> SEQUENCE: 108 agaga                                                                   5

<210> SEQ ID NO 109
<211> LENGTH: 10
<212> TYPE: DNA
<213> ORGANISM: homo sapiens

<400> SEQUENCE: 109
acggtgacta                                                             10
```

```
<210> SEQ ID NO 110
<211> LENGTH: 5
<212> TYPE: DNA
<213> ORGANISM: homo sapiens

<400> SEQUENCE: 110 cgaat                                                                5

<210> SEQ ID NO 111
<211> LENGTH: 7
<212> TYPE: DNA
<213> ORGANISM: homo sapiens

<400> SEQUENCE: 111 tactact                                                              7

<210> SEQ ID NO 112
<211> LENGTH: 6
<212> TYPE: DNA
<213> ORGANISM: homo sapiens

<400> SEQUENCE: 112 gagaca                                                               6

<210> SEQ ID NO 113
<211> LENGTH: 18
<212> TYPE: DNA
<213> ORGANISM: homo sapiens

<400> SEQUENCE: 113
tgtatcgtat tactatgt                                                 18

<210> SEQ ID NO 114
<211> LENGTH: 19
<212> TYPE: DNA
<213> ORGANISM: homo sapiens

<400> SEQUENCE: 114
ttcggggagt tattataac                                                19

<210> SEQ ID NO 115
<211> LENGTH: 6
<212> TYPE: DNA
<213> ORGANISM: homo sapiens

<400> SEQUENCE: 115 ctttga                                                               6

<210> SEQ ID NO 116
<211> LENGTH: 6
<212> TYPE: DNA
<213> ORGANISM: homo sapiens

<400> SEQUENCE: 116 ttaccc                                                               6

<210> SEQ ID NO 117
<211> LENGTH: 7
<212> TYPE: DNA
<213> ORGANISM: homo sapiens

<400> SEQUENCE: 117 gctcact                                                              7
```

```
<210> SEQ ID NO 118
<211> LENGTH: 6
<212> TYPE: DNA
<213> ORGANISM: homo sapiens

<400> SEQUENCE: 118 aaactc                                                              6

<210> SEQ ID NO 119
<211> LENGTH: 8
<212> TYPE: DNA
<213> ORGANISM: homo sapiens

<400> SEQUENCE: 119 tcactttc                                                            8

<210> SEQ ID NO 120
<211> LENGTH: 6
<212> TYPE: DNA
<213> ORGANISM: homo sapiens

<400> SEQUENCE: 120 ttaccc                                                              6

<210> SEQ ID NO 121
<211> LENGTH: 6
<212> TYPE: DNA
<213> ORGANISM: homo sapiens

<400> SEQUENCE: 121 gagaga                                                              6

<210> SEQ ID NO 122
<211> LENGTH: 7
<212> TYPE: DNA
<213> ORGANISM: homo sapiens

<400> SEQUENCE: 122 ggataca                                                             7

<210> SEQ ID NO 123
<211> LENGTH: 9
<212> TYPE: DNA
<213> ORGANISM: homo sapiens

<400> SEQUENCE: 123 atatgctgg                                                           9

<210> SEQ ID NO 124
<211> LENGTH: 8
<212> TYPE: DNA
<213> ORGANISM: homo sapiens

<400> SEQUENCE: 124 ttactact                                                            8

<210> SEQ ID NO 125
<211> LENGTH: 6
<212> TYPE: DNA
<213> ORGANISM: homo sapiens

<400> SEQUENCE: 125
```

-continued cgagag                                                          6

<210> SEQ ID NO 126
<211> LENGTH: 18
<212> TYPE: DNA
<213> ORGANISM: homo sapiens

<400> SEQUENCE: 126
gggtatagca gtggctgg                                            18

<210> SEQ ID NO 127
<211> LENGTH: 6
<212> TYPE: DNA
<213> ORGANISM: homo sapiens

<400> SEQUENCE: 127 tactac                                                          6

<210> SEQ ID NO 128
<211> LENGTH: 6
<212> TYPE: DNA
<213> ORGANISM: homo sapiens

<400> SEQUENCE: 128 gagaga                                                          6

<210> SEQ ID NO 129
<211> LENGTH: 18
<212> TYPE: DNA
<213> ORGANISM: homo sapiens

<400> SEQUENCE: 129
ggatacagct atggttac                                            18

<210> SEQ ID NO 130
<211> LENGTH: 6
<212> TYPE: DNA
<213> ORGANISM: homo sapiens

<400> SEQUENCE: 130 ctacta                                                          6

<210> SEQ ID NO 131
<211> LENGTH: 6
<212> TYPE: DNA
<213> ORGANISM: homo sapiens

<400> SEQUENCE: 131 gagaca                                                          6

<210> SEQ ID NO 132
<211> LENGTH: 6
<212> TYPE: DNA
<213> ORGANISM: homo sapiens

<400> SEQUENCE: 132 tggatc                                                          6

<210> SEQ ID NO 133
<211> LENGTH: 30
<212> TYPE: DNA
<213> ORGANISM: homo sapiens

<400> SEQUENCE: 133

-continued

```
gtattattat ggttcggaga cttattataa                              30

<210> SEQ ID NO 134
<211> LENGTH: 6
<212> TYPE: DNA
<213> ORGANISM: homo sapiens

<400> SEQUENCE: 134 ctttga                                                         6

<210> SEQ ID NO 135
<211> LENGTH: 6
<212> TYPE: DNA
<213> ORGANISM: homo sapiens

<400> SEQUENCE: 135 gagaca                                                         6

<210> SEQ ID NO 136
<211> LENGTH: 21
<212> TYPE: DNA
<213> ORGANISM: homo sapiens

<400> SEQUENCE: 136
gtggatgtag gggctacgat t                                       21

<210> SEQ ID NO 137
<211> LENGTH: 6
<212> TYPE: DNA
<213> ORGANISM: homo sapiens

<400> SEQUENCE: 137 ggggat                                                         6

<210> SEQ ID NO 138
<211> LENGTH: 8
<212> TYPE: DNA
<213> ORGANISM: homo sapiens

<400> SEQUENCE: 138 attactac                                                       8

<210> SEQ ID NO 139
<211> LENGTH: 6
<212> TYPE: DNA
<213> ORGANISM: homo sapiens

<400> SEQUENCE: 139 gagaga                                                         6

<210> SEQ ID NO 140
<211> LENGTH: 18
<212> TYPE: DNA
<213> ORGANISM: homo sapiens

<400> SEQUENCE: 140
attactatga tagtagtg                                           18

<210> SEQ ID NO 141
<211> LENGTH: 7
<212> TYPE: DNA
<213> ORGANISM: homo sapiens
```

```
<400> SEQUENCE: 141 attatct                                                              7

<210> SEQ ID NO 142
<211> LENGTH: 6
<212> TYPE: DNA
<213> ORGANISM: homo sapiens

<400> SEQUENCE: 142 ctacta                                                               6

<210> SEQ ID NO 143
<211> LENGTH: 6
<212> TYPE: DNA
<213> ORGANISM: homo sapiens

<400> SEQUENCE: 143 cgagag                                                               6

<210> SEQ ID NO 144
<211> LENGTH: 19
<212> TYPE: DNA
<213> ORGANISM: homo sapiens

<400> SEQUENCE: 144
tattactatg atagtagtg                                                19

<210> SEQ ID NO 145
<211> LENGTH: 7
<212> TYPE: DNA
<213> ORGANISM: homo sapiens

<400> SEQUENCE: 145 attatct                                                              7

<210> SEQ ID NO 146
<211> LENGTH: 6
<212> TYPE: DNA
<213> ORGANISM: homo sapiens

<400> SEQUENCE: 146 ctacta                                                               6

<210> SEQ ID NO 147
<211> LENGTH: 6
<212> TYPE: DNA
<213> ORGANISM: homo sapiens

<400> SEQUENCE: 147 gagaca                                                               6

<210> SEQ ID NO 148
<211> LENGTH: 6
<212> TYPE: DNA
<213> ORGANISM: homo sapiens

<400> SEQUENCE: 148 tggatc                                                               6

<210> SEQ ID NO 149
<211> LENGTH: 31
<212> TYPE: DNA
<213> ORGANISM: homo sapiens
```

<400> SEQUENCE: 149
gtattactat aattcgggga gttattataa c                                            31

<210> SEQ ID NO 150
<211> LENGTH: 6
<212> TYPE: DNA
<213> ORGANISM: homo sapiens

<400> SEQUENCE: 150 ctttga                                                                        6

<210> SEQ ID NO 151
<211> LENGTH: 6
<212> TYPE: DNA
<213> ORGANISM: homo sapiens

<400> SEQUENCE: 151 cgagag                                                                        6

<210> SEQ ID NO 152
<211> LENGTH: 25
<212> TYPE: DNA
<213> ORGANISM: homo sapiens

<400> SEQUENCE: 152
atattgtagt ggtggtagct gctac                                                  25

<210> SEQ ID NO 153
<211> LENGTH: 6
<212> TYPE: DNA
<213> ORGANISM: homo sapiens

<400> SEQUENCE: 153 actact                                                                        6

<210> SEQ ID NO 154
<211> LENGTH: 6
<212> TYPE: DNA
<213> ORGANISM: homo sapiens

<400> SEQUENCE: 154 gagagg                                                                        6

<210> SEQ ID NO 155
<211> LENGTH: 20
<212> TYPE: DNA
<213> ORGANISM: homo sapiens

<400> SEQUENCE: 155
gtggatacag ctatggttac                                                        20

<210> SEQ ID NO 156
<211> LENGTH: 6
<212> TYPE: DNA
<213> ORGANISM: homo sapiens

<400> SEQUENCE: 156 actact                                                                        6

<210> SEQ ID NO 157
<211> LENGTH: 6
<212> TYPE: DNA

```
<213> ORGANISM: homo sapiens

<400> SEQUENCE: 157 cgagag                                                               6

<210> SEQ ID NO 158
<211> LENGTH: 25
<212> TYPE: DNA
<213> ORGANISM: homo sapiens

<400> SEQUENCE: 158
atattgtagt ggtggtagct gctac                                         25

<210> SEQ ID NO 159
<211> LENGTH: 6
<212> TYPE: DNA
<213> ORGANISM: homo sapiens

<400> SEQUENCE: 159 actact                                                               6

<210> SEQ ID NO 160
<211> LENGTH: 6
<212> TYPE: DNA
<213> ORGANISM: homo sapiens

<400> SEQUENCE: 160 cgagag                                                               6

<210> SEQ ID NO 161
<211> LENGTH: 7
<212> TYPE: DNA
<213> ORGANISM: homo sapiens

<400> SEQUENCE: 161 tgttgaa                                                              7

<210> SEQ ID NO 162
<211> LENGTH: 24
<212> TYPE: DNA
<213> ORGANISM: homo sapiens

<400> SEQUENCE: 162
tattactatg atggtagtgg ttat                                          24

<210> SEQ ID NO 163
<211> LENGTH: 6
<212> TYPE: DNA
<213> ORGANISM: homo sapiens

<400> SEQUENCE: 163 actact                                                               6

<210> SEQ ID NO 164
<211> LENGTH: 6
<212> TYPE: DNA
<213> ORGANISM: homo sapiens

<400> SEQUENCE: 164 gcgaga                                                               6

<210> SEQ ID NO 165
<211> LENGTH: 5
```

<212> TYPE: DNA
<213> ORGANISM: homo sapiens

<400> SEQUENCE: 165 atgag                                                                    5

<210> SEQ ID NO 166
<211> LENGTH: 17
<212> TYPE: DNA
<213> ORGANISM: homo sapiens

<400> SEQUENCE: 166
ggatatagtg gctacga                                                      17

<210> SEQ ID NO 167
<211> LENGTH: 8
<212> TYPE: DNA
<213> ORGANISM: homo sapiens

<400> SEQUENCE: 167 attactac                                                                 8

<210> SEQ ID NO 168
<211> LENGTH: 6
<212> TYPE: DNA
<213> ORGANISM: homo sapiens

<400> SEQUENCE: 168 gagaca                                                                   6

<210> SEQ ID NO 169
<211> LENGTH: 31
<212> TYPE: DNA
<213> ORGANISM: homo sapiens

<400> SEQUENCE: 169
tatgattacg tttggaggaa ttatcggtat a                                      31

<210> SEQ ID NO 170
<211> LENGTH: 5
<212> TYPE: DNA
<213> ORGANISM: homo sapiens

<400> SEQUENCE: 170 caggg                                                                    5

<210> SEQ ID NO 171
<211> LENGTH: 6
<212> TYPE: DNA
<213> ORGANISM: homo sapiens

<400> SEQUENCE: 171 tggttc                                                                   6

<210> SEQ ID NO 172
<211> LENGTH: 6
<212> TYPE: DNA
<213> ORGANISM: homo sapiens

<400> SEQUENCE: 172 ttaccc                                                                   6

<210> SEQ ID NO 173

```
<211> LENGTH: 7
<212> TYPE: DNA
<213> ORGANISM: homo sapiens

<400> SEQUENCE: 173 gctcact                                                              7

<210> SEQ ID NO 174
<211> LENGTH: 6
<212> TYPE: DNA
<213> ORGANISM: homo sapiens

<400> SEQUENCE: 174 ttaccc                                                               6

<210> SEQ ID NO 175
<211> LENGTH: 6
<212> TYPE: DNA
<213> ORGANISM: homo sapiens

<400> SEQUENCE: 175 attcac                                                               6

<210> SEQ ID NO 176
<211> LENGTH: 6
<212> TYPE: DNA
<213> ORGANISM: homo sapiens

<400> SEQUENCE: 176 ttaccc                                                               6

<210> SEQ ID NO 177
<211> LENGTH: 6
<212> TYPE: DNA
<213> ORGANISM: homo sapiens

<400> SEQUENCE: 177 gtggac                                                               6

<210> SEQ ID NO 178
<211> LENGTH: 6
<212> TYPE: DNA
<213> ORGANISM: homo sapiens

<400> SEQUENCE: 178 ttaccc                                                               6

<210> SEQ ID NO 179
<211> LENGTH: 6
<212> TYPE: DNA
<213> ORGANISM: homo sapiens

<400> SEQUENCE: 179 gtggac                                                               6

<210> SEQ ID NO 180
<211> LENGTH: 6
<212> TYPE: DNA
<213> ORGANISM: homo sapiens

<400> SEQUENCE: 180 ctacaa                                                               6
```

-continued

```
<210> SEQ ID NO 181
<211> LENGTH: 14
<212> TYPE: DNA
<213> ORGANISM: homo sapiens

<400> SEQUENCE: 181
tctctcatgt gcag                                                        14

<210> SEQ ID NO 182
<211> LENGTH: 6
<212> TYPE: DNA
<213> ORGANISM: homo sapiens

<400> SEQUENCE: 182 ttttgg                                                                  6

<210> SEQ ID NO 183
<211> LENGTH: 6
<212> TYPE: DNA
<213> ORGANISM: homo sapiens

<400> SEQUENCE: 183 tgcccc                                                                  6

<210> SEQ ID NO 184
<211> LENGTH: 6
<212> TYPE: DNA
<213> ORGANISM: homo sapiens

<400> SEQUENCE: 184 gctcac                                                                  6

<210> SEQ ID NO 185
<211> LENGTH: 6
<212> TYPE: DNA
<213> ORGANISM: homo sapiens

<400> SEQUENCE: 185 tgcccc                                                                  6

<210> SEQ ID NO 186
<211> LENGTH: 6
<212> TYPE: DNA
<213> ORGANISM: homo sapiens

<400> SEQUENCE: 186 gtggac                                                                  6

<210> SEQ ID NO 187
<211> LENGTH: 6
<212> TYPE: DNA
<213> ORGANISM: homo sapiens

<400> SEQUENCE: 187 ttaccc                                                                  6

<210> SEQ ID NO 188
<211> LENGTH: 6
<212> TYPE: DNA
<213> ORGANISM: homo sapiens

<400> SEQUENCE: 188 gtggac                                                                  6
```

```
<210> SEQ ID NO 189
<211> LENGTH: 6
<212> TYPE: DNA
<213> ORGANISM: homo sapiens

<400> SEQUENCE: 189 tgcccc                                                                  6

<210> SEQ ID NO 190
<211> LENGTH: 6
<212> TYPE: DNA
<213> ORGANISM: homo sapiens

<400> SEQUENCE: 190 attcac                                                                  6

<210> SEQ ID NO 191
<211> LENGTH: 6
<212> TYPE: DNA
<213> ORGANISM: homo sapiens

<400> SEQUENCE: 191 ccctcc                                                                  6

<210> SEQ ID NO 192
<211> LENGTH: 6
<212> TYPE: DNA
<213> ORGANISM: homo sapiens

<400> SEQUENCE: 192 gacgtt                                                                  6

<210> SEQ ID NO 193
<211> LENGTH: 6
<212> TYPE: DNA
<213> ORGANISM: homo sapiens

<400> SEQUENCE: 193 tccctc                                                                  6

<210> SEQ ID NO 194
<211> LENGTH: 7
<212> TYPE: DNA
<213> ORGANISM: homo sapiens

<400> SEQUENCE: 194 ggacgtt                                                                 7

<210> SEQ ID NO 195
<211> LENGTH: 6
<212> TYPE: DNA
<213> ORGANISM: homo sapiens

<400> SEQUENCE: 195 caaact                                                                  6

<210> SEQ ID NO 196
<211> LENGTH: 6
<212> TYPE: DNA
<213> ORGANISM: homo sapiens

<400> SEQUENCE: 196 atcacc                                                                  6
```

<210> SEQ ID NO 197
<211> LENGTH: 6
<212> TYPE: DNA
<213> ORGANISM: homo sapiens

<400> SEQUENCE: 197 gctcac                                                                   6

<210> SEQ ID NO 198
<211> LENGTH: 6
<212> TYPE: DNA
<213> ORGANISM: homo sapiens

<400> SEQUENCE: 198 attcac                                                                   6

<210> SEQ ID NO 199
<211> LENGTH: 126
<212> TYPE: PRT
<213> ORGANISM: homo sapiens

<400> SEQUENCE: 199

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Met Ile Thr Phe Gly Gly Val Ile Val His Tyr Gly
            100                 105                 110

Met Asp Val Trp Gly Gln Gly Thr Thr Val Thr Val Ser Ser
        115                 120                 125
```

<210> SEQ ID NO 200
<211> LENGTH: 125
<212> TYPE: PRT
<213> ORGANISM: homo sapiens

<400> SEQUENCE: 200

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Ile Asn Pro Asn Ser Gly Asn Thr Asp Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Ile Tyr Tyr Cys
                85                  90                  95
```

```
Val Arg Gly Phe Gly Tyr Ser Tyr Asn Tyr Asp Tyr Tyr Gly Met
            100                 105                 110

Asp Val Trp Gly Gln Gly Thr Thr Val Thr Val Ser Ser
        115                 120                 125

<210> SEQ ID NO 201
<211> LENGTH: 126
<212> TYPE: PRT
<213> ORGANISM: homo sapiens

<400> SEQUENCE: 201

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Asp Ile Asn Trp Val Arg Gln Ala Thr Gly Gln Gly Leu Glu Trp Met
         35                  40                  45

Gly Trp Met Asn Pro Asn Ser Gly Asn Thr Gly Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Ile Ala Val Ala Gly Thr Tyr Tyr Tyr Tyr Gly
             100                 105                 110

Met Asp Val Trp Gly Gln Gly Thr Thr Val Thr Val Ser Ser
        115                 120                 125

<210> SEQ ID NO 202
<211> LENGTH: 126
<212> TYPE: PRT
<213> ORGANISM: homo sapiens

<400> SEQUENCE: 202

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
             20                  25                  30

Asp Ile Asn Trp Val Arg Gln Ala Thr Gly Gln Gly Leu Glu Trp Met
         35                  40                  45

Gly Trp Met Asn Pro Asn Ser Gly Asn Thr Gly Tyr Ala Gln Lys Phe
     50                  55                  60

Gln Gly Arg Val Thr Met Thr Arg Asn Thr Ser Leu Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ile Val Val Val Ala Ala Thr Asn Tyr Tyr Asn Gly
             100                 105                 110

Met Asp Val Trp Gly Gln Gly Thr Thr Val Thr Val Ser Ser
        115                 120                 125

<210> SEQ ID NO 203
<211> LENGTH: 125
<212> TYPE: PRT
<213> ORGANISM: homo sapiens

<400> SEQUENCE: 203

Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Thr Phe Thr Ser Tyr
                    20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Gly Ser Gly Tyr Ser Gly Tyr Asp Tyr Tyr Gly Met
                100                 105                 110

Asp Val Trp Gly Gln Gly Thr Thr Val Thr Val Ser Ser
            115                 120                 125

<210> SEQ ID NO 204
<211> LENGTH: 126
<212> TYPE: PRT
<213> ORGANISM: homo sapiens

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                    20                  25                  30

Asp Ile Asn Trp Val Arg Gln Ala Thr Gly Gln Gly Leu Glu Trp Met
            35                  40                  45

Gly Trp Met Asn Pro Asn Asn Gly Asn Thr Gly Tyr Ala Gln Lys Phe
        50                  55                  60

Gln Gly Arg Val Thr Met Thr Arg Asn Thr Ser Ile Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Asp Ile Val Val Val Thr Ala Thr Asp Tyr Tyr Tyr Gly
                100                 105                 110

Met Asp Val Trp Gly Gln Gly Thr Thr Val Thr Val Ser Ser
            115                 120                 125

<210> SEQ ID NO 205
<211> LENGTH: 127
<212> TYPE: PRT
<213> ORGANISM: homo sapiens

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                    20                  25                  30

Asp Ile Asn Trp Val Arg Gln Ala Thr Gly Gln Gly Leu Glu Trp Met
            35                  40                  45

Gly Trp Met Asn Pro Asn Ser Gly Asp Thr Gly Tyr Ala Gln Lys Phe
        50                  55                  60

Gln Gly Arg Val Thr Met Thr Arg Asn Thr Ser Ile Ser Thr Ala Tyr
65                      70                  75                  80

Met Glu Leu Ser Ser Leu Arg Ser Glu Asp Thr Ala Val Tyr Phe Cys
```

```
                        85                  90                  95
Ala Arg Met Arg Asp Ile Val Ala Thr Ser Tyr Tyr Tyr Phe Tyr
            100                 105                 110

Gly Met Asp Val Trp Gly Gln Gly Thr Thr Val Thr Val Ser Ser
            115                 120                 125

<210> SEQ ID NO 206
<211> LENGTH: 117
<212> TYPE: PRT
<213> ORGANISM: homo sapiens

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp His Tyr Tyr Asp Ser Ser Asp Tyr Leu Tyr Tyr Tyr Tyr
            100                 105                 110

Gly Leu Asp Val Trp
            115

<210> SEQ ID NO 207
<211> LENGTH: 125
<212> TYPE: PRT
<213> ORGANISM: homo sapiens

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Glu Tyr Tyr Tyr Asp Gly Ser Gly Tyr Tyr Tyr Phe
            100                 105                 110

Asp Tyr Trp Gly Gln Gly Thr Leu Val Thr Val Ser Ser
            115                 120                 125

<210> SEQ ID NO 208
<211> LENGTH: 126
<212> TYPE: PRT
<213> ORGANISM: homo sapiens

<400> SEQUENCE: 208
```

```
Glu Val Gln Leu Val Glu Ser Gly Gly Leu Val Lys Pro Gly Gly
  1               5                  10                 15

Ser Leu Arg Leu Ser Cys Ala Ala Ser Gly Phe Asn Phe Arg Thr Tyr
             20                  25                  30

Asn Met Asn Trp Val Arg Gln Ala Pro Gly Lys Gly Leu Glu Trp Val
         35                  40                  45

Ser Ser Ile Ser Ser Ser Ser Asn Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Ile Met Ile Thr Phe Gly Ile Ile Ala Ser Phe Tyr
            100                 105                 110

Phe Asp Tyr Trp Gly Gln Gly Thr Leu Val Thr Val Ser Ser
            115                 120                 125
```

<210> SEQ ID NO 209
<211> LENGTH: 126
<212> TYPE: PRT
<213> ORGANISM: homo sapiens

<400> SEQUENCE: 209

```
Gln Val Gln Leu Val Glu Ser Gly Gly Gly Val Val Gln Pro Gly Lys
  1               5                  10                 15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Gln Gly Tyr Arg Tyr Ala Gly Tyr Tyr Tyr Asp Tyr Gly
            100                 105                 110

Met Asp Val Trp Gly Gln Gly Thr Thr Val Thr Val Ser Ser
            115                 120                 125
```

<210> SEQ ID NO 210
<211> LENGTH: 126
<212> TYPE: PRT
<213> ORGANISM: homo sapiens

<400> SEQUENCE: 210

```
Gln Val Gln Leu Val Glu Ser Gly Gly Gly Val Val Gln Pro Gly Arg
  1               5                  10                 15

Ser Leu Arg Leu Ser Cys Ala Ala Ser Gly Phe Ser Phe Ser Ser Tyr
             20                  25                  30

Gly Met His Trp Val Arg Gln Ala Pro Gly Lys Gly Leu Glu Trp Val
         35                  40                  45

Ala Asp Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Asp Gln Gly Tyr Ser Tyr Gly Tyr Val Tyr Tyr Asp Tyr Gly
            100                 105                 110

Met Asp Val Trp Gly Gln Gly Thr Thr Val Thr Val Ser Ser
            115                 120                 125
```

<210> SEQ ID NO 211
<211> LENGTH: 127
<212> TYPE: PRT
<213> ORGANISM: homo sapiens

<400> SEQUENCE: 211

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Tyr Asp Gly Asn Asp Lys Tyr Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Asp Ser Ser Asp Tyr Leu Tyr Tyr Tyr Tyr
            100                 105                 110

Gly Met Asp Val Trp Gly Gln Gly Thr Thr Val Thr Val Ser Ser
            115                 120                 125
```

<210> SEQ ID NO 212
<211> LENGTH: 120
<212> TYPE: PRT
<213> ORGANISM: homo sapiens

<400> SEQUENCE: 212

```
Glu Val Gln Leu Val Gln Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Gly Thr Val Thr Thr Asn Tyr Tyr Tyr Gly Met Asp Val Trp Gly Gln
            100                 105                 110

Gly Thr Thr Val Thr Val Ser Ser
            115                 120
```

<210> SEQ ID NO 213
<211> LENGTH: 130
<212> TYPE: PRT
<213> ORGANISM: homo sapiens

<400> SEQUENCE: 213

Glu Val Gln Leu Val Gln Ser Gly Ala Glu Val Lys Lys Pro Gly Glu
1               5                   10                  15

Ser Leu Lys Ile Ser Cys Glu Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Glu Val Gln Leu
    50                  55                  60

Val Gln Ser Gly Ala Glu Val Lys Lys Pro Gly Glu Ser Leu Lys Ile
65                  70                  75                  80

Ser Cys Glu Gly Ser Gly Tyr Ser Phe Thr Ser Tyr Trp Ile Gly Trp
                85                  90                  95

Val Arg Gln Met Pro Gly Lys Gly Leu Glu Trp Met Gly Ile Ile Tyr
            100                 105                 110

Pro Gly Asp Ser Asp Thr Arg Tyr Gly Gln Gly Thr Leu Val Thr Val
        115                 120                 125

Ser Ser
    130

<210> SEQ ID NO 214
<211> LENGTH: 126
<212> TYPE: PRT
<213> ORGANISM: homo sapiens

<400> SEQUENCE: 214

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Ser Tyr Tyr Gly Ser Thr Tyr Tyr Asn Val
            100                 105                 110

Phe Asp Tyr Trp Gly Gln Gly Thr Leu Val Thr Val Ser Ser
        115                 120                 125

<210> SEQ ID NO 215
<211> LENGTH: 129
<212> TYPE: PRT
<213> ORGANISM: homo sapiens

<400> SEQUENCE: 215

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

```
Gly Ile Ile Tyr Pro Gly Asp Ser Asp Thr Arg Tyr Ser Pro Ser Phe
    50                  55                  60
Gln Gly Gln Ala Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg His Val Asp Val Gly Ala Thr Ile Gly Gly Tyr Tyr Tyr Tyr
            100                 105                 110
Tyr His Gly Met Asp Val Trp Gly Gln Gly Thr Thr Val Thr Val Ser
            115                 120                 125
Ser

<210> SEQ ID NO 216
<211> LENGTH: 126
<212> TYPE: PRT
<213> ORGANISM: homo sapiens

<400> SEQUENCE: 216

Glu Val Gln Leu Val Gln Ser Gly Thr Glu Val Lys Lys Pro Gly Glu
1               5                   10                  15
Ser Leu Lys Ile Ser Cys Lys Gly Ser Gly Tyr Arg Phe Thr Ser Tyr
                20                  25                  30
Trp Ile Gly Trp Val Arg Gln Met Pro Gly Lys Gly Leu Glu Trp Met
            35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg His Gly Ser Tyr Tyr Asn Ser Gly Ser Tyr Tyr Asn Val
            100                 105                 110
Phe Asp Tyr Trp Gly Gln Gly Thr Leu Val Thr Val Ser Ser
            115                 120                 125

<210> SEQ ID NO 217
<211> LENGTH: 126
<212> TYPE: PRT
<213> ORGANISM: homo sapiens

<400> SEQUENCE: 217

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
                20                  25                  30
Trp Ile Gly Trp Val Arg Gln Met Pro Gly Lys Gly Leu Glu Trp Met
            35                  40                  45
Gly Ile Ile Tyr Pro Gly Asp Ser Asp Ala Lys Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg His Tyr Asp Tyr Val Trp Arg Asn Tyr Arg Tyr Thr Gly Trp
            100                 105                 110
Phe Asp Pro Trp Gly Gln Gly Thr Leu Val Thr Val Ser Ser
```

115                 120                 125

<210> SEQ ID NO 218
<211> LENGTH: 107
<212> TYPE: PRT
<213> ORGANISM: homo sapiens

<400> SEQUENCE: 218

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Asn Ser Phe Pro Arg
                85                  90                  95

Thr Phe Gly Gln Gly Thr Lys Val Glu Ile Lys
            100                 105

<210> SEQ ID NO 219
<211> LENGTH: 111
<212> TYPE: PRT
<213> ORGANISM: homo sapiens

<400> SEQUENCE: 219

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Leu Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Ile Thr Phe Gly Gln Gly Thr Arg Leu Glu Ile Lys
            100                 105                 110

<210> SEQ ID NO 220
<211> LENGTH: 111
<212> TYPE: PRT
<213> ORGANISM: homo sapiens

<400> SEQUENCE: 220

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Gln Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Leu Thr Phe Gly Gly Gly Thr Lys Val Glu Ile Lys
            100                 105                 110

<210> SEQ ID NO 221
<211> LENGTH: 113
<212> TYPE: PRT
<213> ORGANISM: homo sapiens

<400> SEQUENCE: 221

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met Gln Ala
                 85                  90                  95

Leu Gln Ser Leu Met Cys Ser Phe Gly Gln Gly Thr Lys Leu Glu Ile
            100                 105                 110

Lys

<210> SEQ ID NO 222
<211> LENGTH: 107
<212> TYPE: PRT
<213> ORGANISM: homo sapiens

<400> SEQUENCE: 222

Asp Ile Gln Met Thr Gln Ser Pro Ser Ser Leu Ser Ala Ser Val Gly
  1               5                  10                  15

Asp Arg Val Thr Ile Asn Cys Arg Ala Ser Gln Gly Ile Ser Asn Asp
                 20                  25                  30

Leu Ala Trp Tyr Gln Gln Lys Pro Gly Lys Val Pro Lys Leu Leu Ile
             35                  40                  45

Tyr Ala Ala Ser Thr Leu Gln Leu Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Phe
                 85                  90                  95

Thr Phe Gly Pro Gly Thr Lys Val Asp Ile Lys
            100                 105

<210> SEQ ID NO 223
<211> LENGTH: 107
<212> TYPE: PRT
<213> ORGANISM: homo sapiens

<400> SEQUENCE: 223

Asp Ile Gln Met Thr Gln Ser Pro Ser Ser Leu Ser Ala Ser Val Gly
```

```
                 1               5                  10                 15
Asp Arg Val Thr Ile Thr Cys Arg Ala Ser Gln Gly Ile Ser Asn Tyr
                20                 25                 30

Leu Ala Trp Tyr Gln Gln Lys Pro Gly Lys Val Pro Lys Leu Leu Ile
            35                 40                 45

Tyr Ala Ala Ser Thr Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                  70                 75                 80

Glu Asp Val Ala Thr Tyr Tyr Cys Gln Lys Tyr Asn Ser Ala Pro Leu
                85                 90                 95

Thr Phe Gly Gly Gly Thr Lys Val Glu Ile Lys
            100                105

<210> SEQ ID NO 224
<211> LENGTH: 107
<212> TYPE: PRT
<213> ORGANISM: homo sapiens

<400> SEQUENCE: 224

Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Gly Ile Ser Asn Tyr
                20                 25                 30

Leu Ala Trp Tyr Gln Gln Lys Pro Gly Lys Val Pro Asn Leu Leu Ile
            35                 40                 45

Tyr Ala Ala Ser Thr Leu Gln Ser Gly Val Pro Ser Arg Phe Ser Gly
        50                 55                 60

Ser Gly Ser Gly Thr Asp Phe Ser Leu Thr Ile Ser Ser Leu Gln Pro
65                  70                 75                 80

Glu Asp Val Ala Ala Tyr Tyr Cys Gln Lys Cys Asn Ser Ala Pro Trp
                85                 90                 95

Thr Phe Gly Gln Gly Thr Thr Val Glu Ile Lys
            100                105

<210> SEQ ID NO 225
<211> LENGTH: 108
<212> TYPE: PRT
<213> ORGANISM: homo sapiens

<400> SEQUENCE: 225

Glu Ile Val Leu Thr Gln Ser Pro Gly Thr Leu Ser Leu Ser Pro Gly
1               5                  10                 15

Glu Arg Ala Thr Leu Ser Cys Arg Ala Ser Gln Ser Val Ser Ser Ser
                20                 25                 30

Tyr Leu Ala Trp Tyr Gln Gln Lys Pro Gly Gln Ala Pro Arg Leu Leu
            35                 40                 45

Ile Tyr Ala Thr Ser Ser Arg Ala Thr Gly Ile Pro Asp Arg Phe Ser
        50                 55                 60

Gly Ser Gly Ser Gly Thr Asp Phe Thr Leu Thr Ile Ser Arg Leu Glu
65                  70                 75                 80

Pro Glu Asp Phe Ala Val Tyr Tyr Cys Gln Gln Tyr Gly Ser Ser Pro
                85                 90                 95

Cys Ser Phe Gly Gln Gly Thr Lys Leu Glu Ile Lys
            100                105
```

```
<210> SEQ ID NO 226
<211> LENGTH: 108
<212> TYPE: PRT
<213> ORGANISM: homo sapiens

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Phe Thr Phe Gly Pro Gly Thr Lys Val Asp Ile Lys
            100                 105

<210> SEQ ID NO 227
<211> LENGTH: 107
<212> TYPE: PRT
<213> ORGANISM: homo sapiens

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Asp Pro Cys
                85                  90                  95

Ser Phe Gly Gln Gly Thr Lys Leu Glu Ile Arg
            100                 105

<210> SEQ ID NO 228
<211> LENGTH: 107
<212> TYPE: PRT
<213> ORGANISM: homo sapiens

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Phe Cys Leu Gln His Asn Ser Tyr Pro Phe
                85                  90                  95
Thr Phe Gly Pro Gly Thr Lys Val Asp Ile Lys
            100                 105

<210> SEQ ID NO 229
<211> LENGTH: 107
<212> TYPE: PRT
<213> ORGANISM: homo sapiens

<400> SEQUENCE: 229

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                20                  25                  30

Leu Gly Trp Phe Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 230
<211> LENGTH: 107
<212> TYPE: PRT
<213> ORGANISM: homo sapiens

<400> SEQUENCE: 230

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                20                  25                  30

Leu Gly Trp Tyr Gln Gln Ile Pro Gly Lys Ala Pro Lys Arg Leu Ile
            35                  40                  45

Tyr Ala Ala Ser Ser Leu Gln Arg Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 231
<211> LENGTH: 107
<212> TYPE: PRT
<213> ORGANISM: homo sapiens

<400> SEQUENCE: 231

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                20                  25                  30
```

```
Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
                100                 105

<210> SEQ ID NO 232
<211> LENGTH: 107
<212> TYPE: PRT
<213> ORGANISM: homo sapiens

<400> SEQUENCE: 232

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
                100                 105

<210> SEQ ID NO 233
<211> LENGTH: 107
<212> TYPE: PRT
<213> ORGANISM: homo sapiens

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
                100                 105

<210> SEQ ID NO 234
<211> LENGTH: 107
<212> TYPE: PRT
<213> ORGANISM: homo sapiens
```

```
<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 235
<211> LENGTH: 107
<212> TYPE: PRT
<213> ORGANISM: homo sapiens

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Phe Ala Ala Ser Ser Leu Pro Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Ser Gly Tyr Pro Pro
                85                  90                  95

Thr Phe Gly Gln Gly Thr Lys Val Glu Ile Lys
            100                 105

<210> SEQ ID NO 236
<211> LENGTH: 126
<212> TYPE: PRT
<213> ORGANISM: homo sapiens

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Met Ile Thr Phe Gly Gly Val Ile Val His Tyr Gly
```

-continued

```
                  100                 105                 110
Met Asp Val Trp Gly Gln Gly Thr Thr Val Thr Val Ser Ser
            115                 120                 125

<210> SEQ ID NO 237
<211> LENGTH: 125
<212> TYPE: PRT
<213> ORGANISM: homo sapiens

<400> SEQUENCE: 237

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

Gly Trp Ile Asn Pro Asn Ser Gly Asn Thr Asp Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Ile Tyr Tyr Cys
                 85                  90                  95

Val Arg Gly Phe Gly Tyr Ser Tyr Asn Tyr Asp Tyr Tyr Gly Met
            100                 105                 110

Asp Val Trp Gly Gln Gly Thr Thr Val Thr Val Ser Ser
            115                 120                 125

<210> SEQ ID NO 238
<211> LENGTH: 125
<212> TYPE: PRT
<213> ORGANISM: homo sapiens

<400> SEQUENCE: 238

Gln Val Leu Val Gln Ser Gly Ala Glu Val Lys Lys Pro Gly Ala Ser
  1               5                  10                  15

Val Lys Val Ser Cys Lys Ala Ser Gly Tyr Thr Phe Thr Ser Tyr Asp
                 20                  25                  30

Ile Asn Trp Val Arg Gln Ala Thr Gly Gln Gly Leu Glu Trp Met Gly
             35                  40                  45

Trp Met Asn Pro Asn Ser Gly Asn Thr Gly Tyr Ala Gln Lys Phe Gln
         50                  55                  60

Gly Arg Val Thr Met Thr Arg Asn Thr Ser Ile Ser Thr Ala Tyr Met
 65                  70                  75                  80

Glu Leu Ser Ser Leu Arg Ser Glu Asp Thr Ala Val Tyr Tyr Cys Ala
                 85                  90                  95

Arg Glu Gly Ile Ala Val Ala Gly Thr Tyr Tyr Tyr Tyr Gly Met
            100                 105                 110

Asp Val Trp Gly Gln Gly Thr Thr Val Thr Val Ser Ser
            115                 120                 125

<210> SEQ ID NO 239
<211> LENGTH: 126
<212> TYPE: PRT
<213> ORGANISM: homo sapiens

<400> SEQUENCE: 239

Gln Val Gln Leu Val Gln Ser Gly Ala Glu Val Lys Lys Pro Gly Ala
  1               5                  10                  15
```

-continued

```
Ser Val Lys Val Ser Cys Lys Ala Ser Gly Tyr Thr Phe Thr Thr Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Leu Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Val Val Val Ala Ala Thr Asn Tyr Tyr Asn Gly
                100                 105                 110

Met Asp Val Trp Gly Gln Gly Thr Thr Val Thr Val Ser Ser
            115                 120                 125
```

<210> SEQ ID NO 240
<211> LENGTH: 125
<212> TYPE: PRT
<213> ORGANISM: homo sapiens

<400> SEQUENCE: 240

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Gly Tyr Ser Tyr Gly Tyr Asp Tyr Tyr Tyr Gly Met
                100                 105                 110

Asp Val Trp Gly Gln Gly Thr Thr Val Thr Val Ser Ser
            115                 120                 125
```

<210> SEQ ID NO 241
<211> LENGTH: 126
<212> TYPE: PRT
<213> ORGANISM: homo sapiens

<400> SEQUENCE: 241

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Asn Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Asp Ile Val Val Val Thr Ala Thr Asp Tyr Tyr Tyr Gly
            100                 105                 110

Met Asp Val Trp Gly Gln Gly Thr Thr Val Thr Val Ser Ser
        115                 120                 125

<210> SEQ ID NO 242
<211> LENGTH: 127
<212> TYPE: PRT
<213> ORGANISM: homo sapiens

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
            35                  40                  45

Gly Trp Met Asn Pro Asn Ser Gly Asp Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Met Arg Asp Ile Val Ala Thr Ser Tyr Tyr Tyr Phe Tyr
            100                 105                 110

Gly Met Asp Val Trp Gly Gln Gly Thr Thr Val Thr Val Ser Ser
        115                 120                 125

<210> SEQ ID NO 243
<211> LENGTH: 127
<212> TYPE: PRT
<213> ORGANISM: homo sapiens

<400> SEQUENCE: 243

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp His Tyr Tyr Asp Ser Ser Asp Tyr Leu Tyr Tyr Tyr Tyr
            100                 105                 110

Gly Leu Asp Val Trp Gly Gln Gly Thr Thr Val Thr Val Ser Ser
        115                 120                 125

<210> SEQ ID NO 244
<211> LENGTH: 69
<212> TYPE: PRT
<213> ORGANISM: homo sapiens

<400> SEQUENCE: 244
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Gln Gly Thr Leu
50                  55                  60

Val Thr Val Ser Ser
65
```

<210> SEQ ID NO 245
<211> LENGTH: 126
<212> TYPE: PRT
<213> ORGANISM: homo sapiens

<400> SEQUENCE: 245

```
Gln Val Gln Leu Val Glu Ser Gly Gly Gly Val Val Gln Pro Gly Lys
1               5                   10                  15

Ser Leu Arg Leu Ser Cys Ala Ala Ser Gly Glu Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gln Gly Tyr Arg Tyr Ala Gly Tyr Tyr Asp Tyr Gly
                100                 105                 110

Met Asp Val Trp Gly Gln Gly Thr Thr Val Thr Val Ser Ser
        115                 120                 125
```

<210> SEQ ID NO 246
<211> LENGTH: 126
<212> TYPE: PRT
<213> ORGANISM: homo sapiens

<400> SEQUENCE: 246

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Asp Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gln Gly Tyr Ser Tyr Gly Tyr Val Tyr Tyr Asp Tyr Gly
                100                 105                 110

Met Asp Val Trp Gly Gln Gly Thr Thr Val Thr Val Ser Ser
        115                 120                 125
```

<210> SEQ ID NO 247
<211> LENGTH: 126
<212> TYPE: PRT
<213> ORGANISM: homo sapiens

<400> SEQUENCE: 247

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Asn Asp Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Met Asn Ser Leu Arg Ala Glu Asp Thr Ala Val Tyr Tyr Cys Ala
                85                  90                  95

Arg Gly Tyr Tyr Tyr Asp Ser Ser Asp Tyr Leu Tyr Tyr Tyr Tyr Gly
            100                 105                 110

Met Asp Val Trp Gly Gln Gly Thr Thr Val Thr Val Ser Ser
        115                 120                 125

<210> SEQ ID NO 248
<211> LENGTH: 126
<212> TYPE: PRT
<213> ORGANISM: homo sapiens

<400> SEQUENCE: 248

Glu Val Gln Leu Val Gln Ser Gly Ala Glu Val Lys Lys Pro Gly Glu
1               5                   10                  15

Ser Leu Lys Ile Ser Cys Glu Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Ser Tyr Tyr Val Ser Gly Ser Tyr Tyr Asn Val
            100                 105                 110

Phe Asp Tyr Trp Gly Gln Gly Thr Leu Val Thr Val Ser Ser
        115                 120                 125

<210> SEQ ID NO 249
<211> LENGTH: 126
<212> TYPE: PRT
<213> ORGANISM: homo sapiens

<400> SEQUENCE: 249

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met

-continued

```
                35                  40                  45
Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Ser Tyr Tyr Gly Ser Glu Thr Tyr Tyr Asn Val
                100                 105                 110

Phe Asp Tyr Trp Gly Gln Gly Thr Leu Val Thr Val Ser Ser
            115                 120                 125
```

<210> SEQ ID NO 250
<211> LENGTH: 129
<212> TYPE: PRT
<213> ORGANISM: homo sapiens

<400> SEQUENCE: 250

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Ala Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Asp Val Gly Ala Thr Ile Gly Gly Tyr Tyr Tyr Tyr
                100                 105                 110

Tyr His Gly Met Asp Val Trp Gly Gln Gly Thr Thr Val Thr Val Ser
            115                 120                 125

Ser
```

<210> SEQ ID NO 251
<211> LENGTH: 126
<212> TYPE: PRT
<213> ORGANISM: homo sapiens

<400> SEQUENCE: 251

```
Glu Val Gln Leu Val Gln Ser Gly Thr Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Ser Tyr Tyr Asn Ser Gly Ser Tyr Tyr Asn Val
                100                 105                 110
```

```
Phe Asp Tyr Trp Gly Gln Gly Thr Leu Val Thr Val Ser Ser
        115                 120                 125
```

<210> SEQ ID NO 252
<211> LENGTH: 127
<212> TYPE: PRT
<213> ORGANISM: homo sapiens

<400> SEQUENCE: 252

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Ala Lys Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Ala Thr Ala Met Tyr Tyr
                 85                  90                  95

Cys Ala Arg His Tyr Asp Tyr Val Trp Arg Asn Tyr Arg Tyr Thr Gly
            100                 105                 110

Trp Phe Asp Pro Trp Gly Gln Gly Thr Leu Val Thr Val Ser Ser
        115                 120                 125
```

<210> SEQ ID NO 253
<211> LENGTH: 111
<212> TYPE: PRT
<213> ORGANISM: homo sapiens

<400> SEQUENCE: 253

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Leu Lys Pro Gly Gln Ser
             35                  40                  45

Pro Gln Leu Leu Ile Tyr Leu Gly Ser Ser Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                 85                  90                  95

Leu Gln Thr Ile Thr Phe Gly Gln Gly Thr Arg Leu Glu Ile Lys
            100                 105                 110
```

<210> SEQ ID NO 254
<211> LENGTH: 111
<212> TYPE: PRT
<213> ORGANISM: homo sapiens

<400> SEQUENCE: 254

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Gln Ser
                 20                  25                  30
```

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Thr Phe Gly Gly Gly Thr Lys Val Glu Ile Lys
                100                 105                 110

<210> SEQ ID NO 255
<211> LENGTH: 113
<212> TYPE: PRT
<213> ORGANISM: homo sapiens

<400> SEQUENCE: 255

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Ala
                85                  90                  95

Leu Gln Ser Leu Met Cys Ser Phe Gly Gln Gly Thr Lys Leu Glu Ile
                100                 105                 110

Lys

<210> SEQ ID NO 256
<211> LENGTH: 107
<212> TYPE: PRT
<213> ORGANISM: homo sapiens

<400> SEQUENCE: 256

Asp Ile Gln Met Thr Gln Ser Pro Ser Ser Leu Ser Ala Ser Val Gly
1               5                   10                  15

Asp Arg Val Thr Ile Asn Cys Arg Ala Ser Gln Gly Ile Ser Asn Asp
            20                  25                  30

Leu Ala Trp Tyr Gln Gln Lys Pro Gly Lys Val Pro Lys Leu Leu Ile
            35                  40                  45

Tyr Ala Ala Ser Thr Leu Gln Leu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys
                100                 105

<210> SEQ ID NO 257
<211> LENGTH: 107
<212> TYPE: PRT

<213> ORGANISM: homo sapiens

<400> SEQUENCE: 257

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Ser Asn Tyr
             20                  25                  30
Leu Ala Trp Tyr Gln Gln Lys Pro Gly Lys Val Pro Lys Leu Leu Ile
         35                  40                  45
Tyr Ala Ala Ser Thr Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Lys Tyr Asn Ser Ala Pro Leu
                 85                  90                  95
Thr Phe Gly Gly Gly Thr Lys Val Glu Ile Lys
            100                 105
```

<210> SEQ ID NO 258
<211> LENGTH: 107
<212> TYPE: PRT
<213> ORGANISM: homo sapiens

<400> SEQUENCE: 258

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Ser Asn Tyr
             20                  25                  30
Leu Ala Trp Tyr Gln Gln Lys Pro Gly Lys Val Pro Asn Leu Leu Ile
         35                  40                  45
Tyr Ala Ala Ser Thr Leu Gln Ser Gly Val Pro Ser Arg Phe Ser Gly
 50                  55                  60
Ser Gly Ser Gly Thr Asp Phe Ser Leu Thr Ile Ser Ser Leu Gln Pro
 65                  70                  75                  80
Glu Asp Val Ala Ala Tyr Tyr Cys Gln Lys Cys Asn Ser Ala Pro Trp
                 85                  90                  95
Thr Phe Gly Gln Gly Thr Thr Val Glu Ile Lys
            100                 105
```

<210> SEQ ID NO 259
<211> LENGTH: 108
<212> TYPE: PRT
<213> ORGANISM: homo sapiens

<400> SEQUENCE: 259

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
         35                  40                  45
Ile Tyr Ala Thr Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
```

```
Cys Ser Phe Gly Gln Gly Thr Lys Leu Glu Ile Lys
            100                 105
```

<210> SEQ ID NO 260
<211> LENGTH: 108
<212> TYPE: PRT
<213> ORGANISM: homo sapiens

<400> SEQUENCE: 260

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Leu
             85                  90                  95

Phe Thr Phe Gly Pro Gly Thr Lys Val Asp Ile Lys
            100                 105
```

<210> SEQ ID NO 261
<211> LENGTH: 107
<212> TYPE: PRT
<213> ORGANISM: homo sapiens

<400> SEQUENCE: 261

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln His Asn Ser Asp Pro Cys
             85                  90                  95

Ser Phe Gly Gln Gly Thr Lys Leu Glu Ile Arg
            100                 105
```

<210> SEQ ID NO 262
<211> LENGTH: 107
<212> TYPE: PRT
<213> ORGANISM: homo sapiens

<400> SEQUENCE: 262

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Asp Pro Cys
                85                  90                  95

Ser Phe Gly Gln Gly Thr Lys Leu Glu Ile Arg
            100                 105

<210> SEQ ID NO 263
<211> LENGTH: 107
<212> TYPE: PRT
<213> ORGANISM: homo sapiens

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 264
<211> LENGTH: 107
<212> TYPE: PRT
<213> ORGANISM: homo sapiens

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 265
<211> LENGTH: 107
<212> TYPE: PRT
<213> ORGANISM: homo sapiens

<400> SEQUENCE: 265

Asp Ile Gln Met Thr Gln Ser Pro Ser Ser Leu Ser Ala Ser Val Gly

```
                1               5                   10                  15
Asp Arg Val Thr Ile Thr Cys Arg Ala Ser Gln Gly Ile Arg Asn Asp
                    20                  25                  30

Leu Gly Trp Tyr Gln Gln Lys Pro Gly Lys Ala Pro Lys Arg Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                    85                  90                  95

Thr Phe Gly Gln Gly Thr Lys Leu Glu Ile Lys
                100                 105

<210> SEQ ID NO 266
<211> LENGTH: 107
<212> TYPE: PRT
<213> ORGANISM: homo sapiens

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                    20                  25                  30

Leu Gly Trp Tyr Gln Gln Lys Pro Gly Lys Ala Pro Lys Arg Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                    85                  90                  95

Thr Phe Gly Gln Gly Thr Lys Val Glu Ile Lys
                100                 105

<210> SEQ ID NO 267
<211> LENGTH: 107
<212> TYPE: PRT
<213> ORGANISM: homo sapiens

<400> SEQUENCE: 267

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                    20                  25                  30

Leu Gly Trp Tyr Gln Gln Lys Pro Gly Lys Ala Pro Lys Arg Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                    85                  90                  95

Thr Phe Gly Gly Gly Thr Lys Val Glu Ile Lys
                100                 105
```

```
<210> SEQ ID NO 268
<211> LENGTH: 107
<212> TYPE: PRT
<213> ORGANISM: homo sapiens

<400> SEQUENCE: 268

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 269
<211> LENGTH: 107
<212> TYPE: PRT
<213> ORGANISM: homo sapiens

<400> SEQUENCE: 269

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Phe Ala Ala Ser Ser Leu Pro Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Ser Gly Tyr Pro Pro
                85                  90                  95

Thr Phe Gly Gln Gly Thr Lys Val Glu Ile Lys
            100                 105

<210> SEQ ID NO 270
<211> LENGTH: 126
<212> TYPE: PRT
<213> ORGANISM: homo sapiens

<400> SEQUENCE: 270

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Asn Phe Arg Thr Tyr
            20                  25                  30

Asn Met Asn Trp Val Arg Gln Ala Pro Gly Lys Gly Leu Glu Trp Val
        35                  40                  45

Ser Ser Ile Ser Ser Ser Ser Asn Ile Tyr Tyr Ala Asp Ser Val
 50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Ile Met Ile Thr Phe Gly Gly Ile Ile Ala Ser Phe Tyr
            100                 105                 110

Phe Asp Tyr Trp Gly Gln Gly Thr Val Leu Thr Val Ser Ser
        115                 120                 125

<210> SEQ ID NO 271
<211> LENGTH: 98
<212> TYPE: PRT
<213> ORGANISM: homo sapiens

<400> SEQUENCE: 271

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Ser Ile Ser Ser Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 272
<211> LENGTH: 98
<212> TYPE: PRT
<213> ORGANISM: homo sapiens
<220> FEATURE:
<221> NAME/KEY: VARIANT
<222> LOCATION: 28, 30, 33, 57
<223> OTHER INFORMATION: Xaa = Any Amino Acid
<220> FEATURE:
<221> NAME/KEY: VARIANT
<222> LOCATION: 28, 30, 33, 57
<223> OTHER INFORMATION: Xaa = Any Amino Acid

<400> SEQUENCE: 272

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Xaa Phe Xaa Ser Tyr
             20                  25                  30

Xaa Met Asn Trp Val Arg Gln Ala Pro Gly Lys Gly Leu Glu Trp Val
         35                  40                  45

Ser Ser Ile Ser Ser Ser Ser Xaa Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 273
<211> LENGTH: 108
<212> TYPE: PRT
<213> ORGANISM: homo sapiens
```

-continued

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asn
            20                  25                  30

Asp Leu Gly Trp Phe Gln Gln Lys Pro Gly Lys Ala Pro Lys Arg Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Leu Thr Phe Gly Gly Gly Thr Lys Val Glu Ile Lys
            100                 105

<210> SEQ ID NO 274
<211> LENGTH: 96
<212> TYPE: PRT
<213> ORGANISM: homo sapiens

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asn
            20                  25                  30

Asp Leu Gly Trp Tyr Gln Gln Lys Pro Gly Lys Ala Pro Lys Arg Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

<210> SEQ ID NO 275
<211> LENGTH: 96
<212> TYPE: PRT
<213> ORGANISM: homo sapiens

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asn
            20                  25                  30

Asp Leu Gly Trp Phe Gln Gln Lys Pro Gly Lys Ala Pro Lys Arg Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

<210> SEQ ID NO 276
<211> LENGTH: 120

<212> TYPE: PRT
<213> ORGANISM: homo sapiens

<400> SEQUENCE: 276

| Glu | Val | Gln | Leu | Val | Glu | Ser | Gly | Gly | Gly | Leu | Ile | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Val | Ser | Ser | Asn |
|---|---|---|---|---|---|---|---|---|---|---|---|---|---|---|---|
| | | | 20 | | | | | 25 | | | | | 30 | | |

| Tyr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Val | Ile | Tyr | Ser | Gly | Gly | Ser | Thr | Tyr | Tyr | Ala | Asp | Ser | Val | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Gly | Thr | Val | Thr | Thr | Asn | Tyr | Tyr | Gly | Met | Asp | Val | Trp | Gly | Gln |
|---|---|---|---|---|---|---|---|---|---|---|---|---|---|---|
| | | | | 100 | | | | | 105 | | | | | 110 |

| Gly | Thr | Thr | Val | Thr | Val | Ser | Ser |
|---|---|---|---|---|---|---|---|
| | | 115 | | | | 120 | |

<210> SEQ ID NO 277
<211> LENGTH: 97
<212> TYPE: PRT
<213> ORGANISM: homo sapiens

<400> SEQUENCE: 277

| Glu | Val | Gln | Leu | Val | Glu | Ser | Gly | Gly | Gly | Leu | Ile | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Val | Ser | Ser | Asn |
|---|---|---|---|---|---|---|---|---|---|---|---|---|---|---|---|
| | | | 20 | | | | | 25 | | | | | 30 | | |

| Tyr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Val | Ile | Tyr | Ser | Gly | Gly | Ser | Thr | Tyr | Tyr | Ala | Asp | Ser | Val | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

Arg

<210> SEQ ID NO 278
<211> LENGTH: 96
<212> TYPE: PRT
<213> ORGANISM: homo sapiens

<400> SEQUENCE: 278

| Glu | Val | Gln | Leu | Val | Glu | Ser | Gly | Gly | Gly | Leu | Ile | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Val | Ser | Ser | Asn |
|---|---|---|---|---|---|---|---|---|---|---|---|---|---|---|---|
| | | | 20 | | | | | 25 | | | | | 30 | | |

| Tyr | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Val | Ile | Tyr | Ser | Gly | Gly | Ser | Thr | Tyr | Tyr | Ala | Asp | Ser | Val | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

```
Gln Met Asn Ser Leu Arg Ala Glu Asp Thr Ala Val Tyr Tyr Cys Ala
                85                  90                  95

<210> SEQ ID NO 279
<211> LENGTH: 111
<212> TYPE: PRT
<213> ORGANISM: homo sapiens

<400> SEQUENCE: 279

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Gln Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Leu Thr Phe Gly Gly Gly Thr Lys Val Glu Ile Lys
            100                 105                 110

<210> SEQ ID NO 280
<211> LENGTH: 100
<212> TYPE: PRT
<213> ORGANISM: homo sapiens

<400> SEQUENCE: 280

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 281
<211> LENGTH: 99
<212> TYPE: PRT
<213> ORGANISM: homo sapiens
<220> FEATURE:
<221> NAME/KEY: VARIANT
<222> LOCATION: 31
<223> OTHER INFORMATION: Xaa = Any Amino Acid
<220> FEATURE:
<221> NAME/KEY: VARIANT
<222> LOCATION: 31
<223> OTHER INFORMATION: Xaa = Any Amino Acid

<400> SEQUENCE: 281

Asp Ile Val Met Thr Gln Ser Pro Leu Ser Leu Pro Val Thr Pro Gly
```

```
                 1               5                  10                 15
Glu Pro Ala Ser Ile Ser Cys Arg Ser Ser Gln Ser Leu Leu Xaa Ser
                    20                  25                 30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                    85                  90                  95

Leu Gln Thr
```

<210> SEQ ID NO 282
<211> LENGTH: 126
<212> TYPE: PRT
<213> ORGANISM: homo sapiens

<400> SEQUENCE: 282

```
Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Asp Gln Gly Tyr Arg Tyr Ala Gly Tyr Tyr Tyr Asp Tyr Gly
                100                 105                 110

Met Asp Val Trp Gly Gln Gly Thr Thr Val Thr Val Ser Ser
            115                 120                 125
```

<210> SEQ ID NO 283
<211> LENGTH: 98
<212> TYPE: PRT
<213> ORGANISM: homo sapiens

<400> SEQUENCE: 283

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg
```

<210> SEQ ID NO 284
<211> LENGTH: 98
<212> TYPE: PRT
<213> ORGANISM: homo sapiens

<400> SEQUENCE: 284

```
Gln Val Gln Leu Val Glu Ser Gly Gly Gly Val Val Gln Pro Gly Lys
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 285
<211> LENGTH: 107
<212> TYPE: PRT
<213> ORGANISM: homo sapiens

<400> SEQUENCE: 285

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
                100                 105
```

<210> SEQ ID NO 286
<211> LENGTH: 95
<212> TYPE: PRT
<213> ORGANISM: homo sapiens

<400> SEQUENCE: 286

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80
```

-continued

Glu Asp Phe Ala Thr Tyr Tyr Cys Leu Gln His Asn Ser Tyr Pro
                85                  90                  95

<210> SEQ ID NO 287
<211> LENGTH: 95
<212> TYPE: PRT
<213> ORGANISM: homo sapiens

<400> SEQUENCE: 287

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                85                  90                  95

<210> SEQ ID NO 288
<211> LENGTH: 126
<212> TYPE: PRT
<213> ORGANISM: homo sapiens

<400> SEQUENCE: 288

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Gly Ile Ala Val Ala Gly Thr Tyr Tyr Tyr Tyr Tyr Gly
                100                 105                 110

Met Asp Val Trp Gly Gln Gly Thr Thr Val Thr Val Ser Ser
            115                 120                 125

<210> SEQ ID NO 289
<211> LENGTH: 98
<212> TYPE: PRT
<213> ORGANISM: homo sapiens

<400> SEQUENCE: 289

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

```
Gly Trp Met Asn Pro Asn Ser Gly Asn Thr Gly Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 290
<211> LENGTH: 98
<212> TYPE: PRT
<213> ORGANISM: homo sapiens

<400> SEQUENCE: 290

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
             35                  40                  45

Gly Trp Met Asn Pro Asn Ser Gly Asn Thr Gly Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 291
<211> LENGTH: 107
<212> TYPE: PRT
<213> ORGANISM: homo sapiens

<400> SEQUENCE: 291

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Phe Cys Leu Gln His Asn Ser Tyr Pro Phe
                 85                  90                  95

Thr Phe Gly Pro Gly Thr Lys Val Asp Ile Lys
                100                 105

<210> SEQ ID NO 292
<211> LENGTH: 95
<212> TYPE: PRT
<213> ORGANISM: homo sapiens

<400> SEQUENCE: 292

Asp Ile Gln Met Thr Gln Ser Pro Ser Ser Leu Ser Ala Ser Val Gly
 1               5                  10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 293
<211> LENGTH: 95
<212> TYPE: PRT
<213> ORGANISM: homo sapiens

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln His Asn Ser Tyr Pro
                85                  90                  95

<210> SEQ ID NO 294
<211> LENGTH: 126
<212> TYPE: PRT
<213> ORGANISM: homo sapiens

<400> SEQUENCE: 294

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Met Ile Thr Phe Gly Gly Val Ile Val His Tyr Gly
                100                 105                 110

Met Asp Val Trp Gly Gln Gly Thr Thr Val Thr Val Ser Ser
            115                 120                 125

<210> SEQ ID NO 295
<211> LENGTH: 98
<212> TYPE: PRT
<213> ORGANISM: homo sapiens
```

```
<400> SEQUENCE: 295

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 296
<211> LENGTH: 98
<212> TYPE: PRT
<213> ORGANISM: homo sapiens

<400> SEQUENCE: 296

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 297
<211> LENGTH: 107
<212> TYPE: PRT
<213> ORGANISM: homo sapiens

<400> SEQUENCE: 297

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Asp Pro Cys
                85                  90                  95

Ser Phe Gly Gln Gly Thr Lys Leu Glu Ile Arg
                100                 105
```

<210> SEQ ID NO 298
<211> LENGTH: 95
<212> TYPE: PRT
<213> ORGANISM: homo sapiens

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 299
<211> LENGTH: 95
<212> TYPE: PRT
<213> ORGANISM: homo sapiens
<220> FEATURE:
<221> NAME/KEY: VARIANT
<222> LOCATION: 94
<223> OTHER INFORMATION: Xaa = Any Amino Acid
<220> FEATURE:
<221> NAME/KEY: VARIANT
<222> LOCATION: 94
<223> OTHER INFORMATION: Xaa = Any Amino Acid

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Xaa Pro
                85                  90                  95

<210> SEQ ID NO 300
<211> LENGTH: 126
<212> TYPE: PRT
<213> ORGANISM: homo sapiens

<400> SEQUENCE: 300

Glu Val Gln Leu Val Gln Ser Gly Ala Glu Val Lys Lys Pro Gly Glu
1               5                   10                  15

Ser Leu Lys Ile Ser Cys Glu Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Ser Tyr Tyr Val Ser Gly Ser Tyr Tyr Asn Val
            100                 105                 110

Phe Asp Tyr Trp Gly Gln Gly Thr Leu Val Thr Val Ser Ser
            115                 120                 125
```

<210> SEQ ID NO 301
<211> LENGTH: 98
<212> TYPE: PRT
<213> ORGANISM: homo sapiens

<400> SEQUENCE: 301

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 302
<211> LENGTH: 98
<212> TYPE: PRT
<213> ORGANISM: homo sapiens
<220> FEATURE:
<221> NAME/KEY: VARIANT
<222> LOCATION: 23
<223> OTHER INFORMATION: Xaa = Any Amino Acid
<220> FEATURE:
<221> NAME/KEY: VARIANT
<222> LOCATION: 23
<223> OTHER INFORMATION: Xaa = Any Amino Acid

<400> SEQUENCE: 302

```
Glu Val Gln Leu Val Gln Ser Gly Ala Glu Val Lys Lys Pro Gly Glu
1               5                   10                  15

Ser Leu Lys Ile Ser Cys Xaa Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 303

```
<211> LENGTH: 107
<212> TYPE: PRT
<213> ORGANISM: homo sapiens

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Arg Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 304
<211> LENGTH: 95
<212> TYPE: PRT
<213> ORGANISM: homo sapiens

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 305
<211> LENGTH: 95
<212> TYPE: PRT
<213> ORGANISM: homo sapiens
<220> FEATURE:
<221> NAME/KEY: VARIANT
<222> LOCATION: 56
<223> OTHER INFORMATION: Xaa = Any Amino Acid
<220> FEATURE:
<221> NAME/KEY: VARIANT
<222> LOCATION: 56
<223> OTHER INFORMATION: Xaa = Any Amino Acid

<400> SEQUENCE: 305

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Xaa Gly Val Pro Ser Arg Phe Ser Gly
```

-continued

```
              50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95
```

<210> SEQ ID NO 306
<211> LENGTH: 126
<212> TYPE: PRT
<213> ORGANISM: homo sapiens

<400> SEQUENCE: 306

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Ser Phe Ser Ser Tyr
                 20                  25                  30

Gly Met His Trp Val Arg Gln Ala Pro Gly Lys Gly Leu Glu Trp Val
             35                  40                  45

Ala Asp Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr Ser Tyr Gly Tyr Val Tyr Tyr Asp Tyr Gly
                100                 105                 110

Met Asp Val Trp Gly Gln Gly Thr Thr Val Thr Val Ser Ser
            115                 120                 125
```

<210> SEQ ID NO 307
<211> LENGTH: 98
<212> TYPE: PRT
<213> ORGANISM: homo sapiens

<400> SEQUENCE: 307

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Asp Ile Trp Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 308
<211> LENGTH: 98
<212> TYPE: PRT
<213> ORGANISM: homo sapiens

<400> SEQUENCE: 308

```
Gln Val Gln Leu Val Glu Ser Gly Gly Gly Val Val Gln Pro Gly Arg
  1               5                  10                  15
```

```
Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Asp Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 309
<211> LENGTH: 107
<212> TYPE: PRT
<213> ORGANISM: homo sapiens

<400> SEQUENCE: 309

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asp Asn
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 310
<211> LENGTH: 95
<212> TYPE: PRT
<213> ORGANISM: homo sapiens

<400> SEQUENCE: 310

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asp Asn
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                85                  90                  95

<210> SEQ ID NO 311
<211> LENGTH: 95
<212> TYPE: PRT
<213> ORGANISM: homo sapiens

<400> SEQUENCE: 311
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asp Asn
             20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
             85                  90                  95
```

<210> SEQ ID NO 312
<211> LENGTH: 98
<212> TYPE: PRT
<213> ORGANISM: homo sapiens

<400> SEQUENCE: 312

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg
```

<210> SEQ ID NO 313
<211> LENGTH: 126
<212> TYPE: PRT
<213> ORGANISM: homo sapiens

<400> SEQUENCE: 313

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg His Gly Ser Tyr Tyr Gly Ser Glu Thr Tyr Tyr Asn Val
             100                 105                 110

Phe Asp Tyr Trp Gly Gln Gly Thr Leu Val Thr Val Ser Ser
            115                 120                 125
```

<210> SEQ ID NO 314
<211> LENGTH: 98
<212> TYPE: PRT
<213> ORGANISM: homo sapiens
<220> FEATURE:
<221> NAME/KEY: VARIANT
<222> LOCATION: 28
<223> OTHER INFORMATION: Xaa = Any Amino Acid
<220> FEATURE:
<221> NAME/KEY: VARIANT
<222> LOCATION: 28
<223> OTHER INFORMATION: Xaa = Any Amino Acid

<400> SEQUENCE: 314

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Xaa Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 315
<211> LENGTH: 95
<212> TYPE: PRT
<213> ORGANISM: homo sapiens

<400> SEQUENCE: 315

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 316
<211> LENGTH: 107
<212> TYPE: PRT
<213> ORGANISM: homo sapiens

<400> SEQUENCE: 316

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

```
Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
                100                 105

<210> SEQ ID NO 317
<211> LENGTH: 95
<212> TYPE: PRT
<213> ORGANISM: homo sapiens

<400> SEQUENCE: 317

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95

<210> SEQ ID NO 318
<211> LENGTH: 98
<212> TYPE: PRT
<213> ORGANISM: homo sapiens

<400> SEQUENCE: 318

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 319
<211> LENGTH: 129
<212> TYPE: PRT
<213> ORGANISM: homo sapiens

<400> SEQUENCE: 319

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30
```

-continued

```
Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                      55                      60

Gln Gly Gln Ala Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Val Asp Val Gly Ala Thr Ile Gly Gly Tyr Tyr Tyr Tyr
            100                 105                 110

Tyr His Gly Met Asp Val Trp Gly Gln Gly Thr Thr Val Thr Val Ser
             115                 120                 125

Ser
```

<210> SEQ ID NO 320
<211> LENGTH: 98
<212> TYPE: PRT
<213> ORGANISM: homo sapiens
<220> FEATURE:
<221> NAME/KEY: VARIANT
<222> LOCATION: 68
<223> OTHER INFORMATION: Xaa = Any Amino Acid
<220> FEATURE:
<221> NAME/KEY: VARIANT
<222> LOCATION: 68
<223> OTHER INFORMATION: Xaa = Any Amino Acid

<400> SEQUENCE: 320

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                      55                      60

Gln Gly Gln Xaa Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg
```

<210> SEQ ID NO 321
<211> LENGTH: 100
<212> TYPE: PRT
<213> ORGANISM: homo sapiens

<400> SEQUENCE: 321

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                      55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Val Gly Val Tyr Tyr Cys Met Gln Ala
                85                  90                  95

Leu Gln Thr Pro
            100

<210> SEQ ID NO 322
<211> LENGTH: 114
<212> TYPE: PRT
<213> ORGANISM: homo sapiens

<400> SEQUENCE: 322

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Ala
                85                  90                  95

Leu Gln Thr Pro Leu Met Cys Ser Phe Gly Gln Gly Thr Lys Leu Glu
            100                 105                 110

Ile Lys

<210> SEQ ID NO 323
<211> LENGTH: 99
<212> TYPE: PRT
<213> ORGANISM: homo sapiens

<400> SEQUENCE: 323

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser

<210> SEQ ID NO 324
<211> LENGTH: 98
<212> TYPE: PRT
<213> ORGANISM: homo sapiens

<400> SEQUENCE: 324

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

-continued

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 325
<211> LENGTH: 127
<212> TYPE: PRT
<213> ORGANISM: homo sapiens

<400> SEQUENCE: 325

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp His Tyr Tyr Asp Ser Ser Asp Tyr Leu Tyr Tyr Tyr Tyr
                100                 105                 110

Gly Leu Asp Val Trp Gly Gln Gly Thr Thr Val Thr Val Ser Ser
            115                 120                 125

<210> SEQ ID NO 326
<211> LENGTH: 98
<212> TYPE: PRT
<213> ORGANISM: homo sapiens

<400> SEQUENCE: 326

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 327
<211> LENGTH: 96
<212> TYPE: PRT

<213> ORGANISM: homo sapiens

<400> SEQUENCE: 327

Asp Ile Gln Met Thr Gln Ser Pro Ser Ser Leu Ser Ala Ser Val Gly
1               5                   10                  15

Asp Arg Val Phe Thr Ile Thr Cys Arg Ala Ser Gln Gly Ile Ser Asn
            20                  25                  30

Tyr Leu Ala Trp Tyr Gln Gln Lys Pro Gly Lys Val Pro Lys Leu Leu
        35                  40                  45

Ile Tyr Ala Ala Ser Thr Leu Gln Ser Gly Val Pro Ser Arg Phe Ser
 50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Lys Tyr Asn Ser Ala Pro
                85                  90                  95

<210> SEQ ID NO 328
<211> LENGTH: 108
<212> TYPE: PRT
<213> ORGANISM: homo sapiens

<400> SEQUENCE: 328

Asp Ile Gln Met Thr Gln Ser Pro Ser Ser Leu Ser Ala Ser Val Gly
1               5                   10                  15

Asp Arg Val Phe Thr Ile Thr Cys Arg Ala Ser Gln Gly Ile Ser Asn
            20                  25                  30

Tyr Leu Ala Trp Tyr Gln Gln Lys Pro Gly Lys Val Pro Lys Leu Leu
        35                  40                  45

Ile Tyr Ala Ala Ser Thr Leu Gln Ser Gly Val Pro Ser Arg Phe Ser
 50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Lys Tyr Asn Ser Ala Pro
                85                  90                  95

Leu Thr Phe Gly Gly Gly Thr Lys Val Glu Ile Lys
                100                 105

<210> SEQ ID NO 329
<211> LENGTH: 96
<212> TYPE: PRT
<213> ORGANISM: homo sapiens

<400> SEQUENCE: 329

Asp Ile Gln Met Thr Gln Ser Pro Ser Ser Leu Ser Ala Ser Val Gly
1               5                   10                  15

Asp Arg Val Phe Thr Ile Thr Cys Arg Ala Ser Gln Gly Ile Ser Asn
            20                  25                  30

Tyr Leu Ala Trp Tyr Gln Gln Lys Pro Gly Lys Val Pro Lys Leu Leu
        35                  40                  45

Ile Tyr Ala Ala Ser Thr Leu Gln Ser Gly Val Pro Ser Arg Phe Ser
 50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Lys Tyr Asn Ser Ala Pro
                85                  90                  95

<210> SEQ ID NO 330

-continued

<211> LENGTH: 98
<212> TYPE: PRT
<213> ORGANISM: homo sapiens

<400> SEQUENCE: 330

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 331
<211> LENGTH: 127
<212> TYPE: PRT
<213> ORGANISM: homo sapiens

<400> SEQUENCE: 331

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Asn Asp Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Asp Ser Ser Asp Tyr Leu Tyr Tyr Tyr Tyr
            100                 105                 110

Gly Met Asp Val Trp Gly Gln Gly Thr Thr Val Thr Val Ser Ser
        115                 120                 125

<210> SEQ ID NO 332
<211> LENGTH: 98
<212> TYPE: PRT
<213> ORGANISM: homo sapiens
<220> FEATURE:
<221> NAME/KEY: VARIANT
<222> LOCATION: 56, 57
<223> OTHER INFORMATION: Xaa = Any Amino Acid
<220> FEATURE:
<221> NAME/KEY: VARIANT
<222> LOCATION: 56, 57
<223> OTHER INFORMATION: Xaa = Any Amino Acid

<400> SEQUENCE: 332

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
            35                  40                  45

Ala Ile Ile Trp Tyr Asp Gly Xaa Xaa Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 333
<211> LENGTH: 95
<212> TYPE: PRT
<213> ORGANISM: homo sapiens

<400> SEQUENCE: 333

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
                85                  90                  95

<210> SEQ ID NO 334
<211> LENGTH: 107
<212> TYPE: PRT
<213> ORGANISM: homo sapiens

<400> SEQUENCE: 334

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Asn Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Ser Leu Thr Ile Ser Ser Leu Gln Pro
 65                  70                  75                  80

Glu Asp Val Ala Ala Tyr Tyr Cys Gln Lys Cys Asn Ser Ala Pro Trp
                85                  90                  95

Thr Phe Gly Gln Gly Thr Thr Val Glu Ile Lys
                100                 105

<210> SEQ ID NO 335
<211> LENGTH: 95
<212> TYPE: PRT
<213> ORGANISM: homo sapiens
<220> FEATURE:
<221> NAME/KEY: VARIANT
<222> LOCATION: 45, 85, 91
<223> OTHER INFORMATION: Xaa = Any Amino Acid
```

```
<220> FEATURE:
<221> NAME/KEY: VARIANT
<222> LOCATION: 45, 85, 91
<223> OTHER INFORMATION: Xaa = Any Amino Acid

<400> SEQUENCE: 335

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Xaa Leu Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Xaa Tyr Tyr Cys Gln Lys Xaa Asn Ser Ala Pro
                85                  90                  95

<210> SEQ ID NO 336
<211> LENGTH: 98
<212> TYPE: PRT
<213> ORGANISM: homo sapiens

<400> SEQUENCE: 336

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg

<210> SEQ ID NO 337
<211> LENGTH: 126
<212> TYPE: PRT
<213> ORGANISM: homo sapiens

<400> SEQUENCE: 337

Glu Val Gln Leu Val Gln Ser Gly Thr Glu Val Lys Lys Pro Gly Glu
 1               5                  10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95
```

```
Ala Arg His Gly Ser Tyr Tyr Asn Ser Gly Ser Tyr Tyr Asn Val
            100                 105                 110
Phe Asp Tyr Trp Gly Gln Gly Thr Leu Val Thr Val Ser Ser
            115                 120                 125
```

<210> SEQ ID NO 338
<211> LENGTH: 98
<212> TYPE: PRT
<213> ORGANISM: homo sapiens
<220> FEATURE:
<221> NAME/KEY: VARIANT
<222> LOCATION: 9, 28
<223> OTHER INFORMATION: Xaa = Any Amino Acid
<220> FEATURE:
<221> NAME/KEY: VARIANT
<222> LOCATION: 9, 28
<223> OTHER INFORMATION: Xaa = Any Amino Acid

<400> SEQUENCE: 338

```
Glu Val Gln Leu Val Gln Ser Gly Xaa Glu Val Lys Lys Pro Gly Glu
1               5                   10                  15
Ser Leu Lys Ile Ser Cys Lys Gly Ser Gly Tyr Xaa Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg
```

<210> SEQ ID NO 339
<211> LENGTH: 95
<212> TYPE: PRT
<213> ORGANISM: homo sapiens

<400> SEQUENCE: 339

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro
                85                  90                  95
```

<210> SEQ ID NO 340
<211> LENGTH: 107
<212> TYPE: PRT
<213> ORGANISM: homo sapiens

<400> SEQUENCE: 340

```
Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
                100                 105

<210> SEQ ID NO 341
<211> LENGTH: 95
<212> TYPE: PRT
<213> ORGANISM: homo sapiens

<400> SEQUENCE: 341

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 342
<211> LENGTH: 98
<212> TYPE: PRT
<213> ORGANISM: homo sapiens

<400> SEQUENCE: 342

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 343
<211> LENGTH: 125
<212> TYPE: PRT
<213> ORGANISM: homo sapiens

<400> SEQUENCE: 343

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Asp Ile Asn Trp Val Arg Gln Ala Thr Gly Gln Gly Leu Glu Trp Met
             35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Gly Ser Gly Tyr Ser Tyr Gly Tyr Asp Tyr Tyr Tyr Gly Met
             100                 105                 110

Asp Val Trp Gly Gln Gly Thr Thr Val Thr Val Ser Ser
             115                 120                 125

<210> SEQ ID NO 344
<211> LENGTH: 98
<212> TYPE: PRT
<213> ORGANISM: homo sapiens

<400> SEQUENCE: 344

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Asp Ile Asn Trp Val Arg Gln Ala Thr Gly Gln Gly Leu Glu Trp Met
             35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg

<210> SEQ ID NO 345
<211> LENGTH: 95
<212> TYPE: PRT
<213> ORGANISM: homo sapiens

<400> SEQUENCE: 345

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
             85                  90                  95
```

```
<210> SEQ ID NO 346
<211> LENGTH: 107
<212> TYPE: PRT
<213> ORGANISM: homo sapiens

<400> SEQUENCE: 346

Asp Ile Gln Met Thr Gln Ser Pro Ser Ser Leu Ser Ala Ser Val Gly
 1               5                  10                  15

Asp Arg Val Thr Ile Asn Cys Arg Ala Ser Gln Gly Ile Ser Asn Asp
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Phe
                 85                  90                  95

Thr Phe Gly Pro Gly Thr Lys Val Asp Ile Lys
            100                 105

<210> SEQ ID NO 347
<211> LENGTH: 95
<212> TYPE: PRT
<213> ORGANISM: homo sapiens
<220> FEATURE:
<221> NAME/KEY: VARIANT
<222> LOCATION: 22, 32, 56
<223> OTHER INFORMATION: Xaa = Any Amino Acid
<220> FEATURE:
<221> NAME/KEY: VARIANT
<222> LOCATION: 22, 32, 56
<223> OTHER INFORMATION: Xaa = Any Amino Acid

<400> SEQUENCE: 347

Asp Ile Gln Met Thr Gln Ser Pro Ser Ser Leu Ser Ala Ser Val Gly
 1               5                  10                  15

Asp Arg Val Thr Ile Xaa Cys Arg Ala Ser Gln Gly Ile Ser Asn Xaa
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Xaa Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
                 85                  90                  95

<210> SEQ ID NO 348
<211> LENGTH: 98
<212> TYPE: PRT
<213> ORGANISM: homo sapiens

<400> SEQUENCE: 348

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Asp Ile Asn Trp Val Arg Gln Ala Thr Gly Gln Gly Leu Glu Trp Met
         35                  40                  45
```

-continued

```
Gly Trp Met Asn Pro Asn Ser Gly Asn Thr Gly Tyr Ala Gln Lys Phe
         50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 349
<211> LENGTH: 126
<212> TYPE: PRT
<213> ORGANISM: homo sapiens

<400> SEQUENCE: 349

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Tyr
                 20                  25                  30

Asp Ile Asn Trp Val Arg Gln Ala Thr Gly Gln Gly Leu Glu Trp Met
             35                  40                  45

Gly Trp Met Asn Pro Asn Ser Gly Asn Thr Gly Tyr Ala Gln Lys Phe
         50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ile Val Val Val Thr Ala Thr Asp Tyr Tyr Tyr Gly
                100                 105                 110

Met Asp Val Trp Gly Gln Gly Thr Thr Val Thr Val Ser Ser
            115                 120                 125

<210> SEQ ID NO 350
<211> LENGTH: 98
<212> TYPE: PRT
<213> ORGANISM: homo sapiens
<220> FEATURE:
<221> NAME/KEY: VARIANT
<222> LOCATION: 55
<223> OTHER INFORMATION: Xaa = Any Amino Acid
<220> FEATURE:
<221> NAME/KEY: VARIANT
<222> LOCATION: 55
<223> OTHER INFORMATION: Xaa = Any Amino Acid

<400> SEQUENCE: 350

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

Gly Trp Met Asn Pro Asn Xaa Gly Asn Thr Gly Tyr Ala Gln Lys Phe
         50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

```
<210> SEQ ID NO 351
<211> LENGTH: 95
<212> TYPE: PRT
<213> ORGANISM: homo sapiens

<400> SEQUENCE: 351

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95

<210> SEQ ID NO 352
<211> LENGTH: 107
<212> TYPE: PRT
<213> ORGANISM: homo sapiens

<400> SEQUENCE: 352

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Phe Ala Ala Ser Ser Leu Pro Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Ser Gly Tyr Pro Pro
                 85                  90                  95

Thr Phe Gly Gln Gly Thr Lys Val Glu Ile Lys
                100                 105

<210> SEQ ID NO 353
<211> LENGTH: 95
<212> TYPE: PRT
<213> ORGANISM: homo sapiens
<220> FEATURE:
<221> NAME/KEY: VARIANT
<222> LOCATION: 55, 92, 93
<223> OTHER INFORMATION: Xaa = Any Amino Acid
<220> FEATURE:
<221> NAME/KEY: VARIANT
<222> LOCATION: 55, 92, 93
<223> OTHER INFORMATION: Xaa = Any Amino Acid

<400> SEQUENCE: 353

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
```

```
                    35                  40                  45
Tyr Ala Ala Ser Ser Leu Xaa Ser Gly Val Pro Ser Arg Phe Ser Gly
             50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Xaa Xaa Tyr Pro
                 85                  90                  95
```

<210> SEQ ID NO 354
<211> LENGTH: 126
<212> TYPE: PRT
<213> ORGANISM: homo sapiens

<400> SEQUENCE: 354

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Val Glu Tyr Tyr Tyr Asp Gly Ser Gly Tyr Tyr Tyr Tyr
                100                 105                 110

Phe Asp Tyr Trp Gly Gln Gly Thr Leu Val Thr Val Ser Ser
            115                 120                 125
```

<210> SEQ ID NO 355
<211> LENGTH: 98
<212> TYPE: PRT
<213> ORGANISM: homo sapiens

<400> SEQUENCE: 355

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg
```

<210> SEQ ID NO 356
<211> LENGTH: 98
<212> TYPE: PRT
<213> ORGANISM: homo sapiens

<400> SEQUENCE: 356

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg

<210> SEQ ID NO 357
<211> LENGTH: 108
<212> TYPE: PRT
<213> ORGANISM: homo sapiens

<400> SEQUENCE: 357

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Ser Tyr Tyr Cys Gln Gln Ser Asn Ser Phe Pro Arg
                 85                  90                  95

Phe Thr Phe Gly Gln Gly Thr Lys Val Glu Ile Lys
            100                 105

<210> SEQ ID NO 358
<211> LENGTH: 95
<212> TYPE: PRT
<213> ORGANISM: homo sapiens

<400> SEQUENCE: 358

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ile Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                 85                  90                  95

<210> SEQ ID NO 359
<211> LENGTH: 95
<212> TYPE: PRT
```

```
<213> ORGANISM: homo sapiens
<220> FEATURE:
<221> NAME/KEY: VARIANT
<222> LOCATION: 53
<223> OTHER INFORMATION: Xaa = Any Amino Acid
<220> FEATURE:
<221> NAME/KEY: VARIANT
<222> LOCATION: 53
<223> OTHER INFORMATION: Xaa = Any Amino Acid

<400> SEQUENCE: 359
```

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Xaa Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Asn Ser Phe Pro
                85                  90                  95

```
<210> SEQ ID NO 360
<211> LENGTH: 127
<212> TYPE: PRT
<213> ORGANISM: homo sapiens

<400> SEQUENCE: 360
```

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asp Thr Gly Tyr Ala Gln Lys Phe
 50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Met Arg Asp Ile Val Ala Thr Ser Tyr Tyr Tyr Phe Tyr
            100                 105                 110

Gly Met Asp Val Trp Gly Gln Gly Thr Thr Val Thr Val Ser Ser
        115                 120                 125

```
<210> SEQ ID NO 361
<211> LENGTH: 98
<212> TYPE: PRT
<213> ORGANISM: homo sapiens

<400> SEQUENCE: 361
```

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

```
Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 362
<211> LENGTH: 98
<212> TYPE: PRT
<213> ORGANISM: homo sapiens
<220> FEATURE:
<221> NAME/KEY: VARIANT
<222> LOCATION: 57
<223> OTHER INFORMATION: Xaa = Any Amino Acid
<220> FEATURE:
<221> NAME/KEY: VARIANT
<222> LOCATION: 57
<223> OTHER INFORMATION: Xaa = Any Amino Acid

<400> SEQUENCE: 362

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

Gly Trp Met Asn Pro Asn Ser Gly Xaa Thr Gly Tyr Ala Gln Lys Phe
        50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg

<210> SEQ ID NO 363
<211> LENGTH: 111
<212> TYPE: PRT
<213> ORGANISM: homo sapiens

<400> SEQUENCE: 363

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Leu Lys Pro Gly Gln Ser
             35                  40                  45

Pro Gln Leu Leu Ile Tyr Leu Gly Ser Ser Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Thr
                 85                  90                  95

Leu Gln Thr Ile Thr Phe Gly Gln Gly Thr Arg Leu Glu Ile Lys
                100                 105                 110

<210> SEQ ID NO 364
<211> LENGTH: 100
```

```
<212> TYPE: PRT
<213> ORGANISM: homo sapiens

<400> SEQUENCE: 364

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Leu Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 365
<211> LENGTH: 99
<212> TYPE: PRT
<213> ORGANISM: homo sapiens
<220> FEATURE:
<221> NAME/KEY: VARIANT
<222> LOCATION: 43, 58, 96
<223> OTHER INFORMATION: Xaa = Any Amino Acid
<220> FEATURE:
<221> NAME/KEY: VARIANT
<222> LOCATION: 43, 58, 96
<223> OTHER INFORMATION: Xaa = Any Amino Acid

<400> SEQUENCE: 365

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Xaa Lys Pro Gly Gln Ser
        35                  40                  45

Pro Gln Leu Leu Ile Tyr Leu Gly Ser Xaa Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Xaa
                85                  90                  95

Leu Gln Thr

<210> SEQ ID NO 366
<211> LENGTH: 126
<212> TYPE: PRT
<213> ORGANISM: homo sapiens

<400> SEQUENCE: 366

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

```
Gly Ile Ile Tyr Pro Gly Asp Ser Asp Ala Lys Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Tyr Asp Tyr Val Trp Arg Asn Tyr Arg Tyr Thr Gly Trp
            100                 105                 110

Phe Asp Pro Trp Gly Gln Gly Thr Leu Val Thr Val Ser Ser
            115                 120                 125
```

<210> SEQ ID NO 367
<211> LENGTH: 98
<212> TYPE: PRT
<213> ORGANISM: homo sapiens

<400> SEQUENCE: 367

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg
```

<210> SEQ ID NO 368
<211> LENGTH: 98
<212> TYPE: PRT
<213> ORGANISM: homo sapiens
<220> FEATURE:
<221> NAME/KEY: VARIANT
<222> LOCATION: 58
<223> OTHER INFORMATION: Xaa = Any Amino Acid
<220> FEATURE:
<221> NAME/KEY: VARIANT
<222> LOCATION: 58
<223> OTHER INFORMATION: Xaa = Any Amino Acid

<400> SEQUENCE: 368

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Xaa Lys Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg
```

```
<210> SEQ ID NO 369
<211> LENGTH: 108
<212> TYPE: PRT
<213> ORGANISM: homo sapiens

<400> SEQUENCE: 369

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                 85                  90                  95

Phe Thr Phe Gly Pro Gly Thr Lys Val Asp Ile Lys
            100                 105

<210> SEQ ID NO 370
<211> LENGTH: 96
<212> TYPE: PRT
<213> ORGANISM: homo sapiens

<400> SEQUENCE: 370

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                 85                  90                  95

<210> SEQ ID NO 371
<211> LENGTH: 95
<212> TYPE: PRT
<213> ORGANISM: homo sapiens
<220> FEATURE:
<221> NAME/KEY: VARIANT
<222> LOCATION: 54
<223> OTHER INFORMATION: Xaa = Any Amino Acid
<220> FEATURE:
<221> NAME/KEY: VARIANT
<222> LOCATION: 54
<223> OTHER INFORMATION: Xaa = Any Amino Acid

<400> SEQUENCE: 371

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45
```

```
Ile Tyr Gly Ala Ser Xaa Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser
                 85                  90                  95
```

<210> SEQ ID NO 372
<211> LENGTH: 125
<212> TYPE: PRT
<213> ORGANISM: homo sapiens

<400> SEQUENCE: 372

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

Gly Trp Ile Asn Pro Asn Ser Gly Asn Thr Asp Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Ile Tyr Tyr Cys
                 85                  90                  95

Val Arg Gly Phe Gly Tyr Ser Tyr Asn Tyr Asp Tyr Tyr Gly Met
             100                 105                 110

Asp Val Trp Gly Gln Gly Thr Thr Val Thr Val Ser Ser
         115                 120                 125
```

<210> SEQ ID NO 373
<211> LENGTH: 98
<212> TYPE: PRT
<213> ORGANISM: homo sapiens

<400> SEQUENCE: 373

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
             35                  40                  45

Gly Trp Met Asn Pro Asn Ser Gly Asn Thr Asp Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg
```

<210> SEQ ID NO 374
<211> LENGTH: 98
<212> TYPE: PRT
<213> ORGANISM: homo sapiens
<220> FEATURE:
<221> NAME/KEY: VARIANT
<222> LOCATION: 59, 73, 97
<223> OTHER INFORMATION: Xaa = Any Amino Acid

```
<220> FEATURE:
<221> NAME/KEY: VARIANT
<222> LOCATION: 59, 73, 97
<223> OTHER INFORMATION: Xaa = Any Amino Acid

<400> SEQUENCE: 374
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Ile Asn Pro Asn Ser Gly Asn Thr Xaa Tyr Ala Gln Lys Phe
50                  55                  60

Gln Gly Arg Val Thr Met Thr Arg Xaa Thr Ser Ile Ser Thr Ala Tyr
65                  70                  75                  80

Met Glu Leu Ser Ser Leu Arg Ser Glu Asp Thr Ala Ile Tyr Tyr Cys
                85                  90                  95

Xaa Arg

```
<210> SEQ ID NO 375
<211> LENGTH: 108
<212> TYPE: PRT
<213> ORGANISM: homo sapiens

<400> SEQUENCE: 375
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Ala Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Ser Phe Gly Gln Gly Thr Lys Leu Glu Ile Lys
            100                 105

```
<210> SEQ ID NO 376
<211> LENGTH: 96
<212> TYPE: PRT
<213> ORGANISM: homo sapiens

<400> SEQUENCE: 376
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Ser Pro
                85                  90                  95

<210> SEQ ID NO 377
<211> LENGTH: 96
<212> TYPE: PRT
<213> ORGANISM: homo sapiens

<400> SEQUENCE: 377

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Ala Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95
```